US011731116B2

(12) United States Patent
Milstein et al.

(10) Patent No.: US 11,731,116 B2
(45) Date of Patent: Aug. 22, 2023

(54) MANGANESE BASED COMPLEXES AND USES THEREOF FOR HOMOGENEOUS CATALYSIS

(71) Applicants: YEDA RESEARCH AND DEVELOPMENT CO. LTD., Rehovot (IL); Arkadi Nerush, Rishon LeZion (IL)

(72) Inventors: David Milstein, Rehovot (IL); Alex Nerush, Rehovot (IL); Matthias Vogt, Rehovot (IL); Arup Mukherjee, Rehovot (IL); Noel Angel Espinosa-Jalapa, Rehovot (IL); Subrata Chakraborty, Rehovot (IL)

(73) Assignee: YEDA RESEARCH AND DEVELOPMENT CO. LTD., Rehovot (IL)

( * ) Notice: Subject to any disclaimer, the term of this patent is extended or adjusted under 35 U.S.C. 154(b) by 179 days.

(21) Appl. No.: 16/076,697

(22) PCT Filed: Feb. 8, 2017

(86) PCT No.: PCT/IL2017/050152
§ 371 (c)(1),
(2) Date: Aug. 9, 2018

(87) PCT Pub. No.: WO2017/137984
PCT Pub. Date: Aug. 17, 2017

(65) Prior Publication Data
US 2019/0366316 A1     Dec. 5, 2019

Related U.S. Application Data

(60) Provisional application No. 62/409,392, filed on Oct. 18, 2016.

(30) Foreign Application Priority Data

Feb. 9, 2016    (IL) .......................................... 244052

(51) Int. Cl.
    *B01J 31/00*       (2006.01)
    *B01J 31/18*       (2006.01)
    (Continued)

(52) U.S. Cl.
    CPC ......... *B01J 31/181* (2013.01); *B01J 31/2428* (2013.01); *C07C 249/02* (2013.01);
    (Continued)

(58) Field of Classification Search
    None
    See application file for complete search history.

(56) References Cited

U.S. PATENT DOCUMENTS

| 5,686,645 A | 11/1997 | Faraj |
| 2009/0112005 A1 | 4/2009 | Milstein et al. |
| 2012/0253042 A1 | 10/2012 | Milstein et al. |

OTHER PUBLICATIONS

Voga et al. JACS, 135, 17004-17018 (Year: 2013).*

(Continued)

*Primary Examiner* — Yun Qian
(74) *Attorney, Agent, or Firm* — Mark S. Cohen; Pearl Cohen Zedek Latzer Baratz LLP

(57) ABSTRACT

The present invention relates to novel manganese complexes and their use, inter alia, for homogeneous catalysis in (1) the preparation of imine by dehydrogenative coupling of an alcohol and amine; (2) C—C coupling in Michael addition reaction using nitriles as Michael donors; (3) dehydrogenative coupling of alcohols to give esters and hydrogen gas (4) hydrogenation of esters to form alcohols (including hydrogenation of cyclic esters (lactones) or cyclic di-esters (di-lactones), or polyesters); (5) hydrogenation of amides (including cyclic dipeptides, lactams, diamide, polypeptides and polyamides) to alcohols and amines (or diamine); (6) hydrogenation of organic carbonates (including polycarbonates) to alcohols or hydrogenation of carbamates (including (Continued)

polycarbamates) or urea derivatives to alcohols and amines; (7) dehydrogenation of secondary alcohols to ketones; (8) amidation of esters (i.e., synthesis of amides from esters and amines); (9) acylation of alcohols using esters; (10) coupling of alcohols with water and a base to form carboxylic acids; and (11) preparation of amino acids or their salts by coupling of amino alcohols with water and a hydrogenative coupling of alcohols and amines; (13) preparation of imides from diols.

(51) Int. Cl.
B01J 31/24 (2006.01)
C07C 249/02 (2006.01)
C07B 43/06 (2006.01)
C07B 43/08 (2006.01)

(52) U.S. Cl.
CPC ...... B01J 2231/348 (2013.01); B01J 2531/72 (2013.01); C07B 43/06 (2013.01); C07B 43/08 (2013.01)

(56) References Cited

OTHER PUBLICATIONS

Takai et al.(Chem. Commun., 6360-6362). (Year: 2008).*
Adams JP. "Imines, enamines and oximes" Journal of the Chemical Society, Perkin Transactions 1. 2000(2):125-39.
Alberico et al. "Selective hydrogen production from methanol with a defined iron pincer catalyst under mild conditions" Angewandte Chemie International Edition. Dec. 23, 2013;52(52):14162-6.
Albrecht et al. "Cleavage of unreactive bonds with pincer metal complexes" Dalton Transactions. 2011;40(35):8733-44.
Albrecht et al. "Platinum group organometallics based on "pincer" complexes: Sensors, switches, and catalysts" Angewandte Chemie International Edition. Oct. 15, 2001:40(20):3750-81.
Andérez-Fernández et al. "A stable manganese pincer catalyst for the selective dehydrogenation of methanol" Angewandte Chemie International Edition. Jan. 9, 2017;56(2):559-62.
Andersson PG, Munslow IJ, editors. Modern reduction methods. John Wiley & Sons; Sep. 8, 2008.
Aydin et al. "Stereoselective Pincer-complex catalyzed C—H functionalization of benzyl nitriles under mild conditions. An efficient route to beta-aminonitriles", Org Lett. Nov. 20, 2008;10(22):5175-8.
Bain et al. "Recyclable hydrotalcite catalysts for alcohol imination via acceptorless dehydrogenation", Green Chem., 2015,17, 2271-2280.
Balaraman et al. "Efficient hydrogenation of biomass-derived cyclic di-esters to 1, 2-diols" Chemical Communications. 2012;48(8):1111-3.
Baldauf et al. "δ-Peptides and δ-Amino Acids as Tools for Peptide Structure Design a Theoretical Study" The Journal of organic chemistry. Sep. 17, 2004;69(19):6214-20.
Barta et al. "Catalytic conversion of nonfood woody biomass solids to organic liquids", Acc Chem Res. May 20, 2014;47(5):1503-12.
Bauer et al. "Iron catalysis in organic synthesis" Chemical reviews. Mar. 9, 2015;115(9):3170-387.
Becke AD. "Density-functional exchange-energy approximation with correct asymptotic behavior" Physical review A. Sep. 1, 1988;38(6):3098.
Ben-Ari et al. "Metal-Ligand Cooperation in C—H and H2 Activation by an Electron-Rich PNP Ir (I) System: Facile Ligand Dearomatization—Aromatization as Key Steps" Journal of the American Chemical Society. Dec. 6, 2006:128(48):15390-1.
Benito-Garagorri et al. "Modularly designed transition metal PNP and PGP pincer complexes based on aminophosphines: synthesis and catalytic applications" Accounts of chemical research. Jan. 23, 2008;41(2):201-13.
Bertoli et al. "Osmium and ruthenium catalysts for dehydrogenation of alcohols" Organometallics. Jun. 6, 2011;30(13):3479-82.
Bielinski et al. "Base-free methanol dehydrogenation using a pincer-supported iron compound and Lewis acid co-catalyst" ACS Catalysis. Mar. 16, 2015;5(4):2404-15.
Blackburn et al. "In situ oxidation-imine formation-reduction routes from alcohols to amines", Org Lett. May 31, 2001;3(11):1637-9.
Bornschein et al. "Mild and selective hydrogenation of aromatic and aliphatic (di) nitriies with a well-defined iron pincer complex" Nature communications. Jun. 27, 2014;5:4111.
Brittain et al. "Tetrahydrofuran amino acids—versatile building blocks for unnatural biopolymers: lack of secondary structure in oligomeric carbopeptoids derived from a D-galacto-5-

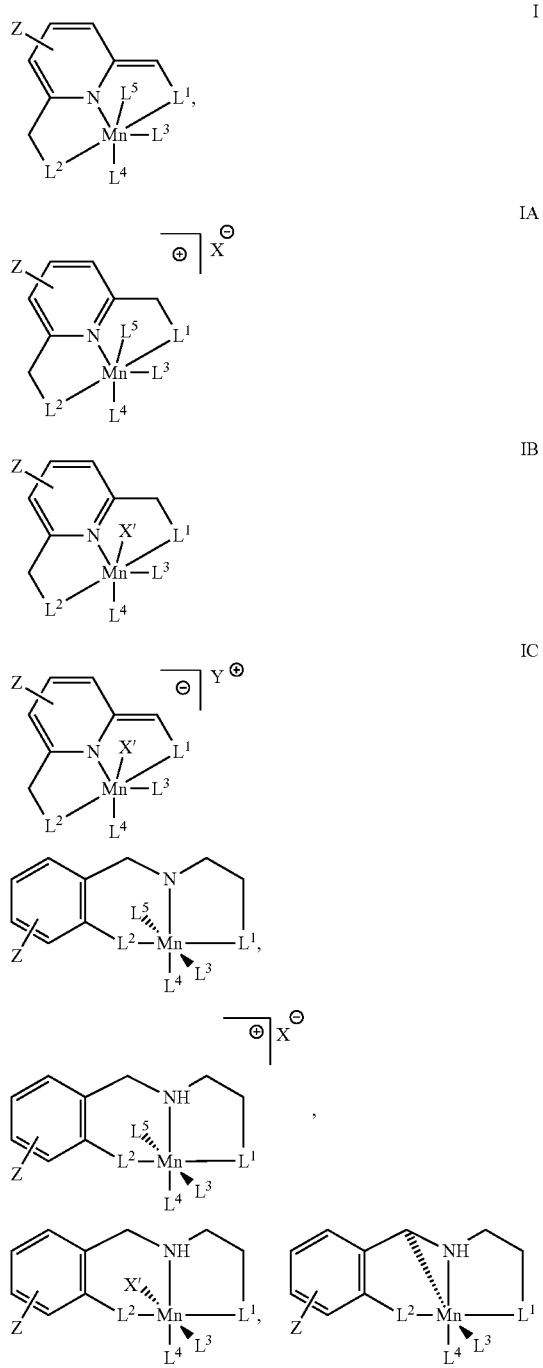

12 Claims, 19 Drawing Sheets

(56) References Cited

OTHER PUBLICATIONS (aminomethyl) tetrahydrofuran-2-carboxylic acid" Journal of the Chemical Society, Perkin Transactions 1. 2000(21):3655-65.
Budzelaar et al. "Metal-to-Ligand Electron Transfer in Diiminopyridine Complexes of Mn—Zn" A Theoretical Study. Inorganic chemistry. Aug. 27, 2001;40(18):4649-55.
Bullock RM, editor. "Catalysis without precious metals" John Wiley & Sons; Aug. 2, 2011.
Chakraborty et al. "Homogeneous Hydrogenation of Nitriies Catalyzed by Molybdenum and Tungsten Amides", ACS Catal., 2014, 4 (7), pp. 2191-2194.
Chakraborty et al. "Nickel and iron pincer complexes as catalysts for the reduction of carbonyl compounds" Accounts of chemical research. Jun. 22, 2015;48(7):1995-2003.
Chakraborty et al. "Iron-based catalysts for the hydrogenation of esters to alcohols" Journal of the American Chemical Society. May 22, 2014;136(22):7869-72.
Chakraborty et al. "Iron-Catalyzed Mild and Selective Hydrogenative Gross-Coupling of Nitriles and Amines to Form Secondary Aldimines" Angewandte Chemie. Feb. 13, 2017;129(8):2106-10.
Chakraborty et al. "Selective hydrogenation of nitriles to primary amines catalyzed by a novel iron complex" Chemical Communications. 2016;52(9):1812-5.
Chan et al. "Rhodium-Catalyzed Ketone Methylation Using Methanol Under Mild Conditions: Formation of α-Branched Products" Angewandte Chemie International Edition. Jan. 13, 2014;53(3):761-5.
Chen et al. "Metal-free and solvent-free oxidative coupling of amines to imines with mesoporous carbon from macrocyclic compounds" Acs catalysis. Mar. 30, 2015:5(5):2788-94.
Chen et al. "Recent advances in aerobic oxidation of alcohols and amines to imines" ACS catalysis. Sep. 3, 2015,5(10):5851-76.
Chen et al. "A new facile method for the synthesis of 1-arylimidazole-5-carboxylates" Tetrahedron Letters. Jul. 15, 2000;41(29):5453-6.
Chirik PJ. "Iron- and cobalt-catalyzed alkene hydrogenation: catalysis with both redox-active and strona field ligands" Accounts of chemical research. Jun. 4, 2015;48(6):1687-95.
Christoffers J. "Transition-metal catalysis of the Michael reaction of 1, 3-dicarbonyl compounds and acceptor-activated alkenes" European journal of organic chemistry. Jul. 1998;1998(7):1259-66.
Cifre et al. "Renewable hydrogen utilisation for the production of methanol" Energy conversion and management. Feb. 1, 2007;48(2):519-27.
Comelles et al. "Michael additions catalyzed by transition metals and lanthanide species. A review" Arkivoc. Jan. 1, 2005;9:207-38.
Corey et al. "Conversion of ketones having δ, επ-functions to cyclopentanols by zinc-trimethylchlorosilane" Tetrahedron Letters. Jan. 1, 1983;24(28):2821-4.
Das Neves Gomes et al. "A diagonal approach to chemical recycling of carbon dioxide: organocatalytic transformation for the reductive functionalization of CO2" Angewandte Chemie International Edition. Jan. 2, 2012;51(1):187-90.
De Boer et al. "CuI click catalysis with cooperative noninnocent pyridylphosphine ligands" Inorganica Chimica Acta. Jan. 15, 2012;380:336-42.
Deibl et al. "Genera! and mild cobalt-catalyzed C-alkylation of unactivated amides and esters with alcohols" Journal of the American Chemical Society. Aug. 16, 2016:138(34):10786-9.
Dine et al. "Formamide synthesis through borinic acid catalysed transamidation under mild conditions" Chemistry—A European Journal. Apr. 19, 2016;22(17):5894-8.
Dolg M. "Effective Core Potentials" in Modern Methods and Algorithms of Quantum Chemistry Grotendorst, J., Ed. 2000.
Downie et al. "Vilsmeier formylation and glyoxylation reactions of nucleophilic aromatic compounds using pyrophosphoryl chloride" Tetrahedron. May 7, 1993,49(19):4015-34.
Dunlap BI. "Fitting the Coulomb potential variationally in X α molecular calculations" The Journal of Chemical Physics. Mar. 15, 1983;78(6):3140-2.

Dunlap BI. "Robust and variational fitting: Removing the four-center integrals from center stage in quantum chemistry" Journal of Molecular Structure: THEOCHEM. Sep. 8, 2000;529(1-3):37-40.
Elangovan et al. "Efficient and selective N-alkylation of amines with alcohols catalysed by manganese pincer complexes" Nature communications. Oct. 6, 2016;7:12641.
Elangovan et al. "Selective catalytic hydrogenations of nitriles, ketones, and aldehydes by well-defined manganese pincer complexes" Journal of the American Chemical Society. Jul. 6, 2016;138(28):8809-14.
Elangovan et al. "Hydrogenation of esters to alcohols catalyzed by defined manganese pincer complexes" Angewandte Chemie International Edition. Dec. 5, 2016,55(49):15364-8.
Éll et al. "Dehydrogenation of aromatic amines to imines via ruthenium-catalyzed hydrogen transfer" Chemical Communications. 2002(10):1144-5.
Espinosa-Jalapa et al. "Manganese-Catalyzed Hydrogenation of Esters to Alcohols" Chemistry—A European Journal. May 2, 2017;23(25):5934-8.
Federsel et al. "A Well-Defined Iron Catalyst for the Reduction of Bicarbonates and Carbon Dioxide to Formates. Alkyl Formates, and Formamides" Angewandte Chemie International Edition. Dec. 10, 2010;49(50):9777-80.
Federsel et al. "Catalytic hydrogenation of carbon dioxide and bicarbonates with a well-defined cobalt dihydrogen complex" Chemistry—A European Journal. Jan. 2, 2012;18(1):72-5.
Feller et al. "N—H Activation by Rh (I) via Metal-Ligand Cooperation" Organometallics. May 18, 2012;31(11):4083-101.
Filonenko et al. "Lutidine-derived Ru-CNC hydrogenation pincer catalysts with versatile coordination properties" ACS Catalysis. Jul. 11, 2014;4(8):2667-71.
Filonenko et al. "The impact of metal-ligand cooperation in hydrogenation of carbon dioxide catalyzed by ruthenium PNP pincer" ACS Catalysis. Oct. 11, 2013;3(11):2522-6.
Fleming et al. "Metalated nitriles: Chelation-controlled cyclizations to cis and trans hydrindanes and decalins" The Journal of organic chemistry. Feb. 16, 2007;72(4):1431-6.
Fleming et al. "Metalated Nitriles: Internal 1, 2-Asymmetric Induction" The Journal of organic chemistry. Apr. 4, 2008;73(7):2803-10.
Fleming et al. "Nitrile-containing pharmaceuticals: efficacious roles of the nitrile pharmacophore" Journal of medicinal chemistry. Aug. 30, 2010;53(22):7902-17.
Fogler et al. "New ruthenium nitrosyl pincer complexes bearing an O2 Ligand, mono-oxygen transfer" Inorganic chemistry. Feb. 19, 2015;54(5):2253-63.
Fogler et al. "System with Potential Dual Modes of Metal-Ligand Cooperation: Highly Catalytically Active Pyridine-Based PNNH-Ru Pincer Complexes" Chemistry—A European Journal. Nov. 24, 2014;20(48):15727-31.
Fogler et al. "New CNN-type ruthenium pincer NHC complexes. Mild, efficient catalytic hydrogenation of esters" Organometallics. Jun. 27, 2011;30(14):3826-33.
Friedfeld et al. "Bis (phosphine) cobalt dialkyl complexes for directed catalytic alkene hydrogenation" Journal of the American Chemical Society. Sep. 10, 2014;136(38):13178-81.
Fryzuk et al. "Nature of the catalytically inactive cobalt hydride formed upon hydrogenation of aromatic substrates. Structure and characterization of the binuclear cobalt hydride [{iso-Pr2P (CH2) 3PPr-iso2} Co] 2 (H)(. mu.-H) 3" Inorganic chemistry. May 1991;30(10):2437-41.
Fujita et al. "Hydrogen production from a methanol-water solution catalyzed by an anionic iridium complex bearing a functional bipyridonate ligand under weakly basic conditions" Angewandte Chemie International Edition. Jul. 27, 2015;54(31):9057-60.
Gaertner et al. "Heteroatom-Free Arene-Cobalt and Arene-Iron Catalysts for Hydrogenations" Angewandte Chemie International Edition. Apr. 1, 2014;53(14):3722-6.
Garg et al. "Unprecedented iron-catalyzed selective hydrogenation of activated amides to amines and alcohols" Chemical Communications. 2016;52(30):5285-8.
Gerack et al. "Formylation of amines" Molecules. Jun. 2014;19(6):7689-713.

(56) References Cited

OTHER PUBLICATIONS

Gnanaprakasam et al. "Direct synthesis of imines from alcohols and amines with liberation of H2" Angewandte Chemie International Edition. Feb. 15, 2010;49(8):1468-71.

Grate et al. "Acoustic wave sensors" Sensors update. Oct. 1996;2(1):37-83.

Grimme et al. "A consistent and accurate ab initio parametrization of density functional dispersion correction (DFT-D) for the 94 elements H—Pu" The Journal of chemical physics. Apr. 21, 2010;132(15):154104.

Gu et al. "Dehydrogenation of secondary amines to imines catalyzed by an iridium PGP pincer complex: initial aliphatic or direct amino dehydrogenation?" Journal of Molecular Catalysis A: Chemical. Oct. 16, 2002;189(1):119-24.

Gunanathan et al. "Bond activation and catalysis by ruthenium pincer complexes" Chemical reviews. Nov. 14, 2014;114(24):12024-87.

Gunanathan et al. "Applications of acceptorless dehydrogenation and related transformations in chemical synthesis" Science. Jul. 19, 2013;341(6143):1229712.

Gunanathan et al. "Bond activation by metal-ligand cooperation: Design of "green" catalytic reactions based on aromatization-dearomatization of pincer complexes" in Bifunctional Molecular Catalysis 2011 (pp. 55-84). Springer, Berlin, Heidelberg.

Gunanathan et al. "Metal-ligand cooperation by aromatization-dearomatization: a new paradigm in bond activation and "Green" catalysis" Accounts of chemical research. Jul. 8, 2011;44(8):588-602.

Han et al. "An efficient and convenient synthesis of formamidines" Tetrahedron letters. Aug. 4, 1997;38(31):5423-6.

Hanson et al. "C—H Bond Activation by Rhodium (I) Phenoxide and Acetate Complexes: Mechanism of H—D Exchange between Arenes and Water" Organometallics. Mar. 4, 2008;27(7):1454-63.

Hasanayn et al. "A metathesis model for the dehydrogenative coupling of amines with alcohols and esters into carboxamides by Milstein's [Ru (PNN)(CO)(H)] catalysts" Inorganic chemistry. Jul. 31, 2014;53(16):8334-49.

Hasegawa et al. Enantioselective direct amination of α-Cyanoacetates catalyzed by bifunctional chiral ru and ir amido complexes Journal of the American Chemical Society. Feb. 20, 2008;130(7):2158-9.

He et al. "Manganese-Catalyzed Dehydrogenative [4+2] Annulation of N☐H Imines and Alkynes by C☐H/N☐H Activation" Angewandte Chemie International Edition. May 5, 2014;53(19):4950-3.

Hett et al. "Large-scale synthesis of enantio- and diastereomerically pure (R, R)-formoterol" Organic Process Research & Development. Mar. 20, 1998;2(2):96-9.

Hill et al. "A field Guide to foldamers" Chemical Reviews. Dec. 12, 2001:101(12):3893-4012.

Hoz et al. "Fluoride Ion as a Catalyst for Michael Additions to Nitro-Alkenes" Synthesis. 1975;1975(03):162.

Hu et al. "Reusable homogeneous catalytic system for hydrogen production from methanol and water" Acs Catalysis. Jul. 10, 2014:4(8):2649-52.

Huang et al., "Manganese-catalyzed late-stage aliphatic C—H azidation" Journal of the American Chemical Society. Apr. 14, 2015;137(16):5300-3.

Huff et al. "Reversible carbon-carbon bond formation between carbonyl compounds and a ruthenium pincer complex" Chemical Communications. 2013;49(64):7147-9.

Huff et al. "Role of a Noninnocent Pincer Ligand in the Activation of CO2 at (PNN) Ru (H)(CO)" Organometallics. Jun. 21, 2012;31(13):4643-9.

Hulley et al. "Manganese-based molecular electrocatalysts for oxidation of hydrogen. ACS Catalysis" Oct. 16, 2015;5(11):6838-47.

Hulley et al. "Heterolytic cleavage of H 2 by bifunctional manganese (i) complexes: impact of ligand dynamics, electrophilicity, and base positioning" Chemical Science. 2014;5(12):4729-41.

International Search Report for PCT Application No. PCT/IL2017/050152 dated May 10, 2017.

Ishida et al. "N-Formylation of Amines via the Aerobic Oxidation of Methanol over Supported Gold Nanoparticles" ChemSusChem: Chemistry & Sustainability Energy & Materials. Jun. 22, 2009;2(6):538-41.

Jagtap et al. "First enantioselective organocatalytic allylation of simple aldimines with allyltrichlorosilane" Chemical Communications. 2006(45):4747-9.

Jeletic et al. "A cobalt-based catalyst for the hydrogenation of CO2 under ambient conditions" Journal of the American Chemical Society. Jul. 24, 2013;135(31):11533-6.

Jha SC. "Catalytic, enantioselective michael addition reaction", Thesis 2002.

Jiang et al. "Aromatic δ-peptides" Journal of the American Chemical Society. Mar. 26, 2003;125(12):3448-9.

Jiang et al. "Aromatic δ-peptides: design, synthesis and structural studies of helical, quinoline-derived oligoamide foldamers" Tetrahedron. Oct. 13, 2003;59(42):8365-74.

Jiang et al. "Highly efficient oxidation of amines to imines by singlet oxygen and its application in Ugi-type reactions" Organic letters. Sep. 21, 2009,11(20):4568-71.

Johnson et al. "Imidotitanium complexes as hydroamination catalysts: Substantially enhanced reactivity from an unexpected cyclopentadienide/amide ligand exchange" Journal of the American Chemical Society. Mar. 28, 2001,123(12):2923-4.

Johnson et al. "A post-Hartree-Fock model of intermolecular interactions: Inclusion of higher-order corrections" The Journal of chemical physics. May 7, 2006;124(17):174104.

Jones et al. "Trichlorosilane mediated asymmetric reductions of the C [double bond, length as m-dash] N bond" Organic & biomolecular chemistry. 2012;10(11):2189-200.

Kallmeier et al. "Highly active and selective manganese C=O bond hydrogenation catalysts: the importance of the multidentate ligand, the ancillary ligands, and the oxidation state" Angewandte Chemie International Edition. Sep. 19, 2016;55(39):11806-9.

Kang et al. "Hydrogen Acceptor- and Base-Free N-Formylation of Nitriles and Amines using Methanol as C1 Source" Advanced Synthesis & Catalysis. Mar. 9, 2015;357(4):834-40.

Kariyone K. "Studies on Insecticides" VI. Synthesis of Proline Derivatives. Chemical and Pharmaceutical Bulletin. Dec. 25, 1960;8(12):1110-3.

Kersten et al. ""[Cp* Co☐ CoCp*]" is a Hydride" Angewandte Chemie International Edition in English. Oct. 1992;31(10):1341-3.

Kesharwani et al. "Explicitly correlated coupled cluster benchmarks with realistic-sized ligands for some late-transition metal reactions: basis sets convergence and performance of more approximate methods" in Thom H. Dunning, Jr. 2015 (pp. 233-246). Springer, Berlin, Heidelberg.

Khaskin et al. "N—H Activation of Amines and Ammonia by Ru via Metal-Ligand Cooperation" Journal of the American Chemical Society. Jun. 4, 2010;132(25):8542-3.

Khusnutdinova et al. "Metal-ligand cooperation" Angewandte Chemie International Edition. Oct. 12, 2015;54(42):12236-73.

Kloek et al. "C—H Bond Activation by Rhodium (I) Hydroxide and Phenoxide Complexes" Angewandte Chemie International Edition. Jun. 18, 2007;46(25):4736-8.

Knijnenburg et al. "Olefin hydrogenation using diimine pyridine complexes of Co and Rh" Journal of Molecular Catalysis A: Chemical. May 3, 2005;232(1-2):151-9.

Kobayashi et al. "Synthesis of 1-formyl-1,2-dihydroquinoline derivatives by a Lewis acid-catalyzed cyclization of o-(1-hydroxy-2-alkenyl) phenyl isocyanides" Chemistry letters. Jul. 1995;24(7):575-6.

Kobayashi et al. "Facile and highly stereoselective synthesis of homoallylic alcohols using organosilicon intermediates" The Journal of Organic Chemistry. Nov. 1994;59(22):6620-8.

Kobayashi et al. "Trichlorosilane-dimethylformamide (Cl3SiH-DMF) as an efficient reducing agent. Reduction of aldehydes and imines and reductive amination of aldehydes under mild conditions using hypervalent hydridosilicates" Chemistry Letters. May 1996;25(5):407-8.

Kohl et al. "Consecutive thermal H2 and light-induced O2 evolution from water promoted by a metal complex" Science. Apr. 3, 2009;324(5923):74-7.

(56) References Cited

OTHER PUBLICATIONS

Korstanje et al. "Hydrogenation of carboxylic acids with a homogeneous cobalt catalyst" Science. Oct. 16, 2015;350(6258):298-302.
Kuriyama et al. "Catalytic hydrogenation of esters. Development of an efficient catalyst and processes for synthesising (R)-1, 2-propanediol and 2-(I-menthoxy) ethanol" Organic Process Research & Development. Dec. 22, 2011;16(1):166-71.
Kwon et al. "One-pot synthesis of imines and secondary amines by Pd-catalyzed coupling of benzyl alcohols and primary amines" The Journal of organic chemistry. Mar. 5, 2009;74(7):2877-9.
Lagaditis et al. "Iron (II) complexes containing unsymmetrical P—N—P' pincer ligands for the catalytic asymmetric hydrogenation of ketones and imines" Journal of the American Chemical Society. Jan. 21, 2014;136(4):1367-80.
Langer et al. "Efficient hydrogenation of ketones catalyzed by an iron pincer complex" Angewandte Chemie International Edition. Feb. 25, 2011;50(9):2120-4.
Langer et al. Low-pressure hydrogenation of carbon dioxide catalyzed by an iron pincer complex exhibiting noble metal activity. Angewandte Chemie International Edition. Oct. 10, 2011:50(42):9948-52.
Largeron et al. "Environmentally friendly chemoselective oxidation of primary aliphatic amines by using a biomimetic electrocatalytic system" Chemistry—A European Journal. Jan. 18, 2008;14(3):996-1003.
Li et al. "Titanium hydrazide and imido complexes: Synthesis, structure, reactivity, and relevance to alkyne hydroamination" Journal of the American Chemical Society. Feb. 18, 2004;126(6):1794-803.
Li et al. "Selective ruthenium-catalyzed methylation of 2-arylethanols using methanol as C1 feedstock" Chemical Communications. 2014;50(95):14991-4.
Li et al. "Acceptoriess Dehydrogenative Coupling of o-Aminobenzamides with the Activation of Methanol as a C1 Source for the Construction of Quinazolinones" Organic letters. May 23, 2016;1 8(11):2580-3.
Lin et al. "A study of ethanol dehydrogenation reaction in a palladium membrane reactor" Catalysis today. Oct. 27, 2004;97(2-3):181-8.
Lin et al. "Boryl-metal bonds facilitate cobalt/nickel-catalyzed olefin hydrogenation" Journal of the American Chemical Society. Sep. 17, 2014;136(39):13672-83.
Lin et al. "Boryl-mediated reversible H2 activation at cobalt: Catalytic hydrogenation, dehydrogenation, and transfer hydrogenation" Journal of the American Chemical Society. Oct. 7, 2013;135(41):15310-3.
Liu et al. "Manganese (I)-Catalyzed C—H Aminocarbonyiation of Heteroarenes" Angewandte Chemie International Edition. Nov. 16, 2015;54(47):14137-40.
Liu et al. "Manganese-catalyzed C—H activation" ACS Catalysis. May 11, 2016;6(6):3743-52.
Liu et al. "Manganese-Catalyzed Oxidative Benzylic C—H Fluorination by Fluoride Ions" Angewandte Chemie International Edition. Jun. 3, 2013;52(23):6024-7.
López et al. "Cyanoalkylation: Alkyinitriles in Catalytic C☐ C Bond-Forming Reactions" Angewandte Chemie International Edition. Nov. 2, 2015;54(45):13170-84.
Maggi et al. "Dehydrogenative synthesis of imines from alcohols and amines catalyzed by a ruthenium N-heterocyclic carbene complex" Organometallics. Dec. 7, 2011;31(1):451-5.
Marenich et al. "Universal solvation model based on solute electron density and on a continuum model of the solvent defined by the bulk dielectric constant and atomic surface tensions" The Journal of Physical Chemistry B. Apr. 14, 2009;113(18):6378-96.
Mastalir et al. "Divergent coupling of alcohols and amines catalyzed by isoeiectronic hydride Mnl and Fell PNP pincer complexes" Chemistry—A European Journal. Aug. 22, 2016;22(35):12316-20.

McNeill et al. "1,4-Functionalization of 1,3-dienes with low-valent iron catalysts" Accounts of chemical research. Jul. 27, 2015;48(8):2330-43.
Mikhailine et al. "The Mechanism of Efficient Asymmetric Transfer Hydrogenation of Acetophenone Using an Iron (II) Complex Containing an (S, S)-Ph2PCH2CH☐ NCHPhCHPhN☐ CHCH2PPh2 Ligand: Partial Ligand Reduction Is the Key" Journal of the American Chemical Society. Jul. 13, 2012;134(29):12266-80.
Mikhailine et al. "Efficient asymmetric transfer hydrogenation of ketones catalyzed by an iron complex containing a P—N—N—P tetradentate ligand formed by template synthesis" Journal of the American Chemical Society. Jan. 9, 2009;131(4):1394-5.
Mikhailine et al. "Asymmetric transfer hydrogenation of ketimines using well-defined iron (II)-based precatalysts containing a PNNP ligand" Organic letters. Aug. 27, 2012;14(17):4638-41.
Milstein D. "Metal-ligand cooperation by aromatization-dearomatization as a tool in single bond activation" Philosophical Transactions of the Royal Society A: Mathematical, Physical and Engineering Sciences. Mar. 13, 2015;373(2037):20140189.
Milstein D. "Discovery of environmentally benign catalytic reactions of alcohols catalyzed by pyridine-based pincer Ru complexes, based on metal-ligand cooperation" Topics in Catalysis. Aug. 1, 2010;53(13-14):915-23.
Mondal et al. "Control in the rate-determining step provides a promising strategy to develop new catalysts for CO2 Hydrogenation: a local pair natural orbital coupled cluster theory study" Inorganic chemistry. Jul. 23, 2015;54(15):7192-8.
Monfette et al. "Enantiopure C 1-symmetric bis (imino) pyridine cobait complexes for asymmetric alkene hydrogenation" Journal of the American Chemical Society. Mar. 6, 2012;134(10):4561-4.
Monney et al. "Base-free hydrogen generation from methanol using a bi-catalytic system" Chemical Communications. 2014;50(6):707-9.
Montag et al. "Aldehyde binding through reversible C—C coupling with the pincer ligand upon alcohol dehydrogenation by a PNP-ruthenium catalyst" Journal of the American Chemical Society. Jun. 15, 2012:134(25):10325-8.
Morales-Morales et al. "The chemistry of PGP pincer phosphinite transition metal complexes" in Morales-Morales et al. The Chemistry of Pincer Compounds 2007 pp. 152-179.
Moran et al. "Iridium-catalysed direct C—C coupling of methanol and allenes" Nature chemistry. Apr. 2011;3(4):287.
Morris RH. Exploiting metal-ligand bifunctional reactions in the design of iron asymmetric hydrogenation catalysts Accounts of chemical research. Apr. 21, 2015;48(5):1494-502.
Morton D. "cole-Hamilton, DJJ Chem. Soc." Chem. Commun. 1988:1154.
Mukherjee et al. "Selective hydrogenation of nitriles to primary amines catalyzed by a cobalt pincer complex" Journal of the American Chemical Society. Jul. 10, 2015;137(28):8888-91.
Mukherjee et al. "Manganese-catalyzed environmentally benign dehydrogenative coupling of alcohols and amines to form aldimines and H2: a catalytic and mechanistic study" Journal of the American Chemical Society. Mar. 25, 2016;138(13):4298-301.
Murahashi et al. "Ruthenium-catalyzed aldol and Michael reactions of nitriles. Carbon-carbon bond formation by. alpha.-CH activation of nitriles" Journal of the American Chemical Society. Dec. 1995;117(50):12436-51.
Naota et al. "Synthesis and characterization of C- and N-bound isomers of transition metal α-cyanocarbanions" Journal of the American Chemical Society. Mar. 29, 2000;122(12):2960-1.
Naota et al. "Ruthenium-catalyzed aldol and Michael reactions of activated nitriles" Journal of the American Chemical Society. Jul. 1989;111(15):5954-5.
Nerush et al. "Template Catalysis by Metal-Ligand Cooperation, C—C Bond Formation via Conjugate Addition of Non-activated Nitriles under Mild, Base-free Conditions Catalyzed by a Manganese Pincer Complex" Journal of the American Chemical Society. May 24, 2016;138(22):6985-97.
Neumann et al. "Improved and General Manganese-Cataiyzed N-Methylation of Aromatic Amines Using Methanol" Chemistry—A European Journal. Apr. 24, 2017;23(23):5410-3.

(56) References Cited

OTHER PUBLICATIONS

Nielsen et al. "Low-temperature aqueous-phase methanol dehydrogenation to hydrogen and carbon dioxide" Nature. Mar. 2013;495(7439):85.
Noyori et al. "Asymmetric transfer hydrogenation catalyzed by chiral ruthenium complexes" Accounts of Chemical Research. Feb. 13, 1997;30(2):97-102.
Noyori et al. "Asymmetric catalysis by architectural and functional molecular engineering: practical chemo- and stereoselective hydrogenation of ketones" Angewandte Chemie International Edition. Jan. 5, 2001;40(1):40-73.
Ogawa et al. "Iridium-catalyzed selective α-methylation of ketones with methanol" Chemical Communications. 2014;50(19):2491-3.
Olah et al., "Formylating agents" Chemical Reviews, Aug. 1, 1987;87(4):671-86.
Oldenhuis et al. "Catalytic acceptorless dehydrogenations: Ru-Macho catalyzed construction of amides and imines" Tetrahedron. Jul. 8, 2014;70(27-28):4213-8.
Ortega et al. "N-formylation of amines by methanol activation" Organic letters. Mar. 22, 2013;15(7):1776-9.
Paradine et al. "A manganese catalyst for highly reactive yet chemoselective intramolecular C (sp 3)—H amination" Nature chemistry. Dec. 2015;7(12):987.
Peña-López et al. "Manganese-Catalyzed Hydrogen-Autotransfer C—C Bond Formation: α-Alkylation of Ketones with Primary Alcohols" Angewandte Chemie International Edition. Nov. 21, 2016;55(48):14967-71.
Perdew JP. "Density-functional approximation for the correlation energy of the inhomogeneous electron gas" Physical Review B. Jun. 15, 1986;33(12):8822.
Perdriau et al. "Metal-Ligand Cooperative Pathway for Intermolecuiar Oxa-Michael Additions to Unsaturated Nitriles" Angewandte Chemie International Edition. Mar. 27, 2015;54(14):4236-40.
Perlmutter "Conjugate Addition Reactions in Organic Synthesis" Angewandte Chemie. Nov. 1993;105(11):1738-9.
Pohlki et al. "The Mechanism of the [Cp2TiMe2]-Catalyzed Intermolecuiar Hydroamination of Alkynes" Angewandte Chemie International Edition. Jun. 18, 2001;40(12):2305-8.
Pouilloux et al. "Selective hydrogenation of methyl oleate into unsaturated alcohols: relationships between catalytic properties and composition of cobalt-tin catalysts" Catalysis Today. Dec. 10, 2000;63(1):87-100.
Prechtl et al. "H/D exchange at aromatic and heteroaromatic hydrocarbons using D2O as the deuterium source and ruthenium dihydrogen complexes as the catalyst" Angewandte Chemie International Edition. Mar. 19, 2007;46(13):2269-72.
Preedasuriyachai et al. "N-Formylation of amines catalyzed by nanogold under aerobic oxidation conditions with MeOH or formalin" Chemistry letters. Oct. 9, 2010;39(11):1174-6.
Qian et al. "Formaldehyde synthesis from methanol over silver catalysts" Applied Catalysis A: General. Jan. 20, 2003;238(2):211-22.
Radosevich et al. "Ligand reactivity in diarylamido/bis (phosphine) PNP complexes of Mn (CO) 3 and Re (CO) 3" Inorganic chemistry, Sep. 8, 2009;48(19):9214-21.
Ren et al. "Manganese-Catalyzed Oxidative Azidation of Cyclobutanols: Regiospecific Synthesis of Alkyl Azides by C☐ G Bond Cleavage" Angewandte Chemie International Edition. Oct. 19, 2015;54(43):12692-6.
Rieke et al. "Fatty methyl ester hydrogenation to fatty alcohol part I: correlation between catalyst properties and activity/selectivity" Journal of the American Oil Chemists' Society. Apr. 1, 1997;74(4):333-9.
Rodriguez-Lugo et al. "A homogeneous transition metal complex for clean hydrogen production from methanol-water mixtures" Nature chemistry. Apr. 2013;5(4):342.
Rösler et al. "Cobalt-Catalyzed Alkylation of Aromatic Amines by Alcohols" Angewandte Chemie International Edition. Dec. 7, 2015;54(50):15046-50.

Rosler et al. "A Highly Active and Easily Accessible Cobalt Catalyst for Selective Hydrogenation of C☐ O Bonds" Journal of the American Chemical Society. Jun. 19, 2015;137(25):7998-8001.
Ruch et al. "New iridium Catalysts for the Selective Alkylation of Amines by Alcohols under Mild Conditions and for the Synthesis of Quinolines by Acceptor-less Dehydrogenative Condensation" Chemistry—A European Journal. Oct. 6, 2014:20(41):13279-85.
Russell et al. "Synthesis and electronic structure of reduced Bis (Imino) pyridine manganese compounds" European Journal of Inorganic Chemistry. Jan. 2012;2012(3):535-45.
Saha et al. "Metal-ligand cooperation on a diruthenium platform: selective imine formation through acceptorless dehydrogenative coupling of alcohols with amines" Chemistry—A European Journal. May 19, 2014;20(21):6542-51.
Samec et al. "Efficient ruthenium-catalyzed aerobic oxidation of amines by using a biomimetic coupled catalytic system" Chemistry—A European Journal. Apr. 8, 2005;11(8):2327-34.
Sampson et al. "Manganese catalysts with bulky bipyridine ligands for the electrocatalytic reduction of carbon dioxide: Eliminating dimerization and altering catalysis" Journal of the American Chemical Society. Mar. 31, 2014;136(14):5460-71.
Saudan et al. "Dihydrogen reduction of carboxylic esters to alcohols under the catalysis of homogeneous ruthenium complexes: high efficiency and unprecedented chemoselectivity" Angewandte Chemie International Edition. Oct. 1, 2007;46(39):7473-6.
Schneck et al. "Selective hydrogenation of amides to amines and alcohols catalyzed by improved iron pincer complexes" Organometallics. May 23, 2016;35(11):1931-43.
Schwalbe et al. "δ-Peptide Analogues of Pyranosyl-RNA, Part 2, Nucleo-δ-peptides Derived from Conformationally Constrained Nucleo-δ-amino Acids: NMR Study of the Duplex Formed by Self-pairing of the (1' S, 2' S, 4' S)-(phba)-Nucieo-δ-peptide-(AATAT)" Helvetica Chimica Acta. Jun. 7, 2000:83(6):1079-107.
Schwartsburd et al. "Dearomatized Anionic PNP Pincer Rhodium Complex: C—H and H—H Bond Activation by Metal-Ligand Cooperation and Inhibition by Dinitrogen" Organometallics. Apr. 22, 2011;30(10):2721-9.
Schwartsburd et al. "Synthesis and Reactivity of an Iridium (I) Acetonyl PNP Complex. Experimental and Computational Study of Metal-Ligand Cooperation in H—H and C—H Bond Activation via Reversible Ligand Dearomatization" Organometallics. Aug. 9, 2010;29(17):3817-27.
Seyden-Penne J. "Reductions by the alumino- and borohydrides in organic synthesis" John Wiley & Sons; Sep. 1, 1997.
Sharma et al. "Synthesis and structure of α/δ-hybrid peptides—access to novel helix patterns in foldamers" Chemistry—A European Journal. May 25, 2009;15(22):5552-66.
Shimizu KI. "Heterogeneous catalysis for the direct synthesis of chemicals by borrowing hydrogen methodology" Catalysis Science & Technology. 2015;5(3):1412-27.
Shinoda et al. "One-step formation of methyl acetate with methanol used as the sole source and catalysis by RuII—SnII cluster complexes" Journal of the Chemical Society, Chemical Communications. Jan. 1, 1990(21):1511-2.
Shono et al. "Electroorganic chemistry. 140. Electroreductively promoted intra- and intermolecuiar couplings of ketones with nitriles" The Journal of Organic Chemistry. Dec. 1992;57(26):7175-87.
Smith et al. "Secondary structure in oligomers of carbohydrate amino acids" Chemical Communications. 1998(18):2041-2.
Sonobe et al. "Catalytic aerobic production of imines en route to mild, green, and concise derivatlzatlons of amines" Chemical Science. 2012;3(11):3249-55.
Srimani et al. "Direct catalytic olefination of alcohols with sulfones" Angewandte Chemie International Edition. Oct. 6, 2014;53(41):11092-5.
Srimani et al. "Catalytic coupling of nitriles with amines to selectively form imines under mild hydrogen pressure" Chemical Communications. 2012;48(97):11853-5.
Srimani et al. "Iron Pincer Complex Catalyzed, Environmentally Benign, E-Selective Semi-Hydrogenation of Alkynes" Angewandte Chemie International Edition. Dec. 23, 2013;52(52):14131-4.

(56) References Cited

OTHER PUBLICATIONS

Srimani et al. "Cobalt-Catalyzed Hydrogenation of Esters to Alcohols: Unexpected Reactivity Trend Indicates Ester Enolate Intermediacy" Angewandte Chemie International Edition. Oct. 12, 2015;54(42):12357-60.
Srimani et al. "Direct Synthesis of Pyrroles by Dehydrogenative Coupling of β-Aminoalcohols with Secondary Alcohols Catalyzed by Ruthenium Pincer Complexes" Angewandte Chemie International Edition. Apr. 2, 2013;52(14):4012-5.
Stor et al. "Coordination of the potentially tridentate ligands 2,6-diacetylpyridine-bis (anil)(dapa) and 2-(2-(2'-methylidenepyridyl) aminoethyl) pyridine (map) in the complexes fac-BrMn (CO) 3 L, fac-(CO) 5MM'(CO) 3L (M, M'=Mn, Re; L=dapa, map) and their photoproducts. The crystal structure of BrMn (CO) 2 (N, N, N-dapa)" Journal of organometallic chemistry. Nov. 29, 1994;482(1-2):15-29.
Streuff J. "A Titanium (III)-Catalyzed Redox Umpolung Reaction for the Reductive Cross-Coupling of Enones with Acrylonitriles" Chemistry—A European Journal. May 9, 2011;17(20):5507-10.
Streuff et al. "Enantioselective Titanium (III)-catalyzed reductive cyclization of ketonitriles" Angewandte Chemie International Edition. Aug. 20, 2012;51(34):8661-4.
Su et al. "Aerobic oxidative coupling of amines by carbon nitride photocatalysis with visible light" Angewandte Chemie International Edition. Jan. 17, 2011;50(3):657-60.
Su et al. "Exploration of earth-abundant transition metals (Fe, Co, and Ni) as catalysts in unreactive chemical bond activations" Accounts of chemical research. Feb. 13, 2015;48(3):886-96.
Takaya et al. "Rhenium-Catalyzed Addition of Carbonyl Compounds to the Carbon-Nitrogen Triple Bonds of Nitriles: α-C—H Activation of Carbonyl Compounds" Journal of the American Chemical Society. Jul. 16, 2009;131(31):10824-5.
Tamura et al. "Redox properties of CeO2 at low temperature: the direct synthesis of imines from alcohol and amine" Angewandte Chemie International Edition. Jan. 12, 2015;54(3):864-7.
Tani et al. "Efficient transfer hydrogenation of alkynes and alkenes with methanol catalysed by hydrido (methoxo) iridium (III) complexes" Chemical Communications. Jan. 1, 1999(18):1821-2.
Tao et al. "Climbing the density functional ladder: Nonempirical meta-generalized gradient approximation designed for molecules and solids" Physical Review Letters. Sep. 30, 2003;91(14):146401.
Tlili et al. "Reductive functionalization of CO 2 with amines: an entry to formamide, formamidine and methylamine derivatives" Green Chemistry. 2015;17(1):157-68.
Umehara et al. "Synthesis, structures, and reactivities of iron, cobalt, and manganese complexes bearing a pincer ligand with two protic pyrazole arms" Inorganica Chimica Acta. Mar. 24, 2014;413:136-42.
Van Der Vlugt JI. "Cooperative catalysis with first-row late transition metals" European Journal of Inorganic Chemistry. Jan. 2012;2012(3):363-75.
Van Der Vlugt et al. "Neutral tridentate PNP ligands and their hybrid analogues: Versatile non-innocent scaffolds for homogeneous Catalysis" Angewandte Chemie International Edition. Nov. 9, 2009;48(47):8832-46.
Van Der Vlugt et al. "Dinuclear copper (I) thioate complexes with a bridging noninnocent PNP ligand" Chemistry—A European Journal. Mar. 28, 2011;17(14):3850-4.
Van Der Vlugt et al. "Cationic and neutral Ni II complexes containing a non-innocent PNP ligand: formation of alkyl and thioiate species" Dalton Transactions. 2009(6):1016-23.
Van Der Waals et al. "Ruthenium-Catalyzed Methylation of Amines with Paraformaldehyde in Water under Mild Conditions" ChemSusChem. Sep. 8, 2016;9(17):2343-7.
Vogt et al. "Activation of nitriles by metal ligand cooperation. Reversible formation of ketimido- and enamido-rhenium PNP pincer complexes and relevance to catalytic design" Journal of the American Chemical Society. Nov. 5, 2013;135(45):17004-18.
Vogt et al. "A New Mode of Activation of CO2 by Metal-Ligand Cooperation with Reversible CC and MO Bond Formation at Ambient Temperature" Chemistry—A European Journal. Jul. 23, 2012;18(30):9194-7.
Vogt et al. "Reversible CO 2 binding triggered by metal-ligand cooperation in a rhenium (I) PNP pincer-type complex and the reaction with dihydrogen" Chemical Science. 2014;5(5):2043-51.
Weigend et al. "Balanced basis sets of spilt valence, triple zeta valence and quadruple zeta valence quality for H to Rn: Design and assessment of accuracy" Physical Chemistry Chemical Physics. Aug. 30, 2005;7(18):3297-305.
Weigend F. "Accurate Coulomb-fitting basis sets for H to Rn" Physical chemistry chemical physics. 2006;8(9):1057-65.
Weissermel et al. "Industrial organic chemistry" John Wiley & Sons; Jul. 11, 2008.
Werkmeister et al. "Hydrogenation of esters to alcohols with a well-defined iron complex" Angewandte Chemie International Edition. Aug. 11, 2014;53(33):8722-6.
Xu et al. "KOH-mediated transition metal-free synthesis of imines from alcohols and amines" Green Chemistry. 2012;14(9):2384-7.
Yamaguchi et al. "Efficient heterogeneous aerobic oxidation of amines by a supported ruthenium catalyst" Angewandte Chemie International Edition. Apr. 4, 2003:42(13):1480-3.
Yamamoto et al. "The Cp2TiPh-mediated reductive radical cyclization of cyanoketones and related reactions. Efficient trapping of ketyl radicals by Cp2TiPh-coordinated polar multiple bonds" The Journal of organic chemistry. Apr. 30, 1999:64(9):3224-9.
Yan et al. "Iron catalysed direct alkylation of amines with aicohois" Nature communications. Nov. 26, 2014;5:5602.
Yoon et al. "Privileged chiral catalysts" Science. Mar. 14, 2003;299(5613):1691-3.
Yu et al. "Catalytic hydrogenation activity and electronic structure determination of bis (arylimidazol-2-yildene) pyridine cobalt alkyl and hydride complexes" Journal of the American Chemical Society. Aug. 22, 2013;135(35):13168-84.
Yuan et al. "Discovery of a metalioenzyme-like cooperative catalytic system of metal nanoclusters and catechol derivatives for the aerobic oxidation of amines" Journal of the American Chemical Society. Aug. 13, 2012;134(34):13970-3.
Zell et al. "Hydrogenation and dehydrogenation iron pincer catalysts capable of metal-ligand cooperation by aromatization/dearomatization" Accounts of chemical research. Jun. 16, 2015;48(7):1979-94.
Zell et al. "Unprecedented Iron-Catalyzed Ester Hydrogenation. Mild, Selective, and Efficient Hydrogenation of Trifluoroacetic Esters to Alcohols Catalyzed by an Iron Pincer Complex" Angewandte Chemie International Edition. Apr. 25, 2014:53(18):4685-9.
Zell, et al. "Highly efficient, general hydrogenation of aldehydes catalyzed by PNP iron pincer complexes" Catalysis Science & Technology. 2015,5(2):822-6.
Zeng et al. "Insights into Dehydrogenative Coupling of Alcohols and Amines Catalyzed by a (PNN)-Ru (II) Hydride Complex: Unusual Metal-Ligand Cooperation" Inorganic chemistry. Sep. 26, 2011;50(21):10572-80.
Zhang et al. "Highly efficient Ruthenium-catalyzed N-formylation of amines with H2 and CO2" Angewandte Chemie International Edition. May 18, 2015;54(21):6186-9.
Zhang et al. "Mild and homogeneous cobalt-catalyzed hydrogenation of C☐ C, C☐O, and C☐ N bonds" Angewandte Chemie International Edition, Nov. 26, 2012:51(48):12102-6.
Zhang et al. "Cobalt-catalyzed acceptorless alcohol dehydrogenation: synthesis of imines from alcohols and amines" Organic letters. Jan. 11, 2013;15(3):650-3.
Zhang et al. "Understanding the mechanisms of cobalt-catalyzed hydrogenation and dehydrogenation reactions" Journal of the American Chemical Society. May 29, 2013;135(23):8668-81.
Zhang et al. "Efficient homogeneous catalytic hydrogenation of esters to alcohols" Angewandte Chemie International Edition. Feb. 6, 2006;45(7):1113-5.
Zhang et al. "Facile conversion of alcohols into esters and dihydrogen catalyzed by new ruthenium complexes" Journal of the American Chemical Society. Aug. 10, 2005;127(31):10840-1.

(56) References Cited

OTHER PUBLICATIONS

Zhang et al. "Cobalt-catalyzed transfer hydrogenation of C [double bond, length as m-dash] O and C [double bond, length as m-dash] N bonds" Chemicai Communications. 2013;49(86):10151-3.

Zhang et al. "Enantioseiective epoxidation of unfunctionalized olefins catalyzed by salen manganese complexes" Journal of the American Chemical Society. Mar. 1990;112(7):2801-3.

Zotova et al. "Catalysis in flow: Au-catalysed alkylation of amines by alcohols" Green chemistry. 2012;14(1):226-32.

Hu, P., et al. (2016). Rechargeable hydrogen storage system based on the dehydrogenative coupling of ethylenediamine with ethanol. Angewandte Chemie, 128(3), 1673-1076.

Johnson, F. P., et al. (1996). Electrocatalytic Reduction of CO2 Using the Complexes [Re (bpy)(CO) 3L] n (n=+1, L=P (OEt) 3, CH3CN; n=0, L=Cl-, Otf-;bpy=2, 2-Bipyridine; Otf-=CF3SO3) as Catalyst Precursors: Infrared Spectroelectrochemical Investigation. *Organometallics*, 15(15), 3374-3387.

Li, H., Wei, D., et al. (2018). Rhenium and manganese complexes bearing amino-bis (phosphinite) ligands: synthesis, characterization, and catalytic activity in hydrogenation of ketones. *Organometallics*, 37(8), 1271-1279.

Srimani, D., et al. (2013). Formation of Tertiary Amides and Dihydrogen by Dehydrogenative Coupling of Primary Alcohols with Secondary Amines Catalyzed by Ruthenium Bipyridins-Based Pincer Complexes. *Advanced Synthesis & Catalysis*, 355(13), 2525-2530.

\* cited by examiner

Previous work:

R is Aryl

This invention:

R is aryl or an aliphatic group

Manganese complex 6B        Manganese complex 6A'

MANGANESE BASED COMPLEXES AND USES THEREOF FOR HOMOGENEOUS CATALYSIS

CROSS-REFERENCE TO RELATED APPLICATIONS

This application is a National Phase Application of PCT International Application No. PCT/IL2017/050152, International Filing Date Feb. 8, 2017, claiming priority from IL Patent Application No. 244052, filed Feb. 9, 2016, and from United-States provisional Application No. 62/409,392 filed Oct. 18, 2016 which are all hereby incorporated by reference in their entirely.

FIELD OF THE INVENTION

The present invention relates to novel manganese complexes and their use, inter alia, for homogeneous catalysis in (1) the preparation of imine by dehydrogenative coupling of an alcohol and amine; (2) C—C coupling in Michael addition reaction using nitriles as Michael donors; (3) dehydrogenative coupling of alcohols to give esters and hydrogen gas (4) hydrogenation of esters to form alcohols (including hydrogenation of cyclic esters (lactones) or cyclic di-esters (di-lactones), or polyesters); (5) hydrogenation of amides (including cyclic dipeptides, diamide, lactams, polypeptides and polyamides) to alcohols and amines (or diamine); (6) hydrogenation of organic carbonates (including polycarbonates) to alcohols or hydrogenation of carbamates (including polycarbamates) or urea derivatives to alcohols and amines; (7) dehydrogenation of secondary alcohols to ketones; (8) amidation of esters (i.e., synthesis of amides from esters and amines); (9) acylation of alcohols using esters; (10) coupling of alcohols with water and a base to form carboxylic acids; (11) preparation of amino acids or their salts by coupling of amino alcohols with water and a base; and (12) preparation of amides (including formamides, cyclic dipeptides, diamide, lactams, polypeptides and polyamides) by dehydrogenative coupling of alcohols and amines (13) preparation of imides from diols.

BACKGROUND OF THE INVENTION

Manganese is one of the most abundant transition metals on earth crust, second only to iron and titanium and is much more appealing and biocompatible[1] when considering a system for eventual scale-up and industrial use. In contrast to the development of several homogenous catalysts based on iron[2] and cobalt[3, 4, 5] systems, homogeneous manganese-based systems are less exploited.[6] In general, well-defined pincer complexes of Mn are scarce. Reports comprise Mn(I) PNP compounds published by Nocera and Ozerov,[7] a Mn(II) center with pyridine-based NNN-pincer motif bearing two pyrazole 'arms'.[8] and Mn-PDI (PDI=2, 6-bisimino pyridine) species were described by Chirik and co-workers.[9] There is a strong current interest in replacement of expensive noble metal catalysts by more economical, environmentally friendly alternatives.

Catalytic dehydrogenative coupling of alcohols and amines to form imines represents an environmentally benign methodology in organic chemistry. This has been accomplished in recent years mainly with precious-metal-based catalysts. A major goal in homogeneous catalysis is the replacement of typical noble-metal mediated chemistry with inexpensive and earth-abundant metals.

Imines and their derivatives are important synthetic intermediates because of their diverse reactivity. As a result, they have been extensively utilized for the synthesis of dyes, fragrances, fungicides, pharmaceuticals, and agricultural chemicals.[10] Moreover, imines also serve as common ligands in coordination chemistry. Conventionally, imines are synthesized by the condensation reaction of aldehydes or ketones with amines in the presence of an acid catalyst. However, it is desirable to obtain imines by an acid free pathway. Recently, versatile alternative methods have been reported, such as oxidation of secondary amines,[11] self-condensation of primary amines upon oxidation,[12] oxidative coupling of alcohols and amines,[13] hydroamination of alkynes with amines,[14] and the partial hydrogenation of nitriles followed by coupling with the amines[15]. Self-coupling of amines involves use of stoichiometric $O_2$ atmosphere as an oxidant and the products are always limited to symmetric imines. Alternatively, the direct dehydrogenative coupling of alcohols and amines is one of the most promising approaches and "green" pathways to synthesize imines, since alcohols are readily available through a variety of industrial processes and can be obtained renewably via fermentation or catalytic conversion of lignocellulosic biomass[6]. Moreover, only hydrogen and water are produced as by-products in this pathway. An acceptorless dehydrogenative coupling of alcohols and amines to synthesize imines catalyzed by a ruthenium pincer complex was reported.[17] Since then, this field has progressed rapidly and several catalytic systems for such transformation have been developed, mainly with precious metals.[18]

Conjugate addition reactions are fundamental C—C bond formation reactions in organic chemistry.[19] For instance, the Michael addition of 1,3-dicarbonyl compounds to activated olefins is regarded as one of the most important C—C coupling reaction in organic synthesis.[20] However, such Michael reactions require the application of strong bases, which may not be compatible with various functional groups and can lead to undesired side reactions. Transition metal catalyzed Michael-type reactions, that can operate under mild and neutral conditions and exhibit superior chemoselectivity, have been reported.[20, 21]

Nitriles are important functional groups in organic synthesis due to their facile transformation into various functional groups. Furthermore, nitriles themselves are important constituents of modern pharmaceuticals. Common protocols for conjugate addition reactions involving nitriles make use of activated nitriles with acidic α-protons (e.g. malononitriles, benzyl cyanide, ethyl cyanoacetates, cyanoacetamides and the like). The same applies for previously reported transition metal catalyzed Michael addition reactions, therefore significantly limiting the substrate scope. The reaction usually involves C—H activation at the α-carbon at the metal center to generate the Michael donor moieties (i.e. metal stabilized carbanions).[22-27]

Non activated aliphatic nitriles have also been used in transition metal catalyzed C—C bond forming reactions. However, due to the low acidity of the α-protons of aliphatic nitriles, no conjugate addition of nitriles to α,β-unsaturated carbonyl compounds has been achieved so far.[28]

A dearomatized rhenium complex was used as a catalyst, (FIG. 6). The rhenium complex catalyzed conjugate addition was limited to benzylic nitriles.[29]

REFERENCES

References considered to be relevant as background to the presently disclosed subject matter are listed below:

[1] C. Kies, Nutritional Bioavailability of Manganese; ACS Symposium Series, 1987.
[2] Selected examples: a) D. Srimani, Y. Diskin-Posner, Y. Ben-David, D. Milstein, Angew. Chem. Int. Ed. 2013, 52, 14131; Angew. Chem. 2013, 125, 14381; b) R. Langer, G. Leitus, Y. Ben-David, D. Milstein, Angew. Chem. 2011, 123, 2168; Angew. Chem. Int. Ed. 2011, 50, 2120; c) R. Langer, Y. Diskin-Posner, G. Leitus, L. J. W. Shimon, Y. Ben-David, D. Milstein, Angew. Chem. 2011, 123, 10122; Angew. Chem. Int. Ed. 2011, 50, 9948; d) T. Zell, Y. Ben-David, D. Milstein, Angew. Chem. Int. Ed. 2014, 53, 4685; Angew. Chem. 2014, 126, 4773; e) T. Zell, Y. Ben-David, D. Milstein, Catal. Sci. Technol 2015, 5, 822; f) S. Werkmeister, K. Junge, B. Wendt, E. Alberico, H. Jiao, W. Baumann, H. Junge, F. Gallou, M Beller, Angew. Chem. 2014, 126, 8722; Angew. Chem. Int. Ed. 2014, 53, 8722; g) S. Chakraborty, H. Dai, P. Bhattacharya, N. T. Fairweather, M. S. Gibson, J. A. Krause, H. Guan, J. Am. Chem. Soc. 2014, 136, 7869; h) C. Bornschein, S. Werkmeister, B. Wendt, H. Jiao, E. Alberico, W. Baumann, H. Junge, K. Junge, M. Beller, Nat. Commun. 2014, 5, 4111; i) Zell, T.; Milstein, D. Acc. Chem. Res. 2015, 48, 1979.
[3] a) T. Yan, B. L. Feringa, K. Barta Nat. Commun. 2014, 5, 5602; b) S. Rösler, M. Ertl, T. Irrgang, R. Kempe, Angew. Chem. Int. Ed. 2015, 54, 15046.
[4] a) S. Rösler, J. Obenauf, R. Kempe, J. Am. Chem. Soc. 2015, 137, 7998; b) P. J. Chirik, Acc. Chem. Res. 2015, 48, 1687; c) M. R. Friedfeld, G. W. Margulieux, B. A. Schaefer, P. J. Chirik, J. Am. Chem. Soc. 2014, 136, 13178; d) T.-P. Lin, J. C. Peters, J. Am. Chem. Soc. 2014, 136, 13672; e) T.-P. Lin, J. C. Peters, J. Am. Chem. Soc. 2013, 135, 15310; f) S. Monfette, Z. R. Turner, S. P. Semproni, P. J. Chirik, J. Am. Chem. Soc. 2012, 134, 4561; g) Q. Knijnenburg, A. D. Horton, H. van der Heijden, T. M. Kooistra, D. G. H. Hetterscheid, J. M. M. Smits, B. de Bruin, P. H. M. Budzelaar, A. W. Gal, J. Mol. Catal. A 2005, 232, 151; h) D. Grtner, A. Welther, B. R. Rad, R. Wolf, A. J. von Wangelin, Angew. Chem. Int. Ed. 2014, 53, 3722; i) G. Zhang, K. V. Vasudevan, B. L. Scott, S. K. Hanson, J. Am. Chem. Soc. 2013, 135, 8668; j) G. Zhang, B. L. Scott, S. K. Hanson, Angew. Chem. Int. Ed. 2012, 51, 12102; k) G. Zhang, S. K. Hanson, Chem. Commun. 2013, 49, 10151; 1) G. Zhang, S. K. Hanson, Org. Lett. 2013, 15, 650.
[5] a) A. Mukherjee, D. Srimani, S. Chakraborty, Y. Ben-David, D. Milstein, J. Am. Chem. Soc. 2015, 137, 8888; b) D. Srimani, A. Mukherjee, A. F. Goldberg, G. Leitus, Y. Diskin Posner, L. J. Shimon, Y. Ben-David, D. Milstein, Angew. Chem. Int. Ed. 2015, 54, 12357.
[6] Selected examples: a) M. D. Sampson, An D. Nguyen, K. A. Grice, C. E. Moore, A. L. Rheingold, C. P. Kubiak, J. Am. Chem. Soc. 2014, 136, 5460; b) X. Huang, T. M. Bergsten, J. T. Groves, J. Am. Chem. Soc. 2015, 137, 5300; c) W. Liu, J. Bang, Y. Zhang, L. Ackermann, Angew. Chem. Int. Ed. 2015, 54, 14137; d) W. Liu, J. T. Groves, Angew. Chem. Int. Ed. 2013, 52, 6024; e) W. Zhang, J. L. Loebach, S. R. Wilson, E. N. Jacobsen J. Am. Chem. Soc. 1990, 112, 2801; f) T. P. Yoon, E. N. Jacobsen Science 2003, 299, 1691; g) E. B. Hulley, N. Kumar, S. Raugei, R. M. Bullock ACS Catal. 2015, 5, 6838; h) R. He, Z.-T. Huang, Q.-Y. Zheng, C. Wang Angew. Chem. Int. Ed. 2014, 53, 4950; i) R. Ren, H. Zhao, L. Huan, C. Zhu Angew. Chem. Int. Ed. 2015, 54, 12692; j) S. M. Paradine, J. R. Griffin, J. Zhao, A. L. Petronico, S. M. Miller, M. C. White Nat. Chem. 2015, 7, 987.
[7] Radosevich, A. T.; Melnick, J. G.; Stoian, S. A.; Bacciu, D.; Chen, C.-H.; Foxman, B. M.; Ozerov, O. V.; Nocera, D. G. Inorg. Chem. 2009, 48, 9214.
[8] Umehara, K.; Kuwata, S.; Ikariya, T. InorgChim Act. 2014, 413, 136.
[9] Russell, S. K.; Bowman, A. C.; Lobkovsky, E.; Wieghardt, K.; Chirik, P. J. Eur. J. Inorg. Chem. 2012, 3, 535.
[10] a) D. J. Hadjipavlou-Litina, A. A. Geronikaki, Drug Des Discov. 1998, 15, 199; J. P. Adams J Chem Soc Perkin Trans. 1 2000, 2, 125; Z. Rappoport, J. F. Liebman The Chemistry of Hydroxylamines, Oximes and Hydroxamic Acids. New York: Wiley, 2009, 609.
[11] a) A. H. El, J. S. M. Samec, C. Brasse, J.-E. Bäckvall, Chem. Commun. 2002, 1144; b) M. Largeron, A. Chiaroni, M.-B. Fleury, Chem. Eur. J. 2008, 14, 996; c) J. S. M. Samec, A. H. Ell, J.-E. Bäckvall, Chem. Eur. J. 2005, 11, 2327; e) G. Jiang, J. Chen, J.-S. Huang, C.-M. Che, Org. Lett. 2009, 11, 4568; f) X.-Q. Gu, W. Chen, D. Morales-Morales, C. M. Jensen, J. Mol. Catal. A 2002, 189, 119; g) K. Yamaguchi, N. Mizuno, Angew. Chem. Int. Ed. 2003, 42, 1480; h) T. Sonobe, K. Oisaki, M. Kanai, Chem. Sci. 2012, 3, 3249; i) H. Yuan, W.-J. Yoo, H. Miyamura, S. Kobayashi J. Am. Chem. Soc. 2012, 134, 13970. J. W. Grate, G. C. Frye in Sensors Update, Vol. 2 (Eds.: H. Baltes, W. Göpel, J. Hesse), Wiley-VCH, Weinheim, 1996, pp. 10-20.
[12] a) F. Su, S. C. Mathew, L. Mohlmann, M. Antonietti, X. Wang, S. Blechert, Angew. Chem. Int. Ed. 2011, 50, 657; b) B. Chen, L. Wang, W. Dai, S. Shang, Y. Lv, S. Gao, ACS Catal. 2015, 5, 2788; c) B. Chen, L. Wang, S. Gao, ACS Catal. 2015, 5, 5851.
[13] a) L. Blackburn, R. J. K. Taylor, Org. Lett. 2001, 3, 1637; b) M. Tamura, K. Tomishige, Angew. Chem. Int. Ed. 2014, 53, 864.
[14] a) F. Pohlki, S. Doye, Angew. Chem. Int. Ed. 2001, 40, 2305; b) J. S. Johnson, R. G. Bergman, J. Am. Chem. Soc. 2001, 123, 2923; c) Y. Li, Y. Shi, A. L. Odom, J. Am. Chem. Soc. 2004, 126, 1794.
[15] a) D. Srimani; M. Feller, Y. Ben-David, D. Milstein Chem. Commun. 2012, 48, 11853; b) S. Chakraborty, H. Berke ACS Catal. 2014, 4, 2191.
[16] K. Barta, P. C. Ford, Acc. Chem Res. 2014, 47, 1503.
[17] B. Gnanaprakasam, J. Zhang, D. Milstein, Angew. Chem. Int. Ed. 2010, 49, 1468.
[18] Selected examples: a) B. Saha, S. M. W. Rahaman, P. Daw, G. Sengupta, J. K. Bera, Chem. Eur. J. 2014, 20, 6542; b) J. Bain, P. Cho, A. Voutchkova-Kostal, Green Chem. 2015, 17, 2271; c) F. Hasanayn, H. Harb, Inorg. Chem. 2014, 53, 8334; c) Nathan J. Oldenhuis, Vy M. Dong, Zhibin Guan, Tetrahedron, 2014, 70, 27; d) S. Ruch, T. Irrgang, R. Kempe, Chem. Eur. J., 2014, 20, 41; e) D. Srimani, Y. Ben-David, D. Milstein, Angew. Chem. Int. Ed., 2013, 52, 14; f) A. Maggi, R. Madsen, Organometallics, 2012, 31, 451; g) G. Zeng, S. Li, Inorg. Chem., 2011, 50, 10572.
[19] Perlmutter, P.; Baldwin, J. E. Conjugate Addition Reactions in Organic Synthesis; Elsevier Science, 2013.
[20] Christoffers, J. Eur. J. Org. Chem. 1998, 1998, 1259.
[21] Comelles, J.; Moreno-Mañas, M.; Vallribera, A. Arkivoc. 2005, 207.
[22] Takaya, H.; Ito, M.; Murahashi, S.-I. J. Am. Chem. Soc. 2009, 131, 10824.
[23] Fleming, F. F.; Vu, V. A.; Shook, B. C.; Rahman, M.; Steward, O. W. J. Org. Chem. 2007, 72, 1431.

[24] Murahashi, S.-I.; Naota, T.; Taki, H.; Mizuno, M.; Takaya, H.; Komiya, S.; Mizuho, Y.; Oyasato, N.; Hiraoka, M. J. Am. Chem. Soc. 1995, 117, 12436.

[25] Naota, T.; Tannna, A.; Murahashi, S.-I. J. Am. Chem. Soc. 2000, 122, 2960.

[26] Aydin, J.; Conrad, C. S.; Szabó, K. J. Org. Lett. 2008, 10, 5175.

[27] Naota, T.; Taki, H.; Mizuno, M.; Murahashi, S. J. Am. Chem. Soc. 1989, 111, 5954.

[28] Lopez, R.; Palomo, C. Angew. Chem. Int. Ed. 2015, 54, 2.

[29] Vogt, M.; Nerush, A.; Iron, M. A.; Leitus, G.; Diskin-Posner, Y.; Shimon, L. J. W.; Ben-David, Y.; Milstein, D. J. Am. Chem. Soc. 2013, 135, 17004.

SUMMARY OF THE INVENTION

In one embodiment, this invention is directed to a manganese complex represented by the structure of formula I, IA, IB, IC or their isomers or salts thereof:

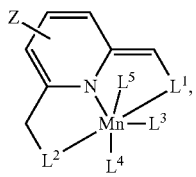

I

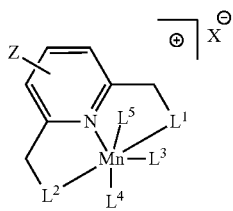

IA

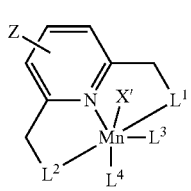

IB

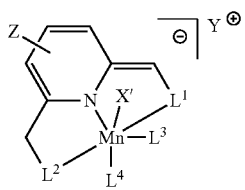

IC wherein $L^1$ is $(PR^aR^b)$, $(NR^aR^b)$, imine; oxazoline, sulfide $(SR^a)$, sulfoxide $(S(=O)R^a)$, heteroaryl containing at least one heteroatom selected from nitrogen and sulfur; $(AsR^aR^b)$, $(SbR^aR^b)$ or a N-heterocyclic carbene represented by the structures:

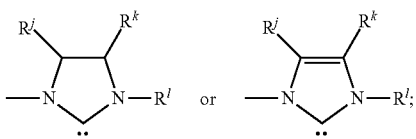

$L^2$ is $(PR^aR^b)$, $(NR^aR^b)$, imine; oxazoline, sulfide $(SR^a)$, sulfoxide $(S(=O)R^a)$, heteroaryl containing at least one heteroatom selected from nitrogen and sulfur; $(AsR^aR^b)$, $(SbR^aR^b)$ or a N-heterocyclic carbene represented by the structures:

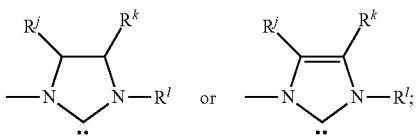

$L^3$ and $L^4$ are each independently a mono-dentate two-electron donor selected from the group consisting of CO, $PR^aR^bR^c$, $P(OR^a)(OR^b)(OR^c)$, $NO^+$, $NR^aR^bR^c$, $AsR^aR^bR^c$, $SbR^aR^bR^c$, $SR^aR^b$, nitrile (RCN), isonitrile (RNC), $N_2$, $PF_3$, CS, heteroaryl, tetrahydrothiophene, alkene, alkyne or $L^3$ and $L^4$ form together with the Mn a ring;

$L^5$ is absent or a mono-dentate two-electron donor selected from the group consisting of CO, $PR^aR^bR^c$, $P(OR^a)(OR^b)(OR^c)$, $NO^+$, $NR^aR^bR^c$, $AsR^aR^bR^c$, $SbR^aR^bR^c$, $SR^aR^b$, nitrile (RCN), isonitrile (RNC), $N_2$, $PF_3$, CS, heteroaryl, tetrahydrothiophene, alkene or alkyne;

X is halide, OCOR, $OCH_2Q$, $OCOCF_3$, $OSO_2R$, $OSO_2CF_3$, CN, OR, $N(R)_2$ and RS, $BF_4$, $B(C_6H_5)_4$, $B(C_6F_5)_4$, $B[(C_6H_4)(CF_3)_2]$, $PF_6$ or $ClO_4$;

X' is H, halide, OCOR, $OCH_2Q$, $OCOCF_3$, $OSO_2R$, $OSO_2CF_3$, CN, OR, $N(R)_2$ or RS; and Q is hydrogen, alkyl, cycloalkyl, aryl, heterocyclyl, heteroaryl, alkylcycloalkyl, alkylaryl, alkylheterocyclyl or alkylheteroaryl;

$Y^+$ is a cationic group bearing a single positive charge;

Z represents zero, one, two or three substituents wherein each such substituent is independently selected from the group consisting of alkyl, cycloalkyl, aryl, heterocyclyl, heteroaryl, alkylcycloalkyl, alkylaryl, alkylheterocyclyl, alkylheteroaryl, halide, nitro, amide, ester, cyano, alkoxy, alkylamino, arylamino, an inorganic support and a polymeric moiety, or Z forms a fused aromatic or heterocyclic ring with the nitrogen based ring.

R, $R^a$ $R^b$ and $R^c$ are each independently H, alkyl, cycloalkyl, aryl, heterocyclyl, heteroaryl, alkylcycloalkyl, alkylaryl, alkylheterocyclyl or alkylheteroaryl; and $R^j$, $R^k$ and $R^l$ are each independently H, alkyl, cycloalkyl, aryl, heterocyclyl, heteroaryl, alkylcycloalkyl, alkylaryl, alkylheterocyclyl or alkylheteroaryl.

In one embodiment, this invention is directed to a manganese complex represented by the structure of formula 1:

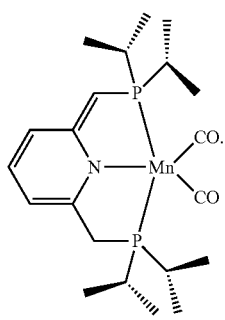

(1)

In one embodiment, this invention is directed to a manganese complex represented by the structure of formula 2:

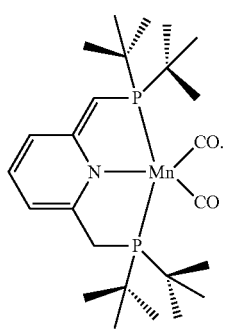

(2)

In one embodiment, this invention is directed to a manganese complex represented by the structure of formula 7. In another embodiment, the manganese complex of formula I in the solid state is a dimer of formula 7:

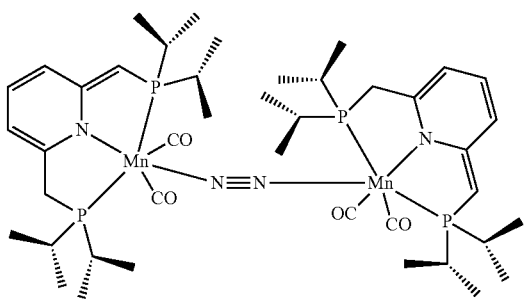

(7)

In one embodiment, this invention is directed to a manganese complex represented by the structure of formula 6A':

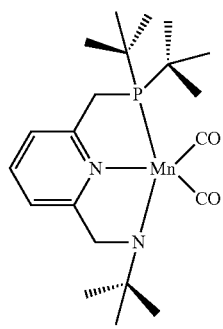

6A'

In one embodiment, this invention is directed to a manganese complex represented by the structure of formula 6B:

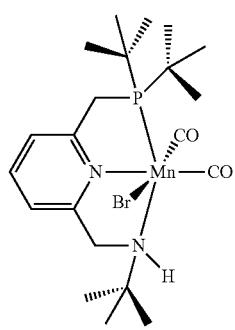

6B

In one embodiment, this invention is directed to a manganese complex represented by the structure of formula VI, VIA, VIB, VIC or their isomers or salts thereof:

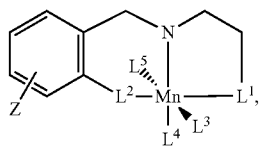

VI

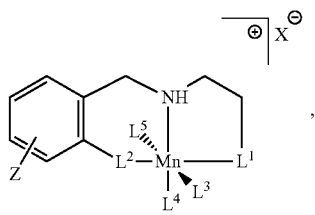

VIA

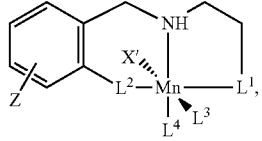

VIB

-continued

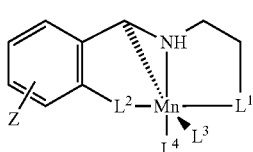
VIC wherein
L¹ is (PR$^a$R$^b$), (NR$^a$R$^b$), imine; oxazoline, sulfide (SR$^a$), sulfoxide (S(=O)R$^a$), heteroaryl containing at least one heteroatom selected from nitrogen and sulfur; (AsR$^a$R$^b$), (SbR$^a$R$^b$) or a N-heterocyclic carbene represented by the structures:

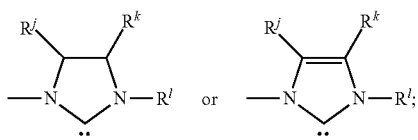

L² is (PR$^a$R$^b$), (NR$^a$R$^b$), imine; oxazoline, sulfide (SR$^a$), sulfoxide (S(=O)R$^a$), heteroaryl containing at least one heteroatom selected from nitrogen and sulfur; (AsR$^a$R$^b$), (SbR$^a$R$^b$) or a N-heterocyclic carbene represented by the structures:

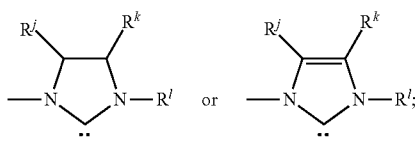

L³ and L⁴ are each independently a mono-dentate two-electron donor selected from the group consisting of CO, PR$^a$R$^b$R$^c$, P(OR$^a$)(OR$^b$)(OR$^c$), NO, AsR$^a$R$^b$R$^c$, SbR$^a$R$^b$R$^c$, NR$^a$R$^b$R$^c$, SR$^a$R$^b$, nitrile (RCN), isonitrile (RNC), N₂, PF₃, CS, heteroaryl, tetrahydrothiophene, alkene, alkyne or L³ and L⁴ form together with the Mn a ring;
L⁵ is absent or a mono-dentate two-electron donor selected from the group consisting of, CO, PR$^a$R$^b$R$^c$, P(OR$^a$)(OR$^b$)(OR$^c$), NO⁺, NR$^a$R$^b$R$^c$, AsR$^a$R$^b$R$^c$, SbR$^a$R$^b$R$^c$, SR$^a$R$^b$, nitrile (RCN), isonitrile (RNC), N₂, PF₃, CS, heteroaryl, tetrahydrothiophene, alkene or alkyne;
X is halide, OCOR, OCH₂Q, OCOCF₃, OSO₂R, OSO₂CF₃, CN, OR, N(R)₂ and RS, BF₄, B(C₆H₅)₄, B(C₆F₅)₄, B[(C₆H₄)(CF₃)₂], PF₆ or ClO₄;
X' is H, halide, OCOR, OCH₂Q, OCOCF₃, OSO₂R, OSO₂CF₃, CN, OR, N(R)₂ or RS;
Q is hydrogen, alkyl, cycloalkyl, aryl, heterocyclyl, heteroaryl, alkylcycloalkyl, alkylaryl, alkylheterocyclyl or alkylheteroaryl;
Y⁺ is a cationic group bearing a single positive charge;
R, R$^a$ R$^b$ and R$^c$ are each independently H, alkyl, cycloalkyl, aryl, heterocyclyl, heteroaryl, alkylcycloalkyl, alkylaryl, alkylheterocyclyl or alkylheteroaryl; and
R$^j$, R$^k$ and R$^l$ are each independently H, alkyl, cycloalkyl, aryl, heterocyclyl, heteroaryl, alkylcycloalkyl, alkylaryl, alkylheterocyclyl or alkylheteroaryl.

In embodiment, this invention is directed to a manganese complex represented by the structure of formula 18:

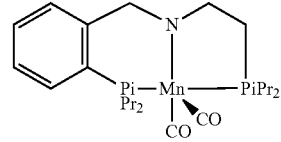
(18)

In one embodiment, this invention is directed to a manganese complex represented by the structure of formula 19:

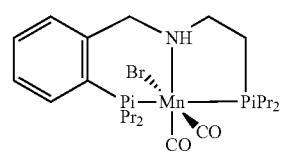
(19)

In one embodiment, this invention is directed to a manganese complex represented by the structure of formula 20:

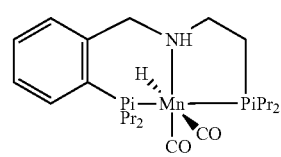
(20)

In one embodiment, this invention is directed to a manganese complex represented by the structure of formula 21:

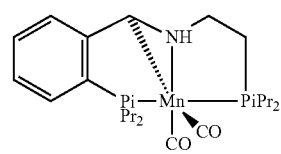
(21)

In one embodiment, this invention provides a catalytic process for preparing an imine by dehydrogenative coupling of an alcohol of the formula RCH₂OH and an amine of the formula R₁NH₂:

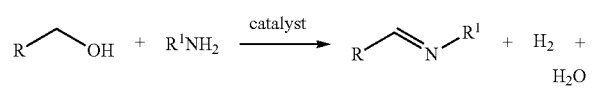

wherein,
R is an unsubstituted or substituted alkyl, alkoxyalkyl, cycloalkyl, aryl, alkylaryl, heterocyclyl and heteroaryl;
R¹ is unsubstituted or substituted alkyl, alkoxyalkyl, cycloalkyl, aryl, alkylaryl, heterocyclyl and heteroaryl;
wherein said process comprising the step of reacting said alcohol and said amine in the presence of the manganese complex of this invention. In another embodiment, if complex IA or IB is used as a catalyst, an amount of base equivalent to the amount of catalyst or higher is required.

In one embodiment, this invention provides a catalytic process for preparing an imine by dehydrogenative coupling of an alcohol of the formula $RCH_2OH$ and an amine of the formula $R^1NH_2$:

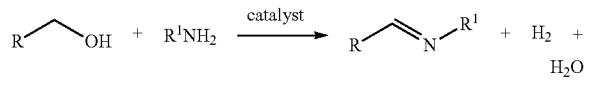

wherein R is, an unsubstituted or substituted alkyl, alkoxyalkyl, cycloalkyl, aryl, alkylaryl, heterocyclyl and heteroaryl;
$R^1$ is unsubstituted or substituted alkyl, alkoxyalkyl, cycloalkyl, aryl, alkylaryl, heterocyclyl and heteroaryl;
wherein said method comprising the step of reacting said alcohol and said amine in the presence of a catalytic amount of the manganese complex of formula I, IA, IB or IC; wherein said complex reacts in the catalytic cycle with said alcohol to obtain the intermediate complex of formula IIIA or IIIB:

IIIA
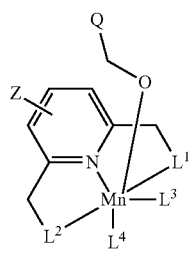

IIIB
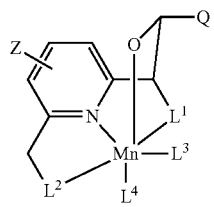

which is further reacted with said amine and thereby generating an imine,
wherein Q is hydrogen, alkyl, cycloalkyl, aryl, heterocyclyl, heteroaryl, alkylcycloalkyl, alkylaryl, alkylheterocyclyl or alkylheteroaryl; and $L^1$, $L^2$, $L^3$, $L^4$ and Z are as defined for the structures of formula I, IA, or IB; wherein if complex IA or IB is used as a catalyst an amount of base equivalent to the amount of catalyst or higher is required.

In one embodiment, this invention provides a catalytic process for C—C bond formation via Michael addition of unactivated nitriles of the formula $R^2CH_2CN$ wherein $R^2$ is H, unsubstituted or substituted alkyl, cycloalkyl, aryl, alkylaryl or heterocyclyl;
wherein said process comprises reacting an unactivated nitrile of formula $R^2CH_2CN$ and a Michael acceptor in the presence of the manganese complex of this invention thereby generating a new C—C bond. In another embodiment, if complex IA or IB is used as a catalyst an amount of base equivalent to the amount of catalyst or higher is required.

In one embodiment, this invention provides a catalytic process for C—C bond formation via Michael addition of unactivated nitriles of the formula $R^2CH_2CN$ wherein $R^2$ is H, unsubstituted or substituted alkyl, cycloalkyl, aryl, alkylaryl or heterocyclyl;
wherein said process comprises reacting an unactivated nitrile of formula $R^2CH_2CN$ and a Michael acceptor in the presence of the manganese complex of formula I, IA, IB or IC; wherein said catalyst of formula of formula I IA IB or IC reacts with said nitrile to obtain the complex of formula IVA or IVB:

IVA
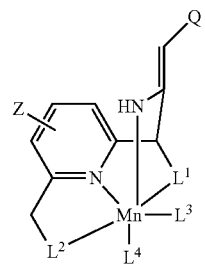

IVB
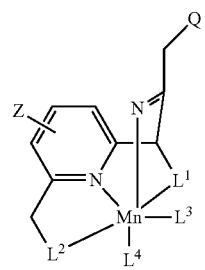

which is further reacted with said Michael acceptor and thereby generating a new C—C bond; wherein Q is hydrogen, alkyl, cycloalkyl, aryl, heterocyclyl, heteroaryl, alkylcycloalkyl, alkylaryl, alkylheterocyclyl or alkylheteroaryl; $L^1$, $L^2$, $L^3$, $L^4$ and Z are as defined for the structures of formula I, IA, IB or IC; wherein if complex IA or IB is used an amount of base equivalent to the amount of catalyst or higher is required.

In one embodiment, this invention provides a process for C—C bond formation via Michael addition; wherein said process comprises reacting an unactivated nitriles of the formula $R^2CH_2CN$ and a Michael acceptor of formula $R^3C(R^4)=C(R^5)EWG$:

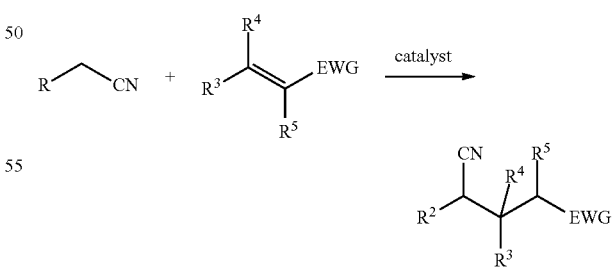

wherein $R^2$ is H, unsubstituted or substituted alkyl, cycloalkyl, aryl, alkylaryl or heterocyclyl; and
$R^3$, $R^4$, $R^5$ are each independently selected from H, nsubstituted or substituted alkyl, cycloalkyl, alkoxy (O-alkyl), aryloxy (O-aryl), aryl, alkylaryl or heterocyclyl or $R^3$ and $R^5$ form a cyclic ring; or $R_4$ and $R^5$ form a cyclic ring; or $R_3$ and $R_4$ form a cyclic ring; wherein EWG is an electron withdrawing group comprising C(=O)R, C(=O)OR', SO₂R', CON(R)₂, NO₂ or CN, wherein R is H, alkyl, aryl, heteroaryl, cycloalkyl or heterocycloalkyl; and R' is alkyl, aryl, heteroaryl, cycloalkyl or heterocycloalkyl In another embodiment, if complex IA or IB is used as a catalyst, an amount of base equivalent to the amount of catalyst or higher is required.

In one embodiment, the manganese complex of formula I, IA IB or IC is a catalyst. In another embodiment, the manganese complex of formula IA IB or IC is a precursor of the complex of formula I. In one embodiment, the manganese precursor of formula IA or IB in the present of a base, yields the manganese complex of formula I.

In one embodiment, this invention provides a catalytic process for hydrogenation of an ester to an alcohol wherein said process comprises reacting an ester, and a complex of this invention, in the presence of hydrogen; wherein said complex reacts with said ester to obtain an alcohol wherein if a manganese complex of formula IA, IB, VIA or VIB is used as a catalyst, an amount of base equivalent to the amount of catalyst or higher is required.

In one embodiment, this invention provides a catalytic process for hydrogenation of an ester to an alcohol wherein said process comprises reacting an ester of formula R⁷C(O)OR⁸, and a complex of this invention, in the presence of hydrogen; wherein said complex reacts with said ester to obtain an alcohol R⁷CH²OH:

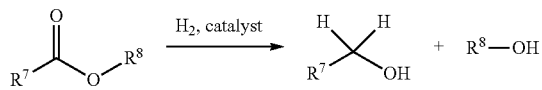

wherein R⁷ is selected from the group consisting of H, an unsubstituted or substituted alkyl, alkoxyalkyl, cycloalkyl, aryl, alkylaryl, heterocyclyl and heteroaryl; and R⁸ is selected from the group consisting of an unsubstituted or substituted alkyl, alkoxyalkyl, cycloalkyl, aryl, alkylaryl, heterocyclyl and heteroaryl.

In one embodiment, this invention provides a catalytic process for the preparation of esters by dehydrogenative coupling of alcohols, said process comprises reacting an alcohol, and a complex of this invention wherein said complex reacts with said alcohol to obtain an ester wherein if a manganese complex of formula IA, IB, VIA or VIB is used as a catalyst, an amount of base equivalent to the amount of catalyst or higher is required.

In one embodiment, this invention provides a catalytic process for the preparation of amides by dehydrogenative coupling of alcohols and amines, said process comprises reacting an alcohol and an amine, in the presence of a complex of this invention; to obtain an amide wherein if a manganese complex of formula IA, IB, VIA or VIB is used as a catalyst, an amount of base equivalent to the amount of catalyst or higher is required.

In one embodiment, this invention provides a catalytic process for the preparation of amides comprising reacting an ester and an amine, in the presence of a complex of this invention; to obtain an amide wherein if a manganese complex of formula IA, IB, VIA or VIB is used as a catalyst, an amount of base equivalent to the amount of catalyst or higher is required.

In one embodiment, this invention provides a catalytic process for preparing formamides by dehydrogenative coupling of methanol and amine of formula R²⁷R²⁷'NH:

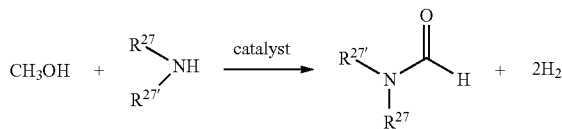

wherein R²⁷ and R²⁷' are each independently selected from the group consisting of H, an unsubstituted or substituted, saturated or unsaturated: alkyl, alkoxyalkyl, cycloalkyl, aryl, alkylaryl, heterocyclyl and heteroaryl;

wherein said process comprising the step of reacting said methanol and said amine in the presence of the manganese complex of formula VI, VIA, VIB, or VIC thereby generating an amide; wherein if a manganese complex of formula VIA or VIB is used as a catalyst, an amount of base equivalent to the amount of catalyst or higher is added;

wherein if a manganese complex of formula VI or VIC is used as a catalyst, an amount of base equivalent to the amount of catalyst or higher is optionally added.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings in which:

FIG. 5A presents the molecular structure of complex 9. FIG. 5B presents the molecular structure of complex 10. FIG. 5C presents the molecular structure of complex 11.

catalyzes conjugate addition of nitriles (where R is aryl or aliphatic group such as alkyl) (down) to Michael acceptors.

Figure 7:
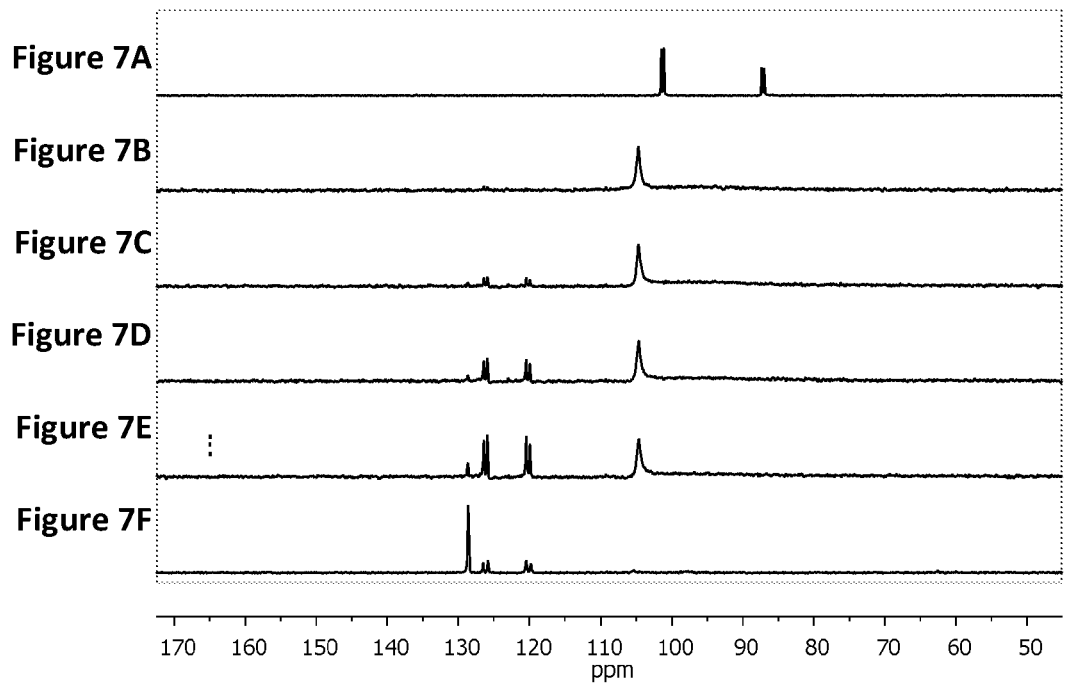

FIG. 7 depicts a selected part of $^{31}P\{^1H\}$ NMR spectra of complex 2 with benzyl alcohol over different time interval: A) complex 2 in $C_6D_6$; B) Complex 2 in neat benzyl alcohol; C) after 20 min of addition; D) after 60 min of addition; E) after 120 min of addition; F) complexes 10 and 11 independently dissolved in benzyl alcohol.

Figure 8:
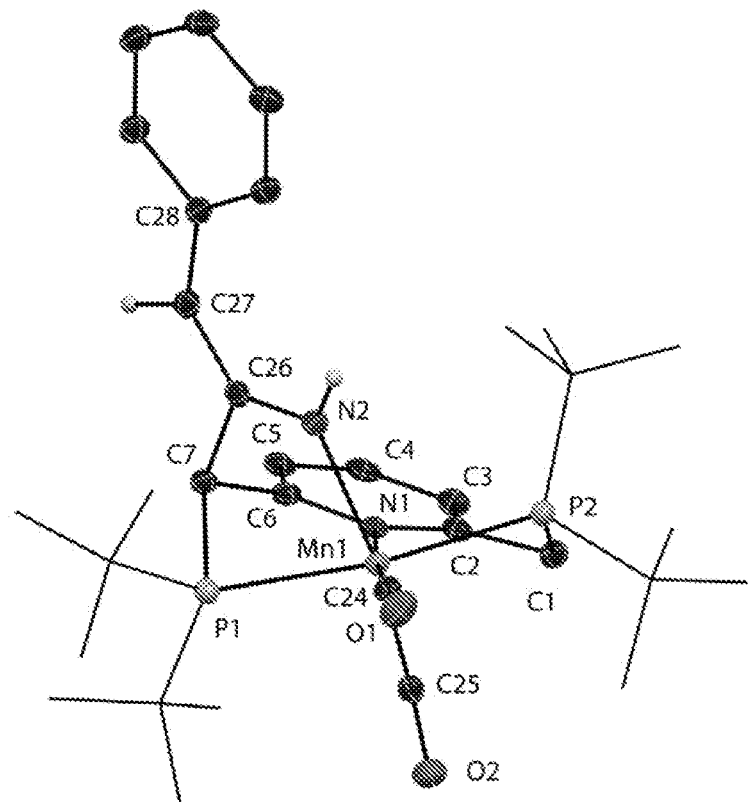

FIG. 8 depicts an ORTEP diagram of [Mn(PNP$^{tBu2}$—HNCH=CHPh)(CO)$_2$]×THF (complex 12) with thermal ellipsoids at 30% probability. The co-crystallized THF solvent molecule is omitted. The P(tert-butyl)$_2$ groups are drawn as wire frames, and hydrogen atoms are partially omitted for clarity. Selected bond lengths: C1-C2=1.502(3) Å, C2-C3=1.385(3)Å, C3-C4=1.387(3) Å, C4-C5=1.375(3) Å, C5-C6=1.390(3)Å, C6-C7=1.499(3) Å, C7-C26=1.540(3) Å, C26-C27=1.383(3)Å, C27-C28=1.446(3) Å, C26-N2=1.345(2) Å, Mn1-N1=2.0519(16) Å, Mn1-N2=2.058(2) Å, Mn1-P1=2.3241(7) Å, Mn1-P2=2.3254(8) Å, Mn1-C24=1.766(2) Å, Mn1-C25=1.780(2) Å, C24-O1=1.173(3) Å, C25-O2=1.167(2) Å.

Figure 9:
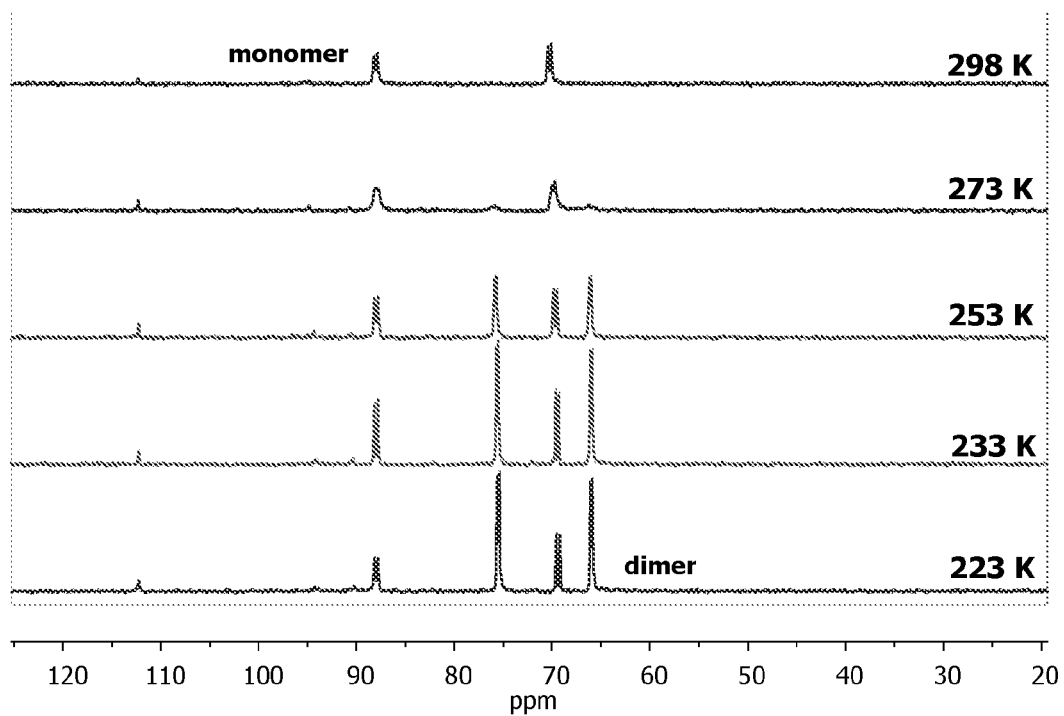

FIG. 9 depicts variable temperature $^{31}P\{^1H\}$ NMR of complex 1.

Figure 10:
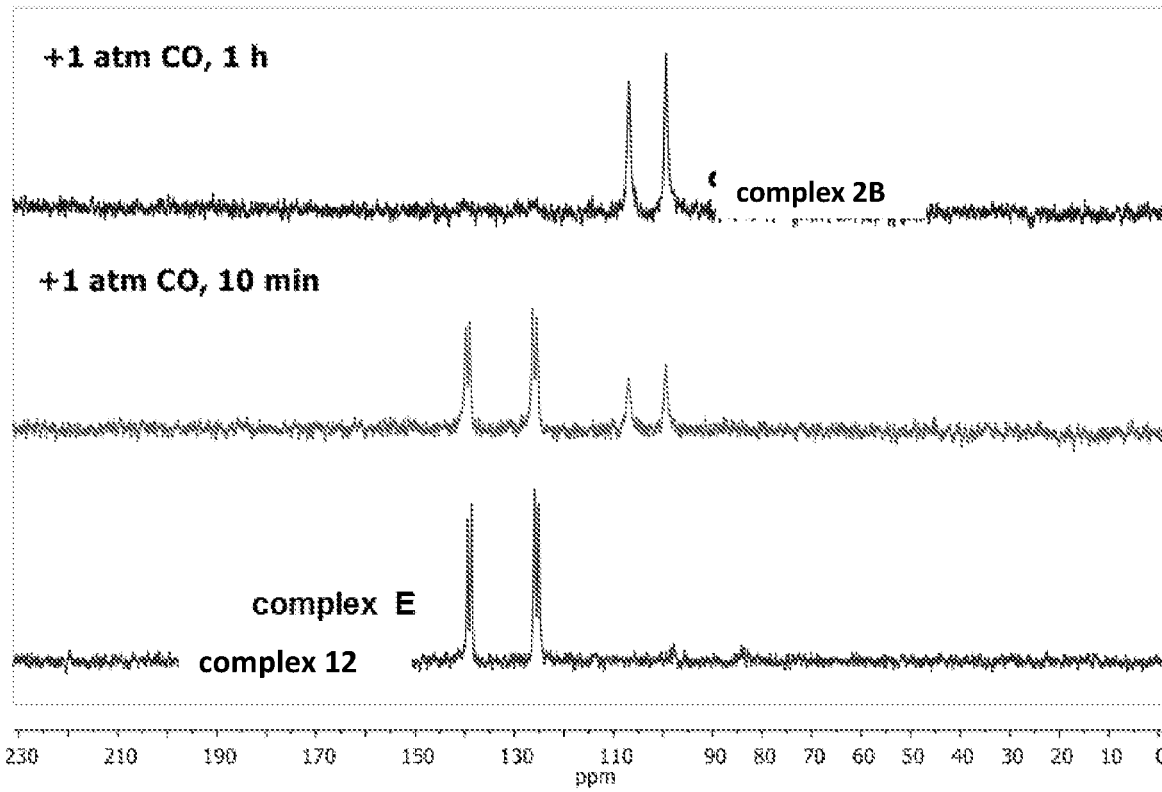

FIG. 10 depicts a $^{31}P\{^1H\}$ NMR spectra of the reaction of complex 12 with 1 atm of CO gas in $C_6D_6$ at ambient temperature. Compound 12 (top); after addition of CO, 10 min (middle); after addition of CO to complex 12, after 1 h (bottom).

Figure 11:
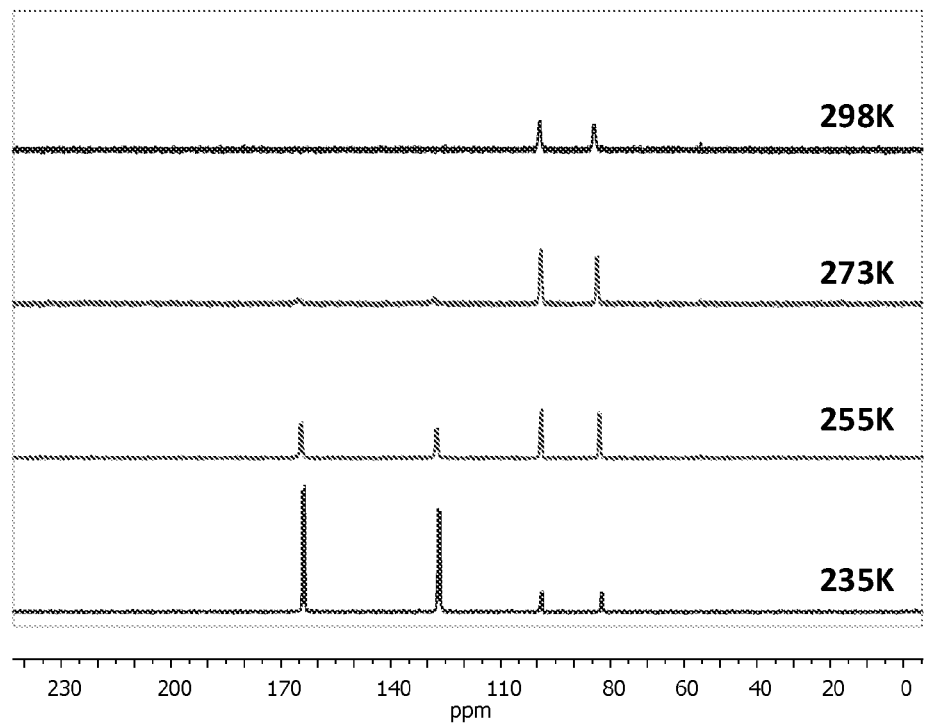

FIG. 11 depicts a $^{31}P\{^1H\}$ NMR spectra at variable temperatures of complex 2 in n-pentane and 12 equivalents of propionitrile.

Figure 12:
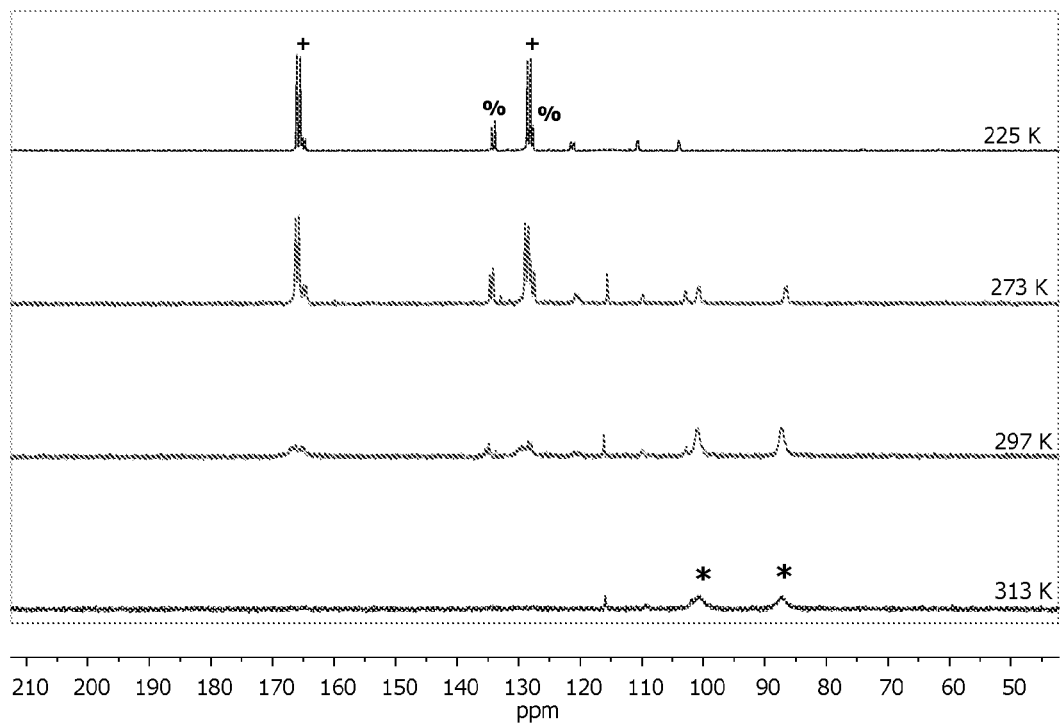

FIG. 8 is a schematic reversible binding of benzyl cyanide to complex 2. P=$^tBu_2P$ FIG. 12 depicts a $^{31}P\{^1H\}$ NMR spectra at variable temperatures of complex 2 in neat propionitrile. Assignment: (*)=complex 2; (+)=complex 14; (%)=complex 15.

Figure 13:
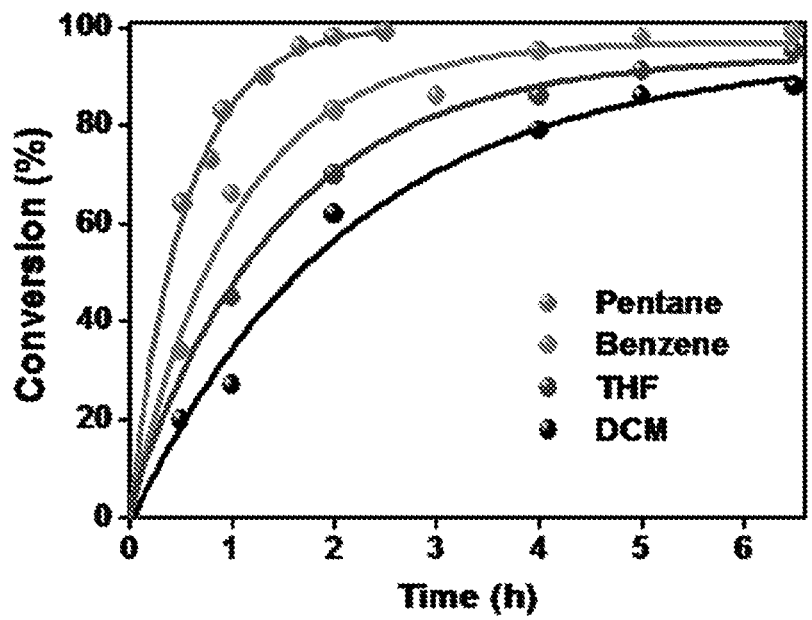

FIG. 13 presents a solvent screening of catalytic Michael addition using complex 2 of propiononitrile to ethyl acrylate in different solvents. Conversion based on NMR integration relative to a standard (toluene for n-pentane, DCM, and THF, and dioxane for the experiment performed in benzene).

Figure 14:
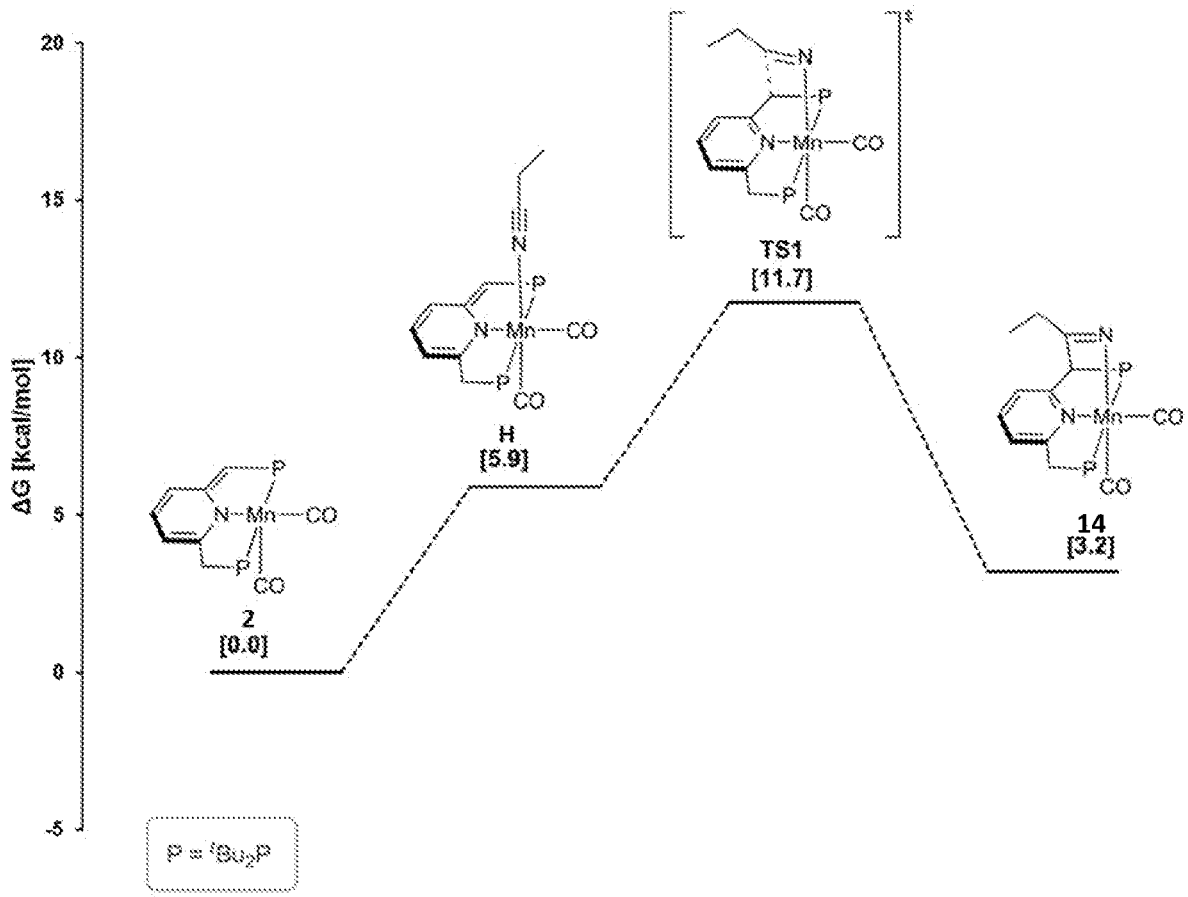

FIG. 14 presents a pathway for the formation of 14. Free Energies with respect to the catalyst and the separated reactants calculated at the TPSS-D3BJ/def2-TZVP//BP86-D3/def2-SV(P) level of theory are given in brackets.

Figure 15:
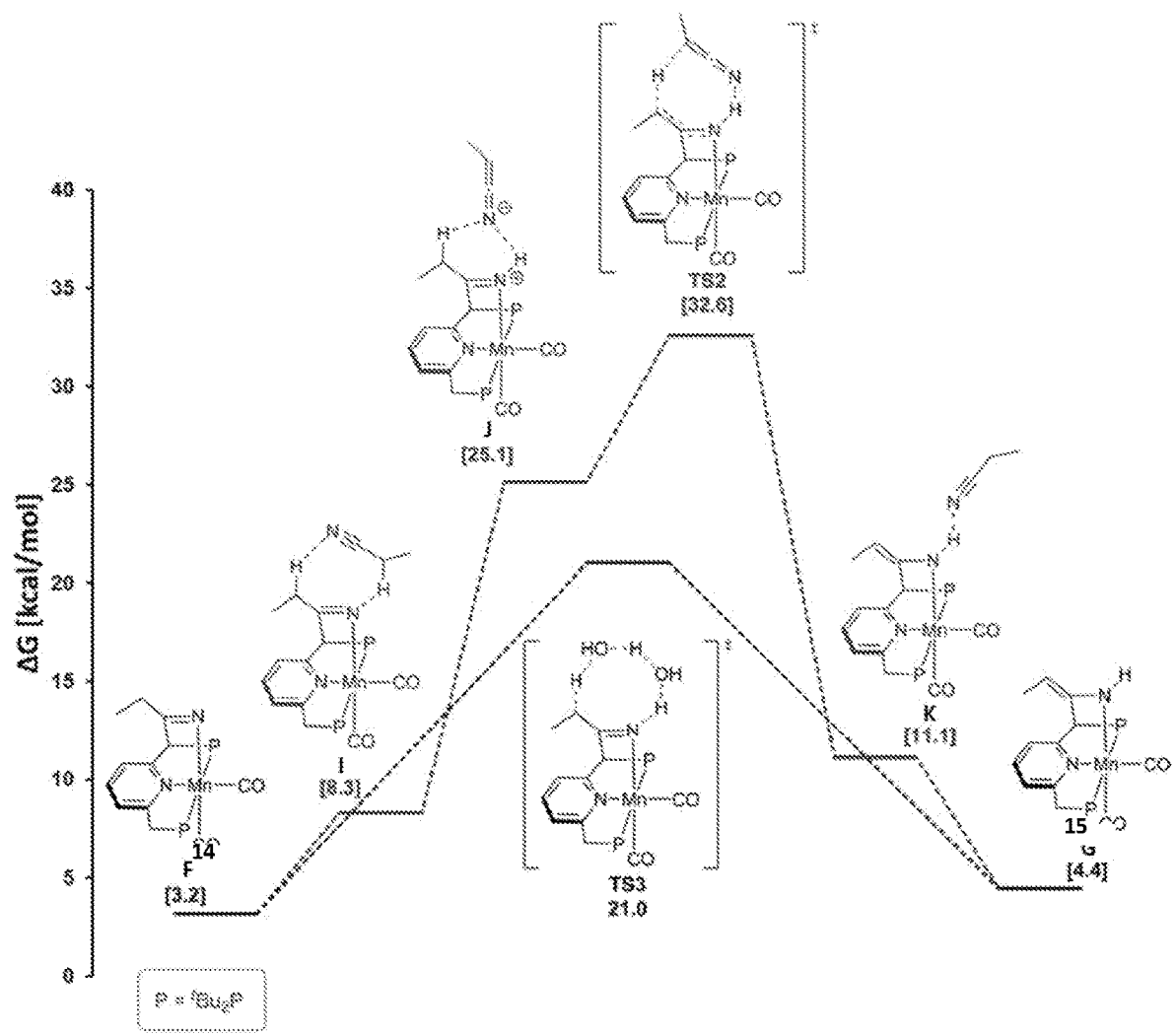
Figure 16:
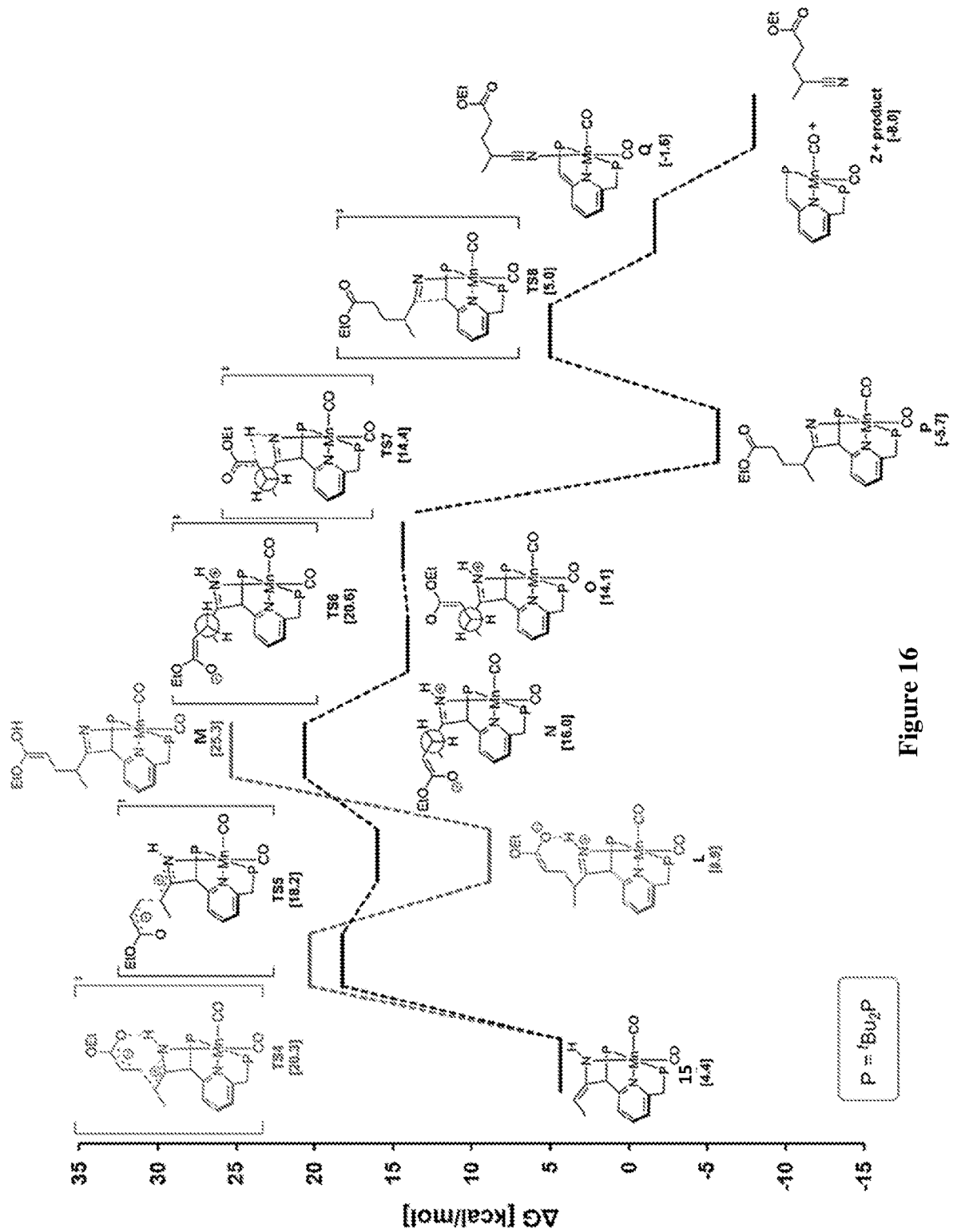

FIG. 15 presents a pathways for the tautomerization of 14. Free Energies with respect to 2 and the separated reactants calculated at the TPSS-D3BJ/def2-TZVP//BP86-D3/def2-SV(P) level of theory are given in brackets FIG. 16 presents a pathway for the product formation starting from the enamido complex 15. For the intermediates N and O and the transition states TS6 and TS7 the new formed carbon-carbon bond is shown in the newman projection. Free Energies with respect to 2 and the separated reactants calculated at the TPSS-D3BJ/def2-TZVP//BP86-D3/def2-SV(P) level of theory are given in brackets.

Figure 17:
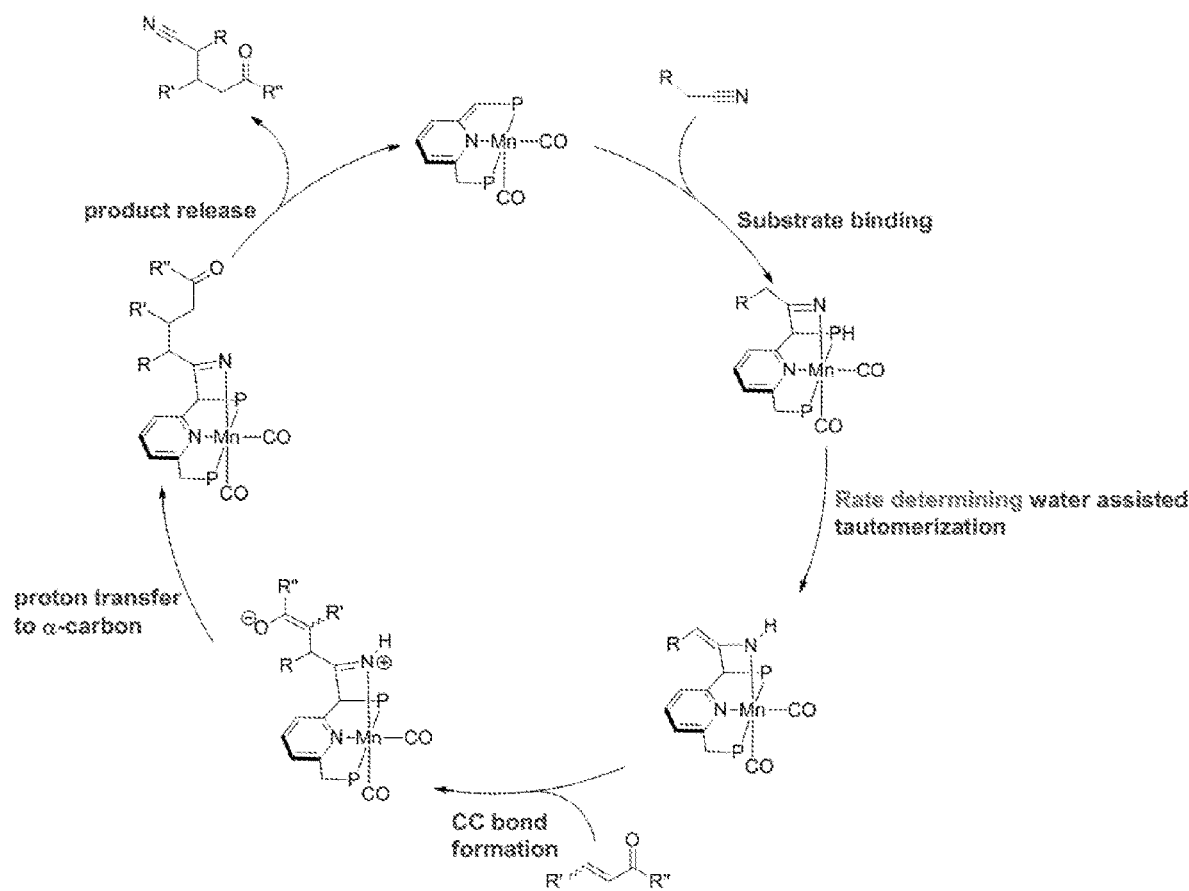

FIG. 17 depicts a simplified catalytic cycle for the conjugate addition of aliphatic nitriles to Michael acceptors catalyzed by 2.

Figure 18:
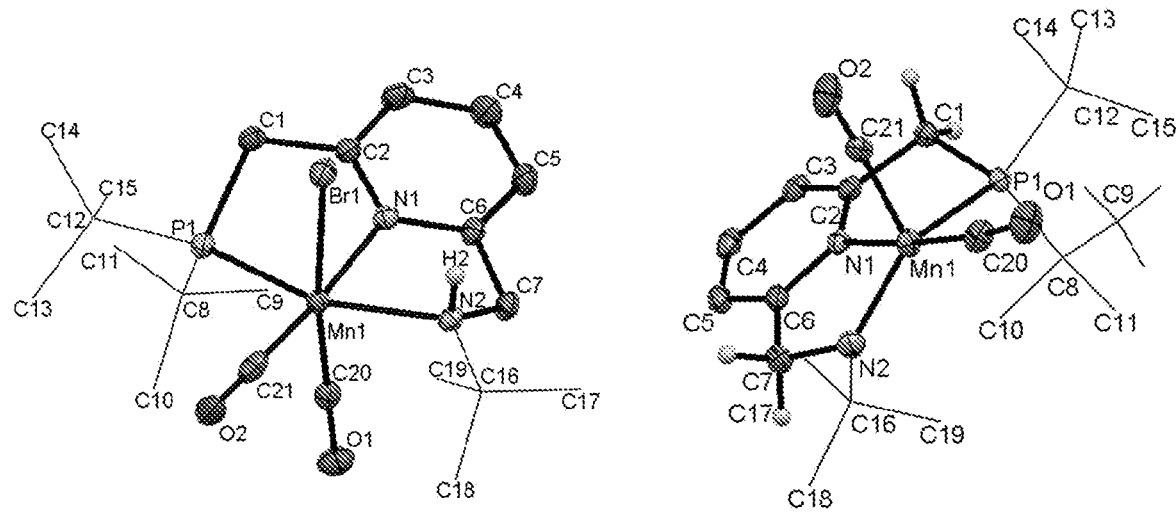

FIG. 18 depicts ORTEP diagrams of [Mn(PNN)(CO)$_2$] (6A') (PNN is an anionic deprotonated PNNH ligand) with thermal ellipsoids at 500 probability and of [Mn(PNNH)(CO)$_2$Br] (6B). The P($^tBu$)$_2$ and N Bu groups are drawn as wire frames, and the hydrogen atoms are partially omitted for clarity. Selected bond lengths and angles are presented in Example 15.

Figure 19:
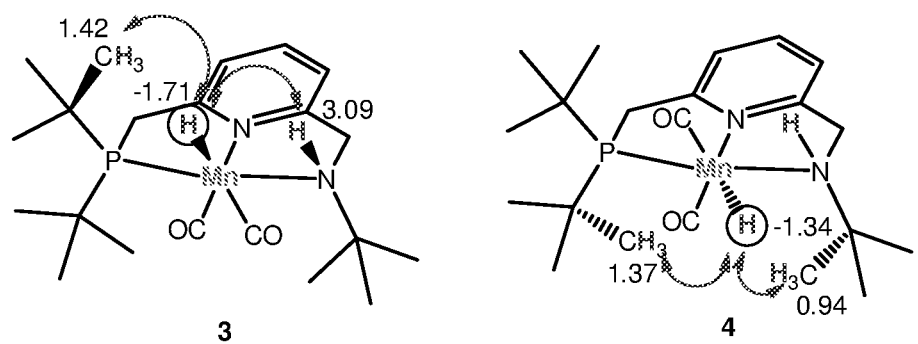

FIG. 19 depicts $^1H$ NMR chemical shifts of the NOE correlations observed under selective irradiation of the hydride resonance for 16 and 17.

Figure 20:
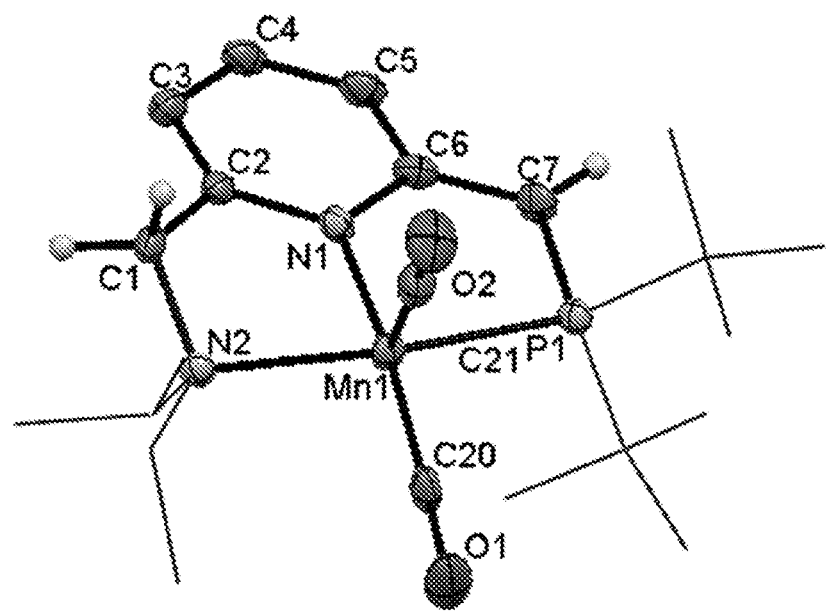

FIG. 20 depicts ORTEP diagram of [Mn(PNN*)(CO)$_2$] (4) (PNN* is a dearomatized PNN ligand) with thermal ellipsoids at 50% probability. The P($^tBu$)$_2$ and N(Et)$_2$ groups are drawn as wire frames, and the hydrogen atoms are partially omitted for clarity. Selected bond lengths and angles are presented in Example 20.

Figure 21:
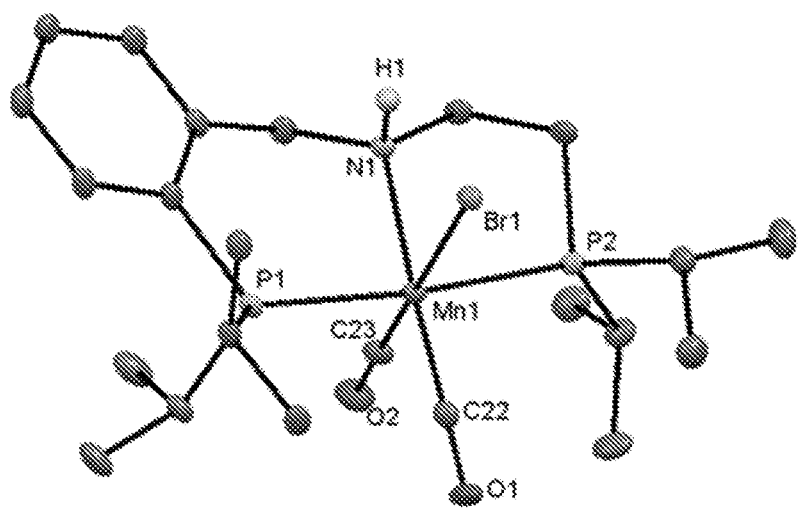

FIG. 21 depicts ORTEP diagrams of Mn(iPr-PN$^H$P)(CO)$_2$Br complex 19 with thermal ellipsoids at 50% probability. The P(iPr)$_2$ groups are drawn as wire frames, and the hydrogen atoms are partially omitted for clarity. Selected bond lengths and angles are presented in Example 21.

Figure 22:
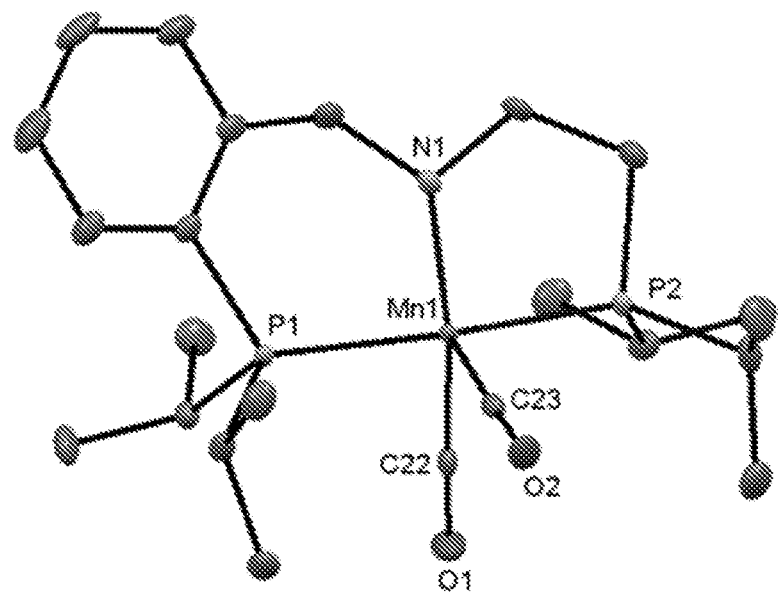

FIG. 22 depicts ORTEP diagrams of (iPr-PNP)Mn(CO)$_2$ complex 18 with thermal ellipsoids at 50% probability. The P(iPr)$_2$ groups are drawn as wire frames, and the hydrogen atoms are partially omitted for clarity. Selected bond lengths and angles are presented in Example 23.

Figure 23:
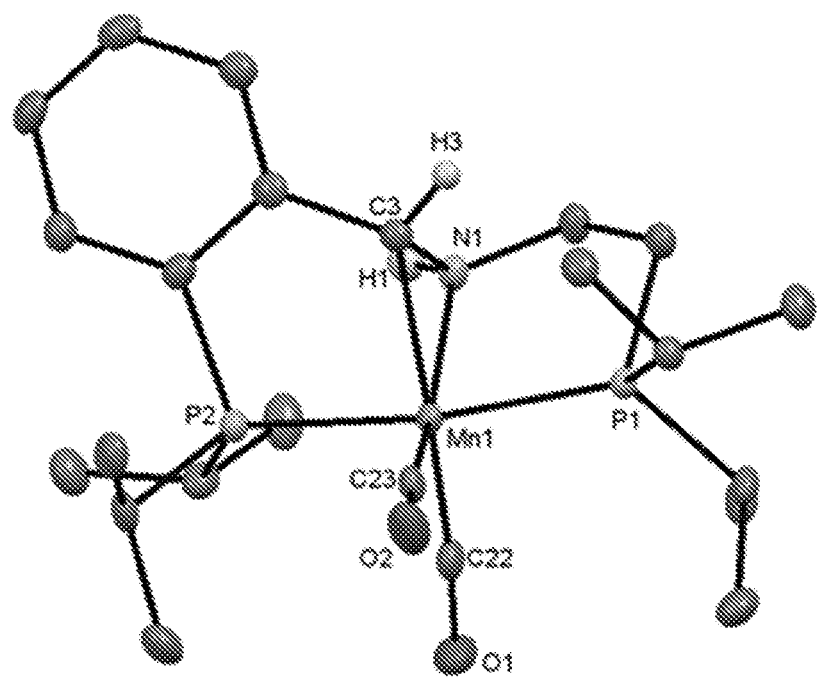

FIG. 23 depicts ORTEP diagrams of (iPr-PN$^H$P)Mn(CO)$_2$ complex 21 with thermal ellipsoids at 50% probability. The P(iPr)$_2$ groups are drawn as wire frames, and the hydrogen atoms are partially omitted for clarity. Selected bond lengths and angles are presented in Example 24.

Figure 24:
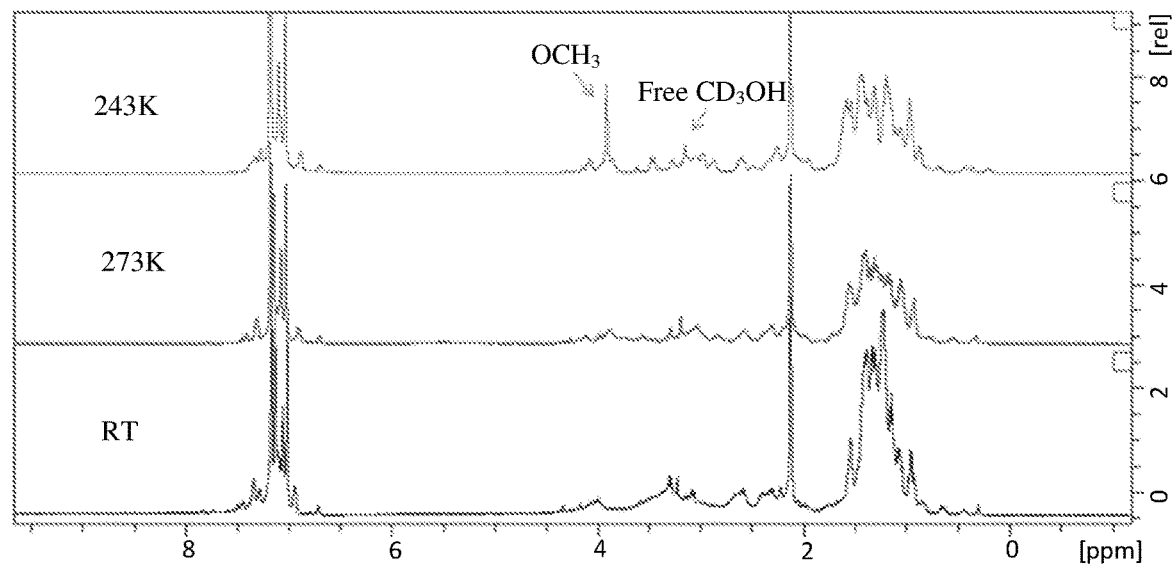

FIG. 24 depicts variable temperature $^1H$ NMR spectra of the reaction of the amido complex 18 and 1 equiv. methanol in toluene-$d_8$ (500 MHz).

Figure 25:
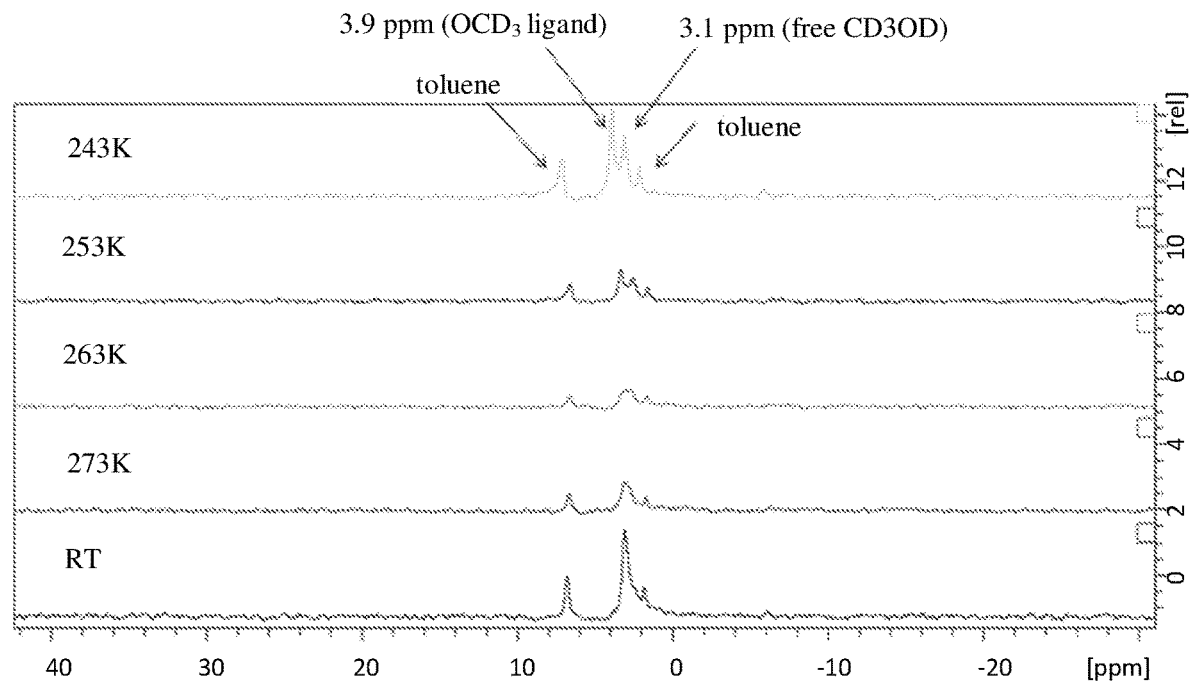

FIG. 25 depicts Variable temperature $^2H$ NMR spectra of the reaction of the amido complex 18 and 1 equiv. methanol in toluene (61.5 MHz).

Figure 26:
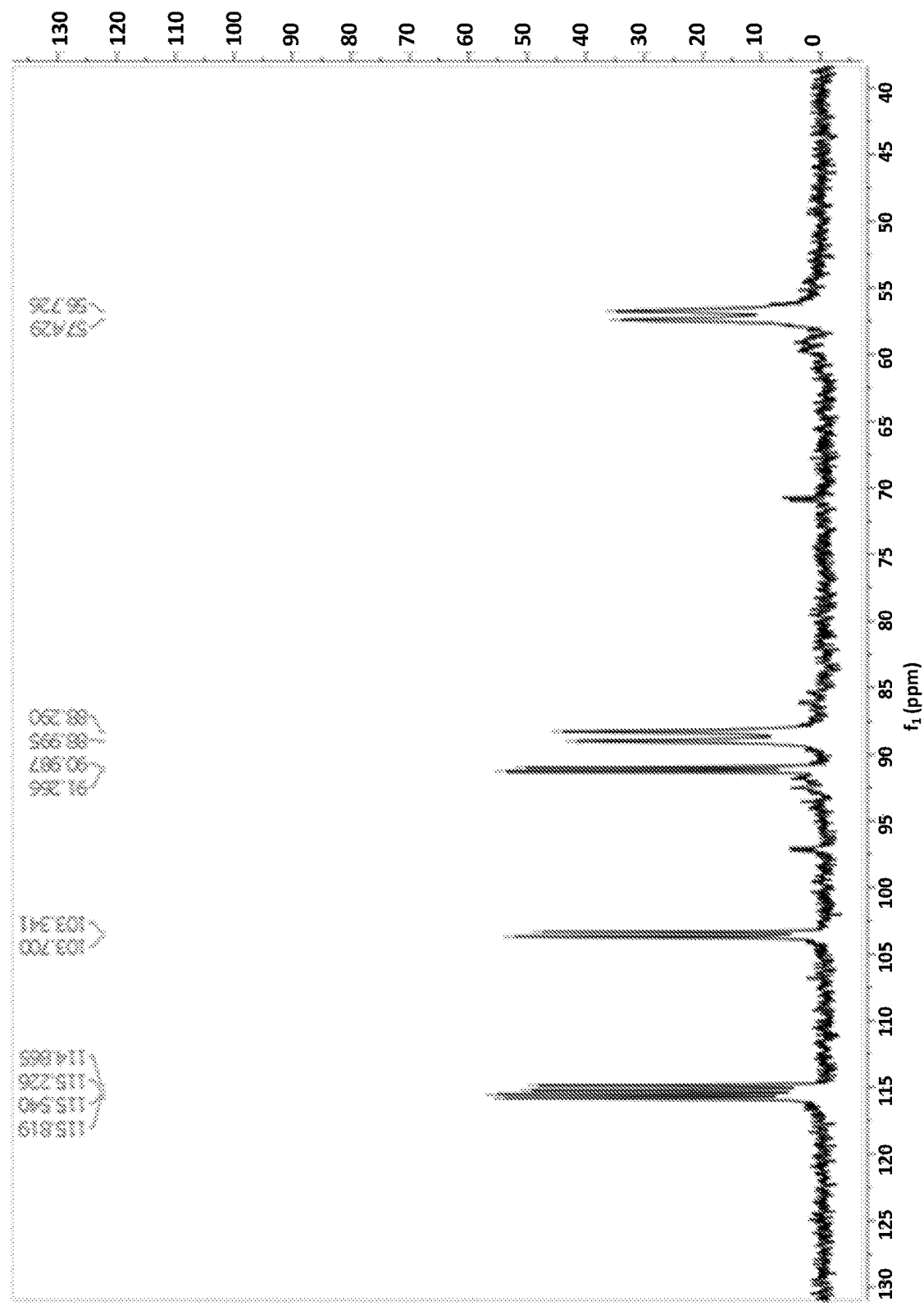

FIG. 26 depicts $^{31}P\{^1H\}$NMR (202 MHz) spectrum of the reaction of amido complex 18 and 1 equiv. methanol in toluene-$d_8$ at −30° C. Signals at 57 and 88 ppm correspond to the methoxy complex 22. Signals at δ=91, 103, 114 and 115 ppm correspond to complex 21 and 20.

Figure 27:
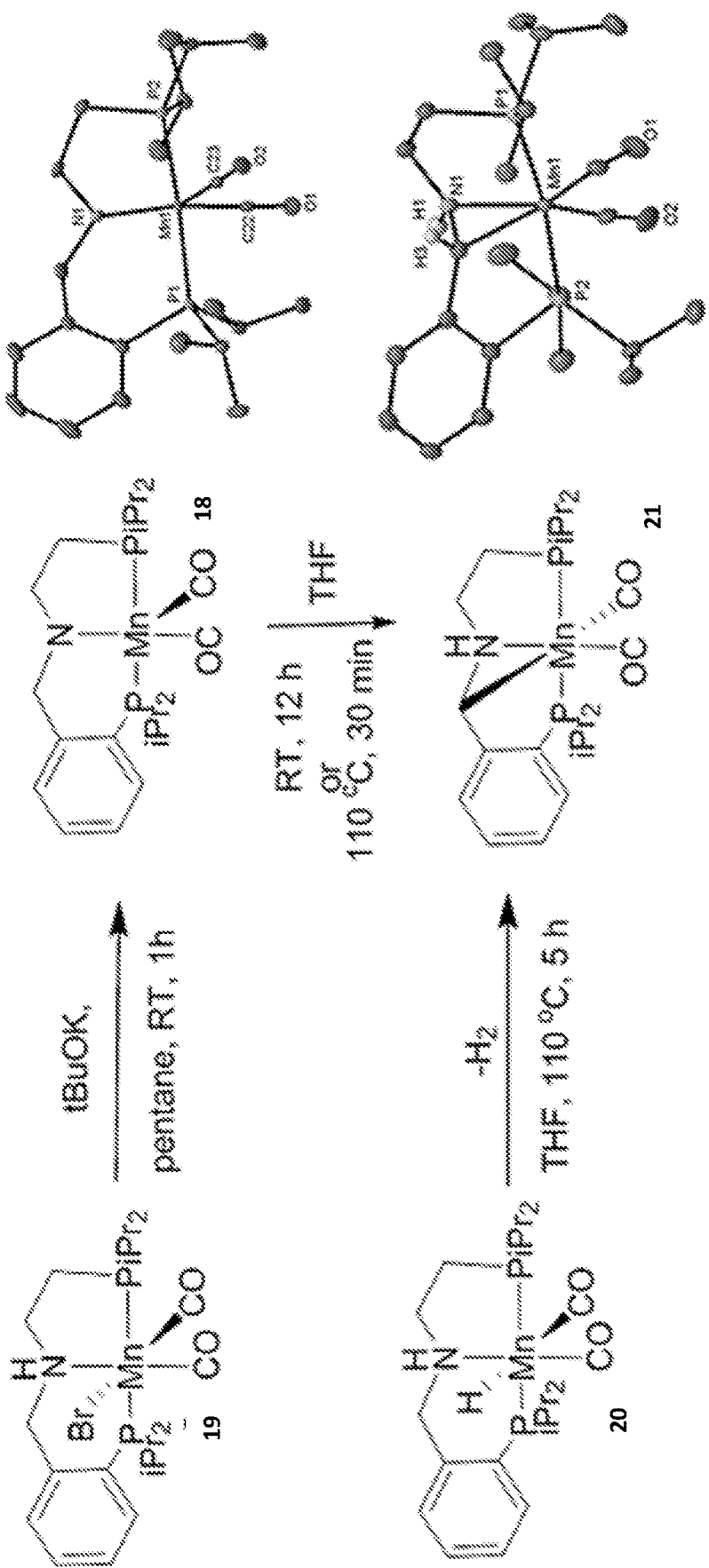

FIG. 27 depicts reactivity of complexes 19 and 20.

Figure 28:
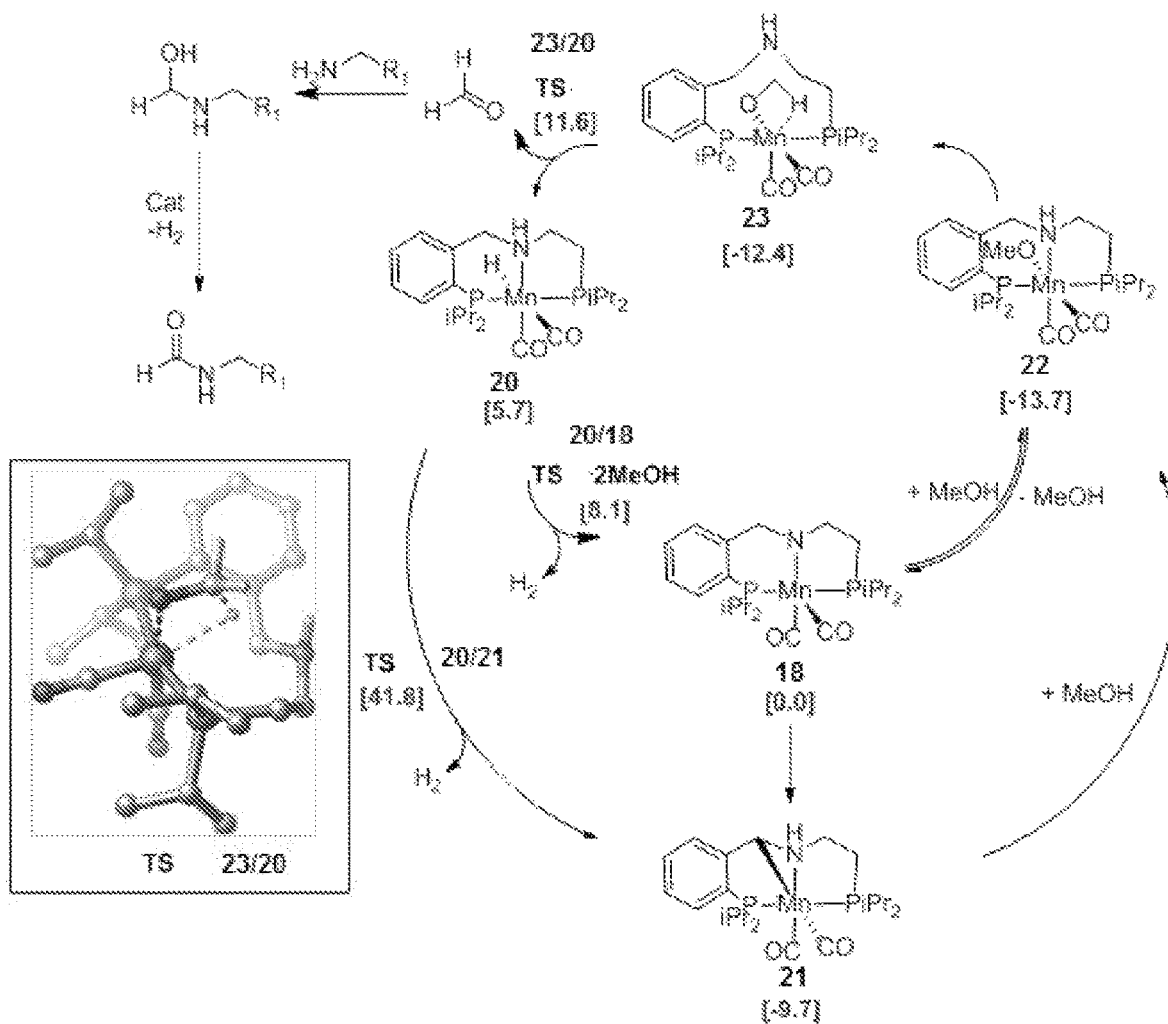

FIG. 28 presents plausible mechanism for the acceptorless dehydrogenative coupling of methanol and amines. $\Delta G_{vib+rot}$ values calculated at the SMD(MeOH)-TPSS-D3BJ/def2-TZVPP//BP86-D3/def2-SV(P) level of theory are given in square brackets. The transition state $TS_{23/20}$ is shown as inset.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF THE PRESENT INVENTION

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

In one embodiment this invention is directed to manganese based complexes and the use of such complexes for, inter alia, (1) the preparation of imine by dehydrogenative coupling of an alcohol and amine; (2) C—C coupling in Michael addition reaction using nitriles as Michael donors; (3) dehydrogenative coupling of alcohols to give esters and hydrogen gas (4) hydrogenation of esters to form alcohols (including hydrogenation of cyclic esters (lactones) or cyclic di-esters (di-lactones), or polyesters); (5) hydrogenation of amides (including cyclic dipeptides, lactams, diamide, polypeptides and polyamides) to alcohols and amines (or diamine); (6) hydrogenation of organic carbonates (including polycarbonates) to alcohols or hydrogenation of carbamates (including polycarbamates) or urea derivatives to alcohols and amines; (7) dehydrogenation of secondary alcohols to ketones; (8) amidation of esters (i.e., synthesis of amides from esters and amines); (9) acylation of alcohols using esters; (10) coupling of alcohols with water and a base to form carboxylic acids; (11) preparation of amino acids or their salts by coupling of amino alcohols with water and a base; (12) preparation of amides (including cyclic dipeptides, diamide, lactams, polypeptides and polyamides) by dehydrogenative coupling of alcohols and amines.

Manganese Complexes

The complexes described herein function as catalysts in the processes described hereinbelow, and are based on abundant, environmentally friendly and inexpensive manganese.

In one embodiment, this invention is directed to a manganese complex represented by the structure of any of formula I or its isomer or salt thereof:

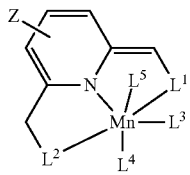

I wherein
L¹ is (PR$^a$R$^b$), (NR$^a$R$^b$), imine; oxazoline, sulfide (SR$^a$), sulfoxide (S(=O)R$^a$), heteroaryl containing at least one heteroatom selected from nitrogen and sulfur; (AsR$^a$R$^b$), (SbR$^a$R$^b$) or a N-heterocyclic carbene represented by the structures:

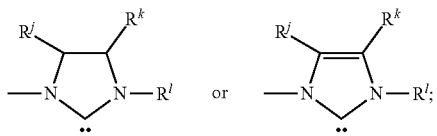

L² is (PR$^a$R$^b$), (NR$^a$R$^b$), imine; oxazoline, sulfide (SR$^a$), sulfoxide (S(=O)R$^a$), heteroaryl containing at least one heteroatom selected from nitrogen and sulfur; (AsR$^a$R$^b$), (SbR$^a$R$^b$) or a N-heterocyclic carbene represented by the structures:

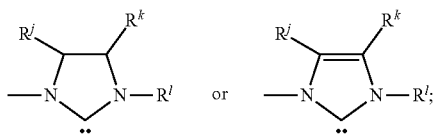

L³ and L⁴ are each independently a mono-dentate two-electron donor selected, from the group consisting of CO, PR$^a$R$^b$R$^c$, P(OR$^a$)(OR$^b$)(OR$^c$), NO⁺, NR$^a$R$^b$R$^c$, AsR$^a$R$^b$R$^c$, SbR$^a$R$^b$R$^c$, SR$^a$R$^b$, nitrile (RCN), isonitrile (RNC), N₂, PF₃, CS, heteroaryl, tetrahydrothiophene, alkene, alkyne or L³ and L⁴ form together with the Mn a ring;

L⁵ is a absent or mono-dentate two-electron donor selected, from the group consisting of CO, PR$^a$R$^b$R$^c$, P(OR$^a$)(OR$^b$)(OR$^c$), NO⁺, NR$^a$R$^b$R$^c$, AsR$^a$R$^b$R$^c$, SbR$^a$R$^b$R$^c$, SR$^a$R$^b$, nitrile (RCN), isonitrile (RNC), N₂, PF₃, CS, heteroaryl, tetrahydrothiophene, alkene or alkyne;

Z represents zero, one, two or three substituents wherein each such substituent is independently selected from the group consisting of alkyl, cycloalkyl, aryl, heterocyclyl, heteroaryl, alkylcycloalkyl, alkylaryl, alkylheterocyclyl, alkylheteroaryl, halogen, nitro, amide, ester, cyano, alkoxy, alkylamino, arylamino, an inorganic support and a polymeric moiety R, R$^a$ R$^b$ and R$^c$ are each independently H, alkyl, cycloalkyl, aryl, heterocyclyl, heteroaryl, alkylcycloalkyl, alkylaryl, alkylheterocyclyl or alkylheteroaryl; and R$^j$, R$^k$ and R$^l$ are each independently H, alkyl, cycloalkyl, aryl, heterocyclyl, heteroaryl, alkylcycloalkyl, alkylaryl, alkylheterocyclyl or alkylheteroaryl.

In one embodiment, the oxidation state of the manganese in the complex of formula I is Mn(I). In one embodiment, if L³, L⁴ or L⁵ is H, then the dearomatised manganese complex I is anionic and may be in equilibrium with the aromatic anionic complex resulting from proton migration to the "arm", forming a Mn(–1) oxidation state:

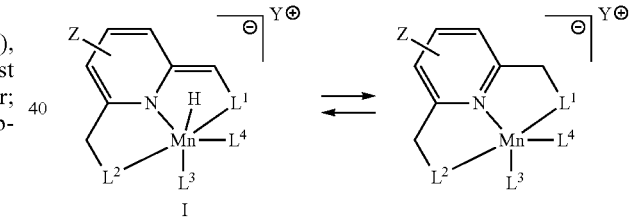

In one embodiment, this invention is directed to a manganese complex represented by the structure of any of formula IA, or its isomer or salt thereof:

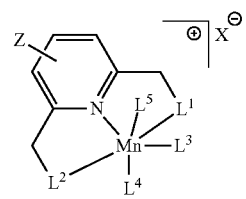

IA wherein
L¹ is (PR$^a$R$^b$), (NR$^a$R$^b$), imine; oxazoline, sulfide (SR$^a$), sulfoxide (S(=O)R$^a$), heteroaryl containing at least one heteroatom selected from nitrogen and sulfur; (AsR$^a$R$^b$), (SbR$^a$R$^b$) or a N-heterocyclic carbene represented by the structures:

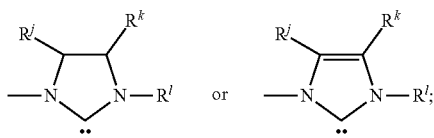

$L^2$ is ($PR^aR^b$), ($NR^aR^b$), imine; oxazoline, sulfide ($SR^a$), sulfoxide (S(=O)$R^a$), heteroaryl containing at least one heteroatom selected from nitrogen and sulfur; ($AsR^aR^b$), ($SbR^aR^b$) or a N-heterocyclic carbene represented by the structures:

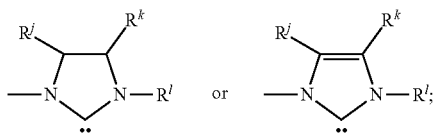

$L^3$ and $L^4$ are each independently a mono-dentate two-electron donor selected from the group consisting of CO, $PR^aR^bR^c$, $P(OR^a)(OR^b)(OR^c)$, $NO^+$, $NR^aR^bR^c$, $AsR^aR^bR^c$, $SbR^aR^bR^c$, $SR^aR^b$, nitrile (RCN), isonitrile (RNC), $N_2$, $PF_3$, CS, heteroaryl, tetrahydrothiophene, alkene, alkyne or $L^3$ and $L^4$ form together with the Mn a ring;

$L^5$ is a mono-dentate two-electron donor selected from the group consisting of CO, $PR^aR^bR^c$, $P(OR^a)(OR^b)(OR^c)$, $NO^+$, $NR^aR^bR^c$, $AsR^aR^bR^c$, $SbR^aR^bR^c$, $SR^aR^b$, nitrile (RCN), isonitrile (RNC), $N_2$, $PF_3$, CS, heteroaryl, tetrahydrothiophene, alkene or alkyne;

X is halide, OCOR, $OCH_2Q$, $OCOCF_3$, $OSO_2R$, $OSO_2CF_3$, CN, OR, $N(R)_2$ and RS, $BF_4$, $B(C_6H_5)_4$, $B(C_6F_5)_4$, $B[(C_6H_4)(CF_3)_2]$, $PF_6$ or $ClO_4$;

Q is hydrogen, alkyl, cycloalkyl, aryl, heterocyclyl, heteroaryl, alkylcycloalkyl, alkylaryl, alkylheterocyclyl or alkylheteroaryl;

Z represents zero, one, two or three substituents wherein each such substituent is independently selected from the group consisting of alkyl, cycloalkyl, aryl, heterocyclyl, heteroaryl, alkylcycloalkyl, alkylaryl, alkylheterocyclyl, alkylheteroaryl, halide, nitro, amide, ester, cyano, alkoxy, alkylamino, arylamino, an inorganic support and a polymeric moiety; or Z forms a fused aromatic or heterocyclic ring with the nitrogen based ring;

R, $R^a$ $R^b$ and $R^c$ are each independently H, alkyl, cycloalkyl, aryl, heterocyclyl, heteroaryl, alkylcycloalkyl, alkylaryl, alkylheterocyclyl or alkylheteroaryl; and $R^j$, $R^k$ and $R^l$ are each independently H, alkyl, cycloalkyl, aryl, heterocyclyl, heteroaryl, alkylcycloalkyl, alkylaryl, alkylheterocyclyl or alkylheteroaryl.

In one embodiment, the oxidation state of the manganese complex of formula IA is Mn(I). In another embodiment, the manganese complex of formula IA is a precursor of the complex of formula I.

In one embodiment, this invention is directed to a precursor of the manganese complex of formula IB, or its isomer or salt thereof

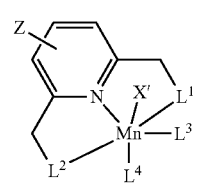

IB wherein $L^1$ is ($PR^aR^b$), ($NR^aR^b$), imine; oxazoline, sulfide ($SR^a$), sulfoxide (S(=O)$R^a$), heteroaryl containing at least one heteroatom selected from nitrogen and sulfur; ($AsR^aR^b$), ($SbR^aR^b$) or a N-heterocyclic carbene represented by the structures:

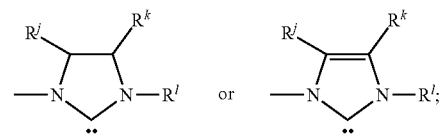

$L^2$ is ($PR^aR^b$), ($NR^aR^b$), imine; oxazoline, sulfide ($SR^a$), sulfoxide (S(=O)$R^a$), heteroaryl containing at least one heteroatom selected from nitrogen and sulfur; ($AsR^aR^b$), ($SbR^aR^b$) or a N-heterocyclic carbene represented by the structures:

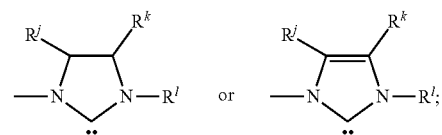

$L^3$ and $L^4$ are each independently a mono-dentate two-electron donor selected from the group consisting of CO, $PR^aR^bR^c$, $P(OR^a)(OR^b)(OR)$, $NO^+$, $NR^aR^bR^c$, $AsR^aR^bR^c$, $SbR^aR^bR^c$, $SR^aR^b$, nitrile (RCN), isonitrile (RNC), $N_2$, $PF_3$, CS, heteroaryl, tetrahydrothiophene, alkene, alkyne or $L^3$ and $L^4$ form together with the Mn a ring;

X' is H, halide, OCOR, $OCH_2Q$, $OCOCF_3$, $OSO_2R$, $OSO_2CF_3$, CN, OR, $N(R)_2$ and RS;

Q is hydrogen, alkyl, cycloalkyl, aryl, heterocyclyl, heteroaryl, alkylcycloalkyl, alkylaryl, alkylheterocyclyl or alkylheteroaryl;

Z represents zero, one, two or three substituents wherein each such substituent is independently selected from the group consisting of alkyl, cycloalkyl, aryl, heterocyclyl, heteroaryl, alkylcycloalkyl, alkylaryl, alkylheterocyclyl, alkylheteroaryl, halide, nitro, amide, ester, cyano, alkoxy, alkylamino, arylamino, an inorganic support and a polymeric moiety; or Z forms a fused aromatic or heterocyclic ring with the nitrogen based ring;

R, $R^a$ $R^b$ and $R^c$ are each independently H, alkyl, cycloalkyl, aryl, heterocyclyl, heteroaryl, alkylcycloalkyl, alkylaryl, alkylheterocyclyl or alkylheteroaryl; and $R^j$, $R^k$ and $R^l$ are each independently H, alkyl, cycloalkyl, aryl, heterocyclyl, heteroaryl, alkylcycloalkyl, alkylaryl, alkylheterocyclyl or alkylheteroaryl.

In one embodiment, the oxidation state of the manganese in the precursor complex of formula IB is Mn(I). In another embodiment, the manganese complex of formula IB is a precursor of the complex of formula I.

In one embodiment, this invention is directed to a precursor of the manganese complex of formula IC, or its isomer or salt thereof:

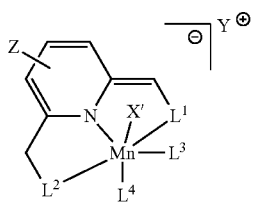

IC wherein
L¹ is (PR$^a$R$^b$), (NR$^a$R$^b$), imine; oxazoline, sulfide (SR$^a$), sulfoxide (S(=O)R$^a$), heteroaryl containing at least one heteroatom selected from nitrogen and sulfur; (AsR$^a$R$^b$), (SbR$^a$R$^b$) or a N-heterocyclic carbene represented by the structures:

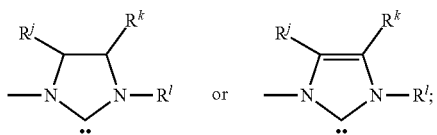

L² is (PR$^a$R$^b$), (NR$^a$R$^b$), imine; oxazoline, sulfide (SR$^a$), sulfoxide (S(=O)R$^a$), heteroaryl containing at least one heteroatom selected from nitrogen and sulfur; (AsR$^a$R$^b$), (SbR$^a$R$^b$) or a N-heterocyclic carbene represented by the structures:

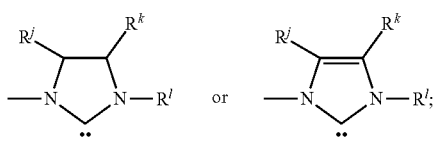

L³ and L⁴ are each independently a mono-dentate two-electron donor selected from the group consisting of CO, PR$^a$R$^b$R$^c$, P(OR$^a$)(OR$^b$)(OR$^c$), NO⁺, NR$^a$R$^b$R$^c$, AsR$^a$R$^b$R$^c$, SbR$^a$R$^b$R$^c$, SR$^a$R$^b$, nitrile (RCN), isonitrile (RNC), N₂, PF₃, CS, heteroaryl, tetrahydrothiophene, alkene, alkyne or L³ and L⁴ form together with the Mn a ring;
X' is H, halide, OCOR, OCH₂Q, OCOCF₃, OSO₂R, OSO₂CF₃, CN, OR, N(R)₂ and RS;
Q is hydrogen, alkyl, cycloalkyl, aryl, heterocyclyl, heteroaryl, alkylcycloalkyl, alkylaryl, alkylheterocyclyl or alkylheteroaryl;
Y⁺ is a cationic group bearing a single positive charge;
Z represents zero, one, two or three substituents wherein each such substituent is independently selected from the group consisting of alkyl, cycloalkyl, aryl, heterocyclyl, heteroaryl, alkylcycloalkyl, alkylaryl, alkylheterocyclyl, alkylheteroaryl, halide, nitro, amide, ester, cyano, alkoxy, alkylamino, arylamino, an inorganic support and a polymeric moiety; or Z forms a fused aromatic or heterocyclic ring with the nitrogen based ring;

R, R$^a$ R$^b$ and R$^c$ are each independently H, alkyl, cycloalkyl, aryl, heterocyclyl, heteroaryl, alkylcycloalkyl, alkylaryl, alkylheterocyclyl or alkylheteroaryl; and
R$^j$, R$^k$ and R$^l$ are each independently H, alkyl, cycloalkyl, aryl, heterocyclyl, heteroaryl, alkylcycloalkyl, alkylaryl, alkylheterocyclyl or alkylheteroaryl.

In one embodiment, this invention is directed to a manganese complex represented by the structure of formula I(1), IA(1), IB(1), IC(1) or their isomers or salts thereof:

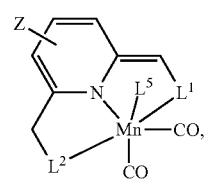

I(1)

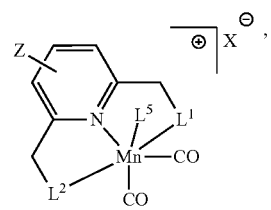

IA(1)

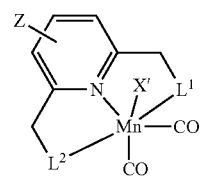

IB(1)

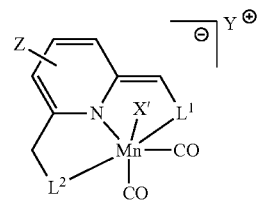

IC(1)

wherein
L¹ is (PR$^a$R$^b$), (NR$^a$R$^b$), imine; oxazoline, sulfide (SR$^a$), sulfoxide (S(=O)R$^a$), heteroaryl containing at least one heteroatom selected from nitrogen and sulfur; (AsR$^a$R$^b$), (SbR$^a$R$^b$) or a N-heterocyclic carbene represented by the structures:

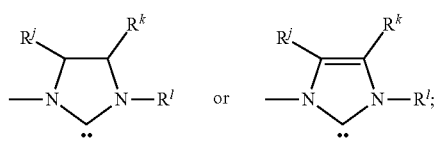

L² is (PR$^a$R$^b$), (NR$^a$R$^b$), imine; oxazoline, sulfide (SR³), sulfoxide (S(=O)R$^a$), heteroaryl containing at least one heteroatom selected from nitrogen and sulfur; (AsR$^a$R$^b$), (SbR$^a$R$^b$) or a N-heterocyclic carbene represented by the structures:

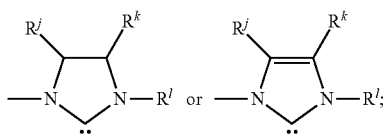

L⁵ is absent or a mono-dentate two-electron donor selected from the group consisting of CO, $PR^aR^bR^c$, $P(OR^a)(OR^b)(OR^c)$, $NO^+$, $NR^aR^bR^c$, $AsR^aR^bR^c$, $SbR^aR^bR^c$, $SR^aR^b$, nitrile (RCN), isonitrile (RNC), $N_2$, $PF_3$, CS, heteroaryl, tetrahydrothiophene, alkene or alkyne X' is H, halide, OCOR, $OCH_2Q$, $OCOCF_3$, $OSO_2R$, $OSO_2CF_3$, CN, OR, $N(R)_2$ and RS;

X is halide, OCOR, $OCH_2Q$, $OCOCF_3$, $OSO_2R$, $OSO_2CF_3$, CN, OR, $N(R)_2$ and RS, $BF_4$, $B(C_6H_5)_4$, $B(C_6F_5)_4$, $B[(C_6H_4)(CF_3)_2]$, $PF_6$ or $ClO_4$;

Q is hydrogen, alkyl, cycloalkyl, aryl, heterocyclyl, heteroaryl, alkylcycloalkyl, alkylaryl, alkylheterocyclyl or alkylheteroaryl;

$Y^+$ is a cationic group bearing a single positive charge

Z represents zero, one, two or three substituents wherein each such substituent is independently selected from the group consisting of alkyl, cycloalkyl, aryl, heterocyclyl, heteroaryl, alkylcycloalkyl, alkylaryl, alkylheterocyclyl, alkylheteroaryl, halide, nitro, amide, ester, cyano, alkoxy, alkylamino, arylamino, an inorganic support and a polymeric moiety; or Z forms a fused aromatic or heterocyclic ring with the nitrogen based ring;

R, $R^a$ and $R^b$ are each independently alkyl, cycloalkyl, aryl, heterocyclyl, heteroaryl, alkylcycloalkyl, alkylaryl, alkylheterocyclyl or alkylheteroaryl; and $R^j$, $R^k$ and $R^l$ are each independently H, alkyl, cycloalkyl, aryl, heterocyclyl, heteroaryl, alkylcycloalkyl, alkylaryl, alkylheterocyclyl or alkylheteroaryl.

In another embodiment, the manganese complex of formula IA(1), IB(1) or IC(I) is a precursor of the complex of formula I(1). In one embodiment, the manganese precursor of formula IA(1) or IB(1) in the present of a base, yields the manganese complex of formula I(1).

In one embodiment, this invention is directed to a manganese complex represented by the structure of formula I(2), IA(2), IB(2), IC(2) or their isomers or salts thereof.

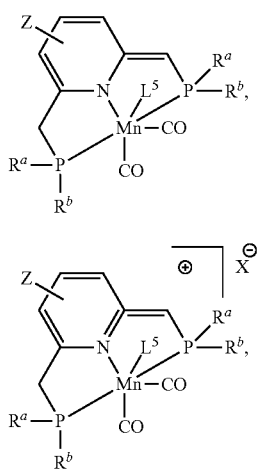

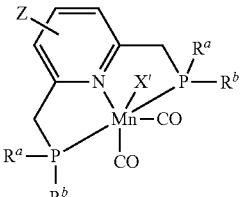

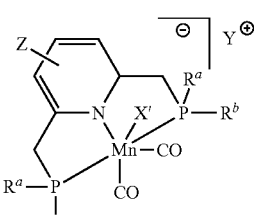

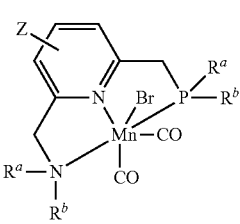

wherein

Z represents zero, one, two or three substituents wherein each such substituent is independently selected from the group consisting of alkyl, cycloalkyl, aryl, heterocyclyl, heteroaryl, alkylcycloalkyl, alkylaryl, alkylheterocyclyl, alkylheteroaryl, halide, nitro, amide, ester, cyano, alkoxy, alkylamino, arylamino, an inorganic support and a polymeric moiety; or Z forms a fused aromatic or heterocyclic ring with the nitrogen based ring;

L⁵ is absent or a mono-dentate two-electron donor selected from the group consisting of, CO, $PR^aR^bR^c$, $P(OR^a)(OR^b)(OR^c)$, $NO^+$, $NR^aR^bR^c$, $AsR^aR^bR^c$, $SbR^aR^bR^c$, $SR^aR^b$, nitrile (RCN), isonitrile (RNC), $N_2$, $PF_3$, CS, heteroaryl, tetrahydrothiophene, alkene or alkyne;

X' is H, halide, OCOR, $OCH_2Q$, $OCOCF_3$, $OSO_2R$, $OSO_2CF_3$, CN, OR, $N(R)_2$ and RS;

X is halide, OCOR, $OCH_2Q$, $OCOCF_3$, $OSO_2R$, $OSO_2CF_3$, CN, OR, $N(R)_2$ and RS, $BF_4$, $B(C_6H_5)_4$, $B(C_6F_5)_4$, $B[(C_6H_4)(CF_3)_2]$, $PF_6$ or $ClO_4$;

Q is hydrogen, alkyl, cycloalkyl, aryl, heterocyclyl, heteroaryl, alkylcycloalkyl, alkylaryl, alkylheterocyclyl or alkylheteroaryl;

$Y^+$ is a cationic group bearing a single positive charge; and

R, $R^a$ and $R^b$ are each independently alkyl, cycloalkyl, aryl, heterocyclyl, heteroaryl, alkylcycloalkyl, alkylaryl, alkylheterocyclyl or alkylheteroaryl.

In another embodiment, the manganese complex of formula IA(2), IB(2) or IC(2) is a precursor of the complex of formula I(2). In one embodiment, the manganese precursor of formula IA(2) or IB(2) in the present of a base, yields the manganese complex of formula I(2).

In one embodiment, this invention provides a manganese complex represented by the following structures:

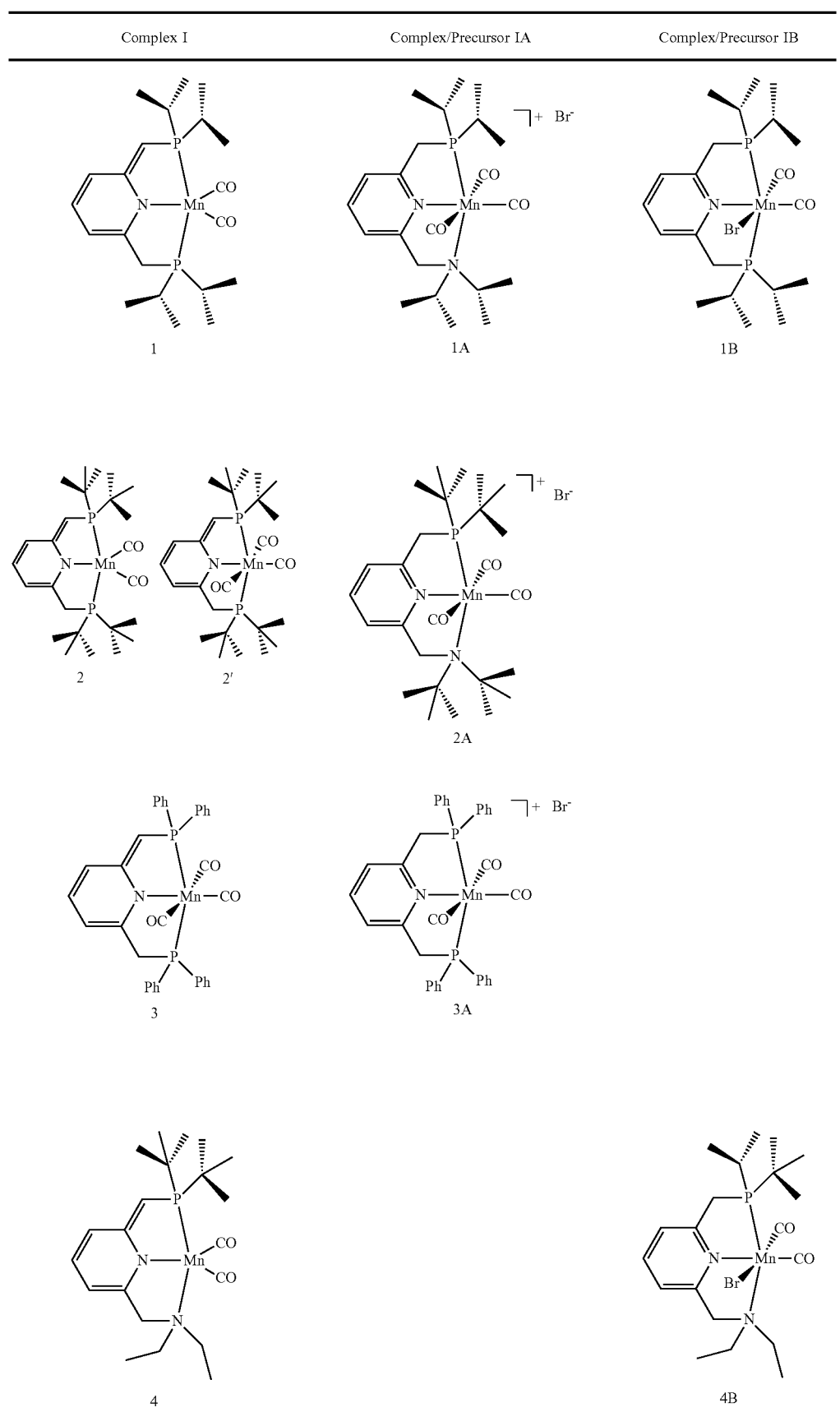

| Complex I | Complex/Precursor IA | Complex/Precursor IB |
|---|---|---|

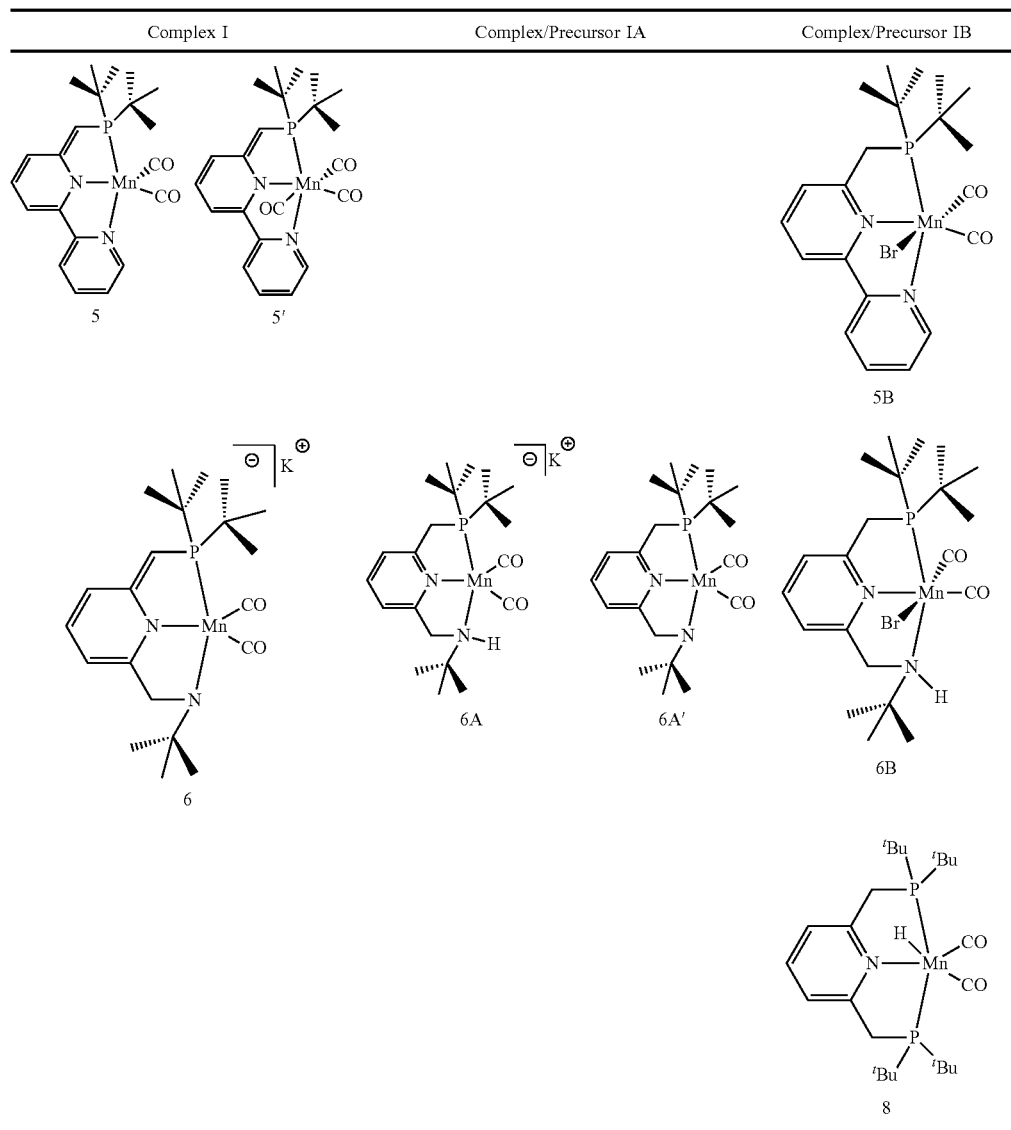

In one embodiment, this invention is directed to a manganese complex represented by the structure of formula 7. In another embodiment, the manganese complex of formula 1 in the solid state is a dimer of formula 7:

In one embodiment, this invention is directed to a manganese complex represented by the structure of any of formula II, IIA, IIB, IIC or its isomer or salt thereof:

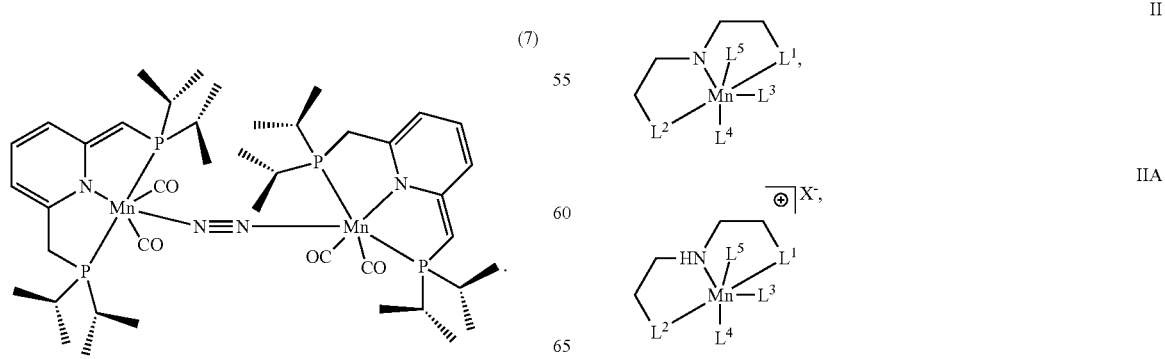

-continued

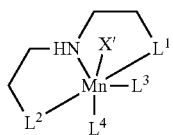
IIB

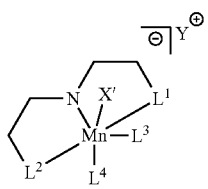
IIC wherein
$L^1$ is $(PR^aR^b)$, $(NR^aR^b)$, imine; oxazoline, sulfide $(SR^a)$, sulfoxide $(S(=O)R^a)$, heteroaryl containing at least one heteroatom selected from nitrogen and sulfur; $(AsR^aR^b)$, $(SbR^aR^b)$ or a N-heterocyclic carbene represented by the structures:

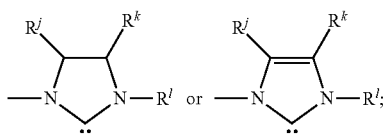

$L^2$ is $(PR^aR^b)$, $(NR^aR^b)$, imine; oxazoline, sulfide $(SR^a)$, sulfoxide $(S(=O)R^a)$, heteroaryl containing at least one heteroatom selected from nitrogen and sulfur; $(AsR^aR^b)$, $(SbR^aR^b)$ or a N-heterocyclic carbene represented by the structures:

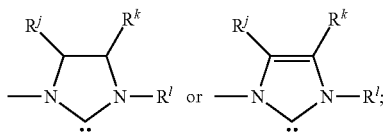

$L^3$ and $L^4$ are each independently a mono-dentate two-electron donor selected from the group consisting of CO, $PR^aR^bR^c$, $P(OR^a)(OR^b)(OR^c)$, $NO^+$, $AsR^aR^bR^c$, $SbR^aR^bR^c$, $NR^aR^bR^c$, $SR^aR^b$, nitrile (RCN), isonitrile (RNC), $N_2$, $PF_3$, CS, heteroaryl, tetrahydrothiophene, alkene, alkyne or $L^3$ and $L^4$ form together with the Mn a ring;
$L^5$ is absent or a mono-dentate two-electron donor selected from the group consisting of, CO, $PR^aR^bR^c$, $P(OR^a)(OR^b)(OR^c)$, $NO^+$, $NR^aR^bR^c$, $AsR^aR^bR^c$, $SbR^aR^bR^c$, $SR^aR^b$, nitrile (RCN), isonitrile (RNC), $N_2$, $PF_3$, CS, heteroaryl, tetrahydrothiophene, alkene or alkyne;
X is an anionic compound, such as halide, OCOR, $OCH_2Q$, $OCOCF_3$, $OSO_2R$, $OSO_2CF_3$, CN, OR, $N(R)_2$ and RS, $BF_4$, $B(C_6H_5)_4$, $B(C_6F_5)_4$, $B[(C_6H_4)(CF_3)_2]$, $PF_6$ or $ClO_4$;
X' is H, halide, OCOR, $OCH_2Q$, $OCOCF_3$, $OSO_2R$, $OSO_2CF_3$, CN, OR, $N(R)_2$ or RS;
Q is hydrogen, alkyl, cycloalkyl, aryl, heterocyclyl, heteroaryl, alkylcycloalkyl, alkylaryl, alkylheterocyclyl or alkylheteroaryl;
$Y^+$ is a cationic group bearing a single positive charge;
R, $R^a$ $R^b$ and $R^c$ are each independently H, alkyl, cycloalkyl, aryl, heterocyclyl, heteroaryl, alkylcycloalkyl, alkylaryl, alkylheterocyclyl or alkylheteroaryl; and
$R^j$, $R^k$ and $R^l$ are each independently H, alkyl, cycloalkyl, aryl, heterocyclyl, heteroaryl, alkylcycloalkyl, alkylaryl, alkylheterocyclyl or alkylheteroaryl.

In one embodiment, the manganese complex of formula II, IIA, IIB or IIC is a catalyst. In another embodiment, the manganese complex of formula IIA, IIB or IIC is a precursor of the complex of formula II. In one embodiment, the manganese precursor of formula IIA, or IIB in the present of a base, yields the manganese complex of formula II. In another embodiment, if complex IIA or IIB is used as a catalyst in the processes or methods of this invention, an amount of base equivalent to the amount of catalyst or higher is required.

In one embodiment, this invention is directed to a manganese complex represented by the structure of any of formula II(1), or its isomer or salt thereof.

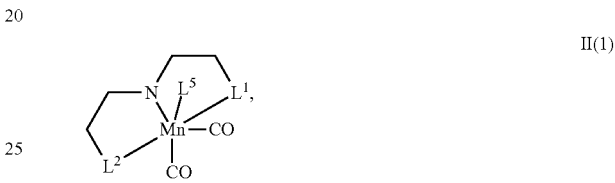
II(1)

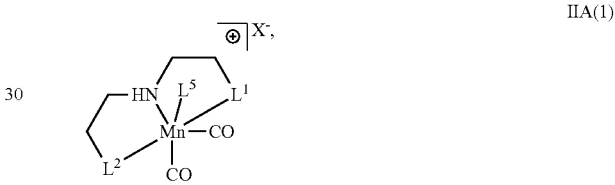
IIA(1)

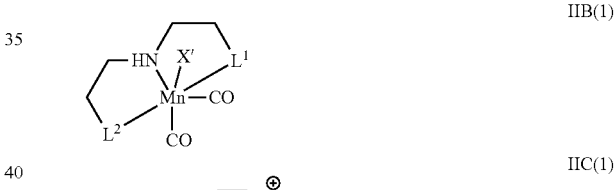
IIB(1)

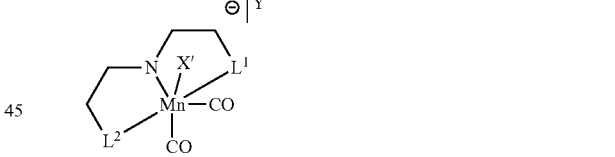
IIC(1)

wherein
$L^1$ is $(PR^aR^b)$, $(NR^aR^b)$, imine; oxazoline, sulfide $(SR^a)$, sulfoxide $(S(=O)R^a)$, heteroaryl containing at least one heteroatom selected from nitrogen and sulfur; $(AsR^aR^b)$, $(SbR^aR^b)$ or a N-heterocyclic carbene represented by the structures:

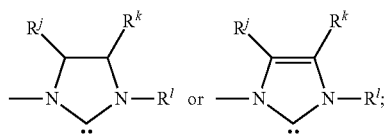

$L^2$ is $(PR^aR^b)$, $(NR^aR^b)$, imine; oxazoline, sulfide $(SR^a)$, sulfoxide $(S(=O)R^a)$, heteroaryl containing at least one heteroatom selected from nitrogen and sulfur; $(AsR^aR^b)$, $(SbR^aR^b)$ or a N-heterocyclic carbene represented by the structures:

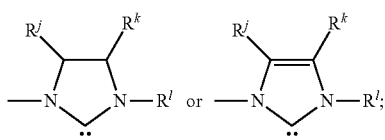

L⁵ is absent or a mono-dentate two-electron donor selected from the group consisting of, CO, $PR^aR^bR^c$, $P(OR^a)(OR^b)(OR^c)$, NO⁺, $NR^aR^bR^c$, $AsR^aR^bR^c$, $SbR^aR^bR^c$, $SR^aR^b$, nitrile (RCN), isonitrile (RNC), $N_2$, $PF_3$, CS, heteroaryl, tetrahydrothiophene, alkene or alkyne;

X is halide, OCOR, $OCH_2Q$, $OCOCF_3$, $OSO_2R$, $OSO_2CF_3$, CN, OR, $N(R)_2$ and RS, $BF_4$, $B(C_6H_5)_4$, $B(C_6F_5)_4$, $B[(C_6H_4)(CF_3)_2]$, $PF_6$ or $ClO_4$;

X' is H, halide, OCOR, $OCH_2Q$, $OCOCF_3$, $OSO_2R$, $OSO_2CF_3$, CN, OR, $N(R)_2$ or RS;

Q is hydrogen, alkyl, cycloalkyl, aryl, heterocyclyl, heteroaryl, alkylcycloalkyl, alkylaryl, alkylheterocyclyl or alkylheteroaryl;

Y⁺ is a cationic group bearing a single positive charge;

R, $R^a$ and $R^b$ are each independently alkyl, cycloalkyl, aryl, heterocyclyl, heteroaryl, alkylcycloalkyl, alkylaryl, alkylheterocyclyl or alkylheteroaryl; and $R^j$, $R^k$ and $R^l$ are each independently H, alkyl, cycloalkyl, aryl, heterocyclyl, heteroaryl, alkylcycloalkyl, alkylaryl, alkylheterocyclyl or alkylheteroaryl.

In one embodiment, the manganese complex of formula II(1), IIA(I), IIB(I) or IIC(I) is a catalyst. In another embodiment, the manganese complex of formula IIA(1) IIB(1) or IIC(1) is a precursor of the complex of formula II(1). In one embodiment, the manganese precursor of formula IIA(1) or IIB(1) in the present of a base, yields the manganese complex of formula II(1). In another embodiment, if complex IIA(1) or IIB(1) as a catalyst is used in the processes or methods of this invention, an amount of base equivalent to the amount of catalyst or higher is required.

In one embodiment, this invention is directed to a manganese complex represented by the structure of any of formula II(2), or its isomer or salt thereof:

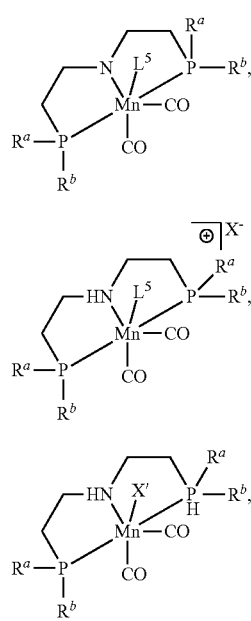

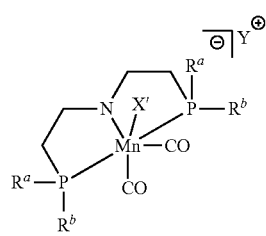

wherein
L⁵ is absent or a mono-dentate two-electron donor selected from the group consisting of CO, $PR^aR^bR^c$, $P(OR^a)(OR^b)(OR^c)$, NO⁺, $AsR^aR^bR^c$, $SbR^aR^bR^c$, $SR^aR^b$, nitrile (RCN), isonitrile (RNC), $N_2$, $PF_3$, CS, heteroaryl, tetrahydrothiophene, alkene or alkyne;

R, $R^a$ and $R^b$ are each independently alkyl, cycloalkyl, aryl, heterocyclyl, heteroaryl, alkylcycloalkyl, alkylaryl, alkylheterocyclyl or alkylheteroaryl.

X is halide, OCOR, $OCH_2Q$, $OCOCF_3$, $OSO_2R$, $OSO_2CF_3$, CN, OR, $N(R)_2$ and RS, $BF_4$, $B(C_6H_5)_4$, $B(C_6F^5)_4$, $B[(C_6H_4)(CF_3)_2]$, $PF_6$ or $ClO_4$;

X' is H, halide, OCOR, $OCH_2Q$, $OCOCF_3$, $OSO_2R$, $OSO_2CF_3$, CN, OR, $N(R)_2$ and RS; 1Q is hydrogen, alkyl, cycloalkyl, aryl, heterocyclyl, heteroaryl, alkylcycloalkyl, alkylaryl, alkylheterocyclyl or alkylheteroaryl; and Y⁺ is a cationic group bearing a single positive charge.

In one embodiment, the manganese complex of formula II(2), IIA(2), IIB(2) or IIC(2) is a catalyst. In another embodiment, the manganese complex of formula IIA(2), IB(2) or IIC(2) is a precursor of the complex of formula II(2). In one embodiment, the manganese precursor of formula IIA(2) or IIB(2) in the present of a base, yields the manganese complex of formula II(2). In another embodiment, if complex IIA(2) or IIB(2) is used as a catalyst in the processes or methods of this invention, an amount of base equivalent to the amount of catalyst or higher is required.

In one embodiment, this invention provides a manganese complex represented by the following structures or its isomer or salt thereof:

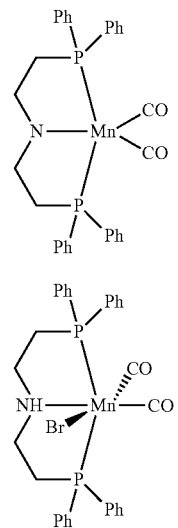

In one embodiment, this invention is directed to a manganese intermediate complex represented by the structure of any of formulae IIIA and IIIB or its isomer or salt thereof:

IIIA

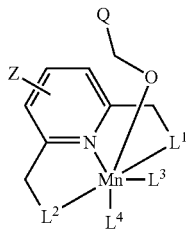

IIIB

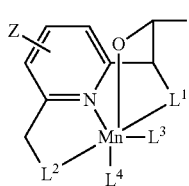

wherein $L^1$ is $(PR^aR^b)$, $(NR^aR^b)$, imine; oxazoline, sulfide $(SR^3)$, sulfoxide $(S(=O)R^a)$, heteroaryl containing at least one heteroatom selected from nitrogen and sulfur; $(AsR^aR^b)$, $(SbR^aR^b)$ or a N-heterocyclic carbene represented by the structures:

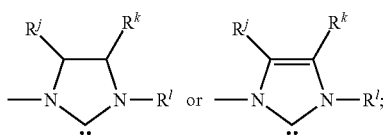

$L^2$ is $(PR^aR^b)$, $(NR^aR^b)$, imine; oxazoline, sulfide $(SR^a)$, sulfoxide $(S(=O)R^a)$, heteroaryl containing at least one heteroatom selected from nitrogen and sulfur; $(AsR^aR^b)$, $(SbR^aR^b)$ or a N-heterocyclic carbene represented by the structures:

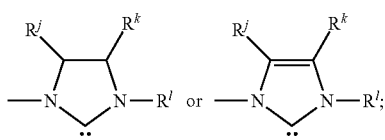

Z represents zero, one, two or three substituents wherein each such substituent is independently selected from the group consisting of alkyl, cycloalkyl, aryl, heterocyclyl, heteroaryl, alkylcycloalkyl, alkylaryl, alkylheterocyclyl, alkylheteroaryl, halide, nitro, amide, ester, cyano, alkoxy, alkylamino, arylamino, an inorganic support and a polymeric moiety; or Z forms a fused aromatic or heterocyclic ring with the nitrogen based ring $L^3$ and $L^4$ are each independently a mono-dentate two-electron donor selected from the group consisting of CO, $PR^aR^bR^c$, $P(OR^a)(OR^b)(OR^c)$, $NO^+$, $AsR^aR^bR^c$, $SbR^aR^bR^c$, $NR^aR^bR^c$, $SR^aR^b$, nitrile (RCN), isonitrile (RNC), $N_2$, $PF_3$, CS, heteroaryl, tetrahydrothiophene, alkene, alkyne or $L^3$ and $L^4$ form together with the Mn a ring;

R, $R^a$ and $R^b$ are each independently H, alkyl, cycloalkyl, aryl, heterocyclyl, heteroaryl, alkylcycloalkyl, alkylaryl, alkylheterocyclyl or alkylheteroaryl;

$R^j$, $R^k$ and $R^l$ are each independently H, alkyl, cycloalkyl, aryl, heterocyclyl, heteroaryl, alkylcycloalkyl, alkylaryl, alkylheterocyclyl or alkylheteroaryl; and Q is hydrogen, alkyl, cycloalkyl, aryl, heterocyclyl, heteroaryl, alkylcycloalkyl, alkylaryl, alkylheterocyclyl or alkylheteroaryl.

In one embodiment, the complex of formula I, IA, IB or IC reacts in a catalytic cycle with an alcohol to obtain the intermediate complex of formula IIIA or IIIB. In another embodiment, if complex IA or IB is used as a catalyst, an amount of base equivalent to the amount of catalyst or higher is required.

In one embodiment, this invention is directed to a manganese complex represented by the structure of any of formulae IIIA(1) and IIIB(2) or its tautomer, isomer or salt thereof:

IIIA(1)

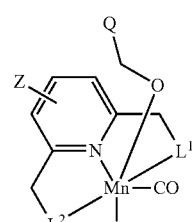

IIIB(1)

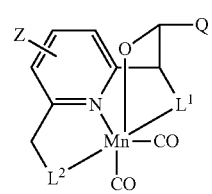

wherein $L^1$ is $(PR^aR^b)$, $(NR^aR^b)$, imine; oxazoline, sulfide $(SR^3)$, sulfoxide $(S(=O)R^a)$, heteroaryl containing at least one heteroatom selected from nitrogen and sulfur; $(AsR^aR^b)$, $(SbR^aR^b)$ or a N-heterocyclic carbene represented by the structures:

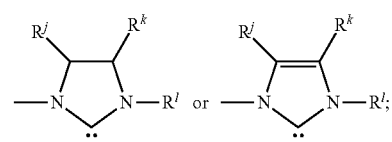

$L^2$ is $(PR^aR^b)$, $(NR^aR^b)$, imine; oxazoline, sulfide $(SR^a)$, sulfoxide $(S(=O)R^a)$, heteroaryl containing at least one heteroatom selected from nitrogen and sulfur; $(AsR^aR^b)$, $(SbR^aR^b)$ or a N-heterocyclic carbene represented by the structures:

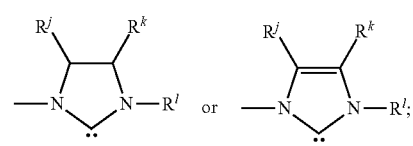

Z represents zero, one, two or three substituents wherein each such substituent is independently selected from the group consisting of alkyl, cycloalkyl, aryl, heterocyclyl, heteroaryl, alkylcycloalkyl, alkylaryl, alkylheterocyclyl, alkylheteroaryl, halide, nitro, amide, ester, cyano, alkoxy, alkylamino, arylamino, an inorganic support and a polymeric moiety;

$R^a$ and $R^b$ are each independently H, alkyl, cycloalkyl, aryl, heterocyclyl, heteroaryl, alkylcycloalkyl, alkylaryl, alkylheterocyclyl or alkylheteroaryl;

$R^j$, $R^k$ and $R^l$ are each independently H, alkyl, cycloalkyl, aryl, heterocyclyl, heteroaryl, alkylcycloalkyl, alkylaryl, alkylheterocyclyl or alkylheteroaryl; and Q is hydrogen, alkyl, cycloalkyl, aryl, heterocyclyl, heteroaryl, alkylcycloalkyl, alkylaryl, alkylheterocyclyl or alkylheteroaryl.

In one embodiment, the complex of formula I, IA IB or IC reacts in a catalytic cycle with an alcohol to obtain the intermediate complex of formula IIIA(1) or IIIB(1). In another embodiment, if complex IA or IB is used as a catalyst, an amount of base equivalent to the amount of catalyst or higher is required.

In one embodiment, the compounds of the structures of formulae IIIA and IIIB are represented by the structures of formulae 10 and 11, respectively.

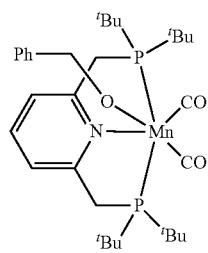

10

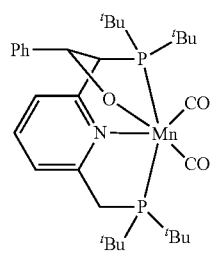

11

In one embodiment, this invention is directed to a manganese intermediate complex represented by the structure of any of formulae IVA and IVB or its isomer or salt thereof:

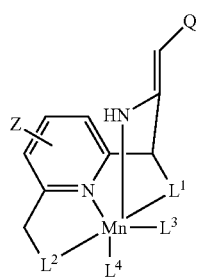

IVA

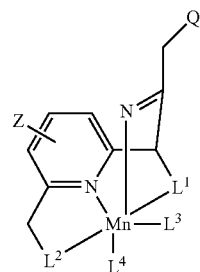

IVB wherein $L^1$ is ($PR^aR^b$), ($NR^aR^b$), imine; oxazoline, sulfide ($SR^a$), sulfoxide (S(=O)$R^a$), heteroaryl containing at least one heteroatom selected from nitrogen and sulfur; ($AsR^aR^b$), ($SbR^aR^b$) or a N-heterocyclic carbene represented by the structures:

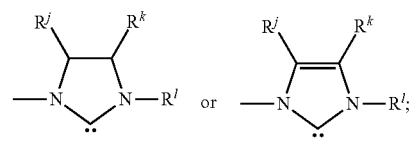

$L^2$ is ($PR^aR^b$), ($NR^aR^b$), imine; oxazoline, sulfide ($SR^a$), sulfoxide (S(=O)$R^a$), heteroaryl containing at least one heteroatom selected from nitrogen and sulfur; ($AsR^aR^b$), ($SbR^aR^b$) or a N-heterocyclic carbene represented by the structures:

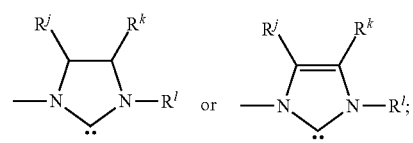

$L^3$ and $L^4$ are each independently a mono-dentate two-electron donor selected from the group consisting of CO, $PR^aR^bR^c$, $P(OR^a)(OR^b)(OR^c)$, $NO^+$, $AsR^aR^bR^c$, $SbR^aR^bR^c$, $NR^aR^bR^c$, SR—$R^b$, nitrile (RCN), isonitrile (RNC), $N_2$, $PF_3$, CS, heteroaryl, tetrahydrothiophene, alkene, alkyne or $L^1$ and $L^4$ form together with the Mn a ring;

Z represents zero, one, two or three substituents wherein each such substituent is independently selected from the group consisting of alkyl, cycloalkyl, aryl, heterocyclyl, heteroaryl, alkylcycloalkyl, alkylaryl, alkylheterocyclyl, alkylheteroaryl, halide, nitro, amide, ester, cyano, alkoxy, alkylamino, arylamino, an inorganic support and a polymeric moiety; or Z forms a fused aromatic or heterocyclic ring with the nitrogen based ring;

R, $R^a$ and $R^b$ are each independently H, alkyl, cycloalkyl, aryl, heterocyclyl, heteroaryl, alkylcycloalkyl, alkylaryl, alkylheterocyclyl or alkylheteroaryl;

$R^j$, $R^k$ and $R^l$ are each independently H, alkyl, cycloalkyl, aryl, heterocyclyl, heteroaryl, alkylcycloalkyl, alkylaryl, alkylheterocyclyl or alkylheteroaryl; and Q is hydrogen, alkyl, cycloalkyl, aryl, heterocyclyl, heteroaryl, alkylcycloalkyl, alkylaryl, alkylheterocyclyl or alkylheteroaryl.

In one embodiment, the complex of formula I, IA IB or IC reacts in a catalytic cycle with an amine to obtain the intermediate complex of formula IVA or IVB. In another embodiment, if complex IA or IB is used as a catalyst, an amount of base equivalent to the amount of catalyst or higher is required.

In one embodiment, this invention is directed to a manganese complex represented by the structure of any of formulae IVA(1) and IVB(1) or its tautomer, isomer or salt thereof:

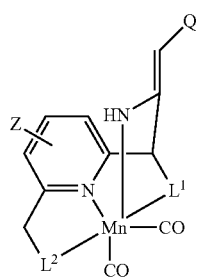

IVA(1)

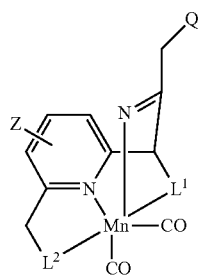

IVB(1)

wherein

L$^1$ is (PR$^a$R$^b$), (NR$^a$R$^b$), imine; oxazoline, sulfide (SR$^a$), sulfoxide (S(=O)R$^a$), heteroaryl containing at least one heteroatom selected from nitrogen and sulfur; (AsR$^a$R$^b$), (SbR$^a$R$^b$) or a N-heterocyclic carbene represented by the structures:

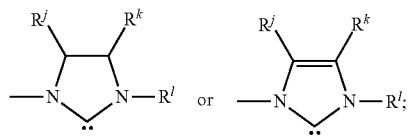

L$^2$ is (PR$^a$R$^b$), (NR$^a$R$^b$), imine; oxazoline, sulfide (SR$^a$), sulfoxide (S(=O)R$^a$), heteroaryl containing at least one heteroatom selected from nitrogen and sulfur; (AsR$^a$R$^b$), (SbR$^a$R$^b$) or a N-heterocyclic carbene represented by the structures:

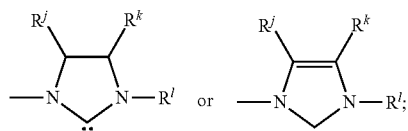

Z represents zero, one, two or three substituents wherein each such substituent is independently selected from the group consisting of alkyl, cycloalkyl, aryl, heterocyclyl, heteroaryl, alkylcycloalkyl, alkylaryl, alkylheterocyclyl, alkylheteroaryl, halide, nitro, amide, ester, cyano, alkoxy, alkylamino, arylamino, an inorganic support and a polymeric moiety; or Z forms a fused aromatic or heterocyclic ring with the nitrogen based ring;

R$^a$ and R$^b$ are each independently H, alkyl, cycloalkyl, aryl, heterocyclyl, heteroaryl, alkylcycloalkyl, alkylaryl, alkylheterocyclyl or alkylheteroaryl;

R$^j$, R$^k$ and R$^l$ are each independently H, alkyl, cycloalkyl, aryl, heterocyclyl, heteroaryl, alkylcycloalkyl, alkylaryl, alkylheterocyclyl or alkylheteroaryl; and Q is hydrogen, alkyl, cycloalkyl, aryl, heterocyclyl, heteroaryl, alkylcycloalkyl, alkylaryl, alkylheterocyclyl or alkylheteroaryl.

In one embodiment, the compounds of the structures of formulae IVA(1) and IVB(1) are represented by the structures of formulae 12, 13, 14 and 15 respectively:

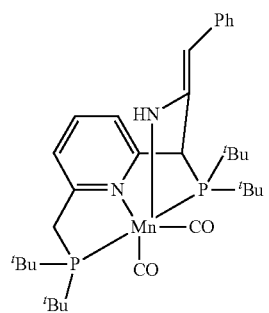

12

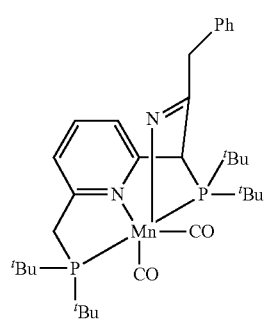

13

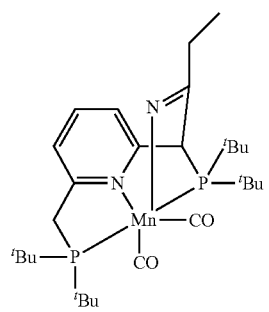

14

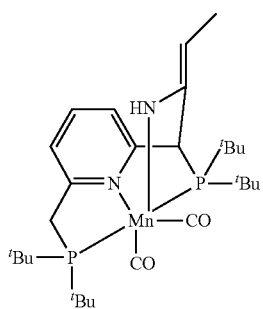

In one embodiment, Z is absent (i.e., the pyridine moiety is unsubstituted). In another embodiment, $L^1$ is phosphine ($PR^aR^b$). In another embodiment, $L^2$ is phosphine ($PR^aR^b$). In another embodiment, $L^1$ and $L^2$ are the same. In another embodiment, $L^1$ and $L^2$ are different. In one embodiment, $R^a$ and $R^b$ are the same. In another embodiment, $R^a$ and $R^b$ are different. In another embodiment, $R^a$ and $R^b$ are isopropyl. In another embodiment, $R^a$ and $R^b$ are tert-butyl.

In one embodiment, this invention is directed to a manganese intermediate complex represented by the structure of any of formulae VA and VB or its isomer or salt thereof:

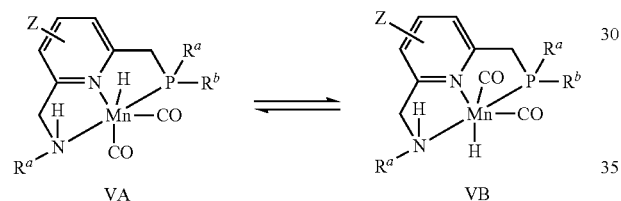

wherein

Z represents zero, one, two or three substituents wherein each such substituent is independently selected from the group consisting of alkyl, cycloalkyl, aryl, heterocyclyl, heteroaryl, alkylcycloalkyl, alkylaryl, alkylheterocyclyl, alkylheteroaryl, halide, nitro, amide, ester, cyano, alkoxy, alkylamino, arylamino, an inorganic support and a polymeric moiety; or Z forms a fused aromatic or heterocyclic ring with the nitrogen based ring;

$R^a$ and $R^b$ are each independently H, alkyl, cycloalkyl, aryl, heterocyclyl, heteroaryl, alkylcycloalkyl, alkylaryl, alkylheterocyclyl or alkylheteroaryl;

In one embodiment, the compounds of the structures of formulae VA(1) and VA(2) are represented by the structures of formulae 16 and 17 respectively:

In one embodiment, this invention is directed to a manganese complex represented by the structure of any of formula VI, VIA, VIB, VIC or their isomer or salt thereof:

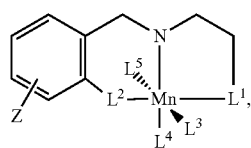

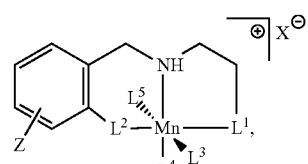

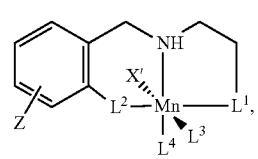

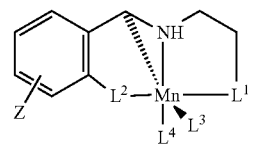

wherein $L^1$ is ($PR^aR^b$), ($NR^aR^b$), imine; oxazoline, sulfide ($SR^a$), sulfoxide ($S(=O)R^a$), heteroaryl containing at least one heteroatom selected from nitrogen and sulfur; ($AsR^aR^b$), ($SbR^aR^b$) or a N-heterocyclic carbene represented by the structures:

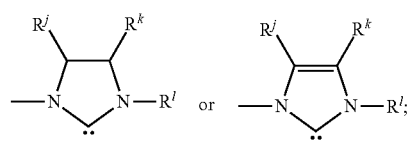

$L^2$ is ($PR^aR^b$), ($NR^aR^b$), imine; oxazoline, sulfide ($SR^a$), sulfoxide ($S(=O)R^a$), heteroaryl containing at least one heteroatom selected from nitrogen and sulfur; ($AsR^aR^b$), ($SbR^aR^b$) or a N-heterocyclic carbene represented by the structures:

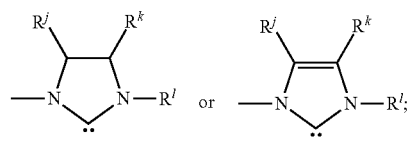

$L^3$ and $L^4$ are each independently a mono-dentate two-electron donor selected from the group consisting of CO, $PR^aR^bR^c$, $P(OR^a)(OR^b)(OR^c)$, $NO^+$, $AsR^aR^bR^c$, $SbR^aR^bR^c$, $NR^aR^bR^c$, $SR^aR^b$, nitrile (RCN), isonitrile (RNC), $N_2$, $PF_3$, CS, heteroaryl, tetrahydrothiophene, alkene, alkyne or $L^3$ and $L^4$ form together with the Mn a ring;

$L^5$ is absent or a mono-dentate two-electron donor selected from the group consisting of, CO, $PR^aR^bR^c$, $P(OR^a)(OR^b)(OR^c)$, $NO^+$, $NR^aR^bR^c$, $AsR^aR^bR^c$, $SbR^aR^bR^c$, $SR^aR^b$, nitrile (RCN), isonitrile (RNC), $N_2$, $PF_3$, CS, heteroaryl, tetrahydrothiophene, alkene or alkyne;

X is halide, OCOR, $OCH_2Q$, $OCOCF_3$, $OSO_2R$, $OSO_2CF_3$, CN, OR, $N(R)_2$ and RS, $BF_4$, $B(C_6H_5)_4$, $B(C_6F_5)_4$, $B[(C_6H_4)(CF_3)_2]$, $PF_6$ or $ClO_4$;

X' is H, halide, OCOR, OCH$_2$Q, OCOCF$_3$, OSO$_2$R, OSO$_2$CF$_3$, CN, OR, N(R)$_2$ or RS;

Q is hydrogen, alkyl, cycloalkyl, aryl, heterocyclyl, heteroaryl, alkylcycloalkyl, alkylaryl, alkylheterocyclyl or alkylheteroaryl;

Y$^+$ is a cationic group bearing a single positive charge;

R, R$^a$ R$^b$ and R$^c$ are each independently H, alkyl, cycloalkyl, aryl, heterocyclyl, heteroaryl, alkylcycloalkyl, alkylaryl, alkylheterocyclyl or alkylheteroaryl; and R$^j$, R$^k$ and R$^l$ are each independently H, alkyl, cycloalkyl, aryl, heterocyclyl, heteroaryl, alkylcycloalkyl, alkylaryl, alkylheterocyclyl or alkylheteroaryl.

In one embodiment, the manganese complex of formula VI, VIA, VIB or VIC is a catalyst. In another embodiment, the manganese complex of formula VI, VIA or VIB is a precursor of the complex of formula VIC. In another embodiment, the manganese complex of formula VIA or VIB is a precursor of the complex of formula VI. In another embodiment, the manganese precursor of formula VIA, VIB in the presence of a base, yields the manganese complex of formula VIC. In another embodiment, the manganese precursor of formula VIA, VIB in the presence of a base, yields the manganese complex of formula VI. In another embodiment, if a manganese complex of formula VIA or VIB is used as a catalyst, an amount of base equivalent to the amount of catalyst or higher is added. In another embodiment, if a manganese complex of formula VI or VIC is used as a catalyst, an amount of base equivalent to the amount of catalyst or higher is optionally added In one embodiment, this invention is directed to a manganese complex represented by the structure of any of formula VI(1), VIA(1), VIB(1), VIC(1), or their isomer or salt thereof.

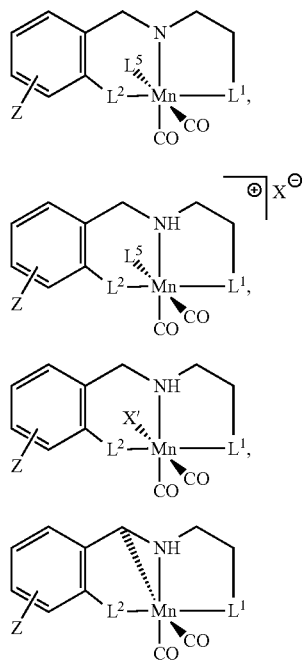

wherein

L$^1$ is (PR$^a$R$^b$), (NR$^a$R$^b$), imine; oxazoline, sulfide (SR$^a$), sulfoxide (S(=O)R$^a$), heteroaryl containing at least one heteroatom selected from nitrogen and sulfur, (AsR$^a$R$^b$), (SbR$^a$R$^b$) or a N-heterocyclic carbene represented by the structures:

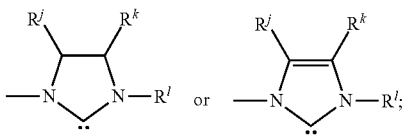

L$^2$ is (PR$^a$R$^b$), (NR$^a$R$^b$), imine; oxazoline, sulfide (SR$^a$), sulfoxide (S(=O)R$^a$), heteroaryl containing at least one heteroatom selected from nitrogen and sulfur; (AsR$^a$R$^b$), (SbR$^a$R$^b$) or a N-heterocyclic carbene represented by the structures:

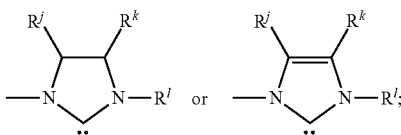

L$^5$ is absent or a mono-dentate two-electron donor selected from the group consisting of, CO, PR$^a$R$^b$R$^c$, P(OR$^a$)(OR$^b$)(OR$^c$), NO$^+$, NR$^a$R$^b$R$^c$, AsR$^a$R$^b$R$^c$, SbR$^a$R$^b$R$^c$, SR$^a$R$^b$, nitrile (RCN), isonitrile (RNC), N$_2$, PF$_3$, CS, heteroaryl, tetrahydrothiophene, alkene or alkyne;

X is halide, OCOR, OCH$_2$Q, OCOCF$_3$, OSO$_2$R, OSO$_2$CF$_3$, CN, OR, N(R)$_2$ and RS, BF$_4$, B(C$_6$H$_5$)$_4$, B(C$_6$F$_5$)$_4$, B[(C$_6$H$_4$)(CF$_3$)$_2$], PF$_6$ or ClO$_4$;

X' is H, halide, OCOR, OCH$_2$Q, OCOCF$_3$, OSO$_2$R, OSO$_2$CF$_3$, CN, OR, N(R)$_2$ or RS;

Z represents zero, one, two or three substituents wherein each such substituent is independently selected from the group consisting of alkyl, cycloalkyl, aryl, heterocyclyl, heteroaryl, alkylcycloalkyl, alkylaryl, alkylheterocyclyl, alkylheteroaryl, halide, nitro, amide, ester, cyano, alkoxy, alkylamino, arylamino, an inorganic support and a polymeric moiety; or Z forms a fused aromatic or heterocyclic ring with the nitrogen based ring;

Q is hydrogen, alkyl, cycloalkyl, aryl, heterocyclyl, heteroaryl, alkylcycloalkyl, alkylaryl, alkylheterocyclyl or alkylheteroaryl;

Y$^+$ is a cationic group bearing a single positive charge;

R, R$^a$ and R$^b$ are each independently alkyl, cycloalkyl, aryl, heterocyclyl, heteroaryl, alkylcycloalkyl, alkylaryl, alkylheterocyclyl or alkylheteroaryl; and R$^j$, R$^k$ and R$^l$ are each independently H, alkyl, cycloalkyl, aryl, heterocyclyl, heteroaryl, alkylcycloalkyl, alkylaryl, alkylheterocyclyl or alkylheteroaryl.

In one embodiment, the manganese complex of formula VI(1), VIA(1), VIB(1) or VIC(1) is a catalyst. In another embodiment, the manganese complex of formula VI(1), VIA(1) or VIB(1) is a precursor of the complex of formula VIC(1). In another embodiment, the manganese complex of formula VIA(1) or VIB(1) is a precursor of the complex of formula VI(1). In another embodiment, the manganese precursor of formula VIA(1), VIB(1) in the presence of a base, yields the manganese complex of formula VIC(1). In another embodiment, the manganese precursor of formula VIA(1), VIB(1) in the presence of a base, yields the manganese complex of formula VI(1). In another embodiment, if a manganese complex of formula VIA(1) or VIB(1) is used as a catalyst, an amount of base equivalent to the amount of catalyst or higher is added. In another embodiment, if a manganese complex of formula VI(1) or VIC(1)

is used as a catalyst, an amount of base equivalent to the amount of catalyst or higher is optionally added.

In one embodiment, this invention is directed to a manganese complex represented by the structure of any of formula VI(2), VIA(2), VIB(2), VIC(2) or their isomer or salt thereof;

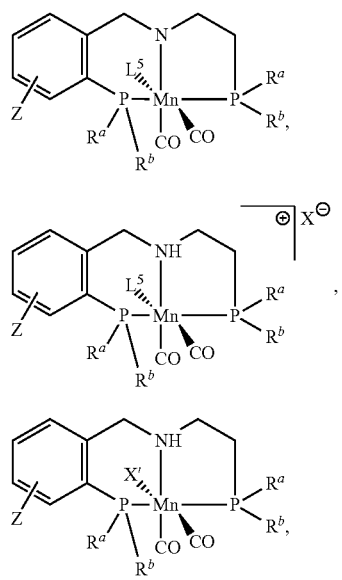

VI(2)

VIA(2)

VIB(2)

-continued

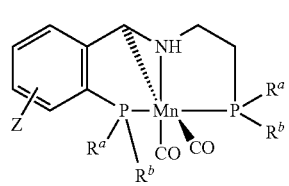

VIC(2)

wherein

L$^5$ is absent or a mono-dentate two-electron donor selected from the group consisting of CO, PR$^a$R$^b$R$^c$, P(OR$^a$)(OR$^b$)(OR$^c$), NO$^+$, AsR$^a$R$^b$R$^c$, SbR$^a$R$^b$R$^c$, SR$^a$R$^b$, nitrile (RCN), isonitrile (RNC), N$_2$, PF$_3$, CS, heteroaryl, tetrahydrothiophene, alkene or alkyne;

R, R$^a$ and R$^b$ are each independently alkyl, cycloalkyl, aryl, heterocyclyl, heteroaryl, alkylcycloalkyl, alkylaryl, alkylheterocyclyl or alkylheteroaryl.

X is halide, OCOR, OCH$_2$Q, OCOCF$_3$, OSO$_2$R, OSO$_2$CF$_3$, CN, OR, N(R)$_2$ and RS, BF$_4$, B(C$_6$H$_5$)$_4$, B(C$_6$F$_5$)$_4$, B[(C$_6$H$_4$)(CF$_3$)$_2$], PF$_6$ or ClO$_4$;

X' is H, halide, OCOR, OCH$_2$Q, OCOCF$_3$, OSO$_2$R, OSO$_2$CF$_3$, CN, OR, N(R)$_2$ and RS;

Z represents zero, one, two or three substituents wherein each such substituent is independently selected from the group consisting of alkyl, cycloalkyl, aryl, heterocyclyl, heteroaryl, alkylcycloalkyl, alkylaryl, alkylheterocyclyl, alkylheteroaryl, halide, nitro, amide, ester, cyano, alkoxy, alkylamino, arylamino, an inorganic support and a polymeric moiety; or Z forms a fused aromatic or heterocyclic ring with the nitrogen based ring;

Q is hydrogen, alkyl, cycloalkyl, aryl, heterocyclyl, heteroaryl, alkylcycloalkyl, alkylaryl, alkylheterocyclyl or alkylheteroaryl; and Y$^+$ is a cationic group bearing a single positive charge.

In one embodiment, this invention provides a manganese complex represented by the following structures:

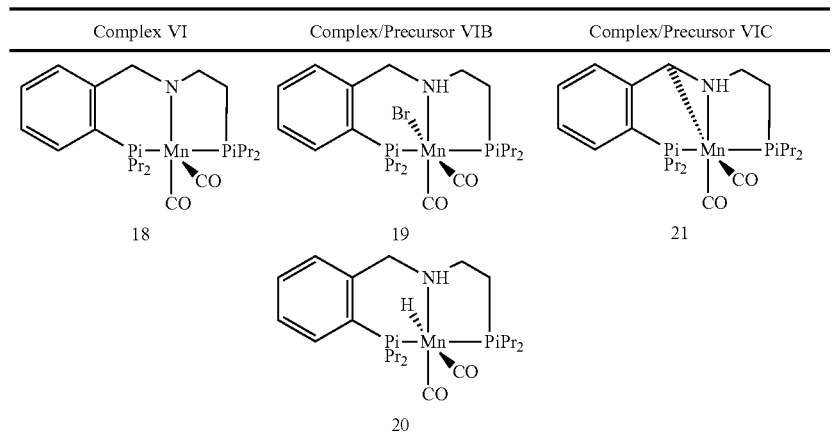

| Complex VI | Complex/Precursor VIB | Complex/Precursor VIC |
|---|---|---|
| 18 | 19 | 21 |
| | 20 | |

In one embodiment, the manganese complex of formula VI(2), VIA(2), VIB(2) or VIC(2) is a catalyst. In another embodiment, the manganese complex of formula VI(2), VIA(2) or VIB(2) is a precursor of the complex of formula VIC(2). In another embodiment, the manganese complex of formula VIA(2) or VIB(2) is a precursor of the complex of formula VI(2). In another embodiment, the manganese precursor of formula VIA(2), VIB(2) in the presence of a base, yields the manganese complex of formula VIC(2). In another embodiment, the manganese precursor of formula VIA(2), VIB(2) in the presence of a base, yields the manganese complex of formula VI(2). In another embodiment, if a manganese complex of formula VIA(2) or VIB(2) is used as a catalyst, an amount of base equivalent to the amount of catalyst or higher is added. In another embodiment, if a manganese complex of formula VI(2) or VIC(2) is used as a catalyst, an amount of base equivalent to the amount of catalyst or higher is optionally added.

In one embodiment, this invention is directed to a manganese intermediate complex represented by the structure of any of formulae VIIA and VIIB or its isomer or salt thereof:

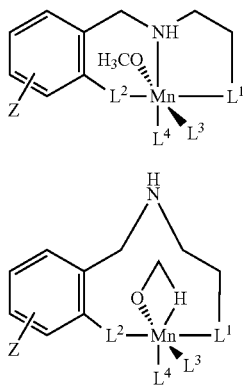

VIIA

VIIB wherein
L$^1$ is (PR$^a$R$^b$), (NR$^a$R$^b$), imine; oxazoline, sulfide (SR$^a$), sulfoxide (S(=O)R$^a$), heteroaryl containing at least one heteroatom selected from nitrogen and sulfur; (AsR$^a$R$^b$), (SbR$^a$R$^b$) or a N-heterocyclic carbene represented by the structures:

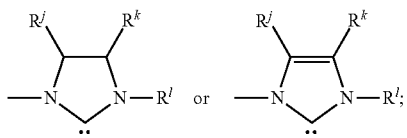

L$^2$ is (PR$^a$R$^b$), (NR$^a$R$^b$), imine; oxazoline, sulfide (SR$^a$), sulfoxide (S(=O)R$^a$), heteroaryl containing at least one heteroatom selected from nitrogen and sulfur; (AsR$^a$R$^b$), (SbR$^a$R$^b$) or a N-heterocyclic carbene represented by the structures:

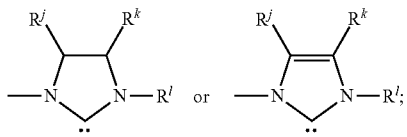

L$^3$ and L$^4$ are each independently a mono-dentate two-electron donor selected from the group consisting of CO, PR$^a$R$^b$R$^c$, P(OR$^a$)(OR$^b$)(OR$^c$), NO$^+$, AsR$^a$R$^b$R$^c$, SbR$^a$R$^b$R$^c$, NR$^a$R$^b$R$^c$, SR$^a$R$^b$, nitrile (RCN), isonitrile (RNC), N$_2$, PF$_3$, CS, heteroaryl, tetrahydrothiophene, alkene, alkyne or L$^3$ and L$^4$ form together with the Mn a ring;
Z represents zero, one, two or three substituents wherein each such substituent is independently selected from the group consisting of alkyl, cycloalkyl, aryl, heterocyclyl, heteroaryl, alkylcycloalkyl, alkylaryl, alkylheterocyclyl, alkylheteroaryl, halide, nitro, amide, ester, cyano, alkoxy, alkylamino, arylamino, an inorganic support and a polymeric moiety; or Z forms a fused aromatic or heterocyclic ring with the nitrogen based ring;

R, R$^a$ and R$^b$ are each independently H, alkyl, cycloalkyl, aryl, heterocyclyl, heteroaryl, alkylcycloalkyl, alkylaryl, alkylheterocyclyl or alkylheteroaryl;
R$^j$, R$^k$ and R$^l$ are each independently H, alkyl, cycloalkyl, aryl, heterocyclyl, heteroaryl, alkylcycloalkyl, alkylaryl, alkylheterocyclyl or alkylheteroaryl.

In one embodiment, the complex of formula VI, VIA VIB or VIC reacts in a catalytic cycle with methanol to obtain the intermediate complex of formula VIIA or VIIB. In another embodiment, if a manganese complex of formula VIA or VIB is used as a catalyst, an amount of base equivalent to the amount of catalyst or higher is added. In another embodiment, if a manganese complex of formula VI or VIC is used as a catalyst, an amount of base equivalent to the amount of catalyst or higher is optionally added In one embodiment, this invention is directed to a manganese complex represented by the structure of any of formulae VIIA(1) and VIIB(1) or its tautomer, isomer or salt thereof:

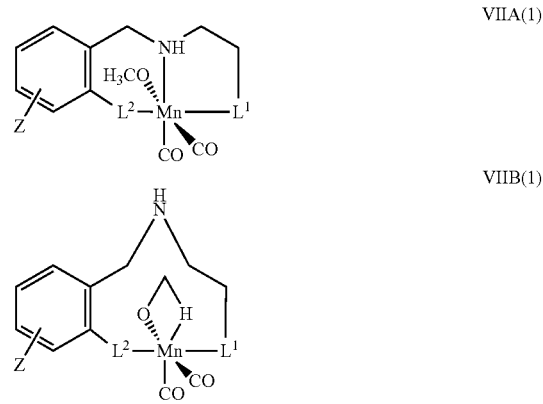

VIIA(1)

VIIB(1)

wherein
L$^1$ is (PR$^a$R$^b$), (NR$^a$R$^b$), imine; oxazoline, sulfide (SR$^a$), sulfoxide (S(=O)R$^a$), heteroaryl containing at least one heteroatom selected from nitrogen and sulfur; (AsR$^a$R$^b$), (SbR$^a$R$^b$) or a N-heterocyclic carbene represented by the structures:

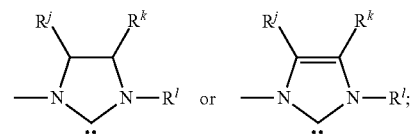

L$^2$ is (PR$^a$R$^b$), (NR$^a$R$^b$), imine; oxazoline, sulfide (SR$^a$), sulfoxide (S(=O)R$^a$), heteroaryl containing at least one heteroatom selected from nitrogen and sulfur; (AsR$^a$R$^b$), (SbR$^a$R$^b$) or a N-heterocyclic carbene represented by the structures:

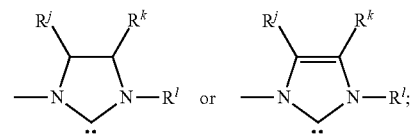

Z represents zero, one, two or three substituents wherein each such substituent is independently selected from the group consisting of alkyl, cycloalkyl, aryl, heterocyclyl, heteroaryl, alkylcycloalkyl, alkylaryl, alkylheterocyclyl, alkylheteroaryl, halide, nitro, amide, ester, cyano, alkoxy, alkylamino, arylamino, an inorganic support and a polymeric moiety; or Z forms a fused aromatic or heterocyclic ring with the nitrogen based ring;

$R^a$ and $R^b$ are each independently H, alkyl, cycloalkyl, aryl, heterocyclyl, heteroaryl, alkylcycloalkyl, alkylaryl, alkylheterocyclyl or alkylheteroaryl;

$R^j$, $R^k$ and $R^l$ are each independently H, alkyl, cycloalkyl, aryl, heterocyclyl, heteroaryl, alkylcycloalkyl, alkylaryl, alkylheterocyclyl or alkylheteroaryl.

In one embodiment, the compounds of the structures of formulae VIIA(1) and VIIB(1) are represented by the structures of formulae 22 and 23 respectively:

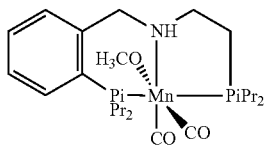

22

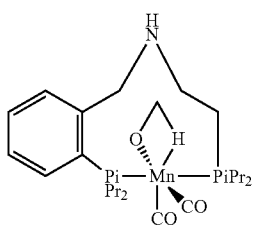

23

In one embodiment, $L^1$ and $L^2$ of formulae I, I(1), IA, IA(1), IB, IB(1), IC, IC(1), II, IIA, IIB, IIC, II(1), IIA(1), IIB(1), IIC(1), IIIA, IIIB, IIIA(1), IIIB(1), IVA, IVB, IVA(1), IVB(1), VI, VIA, VIB, VIC, VI(1), VIA(1), VIB(1) and VIC(1) are each independently ($PR^aR^b$), ($NR^aR^b$), imine; oxazoline, sulfide ($SR^a$), sulfoxide ($S(=O)R^a$), heteroaryl containing at least one heteroatom selected from nitrogen and sulfur; ($AsR^aR^b$), ($SbR^aR^b$) or a N-heterocyclic carbene represented by the structures:

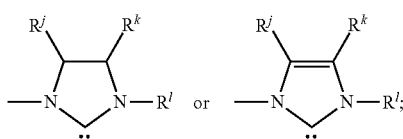

In another embodiment, $L^1$ and $L^2$ of formulae I, I(1), IA, IA(1), IB, IB(1), IC, IC(1), II, II(1), IIA, IIA(1), IIB, IIB(1), IIC, IIC(1), IIIA, IIIB, IIIA(1), IIIB(1), IVA, IVB, IVA(1), IVB(1), VI, VIA, VIB, VIC, VI(1), VIA(1), VIB(1) and VIC(1) are the same. In another embodiment, $L^1$ and $L^2$ of formulae I, I(1), IA, IA(1), II, IB(1), IC, IC(1), II, IIA, IIB, IIC, II(1), IIA(1), IIB(1), IIC(1), IIIA, IIIB, IIIA(1), IIIB(1), IVA, IVB, IVA(1), IVB(1), VI, VIA, VIB, VIC, VI(1), VIA(1), VIB(1) and VIC(1) are different. In another embodiment, $L^1$ and $L^2$ are each independently a phosphine ($PR^aR^b$). In another embodiment, $L^1$ and $L^2$ are each independently ($NR^aR^b$). In another embodiment, $L^1$ and $L^2$ are each independently an imine; In another embodiment, $L^1$ and $L^2$ are each independently an oxazoline. In another embodiment, $L^1$ and $L^2$ are each independently a sulfide ($SR^a$). In another embodiment, $L^1$ and $L^2$ are each independently a sulfoxide ($S(=O)R^a$). In another embodiment, $L^1$ and $L^2$ are each independently a heteroaryl containing at least one heteroatom selected from nitrogen and sulfur; In another embodiment, $L^1$ and $L^2$ are each independently an ($AsR^aR^b$). In another embodiment, $L^1$ and $L^2$ are each independently a ($SbR^aR^b$). In another embodiment, $L^1$ and $L^2$ are each independently a N-heterocyclic carbene represented by the structures:

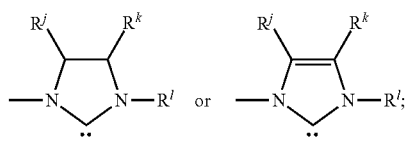

In one embodiment, $R^j$, $R^k$ and $R^l$ are substituents of a N-heterocyclic carbene wherein each independently H, alkyl, cycloalkyl, aryl, heterocyclyl, heteroaryl, alkylcycloalkyl, alkylaryl, alkylheterocyclyl or alkylheteroaryl. In another embodiment, $R^j$, $R^k$ and $R^l$ are each independently a hydrogen. In another embodiment, $R^j$, $R^k$ and $R^l$ are each independently an alkyl. In another embodiment, $R^j$, $R^k$ and $R^l$ are each independently a cycloalkyl. In another embodiment, $R^j$, $R^k$ and $R^l$ are each independently an aryl. In another embodiment, $R^j$, $R^k$ and $R^l$ are each independently a heterocyclyl. In another embodiment, $R^j$, $R^k$ and $R^l$ are each independently heteroaryl. In another embodiment, $R^j$, $R^k$ and $R^l$ are each independently alkylcycloalkyl. In another embodiment, $R^j$, $R^k$ and $R^l$ are each independently an alkylaryl. In another embodiment, $R^j$, $R^k$ and $R^l$ are each independently an alkylheterocyclyl. In another embodiment, $R^j$, $R^k$ and $R^l$ are each independently an alkylheteroaryl.

In another embodiment, $L^3$ and $L^4$ of formulae I, IA, IB, IC, II, IIA, IIB, IIC, IIIA, IIIB, IVA, IVB, VI, VIA, VIB and VIC are the same. In another embodiment, $L^3$ and $L^4$ of formulae I, IA, IB, IC, II, IIA, IIB, HC, IIIA, IIIB, IVA, IVB, VI, VIA, VIB and VIC are different. In another embodiment, $L^3$ and $L^4$ are each independently a mono-dentate two-electron donor selected from the group consisting of CO, $PR^aR^bR^c$, $P(OR^a)(OR^b)(OR^c)$, $NO^+$, $AsR^aR^bR^c$, $SbR^aR^bR^c$, $NR^aR^bR^c$, $SR^aR^b$, nitrile (RCN), isonitrile (RNC), $N_2$, $PF_3$, CS, heteroaryl, tetrahydrothiophene, alkene, alkyne, or $L^3$ and $L^4$ form together with the Mn a ring. In another embodiment, $L^3$ and $L^4$ are each independently CO. In another embodiment, $L^3$ and $L^4$ are each independently $PR^aR^bR^c$. In another embodiment, $L^3$ and $L^4$ are each independently $P(OR^a)(OR^b)(OR^c)$. In another embodiment, $L^3$ and $L^4$ are each independently $NO^+$. In another embodiment, $L^3$ and $L^4$ are each independently $AsR^aR^bR^c$. In another embodiment, $L^3$ and $L^4$ are each independently $SbR^aR^bR^c$. In another embodiment, $L^3$ and $L^4$ are each independently $NR^aR^bR^c$. In another embodiment, $L^3$ and $L^4$ are each independently $SR^aR^b$. In another embodiment, $L^3$ and $L^4$ are each independently a nitrile (RCN). In another embodiment, $L^3$ and $L^4$ are each independently an isonitrile (RNC). In another embodiment, $L^3$ and $L^4$ are each independently $N_2$. In another embodiment, $L^3$ and $L^4$ are each independently $PF_3$. In another embodiment, $L^3$ and $L^4$ are each independently CS. In another embodiment, $L^3$ and $L^4$ are each independently a heteroaryl. In another embodiment, $L^3$ and $L^4$ are each independently tetrahydrothiophene. In another embodiment, $L^3$ and $L^4$ are each independently an alkene. In another embodiment, $L^3$ and $L^4$ are each independently an alkyne. In another embodiment, $L^3$ and $L^4$ form together with the Mn a ring.

In another embodiment, $L^5$ of formulae I, I(1), I(2), IA, IA(1), IA(2), II, IIA, IIB, I(1), IIA(1), II(1), II(2) IIA(2), IIB(2), IV, IVA, IV(1), IVA(1), IV(2) and IVA(2) is absent or a mono-dentate two-electron donor selected from the group consisting of CO, $PR^aR^bR^c$, $P(OR^a)(OR^b)(OR^c)$, $NO^+$, $AsR^aR^bR^c$, $SbR^aR^bR^c$, $NR^aR^bR^c$, $SR^aR^b$, nitrile (RCN), isonitrile (RNC), $N_2$, $PF_3$, CS, heteroaryl, tetrahydrothiophene, alkene or alkyne. In another embodiment, $L^5$ is absent. In another embodiment, $L^5$ is CO. In another embodiment, $L^5$ is $PR^aR^bR^c$. In another embodiment, $L^5$ is $P(OR^a)(OR^b)(OR^c)$. In another embodiment, $L^5$ is $NO^+$. In another embodiment, $L^5$ is $AsR^aR^bR^c$. In another embodiment, $L^5$ is $NR^aR^bR^c$ In another embodiment, $L^5$ is $SbR^aR^bR^c$. In another embodiment, $L^5$ is $SR^aR^b$. In another embodiment, $L^5$ is nitrile (RCN). In another embodiment, $L^5$ is isonitrile (RNC). In another embodiment, $L^5$ is $N_2$. In another embodiment, $L^5$ is $PF_3$. In another embodiment, $L^5$ is CS. In another embodiment, $L^5$ is heteroaryl. In another embodiment, $L^5$ is tetrahydrothiophene. In another embodiment, $L^5$ is alkene. In another embodiment, $L^5$ is alkyne.

In one embodiment, $R^a$ and $R^b$ of formulae I, I(1), I(2), IA, IA(1), IA(2), IB, IB(1), IB(2), IC, IC(1), IC(2), ID(2), II, IIA, IIB, IIC, II(1), IIA(1), IIB(1), IIC(1), II(2), IA(2), IIB(2), IC(2), IIIA, IIIB, IIIB(1), IIC, IIIC(1), IVA, IVA(1), IVB, IVB(1) VA, VB, VI, VIA, VIB, VIC, VI(1), VIA(1), VIB(1), VIC(1), VI(2), VIA(2), VIB(2) and VIC(2) are each independently alkyl, cycloalkyl, aryl, heterocyclyl, heteroaryl, alkylcycloalkyl, alkylaryl, alkylheterocyclyl or alkylheteroaryl. In another embodiment, $R^a$ and $R^b$ are the same. In another embodiment, $R^a$ and $R^b$ are different. In another embodiment, $R^a$ and $R^b$ are each independently a hydrogen. In another embodiment, $R^a$ and $R^b$ are each independently an alkyl. In another embodiment, $R^a$ and $R^b$ are each independently a cycloalkyl. In another embodiment, $R^a$ and $R^b$ are each independently an aryl. In another embodiment, $R^a$ and $R^b$ are each independently a heterocyclyl. In another embodiment, $R^a$ and $R^b$ are each independently a heteroaryl. In another embodiment, $R^a$ and $R^b$ are each independently an alkylcycloalkyl. In another embodiment, $R^a$ and $R^b$ are each independently an alkylaryl. In another embodiment, $R^a$ and $R^b$ are each independently an alkylheterocyclyl. In another embodiment, $R^a$ and $R^b$ are each independently an alkylheteroaryl.

In one embodiment X of formulae IA, IIA, IA(1) IIA(1), IA(2), IIA(2), VIA, VIA(1) and VIA(2) is an anionic compound, such as halide, OCOR, $OCH_2Q$, $OCOCF_3$, $OSO_2R$, $OSO_2CF_3$, CN, OR, $N(R)_2$ and RS, $BF_4$, $B(C_6H_5)_4$, $B(C_6F_5)_4$, $B[(C_6H_4)(CF_3)_2]$, $PF_6$, and $ClO_4$. In another embodiment, X is halide. In another embodiment, X is CO. In another embodiment, X is OCOR. In another embodiment, X is $OCH_2Q$. In another embodiment, X is $OCOCF_3$. In another embodiment, X is $OSO_2R$. In another embodiment, X is $OSO_2CF_3$. In another embodiment, X is CN. In another embodiment, X is OR. In another embodiment, X is $N(R)_2$. In another embodiment, X is RS. In another embodiment, X is $BF_4$. In another embodiment, X is $B(C_6H_5)_4$. In another embodiment, X is $B(C_6F_5)_4$. In another embodiment, X is $B[(C_6H_4)(CF_3)_2]$. In another embodiment, X is $PF_6$. In another embodiment, X is $ClO_4$.

In one embodiment X' of formula IB, IC, IIB, IIC, IB(1), IC(1), IIB(1), IIC(1), IB(2), IC(2), ID(2), IIB(2), IIC(2), VIB, VIC, VIB(1), VIC(1), VIB(2) and VIC(2) is selected from the group consisting of H, halide, CO, OCOR, $OCH_2Q$, $OCOCF_3$, $OSO_2R$, $OSO_2CF_3$, CN, OR, $N(R)_2$ and RS. In another embodiment, X' is H. In another embodiment, X' is halide. In another embodiment, X' is OCOR. In another embodiment, X' is $OCH_2Q$. In another embodiment, X' is $OCOCF_3$. In another embodiment, X' is $OSO_2R$. In another embodiment, X' is $OSO_2CF_3$. In another embodiment, X' is CN. In another embodiment, X' is OR. In another embodiment, X' is $N(R)_2$. In another embodiment, X' is RS.

In one embodiment Q of formulae IA, IA(1), IA(2), IB, IB(1), IB(2), IIIA, IIIA(1), IIIB, IIIB(1), IVA, IVA(1), IVB, IVB(1), VIA, VIA(1) and VIA(2), VIB, VIC, VIB(1), VIC (1), VIB(2) and VIC(2) is hydrogen, alkyl, cycloalkyl, aryl, heterocyclyl, heteroaryl, alkylcycloalkyl, alkylaryl, alkylheterocyclyl or alkylheteroaryl. In another embodiment Q is hydrogen. In another embodiment Q is alkyl. In another embodiment Q is cycloalkyl. In another embodiment Q is aryl. In another embodiment Q is heterocyclyl. In another embodiment Q is heteroaryl. In another embodiment Q is alkylcycloalkyl. In another embodiment Q is alkylaryl. In another embodiment Q is alkylheterocyclyl. In another embodiment Q is alkylheteroaryl.

In one embodiment Z of formula I, I(1), 1(2), IA, IA(1), IA(2), IB, IB(1), IB(2), IC(2), ID(2), IIIA, IIIA(1), IIIB, IIIB(1), IIC, IVA, IVA(1), IVB, IVB(1), VA, VB, VI, VIA, VIB, VIC, VI(1), VIA(1), VIB(1), VIC(1), VI(2), VIA(2), VIB(2) and VIC(2) is zero, one, two or three substituents wherein each such substituent is independently selected from the group consisting of alkyl, cycloalkyl, aryl, heterocyclyl, heteroaryl, alkylcycloalkyl, alkylaryl, alkylheterocyclyl, alkylheteroaryl, halogen, nitro, amide, ester, cyano, alkoxy, alkylamino, arylamino, an inorganic support and a polymeric moiety. In another embodiment, Z is zero substituents (i.e. the pyridine or aryl group is unsubstituted). In another embodiment, Z is a one substituent on the pyridine or aryl group. In another embodiment, Z is two substituents on the pyridine or aryl group. In another embodiment, Z is three substituents on the pyriding or aryl group. In another embodiment, if Z is more than one substituent, the substituents are the same or different. In another embodiment, the substituent is alkyl. In another embodiment, the substituent is cycloalkyl. In another embodiment, the substituent is aryl. In another embodiment, the substituent is heterocyclyl. In another embodiment, the substituent is heteroaryl. In another embodiment, the substituent is alkylcycloalkyl. In another embodiment, the substituent is alkylaryl. In another embodiment, the substituent is alkylheterocyclyl. In another embodiment, the substituent is alkylheteroaryl. In another embodiment, the substituent is halogen. In another embodiment, the substituent is nitro. In another embodiment, the substituent is amide. In another embodiment, the substituent is ester. In another embodiment, the substituent is cyano. In another embodiment, the substituent is alkoxy. In another embodiment, the substituent is alkylamino. In another embodiment, the substituent is arylamino. In another embodiment, the substituent is an inorganic support. In another embodiment, the substituent is a polymeric moiety.

In one embodiment $Y^+$ is a cationic group bearing a single positive charge. In another embodiment $Y^+$ may be selected from the group consisting of $Li^+$, $Cs^+$, $K^+$, $Na^+$, and $N(R)_4^+$ (R=H or alkyl).

In some embodiments, the manganese complex acts as a catalyst (and is thus designated "manganese catalyst").

Chemical Definitions

As used herein, the term alkyl, used alone or as part of another group, refers, in one embodiment, to a "$C_1$ to $C_{12}$ alkyl" and denotes linear and branched, saturated or unsaturated (e.g., alkenyl, alkynyl) groups, the latter only when the number of carbon atoms in the alkyl chain is greater than or equal to two, and can contain mixed structures. Non-limiting examples are alkyl groups containing from 1 to 6 carbon atoms ($C_1$ to $C_6$ alkyls), or alkyl groups containing from 1 to 4 carbon atoms ($C_1$ to $C_4$ alkyls). Examples of saturated alkyl groups include, but are not limited to, methyl, ethyl, n-propyl, isopropyl, n-butyl, iso-butyl, sec-butyl, tert-butyl, amyl, tert-amyl and hexyl. Examples of alkenyl groups include, but are not limited to, vinyl, allyl, butenyl and the like. Examples of alkynyl groups include, but are not limited to, ethynyl, propynyl and the like. Similarly, the term "$C_1$ to $C_{12}$ alkylene" denotes a bivalent radical of 1 to 12 carbons.

The alkyl group can be unsubstituted, or substituted with one or more substituents selected from the group consisting of halogen, hydroxy, alkoxy, aryloxy, alkylaryloxy, heteroaryloxy, oxo, cycloalkyl, phenyl, heteroaryls, heterocyclyl, naphthyl, amino, alkylamino, arylamino, heteroarylamino, dialkylamino, diarylamino, alkylarylamino, alkylheteroarylamino, arylheteroarylamino, acyl, acyloxy, nitro, carboxy, carbamoyl, carboxamide, cyano, sulfonyl, sulfonylamino, sulfinyl, sulfinylamino, thiol, alkylthio, arylthio, or alkylsulfonyl groups. Any substituents can be unsubstituted or further substituted with any one of these aforementioned substituents. By way of illustration, an "alkoxyalkyl" is an alkyl that is substituted with an alkoxy group.

The term "cycloalkyl" used herein alone or as part of another group, refers to a "$C_3$ to $C_8$ cycloalkyl" and denotes any unsaturated or unsaturated (e.g., cycloalkenyl, cycloalkynyl) monocyclic or polycyclic group. Nonlimiting examples of cycloalkyl groups are cyclopropyl, cyclobutyl, cyclopentyl, cyclohexyl or cycloheptyl. Examples or cycloalkenyl groups include cyclopentenyl, cyclohexenyl and the like. The cycloalkyl group can be unsubstituted or substituted with any one or more of the substituents defined above for alkyl. Similarly, the term "cycloalkylene" means a bivalent cycloalkyl, as defined above, where the cycloalkyl radical is bonded at two positions connecting together two separate additional groups.

The term "aryl" used herein alone or as part of another group denotes an aromatic ring system containing from 6-14 ring carbon atoms. The aryl ring can be a monocyclic, bicyclic, tricyclic and the like. Non-limiting examples of aryl groups are phenyl, naphthyl including 1-naphthyl and 2-naphthyl, and the like. The aryl group can be unsubstituted or substituted through available carbon atoms with one or more groups defined hereinabove for alkyl. An alkylaryl group denotes an alkyl group bonded to an aryl group (e.g., benzyl).

The term "heteroaryl" used herein alone or as part of another group denotes a heteroaromatic system containing at least one heteroatom ring atom selected from nitrogen, sulfur and oxygen. The heteroaryl contains 5 or more ring atoms. The heteroaryl group can be monocyclic, bicyclic, tricyclic and the like. Also included in this expression are the benzoheterocyclic rings. If nitrogen is a ring atom, the present invention also contemplates the N-oxides of the nitrogen containing heteroaryls. Nonlimiting examples of heteroaryls include thienyl, benzothienyl, 1-naphthothienyl, thianthrenyl, furyl, benzofuryl, pyrrolyl, imidazolyl, pyrazolyl, pyridyl, pyrazinyl, pyrimidinyl, pyridazinyl, indolyl, isoindolyl, indazolyl, purinyl, isoquinolyl, quinolyl, naphthyridinyl, quinoxalinyl, quinazolinyl, cinnolinyl, pteridinyl, carbolinyl, thiazolyl, oxazolyl, isothiazolyl, isoxazolyl and the like. The heteroaryl group can be unsubstituted or substituted through available atoms with one or more groups defined hereinabove for alkyl.

The term "heterocyclic ring" or "heterocyclyl" used herein alone or as part of another group denotes a five-membered to eight-membered rings that have 1 to 4 heteroatoms, such as oxygen, sulfur and/or nitrogen. These five-membered to eight-membered rings can be saturated, fully unsaturated or partially unsaturated. Non-limiting examples of heterocyclic rings include piperidinyl, piperidinyl, pyrrolidinyl pyrrolinyl, pyrazolinyl, pyrazolidinyl, piperidinyl, morpholinyl, thiomorpholinyl, pyranyl, thiopyranyl, piperazinyl, indolinyl, dihydrofuranyl, tetrahydrofuranyl, dihydrothiophenyl, tetrahydrothiophenyl, dihydropyranyl, tetrahydropyranyl, and the like. The heterocyclyl group can be unsubstituted or substituted through available atoms with one or more groups defined hereinabove for alkyl.

The inorganic support which is attached to the manganese complex can be, for example, silica, silica gel, glass, glass fibers, titania, zirconia, alumina and nickel oxide.

The polymeric moiety which is attached to the manganese complex can be, for example, selected from polyolefins, polyamides, polyethylene terephthalate, polyvinylchloride, polyvinylidenechloride, polystyrene, polymethracrylate, natural rubber, polyisoprene, butadiene-styrene random copolymers, butadiene acrylonitrile copolymers, polycarbonate, polyacetal, polyphenylenesulfide, cyclo-olefin copolymers, styrene-acrylonitrile copolymers, ABS, styrene-maleic anhydride copolymers, chloroprene polymers, isobutylene copolymers, polystyrene, polyethylene, polypropylene, and the like.

In one embodiment, the processes of this invention make use of a manganese complexes as a catalyst. Thus, the manganese complex is used in a catalytic amount in the processes of this invention. A catalytic amount reefers to a significantly smaller amount of the catalyst than the molecular amount of substrates.

Michael addition refers to the 1,4-addition (or conjugate addition) of a nucleophile (also known as donor) to an alkene or alkyne attached to electron withdrawing groups (also known as acceptor). A Michael donor refers to in this invention to nitriles and specifically to aliphatic or unactivated nitriles. In one embodiment a Michael acceptor in this invention is an α β, unsaturated carbonyl. In one embodiment a Michael acceptor is represented by the following formula:

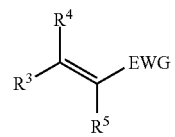

wherein
$R^3$, $R^4$, $R^5$ are each independently selected from H, nsubstituted or substituted alkyl, cycloalkyl, alkoxy (O-alkyl), aryloxy (O-aryl), aryl, alkylaryl or heterocyclyl or $R^3$ and $R^5$ form a cyclic ring; or $R_4$ and $R_5$ form a cyclic ring; or $R_3$ and $R_4$ form a cyclic ring; wherein EWG is an electron withdrawing group comprising C(=O)R, C(=O)OR', $SO_2R'$, $CON(R)_2$, $NO_2$ or CN, wherein R is H, alkyl, aryl, heteroaryl, cycloalkyl or heterocycloalkyl; and R' is alkyl, aryl, heteroaryl, cycloalkyl or heterocycloalkyl; and EWG is an electron withdrawing group comprising C(=O)R, C(=O)OR', $SO_2R'$, $CON(R)_2$, $NO_2$ or CN, wherein R is H, alkyl, aryl, heteroaryl, cycloalkyl or heterocycloalkyl; and R' is alkyl, aryl, heteroaryl, cycloalkyl or heterocycloalkyl.

PNP refers to the ligand of the complexes of this invention including phosphorous, nitrogen and phosphorous atoms. Examples of PNP ligands of this invention include

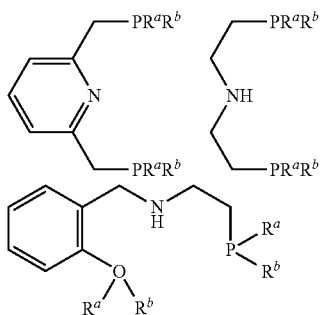

PNP* refers to dearomatized pyridine ligand of the complexes of this invention including the phosphorous, nitrogen and phosphorous atoms. An examples of PNP* ligand of this invention includes

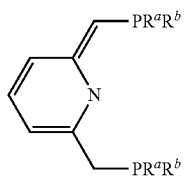

Processes

The present invention further provides various processes which utilize the manganese complexes of the present invention as catalysts.

In general, the processes of the present invention can be conducted in the absence or in the presence of a solvent. When a solvent is present, it can be an organic solvent, including but not limited to benzene, toluene, o-, m- or p-xylene, mesitylene (1,3,5-trimethyl benzene), dioxane, pentane, hexane, DCM, THF, DME, DMSO, anisole and cyclohexane.

The stoichiometric ratios of reagents can vary, and depend on the particular reactants being used, as well as solvent used for the reaction. The reactions of the present invention can be performed for as long as needed so as to effect desired transformation, for example 1 hr to 24 hr or longer than 24 hr. The temperature range can vary from room temperature to heated conditions, for example up to 200° C.

1. Dehydrogenative Coupling of Alcohols and Amines

Direct dehydrogenative coupling of alcohols and amines is one of the most promising approaches and "green" pathway to synthesize imine, since alcohols are readily available through a variety of industrial processes and are highly relevant starting materials in view of recent developments in the field of renewable, as they can be obtained via fermentation or catalytic conversion of lignocellulosic biomass. Moreover, only hydrogen and water are produced as by-products in this pathway. Thus, development of an efficient and general strategy for the synthesis of imines from alcohols and amines is highly imperative because of its potential versatility and wide spread application.

In one embodiment, the present invention provides a process for preparing imines by coupling of alcohols and amines in the presence of the manganese complexes of this invention. In one embodiment, this invention is directed to a process comprising reacting an amine with an alcohol in the presence of a catalyst of this invention to generate an imine compound, a molecular hydrogen ($H_2$) and water ($H_2O$). In one embodiment, the process involves coupling of primary alcohols and primary amines. In another embodiment, the process is described in Example 6.

In one embodiment, the process comprises reacting a manganese complex of formula I, IA, IB or IC with an alcohol to yield the intermediate of formula IIIA, which is then reacted with the amine to yield an imine.

In one embodiment, the process of the invention, i.e., the direct catalytic coupling of primary alcohol and a primary amine into an imine and dihydrogen is illustrated in Scheme 1 using the catalyst of this invention. In accordance with this process, a primary alcohol represented by formula $RCH_2OH$ is reacted with $R_1NH_2$ are converted to an imine represented by the structure $R-C=N-R_1$. This novel, environmentally benign reaction, can be used to produce various imines from very simple substrates and generating no waste. In another embodiment, if the manganese complex IA, IA(1), IA(2), IB, IB(1), IB(2) ID(2), VIA, VIA(1), VIA(2), VIB, VIB(1) or VIB (2) is used as a catalyst, an amount of base equivalent to the amount of catalyst or higher is required. In another embodiment, if a manganese complex of formula VI, VI(1), VI(2), VIC, VIC(1) or VIC(2) is used as a catalyst, an amount of base equivalent to the amount of catalyst or higher is optionally added.

In one embodiment this invention is directed to a process for preparing an imine by dehydrogenative coupling of an alcohol of the formula $RCH_2OH$ and an amine of the formula $R^1NH_2$ as presented in scheme 1:

Scheme 1

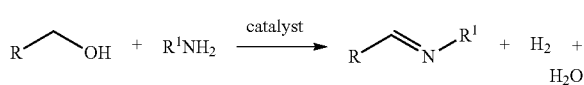

wherein R is an unsubstituted or substituted alkyl, alkoxyalkyl, cycloalkyl, aryl, alkylaryl, heterocyclyl and heteroaryl;

$R^1$ is unsubstituted or substituted alkyl, alkoxyalkyl, cycloalkyl, aryl, alkylaryl, heterocyclyl and heteroaryl;

wherein said process comprising the step of reacting said alcohol and said amine in the presence of the manganese complex as a catalyst of this invention, wherein said catalyst is represented by the structure of formula I, IA, IB or IC thereby generating an imine.

In another embodiment, the catalyst is of formula 1-11, 6A' or 6B, 18-21. In another embodiment, if the manganese complex IA, IA(1), IA(2), ID(2), IB, IB(1), IB(2), VIA, VIA(1), VIA(2), VIB, VIB(1) or VIB (2) is used as a catalyst, an amount of base equivalent to the amount of catalyst or higher is required. In another embodiment, if a manganese complex of formula VI, VI(1), VI(2), VIC, VIC(1) or VIC(2) is used as a catalyst, an amount of base equivalent to the amount of catalyst or higher is optionally added.

In one embodiment, this invention is directed to a process for preparing an imine by dehydrogenative coupling of an alcohol of the formula RCH$_2$OH and an amine of the formula R$^1$NH$_2$ as presented in Scheme 1:

Scheme 1

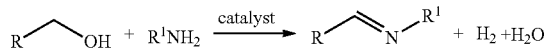

wherein R is an unsubstituted or substituted alkyl, alkoxyalkyl, cycloalkyl, aryl, alkylaryl, heterocyclyl and heteroaryl;
R$^1$ is unsubstituted or substituted alkyl, alkoxyalkyl, cycloalkyl, aryl, alkylaryl, heterocyclyl and heteroaryl;
wherein said method comprising the step of reacting said alcohol and said amine in the presence of the manganese complex as a catalyst of this invention; wherein said catalyst of formula I, IA IB or IC reacts with said alcohol to obtain the catalyst of formula IIIA which is further reacted with said amine and thereby generating an imine. In another embodiment, if the manganese complex IA, IA(1), IA(2), IB, IB(1), IB(2), ID(2), VIA, VIA(1), VIA(2), VIB, VIB(1) or VIB(2) is used as a catalyst an amount of base equivalent to the amount of catalyst or higher is required. In another embodiment, if a manganese complex of formula VI, VI(1), VI(2), VIC, VIC(1) or VIC(2) is used as a catalyst, an amount of base equivalent to the amount of catalyst or higher is optionally added.

Figure 4:
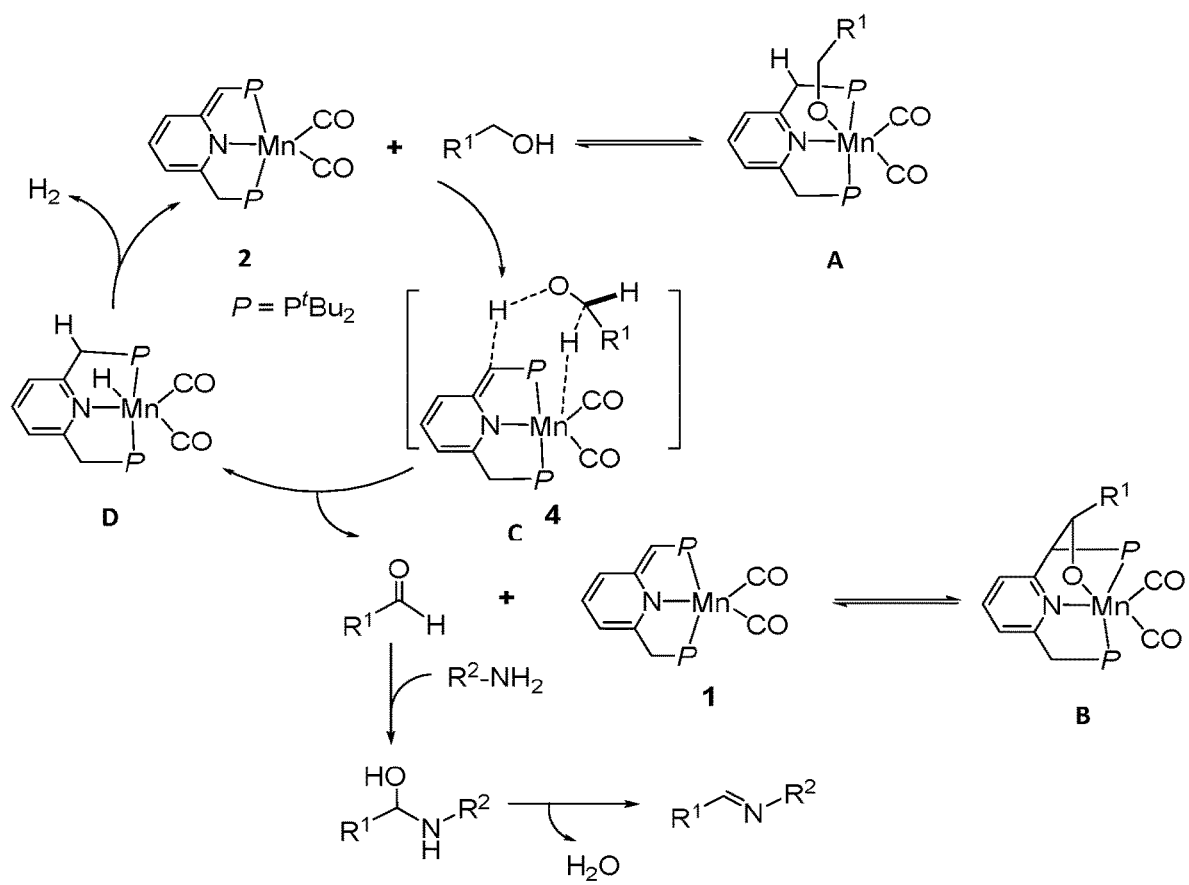
FIG. 4 depicts proposed mechanism for the formation of imine.

In another embodiment, the catalytic cycle for the formation of imine using the complex of this invention is presented in FIG. 4 and in Example 7.

In one embodiment, the hydroxyl compound reacts with the catalyst to obtain an intermediate complex of formula IIIA and/or IIIB.

In one embodiment, the process of this invention for the preparation of imines includes the use of an alcohol of the formula RCH$_2$OH. In another embodiment R is an unsubstituted or substituted alkyl, alkoxyalkyl, cycloalkyl, aryl, alkylaryl, heterocyclyl or heteroaryl. In another embodiment R is unsubstituted or substituted alkyl. In another embodiment R is unsubstituted or substituted alkoxyalkyl. In another embodiment R is unsubstituted or substituted cycloalkyl. In another embodiment R is unsubstituted or substituted aryl. In another embodiment R is unsubstituted or substituted alkylaryl. In another embodiment R is unsubstituted or substituted heterocyclyl. In another embodiment R is unsubstituted or substituted or heteroaryl. Non limiting examples of an alcohol used in the process for the preparation of imines include: ethanol, n-propanol, n-butanol, isobutanoln-pentanol, 1-hexanol, benzyl alcohol, 2-methoxy benzyl alcohol, 4-fluoro benzyl alcohol, 4-chloro-benzyl alcohol, 3-methoxy benzyl alcohol, 3,4-methoxy benzyl alcohol, 4-methoxy benzyl alcohol, I-phenylethanol, and cyclohexane methanol.

In one embodiment, the process of this invention for the preparation of imines includes the use of an amine of the formula R$^1$NH$_2$. In another embodiment R$^1$ unsubstituted or substituted alkyl, alkoxyalkyl, cycloalkyl, aryl, alkylaryl, heterocyclyl or heteroaryl. In another embodiment R$^1$ unsubstituted or substituted alkyl. In another embodiment R$_1$ unsubstituted or substituted alkoxyalkyl. In another embodiment R$^1$ unsubstituted or substituted cycloalkyl. In another embodiment R$^1$ unsubstituted or substituted aryl. In another embodiment R$_1$ unsubstituted or substituted alkylaryl. In another embodiment R$^1$ unsubstituted or substituted heterocyclyl. In another embodiment R$^1$ unsubstituted or substituted heteroaryl. Non limiting examples of an amine used in the process for the preparation of imines include: cyclohexanamine, 2-phenylethanamine, (4-methoxyphenyl)methanamine, (4-fluorophenyl)methanamine phenylmethanamine and hexan-1-amine.

2. Michael Addition

In one embodiment, the present invention provides a process for conjugate addition (C—C bond formation) between nitriles and Michael acceptors using the manganese catalyst of this invention. In another embodiment, the nitrile is an activated nitrile. In another embodiment, the nitrile is a nonactivated nitrile. In another embodiment, the nitrile is an aliphatic nitrile. In one embodiment, the process for conjugate addition is presented in Example 10.

In one embodiment, this invention is directed to a process for C—C bond formation via Michael addition, wherein said process comprises reacting an unactivated nitrile of the formula R$^2$CH$_2$CN wherein R$^2$ is H, unsubstituted or substituted alkyl, cycloalkyl, aryl, alkylaryl or heterocyclyl with a Michael acceptor in the presence of the manganese complex of formula I, IA IB or IC thereby generating a new C—C bond. In another embodiment, the complex is of formula 1-11, 18-21, 6A' or 6B. In another embodiment, the complex is of formula 1, 7 or 2. In another embodiment, if the manganese complex IA, IA(1), IA(2), IB, IB(1), IB(2) or, ID(2), as a catalyst is used an amount of base equivalent to the amount of catalyst or higher is required.

In one embodiment, this invention is directed to a process for C—C bond formation via Michael addition, wherein said process comprises reacting an unactivated nitrile of the formula R$^2$CH$_2$CN wherein R$^2$ is H, unsubstituted or substituted alkyl, cycloalkyl, aryl, alkylaryl or heterocyclyl with a Michael acceptor in the presence of the manganese complex of formula I, IA, IB or IC wherein said complex of formula I IA, IB or IC reacts with said nitrile to obtain the catalyst of formula IVA or IVB which is further reacted with said Michael acceptor and thereby generating a new C—C bond.

In one embodiment, the process of C—C bond formation of this invention make use of a Michael acceptor. In another embodiment, the Michael acceptor is α,β-unsaturated carbonyl compound.

In one embodiment, this invention is directed to a process for C—C bond formation via Michael addition, wherein said process comprises reacting an unactivated nitriles of the formula R$^2$CH$_2$CN and a Michael acceptor of compound of the formula R—C(R$^4$)=C(R$^5$)EWG in the present of a manganese complex of this invention as a catalyst:

Scheme 2

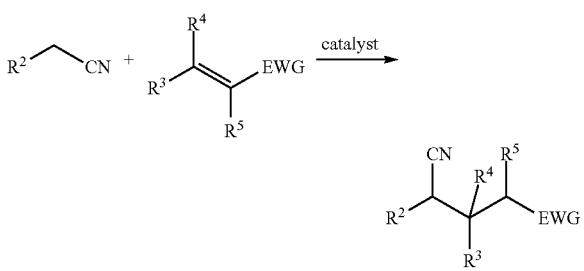

wherein R$^2$ is H, unsubstituted or substituted alkyl, cycloalkyl, aryl, alkylaryl or heterocyclyl; and;
R$^3$, R$^4$, R$^5$ are each independently selected from H, unsubstituted or substituted alkyl, cycloalkyl, alkoxy (O-alkyl), aryloxy (O-aryl), aryl, alkylaryl or heterocyclyl or R$^3$ and R$^5$ form a cyclic ring; or $R_4$ and $R_5$ form a cyclic ring; or $R_3$ and $R_4$ form a cyclic ring; and EWG is an electron withdrawing group comprising C(=O)R, C(=O)OR', $SO_2R'$, $CON(R)_2$, $NO_2$ or CN, wherein R is H, alkyl, aryl, heteroaryl, cycloalkyl or heterocycloalkyl; and R' is alkyl, aryl, heteroaryl, cycloalkyl or heterocycloalkyl.

In one embodiment, the nitrile compound reacts with the catalyst of formula I, IA, IB or IC to obtain an intermediate complex of formula IVA or IVB.

In another embodiment, if the manganese complex IA, IA(1), IA(2), IB, IB(1), IB(2), ID(2), VIA, VIA(1), VIA(2), VIIB, VIB(I) or VIB (2)catalyst is used as the catalyst, an amount of base equivalent to the amount of catalyst or higher is required. In another embodiment, if a manganese complex of formula VI, VI(1), VI(2), VIC, VIC(1) or VIC(2) is used as a catalyst, an amount of base equivalent to the amount of catalyst or higher is optionally added.

In one embodiment, the process of C—C bond formation of this invention make use of a Michael donor of the formula $R^2CH_2CN$. In another embodiment $R^2$ is H, unsubstituted or substituted alkyl, cycloalkyl, aryl, alkylaryl or heterocyclyl. In another embodiment, $R^2$ is H. In another embodiment, $R^2$ is unsubstituted or substituted alkyl. In another embodiment, $R^2$ is unsubstituted or substituted cycloalkyl. In another embodiment, $R^2$ is unsubstituted or substituted aryl. In another embodiment, $R^2$ is unsubstituted or substituted alkylaryl. In another embodiment, $R^2$ is unsubstituted or substituted heterocyclyl.

Non limiting examples of $R^2CH_2CN$ include: acetonitrile, propionitrile, butyronitrile, pentanenitrile and benzyl cyanide.

In one embodiment, the process of C—C bond formation of this invention make use of a Michael acceptor of the formula $R^3C(R^4)=C(R^5)EWG$. In another embodiment $R^3$, $R^4$, $R^5$ are each independently selected from H, unsubstituted or substituted alkyl, cycloalkyl, alkoxy (O-alkyl), aryloxy (O-aryl), aryl, alkylaryl or heterocyclyl or $R^4$ and $R^5$ form a cyclic ring; or $R^4$ and $R^5$ form a cyclic ring; or $R^3$ and $R^4$ form a cyclic ring. In another embodiment, $R^3$ is H. In another embodiment, $R^4$ is H. In another embodiment $R^5$ is H. In another embodiment, $R^3$ is unsubstituted or substituted alkyl. In another embodiment, $R^4$ is unsubstituted or substituted alkyl. In another embodiment $R^5$ is unsubstituted or substituted alkyl. In another embodiment, $R^3$ is unsubstituted or substituted cycloalkyl. In another embodiment, $R^4$ is unsubstituted or substituted cycloalkyl. In another embodiment $R^5$ is unsubstituted or substituted cycloalkyl. In another embodiment, $R^3$ is unsubstituted or substituted alkoxy. In another embodiment, $R^4$ is unsubstituted or substituted alkoxy. In another embodiment $R^5$ is unsubstituted or substituted alkoxy. In another embodiment, $R^3$ is unsubstituted or substituted aryloxy. In another embodiment, $R^4$ is unsubstituted or substituted aryloxy. In another embodiment $R^5$ is unsubstituted or substituted aryloxy. In another embodiment, $R^3$ is unsubstituted or substituted aryl. In another embodiment, $R^4$ is unsubstituted or substituted aryl. In another embodiment $R^5$ is unsubstituted or substituted aryl. In another embodiment, $R^3$ is unsubstituted or substituted alkylaryl. In another embodiment, $R^4$ is unsubstituted or substituted alkylaryl. In another embodiment $R^5$ is unsubstituted or substituted alkylaryl. In another embodiment, $R^3$ is unsubstituted or substituted heterocyclyl. In another embodiment, $R^4$ is unsubstituted or substituted heterocyclyl. In another embodiment $R^5$ is unsubstituted or substituted heterocyclyl. In another embodiment, $R^3$ and $R^5$ form a cyclic ring. In another embodiment $R^4$ and $R^5$ form a cyclic ring. In another embodiment, $R^3$ and $R^4$ form a cyclic ring.

In one embodiment EWG is an electron withdrawing group comprising C(=O)R, C(=O)OR', $SO_2R'$, $CON(R)_2$, $NO_2$ or CN, wherein R is H, alkyl, aryl, heteroaryl, cycloalkyl or heterocycloalkyl; and R' is alkyl, aryl, heteroaryl, cycloalkyl or heterocycloalkyl; In one embodiment EWG is (=O)R. In another embodiment EWG is C(=O)OR'; In another embodiment EWG is $SO_2R'$; In another embodiment EWG is $CON(R)_2$; In another embodiment EWG is $NO_2$. In another embodiment EWG is CN.

Non limiting examples of Michael acceptors include: ethyl acrylate, but-3-en-2-one, 2,2,2-trifluoroethyl acrylate, phenyl acrylate, methyl methacrylate, cyclohex-2-enone or methyl but-2-enoate.

3. Dehydrogenative Coupling of Alcohols to Give Esters and Hydrogen Gas

In one aspect, the present invention provides a process for preparing esters by coupling of alcohols in the presence of the manganese complexes of the present invention, to generate the ester compound and molecular hydrogen.

In one embodiment, the process involves coupling of primary alcohols. In another embodiment, the process involves coupling of a primary and secondary alcohol. Use of dialcohols in the reaction leads to polyesters or to lactones.

Depending on the complex being used, the reaction permits the optional use of one or more equivalents of a base relative to the metal complex. When complexes IA, IA(1), IA(2), IB, IB(1), IB(2), ID(2), VIA, VIA(1), VIA(2), VIB, VIB(1) or VIB (2) are used, the process is conducted in the presence of a base. In another embodiment, when complexes of formula VI, VI(1), VI(2), VIC, VIC(1) or VIC(2) are used, the process is optionally conducted in the presence of a base. When the process of this invention is conducted in the presence of a base, at least one equivalent of a base relative to the metal complex is required. In another embodiment, two or three equivalents of a base relative to the metal complex are required. In another embodiment, the catalyst is a manganese complex 1-11, 18-21. In another embodiment, the catalyst is a manganese complex 6A'. In another embodiment, the catalyst is a manganese complex 6B.

In one embodiment, the process of the invention, i.e., the direct catalytic coupling of primary alcohols into esters and dihydrogen is illustrated in Scheme 3. In accordance with this process, two equivalents of a primary alcohol represented by formula $R^6CH_2OH$ are converted to an ester by the structure $R^6$—C(=O)—$OCH_2R^6$. This novel, environmentally benign reaction, can be used to produce various esters from very simple substrates, with high atom economy and in some embodiments no stoichiometric activating agents, thus generating no waste.

Scheme 3

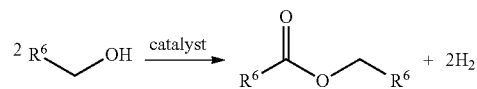

In another embodiment, the process of the invention involves the catalytic coupling of a primary alcohol and a secondary alcohol, as illustrated in Scheme 4.

In Schemes 3 and 4, each of $R^6$ $R^{6'}$ and $R^{6''}$ is independently selected from the group consisting of H, an unsubstituted or substituted alkyl, alkoxyalkyl, cycloalkyl, aryl, alkylaryl, heterocyclyl and heteroaryl.

Scheme 4

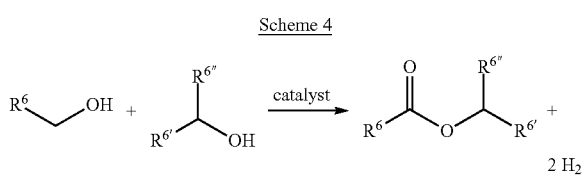

When primary alcohols are used, the process of the invention contemplates symmetric coupling of alcohols to yield symmetric esters (i.e., 2 equivalents of the same alcohol are coupled). However, the present invention further contemplates the generation of asymmetric esters by coupling of different alcohols. In accordance with this embodiment, a first primary alcohol represented by formula $R^6CH_2OH$ is reacted with a second alcohol represented by formula $R^{6'}CH_2OH$ so as to generate an ester by the structure $R^6$—C(=O)—O $CH_2R^{6'}$ or an ester of formula $R^{6'}$—C(=O)—$OCH_2R^6$, as illustrated in Scheme 4:

Scheme 5

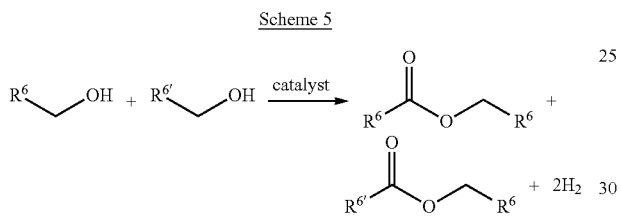

wherein $R^6$ and $R^{6'}$ are the same or different from each other and are each independently selected is from the group consisting of H, an unsubstituted or substituted alkyl, alkoxyalkyl, cycloalkyl, aryl, alkylaryl, heterocyclyl and heteroaryl.

A variety of alcohols can be used in the process of the invention. In some embodiments, the alcohol is selected from the group consisting of methanol, ethanol, n-propanol, iso-propanol, n-butanol, isobutanol, t-butanol, n-pentanol, 2-pentanol, 3-pentanol, 1-hexanol, 2-hexanol, 3-hexanol, 2-methoxyethanol, 2,2,2-trifluoroethanol, 2-methyl-1-butanol, 3-methyl-1-butanol, benzyl alcohol, 2-methoxy benzyl alcohol, 3-methoxy benzyl alcohol, 4-methoxy benzyl alcohol, 1-phenylethanol, and cyclohexane methanol. Each possibility represents a separate embodiment of the present invention.

In another embodiment, the process of the invention can also be applied to bis-acylation reactions with dialcohols to yield polyesters.

The reaction between the alcohols can be inter-molecular (i.e., the two alcohols are separate molecules). Alternatively, the reaction between the alcohols can be intra-molecular, i.e., the alcohol functionalities can be present in the same molecule, resulting in intra-molecular cyclization to generate a lactone. Each possibility represents a separate embodiment of the present invention.

In another embodiment, a process of dehydrogenative coupling of alcohols for the preparation of esters and hydrogen gas are exemplified in Example 18.

4. Hydrogenation of Esters to Alcohols

The manganese complexes of the present invention can also catalyze the hydrogenation of esters to the corresponding alcohols. Thus, in some embodiments, the present invention further provides a process for hydrogenating an ester with molecular hydrogen ($H_2$) in the presence of the manganese complexes of the present invention.

Depending on the complex being used, the reaction permits the optional use of one or more equivalents of a base relative to the metal complex. When complexes IA, IA(1), IA(2), IB, IB(1), IB(2), ID(2), VI, VI(1), VI(2), VIA, VIA(1), VIA(2), VIB, VIB(1) or VIB (2) is used as a catalyst, the process is conducted in the presence of a base. In another embodiment, when complexes of formula VI, VI(1), VI(2), VIC, VIC(1) or VIC(2) are used, the process is optionally conducted in the presence of a base. When the process of this invention is conducted in the presence of a base, an amount of base equivalent to the amount of catalyst or higher is required. In another embodiment, the catalyst is a manganese complex 1-11, 18-21. In another embodiment, the catalyst is a manganese complex 6A'. In another embodiment, the catalyst is a manganese complex 6B.

In one embodiment of the process of the invention, i.e., the direct catalytic conversion of esters to alcohols, is illustrated in Scheme 6, whereby an ester represented by the formula $R^7C(=O)$—$OR^8$ is hydrogenated to the corresponding alcohol or alcohols:

Scheme 6

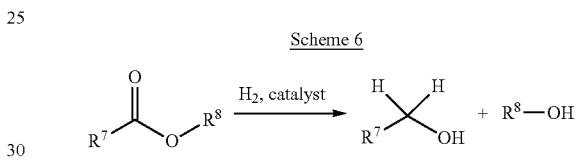

wherein $R^7$ is selected from the group consisting of H, an unsubstituted or substituted alkyl, alkoxyalkyl, cycloalkyl, aryl, alkylaryl, heterocyclyl and heteroaryl; and $R^8$ is selected from the group consisting of an unsubstituted or substituted alkyl, alkoxyalkyl, cycloalkyl, aryl, alkylaryl, heterocyclyl and heteroaryl.

It is apparent to a person of skill in the art that when the ester is symmetric (i.e., $R^7=R^8$), the reaction yields two equivalents of the same alcohol. However, when the ester is asymmetric (i.e., $R^7$ is different from $R^8$), the reaction yields a mixture of two alcohols.

In one embodiment, $R^7$ is H and the process comprises hydrogenating a formate ester of formula H—C(=O)—$OR^8$ to methanol and an alcohol of formula $R^8$—OH.

A variety of esters can be used in the process of the invention. In some embodiments, the ester is selected from the group consisting of hexyl hexanoate, methyl hexanoate, cyclohexyl hexanoate, tert-butyl acetate, cyclohexyl acetate, 2,2,2-trifluoroethyl 2,2,2-trifluoroacetate, benzyl benzoate, ethyl 3-phenylpropanoate, ethyl benzoate, butyl butyrate, methyl formate, ethyl formate, propyl formate butyl formate, methyl trifluoroacetate, methyl difluoroacetate and methyl monofluoroacetate. In other embodiments, the ester is a cyclic ester (a lactone). In yet other embodiments, the ester is a cyclic ester (lactone) or a di-ester (di-lactone), and the process results in a diol. In another embodiment, the cyclic ester is oxepan-2-one and the diol formed is hexane 1,6-diol. In yet other embodiments, the ester is a biomass-derived cyclic di-ester (di-lactone) such as, but not limited to glycolide or lactide. In yet another embodiment, the ester is polyester. Each possibility represents a separate embodiment of the present invention.

In another embodiment, a process of hydrogenation of esters to alcohols are exemplified in Example 16.

Catalytic homogeneous hydrogenation of cyclic di-esters (di-lactone), specifically glycolide and lactide to the corresponding 1,2-diols (vicinal diols) is of significant interest conceptually and practically, since these compounds are produced from biomass sources such as glycolic acid and lactic acid respectively via self-esterification, and their efficient hydrogenation can provide an alternative, mild approach to the indirect transformation of biomass resources to important synthetic building blocks. As contemplated herein, the unprecedented, environmentally benign, atom-economical route for the synthesis of propylene glycol and ethylene glycol are efficiently catalyzed by the manganese complexes as described herein. These catalytic reactions proceed under neutral, homogeneous conditions, at mild temperatures and mild hydrogen pressures. The optical purity of a chiral diol is unaffected during the hydrogenation reactions.

The process of lactone or di-lactone hydrogenation can be catalyzed by any of the complexes of the present invention, as described herein (Scheme 7).

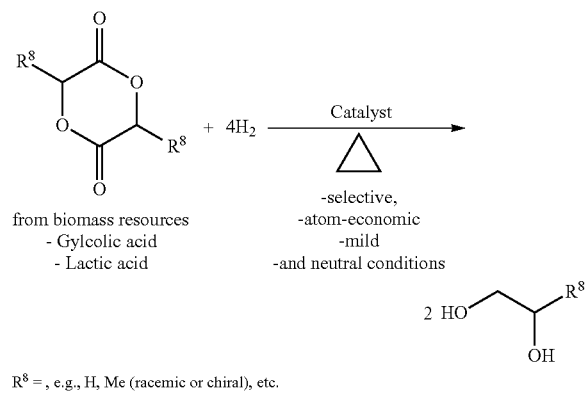

$R^8$ =, e.g., H, Me (racemic or chiral), etc.

wherein $R^8$ is as described above.

A variety of cyclic di-esters (di-lactones) can be used in the process of the invention. In some embodiments, the ester is a biomass-derived cyclic di-ester (di-lactone) such as, but not limited to glycolide or lactide. Each possibility represents a separate embodiment of the present invention.

5. Hydrogenation of Amides to Alcohols and Amines

The present invention provides a process for hydrogenating amides (including cyclic dipeptides, diamide, lactams, polypeptides and polyamides) by reacting the amide with molecular hydrogen ($H_2$) in the presence of the manganese complexes of the present invention to generate the corresponding alcohol and amine. Depending on the complex being used, the reaction permits the optional use of one or more equivalents of a base relative to the metal complex. When complexes IA, IA(1), IA(2), IB, IB(1), IB(2), ID(2), VIA, VIA(1), VIA(2), VIB, VIB(1) or VIB (2) is used as a catalyst, the process is conducted in the presence of a base. In another embodiment, when complexes of formula VI, VI(1), VI(2), VIC, VIC(1) or VIC(2) are used, the process is optionally conducted in the presence of a base. When the process of this invention is conducted in the presence of a base, an amount of base equivalent to the amount of catalyst or higher is required.

The process of the invention, i.e., the direct catalytic conversion of amides to alcohols and amides is illustrated in Scheme 8. This novel, environmentally benign reaction can be used to prepare alcohols and amines from any type of amide, with high atom economy and in some embodiments no stoichiometric activating agents, thus generating no waste. Thus, in one embodiment, the present invention provides a process for hydrogenating an amide represented by the formula $R^{12}C(=O)-N-R^{13}R^{13'}$ to an alcohol of formula $R^{12}CH_2OH$ and amine of formula $R^{13}R^{13'}NH$:

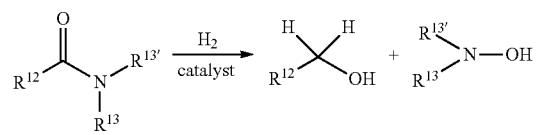

wherein $R^{12}$, $R^{13}$ and $R^{13'}$ are each independently selected from the group consisting of H, an unsubstituted or substituted alkyl, alkoxyalkyl, cycloalkyl, aryl, alkylaryl, heterocyclyl and heteroaryl.

A variety of amides can be used in the process of the invention. In some embodiments, the amide is selected from the group consisting of N-benzyl-2-methoxyacetamide, N-hexyl-2-methoxyacetamide, N-hexyl-3-methyloxetane-3-carboxamide, N-hexyl-2-furanylcarboxamide, N-benzylbenzamide, N-ethylacetamide, N-methylpropionamide, N-cyclohexyl-2-methoxyacetamide, N-phenylacetamide, N-phenylhexylamide, 2-methoxy-N-phenylacetamide, N-phenylbenzamide, Ethylenediamine-N,N'-(2-methoxyacetamide), N-hexanoylmorpholine, N-butanoylmorpholine, N-2-metoxyacetylpyrrolidine, N-formylmorpholine, N,N-dimethylformamide, N,N-diethylbenzamide, benzamide, 4-methylbenzamide, cyclohexanecarboxamide, hexanamide, acetamide, acrylamide and pivalamide. Each possibility represents a separate embodiment of the present invention.

In a similar manner, cyclic amides (lactams) can be hydrogenated to the corresponding amino alcohols. In one embodiment, the lactam is a cyclic peptide, which can be hydrogenated with the Ruthenium complex of the present invention to the respective amino alcohol (Scheme 9). In a similar manner, polyamides can be hydrogenated to amines and alcohols, and polypeptides or polyamides can be hydrogenated to amino alcohols.

In one particular embodiment, the cyclic amide is glycine anhydride (GA) or N,N-dimethyl GA, and the process results in ethanolamine or 2-(methylamino)ethanol.

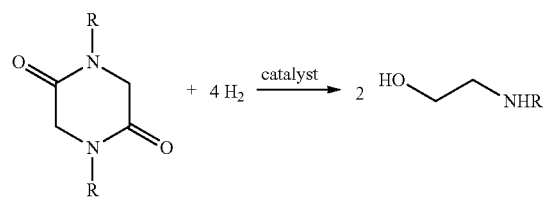

wherein R is H or CH.

As mentioned above, in another embodiment, mixtures of linear peptides and GA/N,N-dimethyl-GA are capable of being hydrogenated back to AE or its N-methyl derivative, as illustrated in Scheme 10b hereinabove.

In another embodiment, the diamide can is hydrogenated to diamine and alcohol. Specifically, the present invention relates to a catalytic process for the preparation of ethylenediamine (ED) and ethanol, the process comprises the steps of reacting N,N'-diacetylethylenediamine (DAE) with molecular hydrogen (H$_2$) in the presence of a catalyst, thereby generating ethylenediamine (ED) and ethanol. This reaction is described in Scheme 10. In one embodiment, the catalyst is a Ruthenium complex as described herein.

Scheme 10

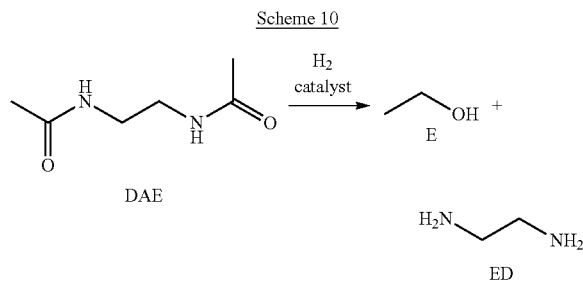

DAE

6. Hydrogenation of Organic Carbonates, Carbamates and Urea Derivatives

Similar to the hydrogenation of amides and esters, the novel manganese complexes of the present invention can also catalyze the hydrogenation of organic carbonates, hydrogenation of carbamates, or hydrogenation of urea derivatives to the corresponding amines and/or alcohols. Thus, in some embodiments, the present invention further provides a process for hydrogenating an organic carbonate, carbamate or urea derivative with molecular hydrogen (H$_2$) in the presence of the manganese complex of the present invention. Depending on the complex being used, the reaction permits the optional use of one or more equivalents of a base relative to the metal complex. When complexes IA, IA(1), IA(2), IB, IB(1), IB(2), ID(2), VIA, VIA(1), VIA(2), VIB, VIB(1) or VIB (2) is used, the process is conducted in the presence of a base. In another embodiment, when complexes of formula VI, VI(1), VI(2), VIC, VIC(1) or VIC(2) are used, the process is optionally conducted in the presence of a base. When the process of this invention is conducted in the presence of a base, an amount of base equivalent to the amount of catalyst or higher is required.

One embodiment of the process of the invention, i.e., the direct catalytic hydrogenation of organic carbonates, is illustrated in Scheme 11, whereby a carbonate represented by the formula R$^{14}$O—C(=O)—OR$^{14'}$ is hydrogenated to the corresponding alcohols(s) and methanol:

Scheme 11

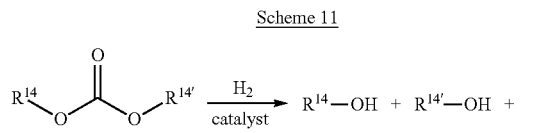

CH$_3$OH wherein R$^{14}$ and R$^{14'}$ are the same or different and are selected from the group consisting of an unsubstituted or substituted alkyl, alkoxyalkyl, cycloalkyl, aryl, alkylaryl, heterocyclyl and heteroaryl.

It is apparent to a person of skill in the art that when the organic carbonate is symmetric (i.e., R$^{14}$=R$^{14'}$) the reaction yields two equivalents of the same alcohol, and one equivalent of methanol. However, when the organic carbonate is asymmetric (i.e., R$^{14}$ is different from R$^{14'}$), the reaction yields a mixture of two alcohols, and methanol.

A variety of organic carbonates can be used in the process of the invention. In some embodiments, the carbonate is dimethyl carbonate, diethyl carbonate, dipropyl carbonate or dibutyl carbonate. In another embodiment, the carbonate is a polycarbonate, such as polyethylene carbonate or polypropylene carbonate. Each possibility represents a separate embodiment of the present invention.

Another embodiment of the process of the present invention, i.e., the direct catalytic hydrogenation of carbamates, is illustrated in Scheme 12, a carbamate represented by the formula R$^{15}$O—C(=O)—NHR$^{16}$ is hydrogenated to the corresponding amine, alcohol and methanol:

Scheme 12

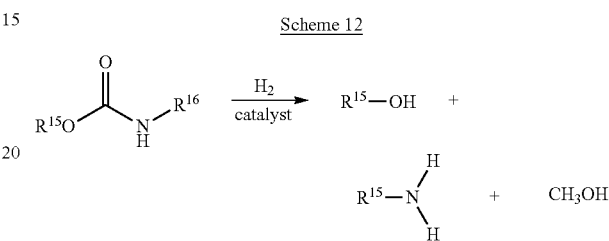

wherein R$^{15}$ is selected from the group consisting of an unsubstituted or substituted alkyl, alkoxyalkyl, cycloalkyl, aryl, alkylaryl, heterocyclyl and heteroaryl; and R$^{16}$ is selected from the group consisting of H or an unsubstituted or substituted alkyl, alkoxyalkyl, cycloalkyl, aryl, alkylaryl, heterocyclyl and heteroaryl.

A variety of organic carbamates can be used in the process of the invention. In some embodiments, the carbamate is methyl benzylcarbamate or methyl 4-methoxybenzylcarbamate. In another embodiment, the carbamate is a polycarbamate. Each possibility represents a separate embodiment of the present invention.

Another embodiment of the process of the present invention, i.e., the direct catalytic hydrogenation of urea derivatives, is illustrated in Scheme 13, whereby a urea derivative is hydrogenated to the corresponding amine(s) and methanol:

Scheme 13

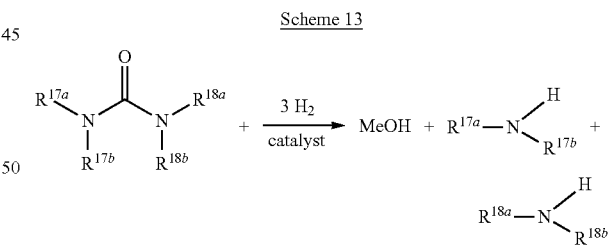

wherein each of R$^{17a}$ and R$^{18a}$, which may be the same or different, is selected from the group consisting of H, an unsubstituted or substituted alkyl, alkoxyalkyl, cycloalkyl, aryl, alkylaryl, and heterocyclyl, and each of Rim and R$^{18b}$, which may be the same or different, is selected from the group consisting of H, an unsubstituted or substituted alkyl, alkoxyalkyl, cycloalkyl, aryl, alkylaryl, and heterocyclyl. Alternatively, at least one of R$^{17a}$ and R$^{17b}$, and/or R$^{16a}$ and R$^{16b}$ together with the nitrogen to which they are attached form a heterocyclic ring A variety of symmetrical (R$^{17a}$=R$^{18a}$, R$^{17b}$=R$^{18b}$) and asymmetrical (R$^{17a}$≠R$^{18a}$, R$^{17b}$≠R$^{18b}$) urea derivatives can be used in the process of the invention, with each possibility representing a separate embodiment of the present invention. In some embodiments, the urea derivative is 1,3-dimethylurea, and the product of the reaction is methanol and two molecules of methylamine. In another embodiment, the urea derivative is selected from the group consisting of 1,3-dipropylurea, 1,3-dihexylurea, 1,3-bis(2-methoxyethyl) urea, 1,3-dicyclohexylurea, 1,3-dibenzylurea, 1,3-bis(4-methylbenzyl)urea, 1,3-bis(4-methylbenzyl)urea, 1,3-diphenylurea, 1,3-bis(4-(tert-butyl)phenyl)urea, 1,1,3,3-tetramethylurea, and di(piperidin-1-yl)methanone. Polyurea derivatives can also be hydrogenated in a similar manner. Each possibility represents a separate embodiment of the present invention.

7. Dehydrogenation of Secondary Alcohols to Ketones

In another aspect, the present invention further relates to a process for preparing a ketone by dehydrogenation of a secondary alcohol, comprising the step of reacting the secondary alcohol in the presence of the manganese complex of the present invention, thereby generating the ketone and molecular hydrogen. Depending on the complex being used, the reaction permits the optional use of one or more equivalents of a base relative to the metal complex. When complexes IA, IA(1), IA(2), IB, IB(1), IB(2), VIA, VIA(1), VIA(2), VIB, VIB(1) or VIB(2) is used, the process is conducted in the presence of a base. In another embodiment, when complexes of formula VI, VI(1), VI(2), VIC, VIC(1) or VIC(2) are used, the process is optionally conducted in the presence of a base. When the process of this invention is conducted in the presence of a base, an amount of base equivalent to the amount of catalyst or higher is required.

The process of the invention, i.e., the direct catalytic conversion of secondary alcohols into ketones and dihydrogen is illustrated in Scheme 14. In accordance with this process, a secondary alcohol represented by formula $R^{19}CH(OH)R^{19'}$ is converted to a ketone represented by the structure $R^{19}$—$C(=O)$—$R^{19'}$:

Scheme 14

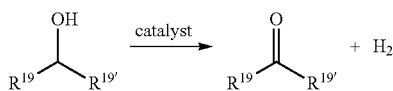

wherein $R^{19}$ and $R^{19'}$ are each independently selected from the group consisting of H or an unsubstituted or substituted alkyl, alkoxyalkyl, cycloalkyl, aryl, alkylaryl, heterocyclyl and heteroaryl.

A variety of alcohols can be used in the process of the invention. In some embodiments, the alcohol is selected from the group consisting of 1-phenyl-1-ethanol, 2-hexanol, cyclohexanol and 2-propanol. Each possibility represents a separate embodiment of the present invention.

8. Synthesis of Amides from Esters and Amines

The present invention further provides a process for preparing amides, by reacting an amine and an ester in the presence of the manganese complex of the present invention, to generate the amide compound and molecular hydrogen ($H_2$). Reactions of esters with diamines lead to diamides. Depending on the complex being used, the reaction permits the optional use of one or more equivalents of a base relative to the metal complex. When complexes IA, IA(1), IA(2), IB, IB(1), IB(2), ID(2), VIA, VIA(1), VIA(2), VIB, VIB(1) or VIB (2) is used, the process is conducted in the presence of a base. In another embodiment, when complexes of formula VI, VI(1), VI(2), VIC, VIC(1) or VIC(2) are used, the process is optionally conducted in the presence of a base. When the process of this invention is conducted in the presence of an amount of base equivalent to the amount of catalyst or higher is required. In another embodiment, the complex is of formula 1-11, 18-21 6A' or 6B.

The process of the invention, i.e., the direct catalytic reaction of esters and amines into amides and dihydrogen is illustrated in Scheme 15. In accordance with this process, an amine represented by formula $R^{20}R^{20'}NH$ is reacted with an ester represented by the formula $R^{21}$—$C(=O)$—$OCH_2R^{21'}$ to generate an amide represented by the structure $R^{21}$—$C(=O)$—$NR^{2R}R^{20}$ or $R^{21'}$—$C(=O)$—$NR^{20}R^{20'}$. This novel, environmentally benign reaction can be used to produce various amides from very simple substrates, with high atom economy and in some embodiments no stoichiometric activating agents, thus generating no waste.

Scheme 15

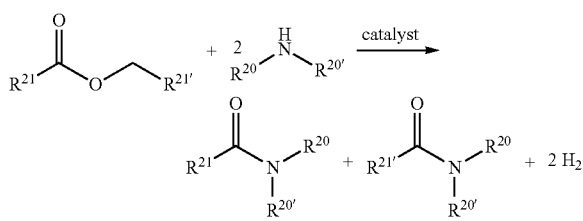

wherein $R^{20}$, $R^{20'}$, $R^{21}$ and $R^{21'}$ are each independently selected from the group consisting of H, an unsubstituted or substituted alkyl, alkoxyalkyl, cycloalkyl, aryl, alkylaryl, heterocyclyl and heteroaryl, wherein $R^{20}$, $R^{20'}$, $R^{21}$ and $R^{21'}$ can be the same or different from each other.

A variety of esters can be used in the process of the invention. In some embodiments, the ester is selected from the group consisting of ethyl acetate, butyl butyrate, pentyl pentanoate and hexyl hexanoate. Each possibility represents a separate embodiment of the present invention.

A variety of primary and secondary amines (as well as ammonia) may be used in the process of the invention. In some embodiments, the amine is selected from the group consisting of pyrrolidine, morpholine, 1-methyl piperazine, piperidine, piperazine, 1-hexylamine and p-tolylmethanamine.

In another embodiment, the process of the invention can also be applied to bis-acylation reactions with diamines. Upon reacting alcohols and diamines, the corresponding bis-amides are produced in high yields.

In another embodiment, a process of amidation of esters and amines are exemplified in Example 20.

9. Acylation of Alcohols Using Esters with Liberation of $H_2$

The present invention further provides a process for preparing esters by acylation of alcohols using esters in the presence of the manganese complex of the present invention, to generate the ester compound and molecular hydrogen. In one embodiment, the process involves reaction of primary alcohols and esters. In another embodiment, the process involves reaction of a secondary alcohols and esters. Depending on the complex being used, the reaction permits the optional use of one or more equivalents of a base relative to the metal complex. When complexes IA, IA(1), IA(2), IB, IB(1), IB(2), ID(2), VIA, VIA(I), VIA(2), VIB, VIB(1) or VIB(2) is used, the process is conducted in the presence of a base. In another embodiment, when complexes of formula VI, VI(1), VI(2), VIC, VIC(1) or VIC(2) are used, the process is optionally conducted in the presence of a base. When the process of this invention is conducted in the presence of a base, an amount of base equivalent to the amount of catalyst or higher is required.

In one embodiment, the process of the invention, i.e., the direct catalytic acylation of alcohols using esters to yield an ester and dihydrogen is illustrated in Scheme 21. In accordance with this process, two equivalents of a primary or secondary alcohol represented by formula $R^{23}R^{23'}$ CHOH reacts with one equivalent an ester by the structure $R^{22}$—C(=O)—OCH$_2$R$^{22'}$ as shown in Scheme 16. This novel, environmentally benign reaction, can be used to produce various esters from very simple substrates, with high atom economy and in some embodiments no stoichiometric activating agents, thus generating no waste.

Scheme 16

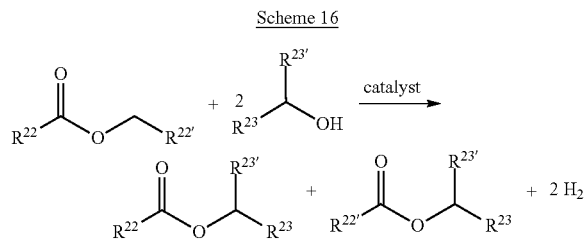

wherein $R^{22}$, $R^{22'}$, $R^{23}$ and $R^{23'}$ are each independently selected from the group consisting of H, an unsubstituted or substituted alkyl, alkoxyalkyl, cycloalkyl, aryl, alkylaryl, heterocyclyl and heteroaryl.

A variety of alcohols can be used in the process of the invention. In some embodiments, the alcohol is selected from the group consisting of cyclohexanol, cyclopentanol, 1-phenylethanol, isopropanol and 3-pentanol. Each possibility represents a separate embodiment of the present invention.

A variety of esters can be used as the starting materials. In some embodiments, the ester is selected from the group consisting of ethyl acetate, hexyl hexanoate, pentyl pentanoate, butyl butyrate, ethyl butyrate and methyl hexanoate.

10. Coupling of Alcohols with Water to Form Carboxylic Acid Salts with Liberation of H$_2$ In another aspect, the present invention further provides a process for preparing carboxylic acids by contacting primary alcohols with water in the presence of the manganese complex of the present invention and a base, to generate the carboxylic acid salt and molecular hydrogen and, if desired, followed by conversion of the carboxylic acid salt to the corresponding carboxylic acid.

Depending on the complex being used, the reaction permits the optional use of one or more equivalents of a base relative to the metal complex. When complexes IA, IA(1), IA(2), IB, IB(1), IB(2), ID(2), VIA, VIA(1), VIA(2), VIB, VIB(1) or VIB(2) are used, the process is conducted in the presence of a base. In another embodiment, when complexes of formula VI, VI(1), VI(2), VIC, VIC(1) or VIC(2) are used, the process is optionally conducted in the presence of a base. When the process of this invention is conducted in the presence of a base, an amount of base equivalent to the amount of catalyst or higher is required.

In one embodiment, the process of the invention, i.e., the direct catalytic conversion of primary alcohols to carboxylic acids and dihydrogen is illustrated in Scheme 22. In accordance with this process, a primary alcohol represented by formula $R^{24}CH_2OH$ is contacted with water and a base (e.g., NaOH) as shown in Scheme 17. This novel, environmentally benign reaction, can be used to produce various carboxylic acids and their salts from very simple substrates, with high atom economy and in some embodiments no stoichiometric activating agents, thus generating no waste. If desired, the salt is neutralized with the appropriate acid to provide the corresponding carboxylic acid.

Scheme 17

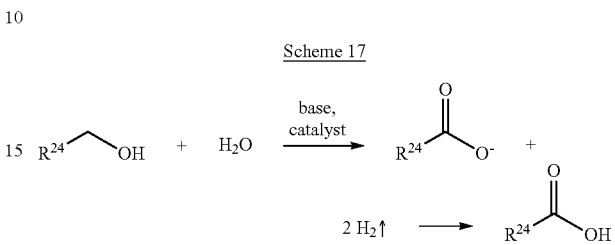

wherein $R^{24}$ is selected from the group consisting of H, an unsubstituted or substituted alkyl, alkoxyalkyl, aminoalkyl, cycloalkyl, aryl, alkylaryl, heterocyclyl and heteroaryl.

A variety of bases can be used for this reaction, non-limiting examples of which include an inorganic or organic base selected from sodium carbonate, potassium carbonate, sodium hydroxide, potassium hydroxide, sodium ethoxide, potassium tert-butoxide, sodium methoxide. The acid used to neutralize the salt can be, e.g. a mineral acid such as hydrochloric acid, hydrobromic acid, and the like. Each possibility represents a separate embodiment of the invention.

A variety of alcohols can be used in the process of the invention. In some embodiments, the alcohol is selected from the group consisting of butanol, pentanol, decanol, 2-methoxyethanol, 2-aminoethanol, 2-aminopropanol, 2-amino-2-phenylethanol, 2-phenylethanol, cyclohexylmethanol, 3-phenylbutan-1-ol, but-3-en-1-ol, (4-methoxyphenyl)methanol, and (2,4-dimethoxyphenyl)methanol. Use of amino alcohols leads to the formation of amino acids. In case of 2-aminoalcohols, natural amino acids are formed. Each possibility represents a separate embodiment of the present invention.

11. Preparing of Amino Acids or their Salts from Amino Alcohols

Thus, in another aspect, the present invention relates to a process for preparing an amino acid or a salt thereof, by contacting an amino alcohol with the manganese complex of the present invention, in the presence of water and a base, under conditions sufficient to generate the amino acid or a salt thereof.

Depending on the complex being used, the reaction permits the optional use of one or more equivalents of a base relative to the metal complex. When complexes IA, IA(1), IA(2), IB, IB(1), IB(2), ID(2), VIA, VIA(1), VIA(2), VIB, VIB(1) or VIB(2) are used, the process is conducted in the presence of a base. In another embodiment, when complexes of formula VI, VI(1), VI(2), VIC, VIC(1) or VIC(2) are used, the process is optionally conducted in the presence of a base. When the process of this invention is conducted in the presence of a base, an amount of base equivalent to the amount of catalyst or higher is required.

In one embodiment, the process of the invention involves the direct catalytic conversion of β- or γ-amino alcohols to amino acids or their salts, as illustrated by Scheme 18:

Scheme 18

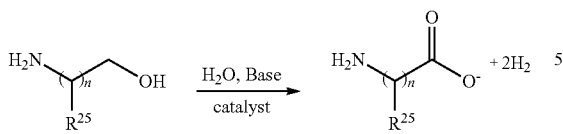

wherein $R^{25}$ is H or an unsubstituted or substituted alkyl; and n is 1 or 2.

A variety of amino alcohols can be used in the process of preparing amino acids in accordance with the principles of the present invention. In some embodiments, the amino alcohol is selected from the group consisting of 2-aminoethanol (ethanolamine), 2-amino-1-butanol, diethanolamine, 2-aminopropanol, N-methylethanolamine, N,N-dimethylethanolamine, N-isopropylethanolamine, t-tert-butylethanolamine, 2-amino-3-methyl-1-butanol, prolinol, 2-amino-3-phenyl-1-propanol, 2-amino-2-phenyl-1-ethanol, 3-aminopropanol, N,N-dimethyl-3-aminopropanol, 3-amino-3-phenyl-1-propanol, and 2-aminobenzyl alcohol, or salts of any of the foregoing. Each possibility represents a separate embodiment of the present invention.

A variety of amino acids can be produced in accordance with the foregoing process. In some embodiments, the amino acid is selected from the group consisting of glycine, α-aminobutyric acid, 2-(2-hydroxyethylamino)acetic acid, alanine, sarcosine, dimethylglycine, N-isopropyl glycine, N-tert-butyl glycine, leucine, proline, phenylalanine, 2-phenylglycine, β-alanine, N,N-dimethyl-β-alanine, 3-amino-3-phenyl propanoic acid, and anthranilic acid, or salts of any of the foregoing. Each possibility represents a separate embodiment of the present invention.

12. Dehydrogenative Coupling of Alcohols and Amines for the Preparation of Amides (Including Cyclic Dipeptides, Diamide, Lactams, Polypeptides and Polyamides)

The present invention provides a process for the preparation of amides (including cyclic dipeptides, diamide, lactams, polypeptides and polyamides) by dehydrogenative coupling of alcohols and amines in the presence of the manganese complexes. Depending on the complex being used, the reaction permits the optional use of one or more equivalents of a base relative to the metal complex. When complex IA, IA(1), IA(2), IB, IB(1), IB(2), ID(2), VIA, VIA(1), VIA(2), VIB, VIB(1) or VIB (2) is used as a catalyst, the process is conducted in the presence of a base. In another embodiment, when complexes of formula VI, VI(1), VI(2), VIC, VIC(1) or VIC(2) are used, the process is optionally conducted in the presence of a base. When the process is conducted in the presence of a base, an amount of base equivalent to the amount of catalyst or higher is required. In another embodiment, the complex is of formula 1-11, 18-21, 6A', 6B, VI, VI(1), VI(2), VIA, VIA(1), VIA (2), VIB, VIB(1). VIB (2), VIC, VIC(1) or VIC(2).

In one embodiment, the process comprises reacting a manganese complex of formula VI, VIA, VIB or VIC with methanol to yield the intermediate of formula VIIA or VIIB, which is then reacted with the amine to yield an amide.

This novel, environmentally benign reaction can be used to prepare amides from any secondary or primary amine and primary alcohols, and it doesn't generate any waste. The process of the invention, i.e., the catalytic conversion of alcohols and amines for the preparation of amides is illustrated for example in Scheme 19. Thus, in one embodiment, the present invention provides a process for the preparation of amides represented by the formula $R^{26}C(=O)-N-R^{27}R^{27'}$ by dehydrogenative coupling of alcohols of formula $R^{26}CH_2OH$ and amine of formula $R^{27}R^{27'}NH$:

Scheme 19

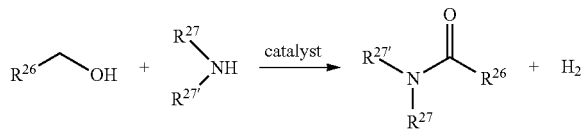

wherein $R^{26}$, $R^{27}$ and $R^{27'}$ are each independently selected from the group consisting of H, an unsubstituted or substituted, saturated or unsaturated: alkyl, alkoxyalkyl, cycloalkyl, aryl, alkylaryl, heterocyclyl and heteroaryl.

The coupling between the alcohol and the amines can be inter-molecular (i.e., the alcohol and the amine are separate molecules). Alternatively, the reaction between the alcohol and amine can be intra-molecular, i.e., the alcohol and amine are in the same molecule, resulting in intra-molecular cyclization to generate a lactam. In another embodiment, coupling a diamine with an alcohol, or coupling a dialcohol with an amine will yield diamides or dipeptides. In another embodiment, a lactam is prepared by coupling an aminoalcohol. In another embodiment, a polyamide or a polypeptide is prepared by coupling a dialcohol with diamine.

A variety of amines can be used in the process of the invention. In some embodiments, the amine is selected from the group consisting substituted or unsubstituted aryl-alkylamine, alkyl amine, alkyl-diamine, cycloalkyl amine, cycloalkyl diamine, hereterocycoalkyl amine, hereterocycoalkyl diamine Non limited examples include phenylmethanamine, 2-phenylethanamine, pentan-1-amine hexan-1-amine, pyrrolidine, cyclohexanamine, (4-methoxyphenyl) methanamine, (4-fluorophenyl)methanamine and 4-benzylpiperidine. Each possibility represents a separate embodiment of the present invention.

A variety of alcohols can be used in the process of the invention. In some embodiments, the alcohol is selected from the group consisting of substituted or unsubstituted: hydroxyalkyl, hydroxyarylalkyl, hydroxycycloalkyl, hydroxyheterocycloalkyl. Non limited examples include methanol, ethanol, n-propanol, iso-propanol, n-butanol, isobutanol, t-butanol, n-pentanol, 2-pentanol, 3-pentanol, 1-hexanol, 2-hexanol, 3-hexanol, 2-methoxyethanol, 2,2,2-trifluoroethanol, 2-methyl-1-butanol, 3-methyl-1-butanol, benzyl alcohol, 2-methoxy benzyl alcohol, 3-methoxy benzyl alcohol, 4-methoxy benzyl alcohol, 1-phenylethanol, and cyclohexane methanol Each possibility represents a separate embodiment of the present invention.

A variety of aminoalcohols can be used in the process of the invention. In some embodiments, the aminolcohol is selected from the group consisting of substituted or unsubstituted: hydroxyalkylamine, hydroxyarylalkylamine, hydroxycycloalkylamine, hydroxyheterocycloalkylamine. Non limited examples include 5-aminopentan-1-ol, 2-aminoethanol (ethanolamine), 2-amino-1-butanol, diethanolamine, 2-aminopropanol, N-methylethanolamine, N,N-dimethylethanolamine, N-isopropylethanolamine, t-tert-butylethanolamine, 2-amino-3-methyl-1-butanol, prolinol, 2-amino-3-phenyl-1-propanol, 2-amino-2-phenyl-1-ethanol, 3-aminopropanol, N,N-dimethyl-3-aminopropanol, 3-amino-3-phenyl-1-propanol, and 2-aminobenzyl alcohol. Each possibility represents a separate embodiment of the present invention.

In another embodiment, a process of dehydrogenative coupling of alcohols and amines for the preparation of amides are exemplified in Example 19.

13. Dehydrogenative Coupling of Methanol and Amines for the Preparation of Formamides In one embodiment, this invention provides a process for the preparation of formamides by dehydrogenative coupling of methanol and amines in the presence of the manganese complexes. Depending on the complex being used, the reaction permits the optional use of one or more equivalents of a base relative to the metal complex. In another embodiment, the complex is of formula VI, VI(1), VI(2), VIA, VIA(1), VIA(2), VIB, VIB(1), VIB (2), VIC, VIC(1) or VIC(2) their isomers or salts thereof. In another embodiment, the complex is a compound 18, 19, 20, 21 their isomers or salts thereof. When complex VIA, VIA(1), VIA (2), VIB, VIB(1) or VIB (2) is used as a catalyst, an amount of base equivalent to the amount of catalyst or higher is required. In another embodiment, when complexes of formula VI, VI(1), VI(2), VIC, VIC(1) or VIC(2) are used, the process is optionally conducted in the presence of a base. In one embodiment, this invention provides a process for the preparation of formamides by dehydrogenative coupling of methanol and amines in the presence of the manganese complexes 18-21, their isomers or salts thereof.

In one embodiment, this invention provides a catalytic process for preparing formamides by dehydrogenative coupling of methanol and amine of formula $R^{27}R^{27'}NH$:

Scheme 19A

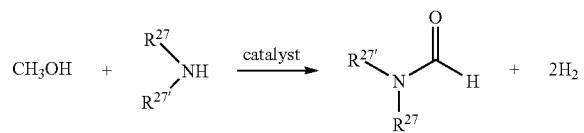

wherein $R^{27}$ and $R^{27'}$ are each independently selected from the group consisting of H, an unsubstituted or substituted, saturated or unsaturated: alkyl, alkoxyalkyl, cycloalkyl, aryl, alkylaryl, heterocyclyl and heteroaryl;

wherein said process comprising the step of reacting said methanol and said amine in the presence of the manganese complex of formula VI, VIA, VIB, or VIC thereby generating an amide; wherein if a manganese complex of formula VIA or VIB is used as a catalyst, an amount of base equivalent to the amount of catalyst or higher is added;

wherein if a manganese complex of formula VI or VIC is used as a catalyst, an amount of base equivalent to the amount of catalyst or higher is optionally added.

In another embodiment, a process of dehydrogenative coupling of alcohols and amines for the preparation of amides are exemplified in Example 27.

Processes for Preparing the Manganese Complexes

Also encompassed by the present invention are processes for preparing the manganese complexes of the present invention, and intermediates used in these processes.

The process for the preparation of the manganese complex of formula I(1) comprises reacting the ligand a in the presence of $Mn(CO)_5Br$ (Scheme 20) to obtain precursor b followed by dearomatization (for example, by using KO$^t$Bu) and decarbonylation (Scheme 20); or followed by decarbonylation and dearomatization (Scheme 21).

Scheme 20

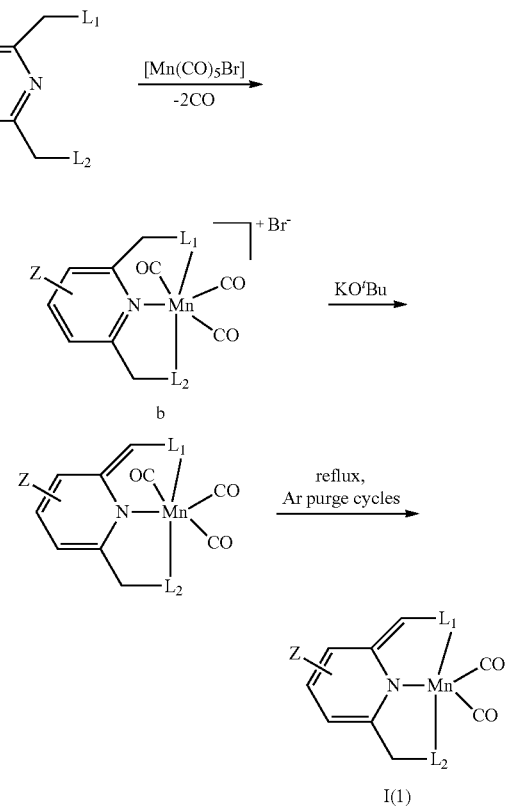

wherein $L^1$, $L^2$ and Z, are as defined above for formula I(1).
wherein $L^1$, $L^2$ and Z, are as defined above for formula I(1).

Scheme 21

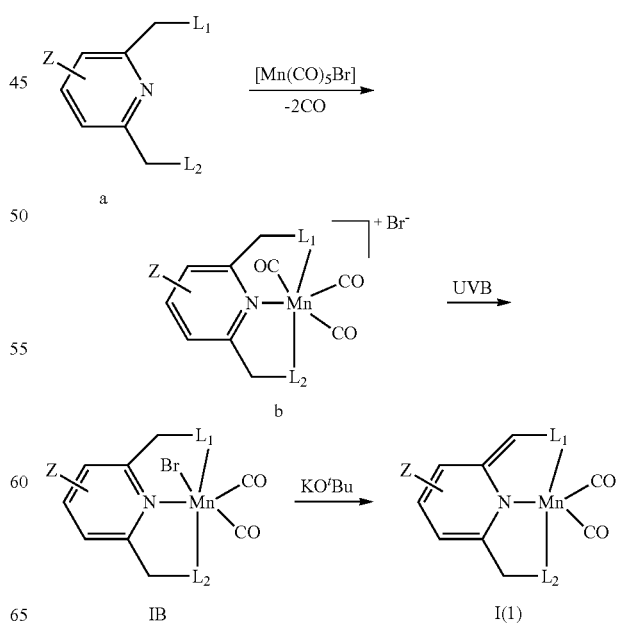

In one embodiment, the process for the preparation of the manganese complex of formula IB, wherein the ligands $L_1$ and $L_2$ are nitrogen and phosphorus, is presented in Scheme 22 and Example 15:

Scheme 22

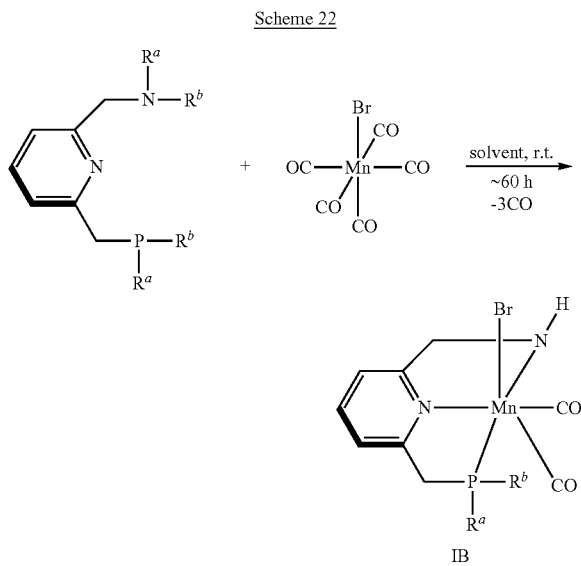

The process for the preparation of the manganese complex of formula VI(I), VIB(I), or VIC(1) comprises reacting the ligand 1 in the presence of Mn(CO)$_5$Br (Scheme 23) to obtain VIB(I)(Br); reduction of the last yields VIB(1)(H), whereas treatment of VIB(1)(Br) with a base provides the compound VI(1); VIC(1) is formed from VI(1), with or without heating.

Scheme 23

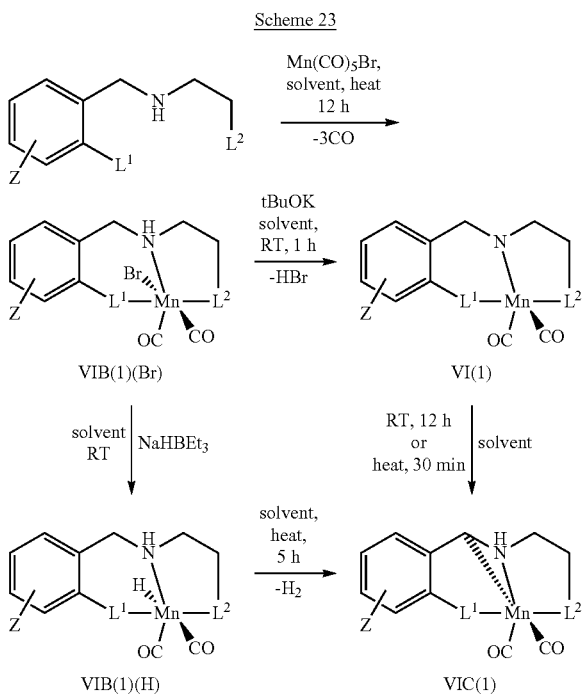

In one embodiment a process for the preparation of complex 1 is presented in Example 1.

In one embodiment a process for the preparation of complex 2 is presented in Example 3.

In one embodiment a process for the preparation of complex 19 is presented in Example 23.

In one embodiment a process for the preparation of complex 20 is presented in Example 24.

In one embodiment a process for the preparation of complex 18 is presented in Example 25.

In one embodiment a process for the preparation of complex 21 is presented in Example 26.

The disclosures of all cited references are incorporated by reference as if fully set forth herein.

The following examples are presented in order to more fully illustrate the preferred embodiments of the invention. They should in no way be construed, however, as limiting the broad scope of the invention.

EXAMPLES

All $^1$H NMR, $^{13}$C{$^1$H} NMR, and $^{31}$P{$^1$H} NMR spectra were recorded on Bruker AMX-300, AMX-400, and AMX-500 NMR spectrometer and reported in ppm (δ). $^1$H NMR, $^{13}$C{$^1$H} NMR, and $^{13}$C{$^1$H}-DEPTQ NMR chemical shifts are referenced with respect to tetramethylsilane, while $^{31}$P{$^1$H} NMR chemical shifts are reported referenced to an external 85% solution of phosphoric acid in D$_2$O. NMR spectroscopy abbreviations: b, broad; s, singlet; d, doublet; t, triplet, q, quartet; m, multiplet. IR spectra were recorded on a Nicolet FT-IR spectrophotometer. Mass spectra were recorded on MicromassPlatform LCZ 4000, using Electro Spray Ionization (ESI) mode. GC-MS was carried out on HP 6890/5973 (MS detector) instruments equipped with a 30 m column (Restek 5MS, 0.32 mm internal diameter) with a 5% phenylmethylsilicone coating (0.25 mm) and helium as carrier gas.

Example 1

Synthesis of Manganese Complex of Formula 1

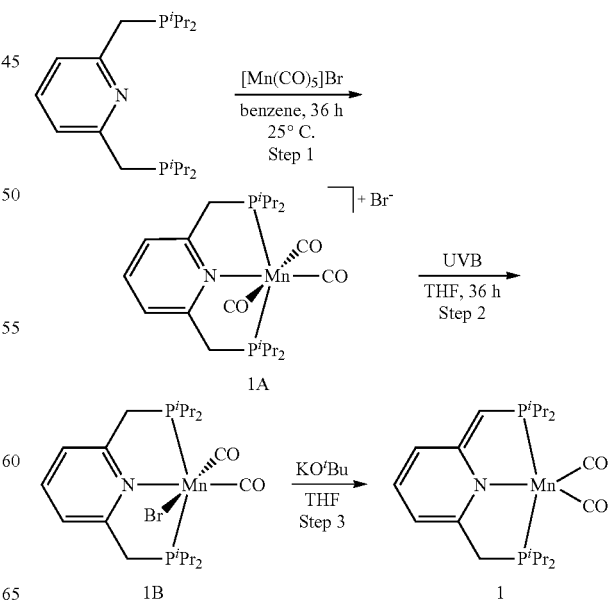

Step 1: Preparation of mer-[Mn(PNP$^{iPr}$)(CO)$_3$]Br (1A)

In a 20 mL vial, 2,6-bis(di-$^i$propyl-phosphinomethyl)pyridine (PNP$^{iPr}$ligand) (340 mg, 1.0 mmol) was dissolved in 5 mL of benzene and slowly added to a stirred suspension of Mn(CO)$_5$Br (280 mg, 1.0 mmol) in 5 mL benzene in a separate 20 mL vial. The mixture was stirred at room temperature for 36 h. The obtained suspension was distributed between 2 vials which were subsequently layered with pentane. The resulting yellow powder was decanted washed with pentane and dried under vacuum until constant mass, Yield: 480 mg, 85.5%.

$^{31}$P{$^1$H} NMR(162.07 MHz, CDCl$_3$, 25° C.): δ 89.2 (s, 2P).

$^1$H NMR (400.36 MHz, CDCl$_3$, 25° C.): δ 1.18 (br, 12H, (CH$_3$)$_2$CHP), 1.28 (br, 12H, (CH$_3$)$_2$CHP), 2.58 (br, 4H, (CH$_3$)$_2$CHP), 3.95 (br, 4H, CH$_2$P), 7.70 (br, 3H, CH$_{pyri}$).

$^{13}$C{$^1$H} QDEPT NMR (100.67 MHz, CDCl$_3$, 25° C.): δ 19.12 (s, 8C, ((H$_3$)$_2$CHP), 27.86 (s, 4C, (CH$_3$)$_2$CHP), 128.13 (s, 3C, CH$_{pyri(3,4,5)}$), 163.09 (s, 2C, CH$_{pyri(2,6)}$), 216.5 (s, 2C, Mn—CO), 222.4 (s, 1C, Mn—CO).

IR (KBr, pellet, cm$^{-1}$): ν$_{3CO}$: 1826, 1911 (large, same intensity), 1945 (small, overlapping).

Elemental analysis calculated (found) for C$_{22}$H$_{35}$BrMnNO$_3$P$_2$: C, 47.33 (48.09), H, 6.35 (6.45), N, 2.51 (1.91) %.

Step 2: Preparation of cis-[Mn(PNP$^{iPr}$)(CO)$_2$Br] (1B)

mer-[Mn(PNP$^{iPr}$)(CO)$_3$]Br (480 mg, 0.85 mmol) was suspended in 20 mL THF, and transferred to a sealed 50 mL Schlenk tube. The solution was irradiated with UVB light under stirring for 36 hours until a clear solution was received (product is completely soluble in THF). During the irradiation (after 24 h and 48 h) the solution was exposed to an argon stream for 5 min (in order to reduce the CO pressure). The solution was transferred to a 20 mL vial and was concentrated under vacuum to a volume of 5 mL. After layering with pentane and letting the solution stand for 48 h at room temperature, the product precipitates as pale yellow powder. The solution was decanted and the solids were washed with pentane and dried under vacuum, Yield: 390 mg 0.73 mmol, 86%.

$^{31}$P{$^1$H} NMR (162.07 MHz, CDCl$_3$, 25° C.): δ 85.71 (s, 2P).

$^1$H NMR (400.36 MHz, CDCl$_3$, 25° C.): δ 1.22, 1.33, 1.40 (overlap, 24H, (CH$_3$)$_2$CHP), 2.53 (br, 2H, (CH$_3$)$_2$CHP), 3.04 (br, 2H, (CH$_3$)$_2$CHP), 3.50 (d, $^3$J$_{HH}$=15.4 Hz, 2H, CH$_2$P), 3.90 (d, $^3$J$_{HH}$=15.6 Hz, 2H, CH$_2$P), 7.22 (br, 2H, CH$_{pyri(3,5)}$), 7.48 (br, 1H, CH$_{pyri(4)}$).

$^{13}$C{$^1$H} QDEPT NMR (100.67 MHz, CDCl$_3$, 25° C.): δ 18.8 (s, 2C, (CH$_3$)$_2$CHP), 19.58 (s, 2C, (CH$_3$)$_2$CHP), 19.93 (s, 4C, (CH$_3$)$_2$CHP), 25.93 (s, 2C, (CH$_3$)$_2$CHP), 26.46 (s, 2C, (CH$_3$)$_2$CHP), 41.17 (s, 2C, CH$_2$P), 120.4 (s, 2C, CH$_{pyri(3,5)}$), 136.72 (s, 1C, CH$_{pyri(4)}$), 163.7 (s, 2C, C$_{pyri(2,6)}$). CO resonances are not observed.

IR (KBr, pellet, cm$^{-1}$): 1827, 1913 (ν$_{2CO\ symmetric}$+ν$_{2CO\ anisymmetric}$, 1:1 ratio).

Elemental analysis calculated (found) for C$_{21}$H$_{35}$MnNO$_2$P$_2$Br: C, 47.56 (47.43), H, 6.65 (6.67), N, 2.64 (2.32) %.

Step 3: Preparation of cis-[Mn(PNP*$^{iPr}$)(CO)$_2$] (1)

cis-[Mn(PNP$^{iPr}$)(CO)$_2$Br] (90 mg, 0.17 mmol) was suspended in 5 mL THF, KO$^t$Bu (20 mg, 0.18 mmol) was dissolved in 5 mL THF and added dropwise to the suspension, which turned dark. The solution was evaporated and redissolved in 10 ml of pentane and filtered through Teflon syringe filter (0.2 μm). The solution was kept in −38° C. freezer for 48 h to form red crystals. The crystals were dacanted and dried under vacuum, Yield: 50 mg, 0.11 mmol, 65%.

$^{31}$P{$^1$H} NMR (202.5 MHz, C$_6$D$_6$, 25° C.): δ 69.51 (d, $^2$J$_{PP}$=72.0 Hz, 1P, PCH=C), 87.17 (d, $^2$J$_{PP}$=72.0 Hz, 1P, PCH$_2$C).

$^1$H NMR (500.13 MHz, C$_6$D$_6$, 25° C.): δ 0.81 (dd, $^3$J$_{PH}$=14.2 Hz, $^3$J$_{HH}$=7.11 Hz, 6H, ((CH$_3$)$_2$CHP), 0.98 (dd, $^3$J$_{PH}$=14.9 Hz, $^3$J$_{HH}$=6.9 Hz, 6H, ((CH$_3$)$_2$CHP), 1.17 (m, 12H, ((CH$_3$)$_3$CP), 1.87 (dd, $^3$J$_{PH}$=15.2 Hz, $^3$J$_{HH}$=7.1 Hz, 2H, ((CH$_3$)$_2$CHP), 2.50 (dd, $^3$J$_{PH}$=14.5 Hz, $^3$J$_{HH}$=6.9 Hz, 2H, ((CH$_3$)$_2$CHP), 2.60 (d, $^2$J$_{HH}$=9.6 Hz, 2H, PCH$_2$), 3.59 (s, 1H, PCH), 5.32 (d, $^3$J$_{HH}$=5.6 Hz, 1H, CH$_{pyri(3)}$), 6.23 (m, 1H, CH$_{pyri(5)}$), 6.32 (m, 1H, CH$_{pyri(4)}$).

$^{13}$C{$^1$H} QDEPT NMR (100.67 MHz, C$_6$D$_6$, 25° C.): δ 18.02, 18.21, 18.7, 19.15 (s, 2C each, (C(H$_3$)$_2$CHP), 25.79 (d, $^1$J$_{CP}$=28.3 Hz, 2C, (CH$_3$)$_2$CHP), 26.51 (d, $^1$J$_{CP}$=21.1 Hz, 2C, (CH$_3$)$_2$CHP), 35.90 (d, $^1$J$_{CP}$=16.6 Hz, 1C, PCH$_2$), 70.32 (d, $^1$J$_{CP}$=43.0 Hz, 1C, PCH=C), 98.95 (d, $^3$J$_{PC}$=10.2 Hz, 1C, CH$_{pyri(3)}$), 118.2 (d, $^3$J$_{PC}$=18.1 Hz, 1C, CH$_{pyri(5)}$), 132.36 (s, 1C, CH$_{pyri(4)}$), 160.38 (s, 1C, C$_{pyri(6)}$), 175.16 (d, $^2$J$_{PC}$=16.2 Hz, 1C, C$_{pyri(2)}$), 238.76 (t, $^2$J$_{CP}$=17.3 Hz, 2C, Mn—CO).

IR (KBr, pellet, cm$^{-1}$): solid state: 1827, 1913 (ν$_{2CO\ symmetric}$+ν$_{2CO\ antisymmetric}$, 1:1 ratio); solution: 1852, 1919 (ν$_{2CO\ symmetric}$+ν$_{2CO\ antisymmetric}$, 1:1 ratio), dinitrogen stretch was not observed.

Example 2

The Manganese Complex of Formula 7

Figure 1:
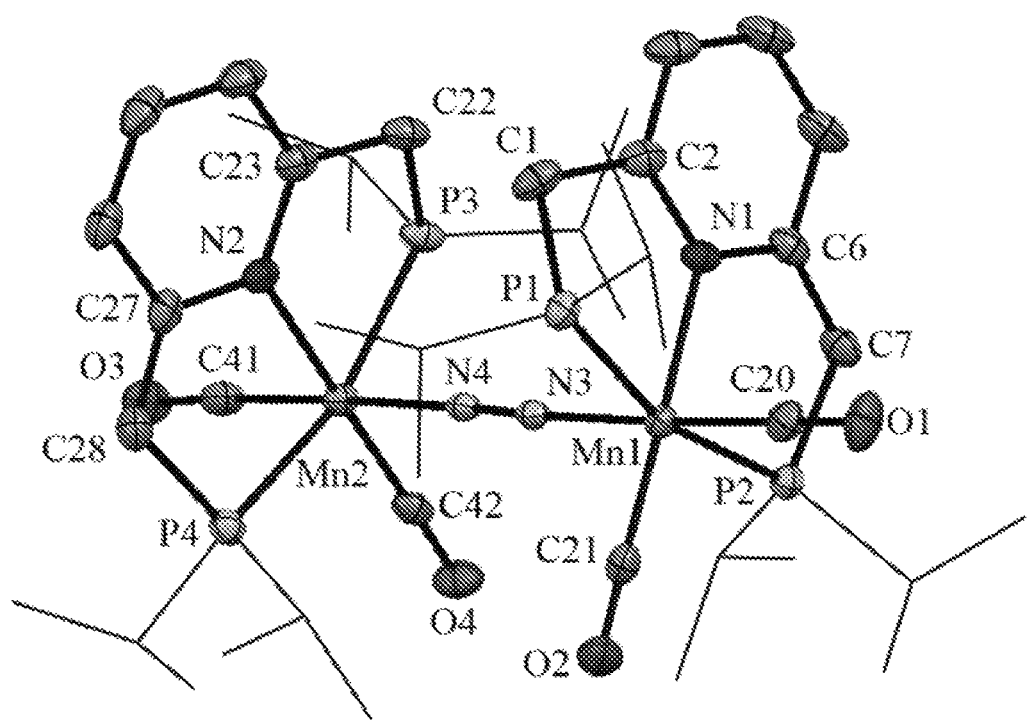
FIG. 1 depicts the molecular structure of manganese complex 7 with thermal ellipsoids set at 50% probability. Hydrogen atoms were omitted for calrity and the P(ᵗBu)₂ groups are drawn as wire frames. Selected bond lengths [Å] and angles [°] of 2: Mn1-P1 2.302(13), Mn1-P2 2.309(12), Mn2-P3 2.289(5), Mn2-P4 2.297(5), Mn1-N3 1.939(4), Mn2-N4 1.940(2); N3-N4 1.1140; P1-Mn1-P2 163.15(5), P3-Mn2-P4 164.11(4), N1-Mn1-C21 177.93(4), N2-Mn2-C42 178.01(4), Mn1-N3-N4 175.81(4), Mn2-N4-N3 177.74 (17); N3-Mn1-C20 176.02(17); N4-Mn2-C41 176.61(17).
Figure 2:
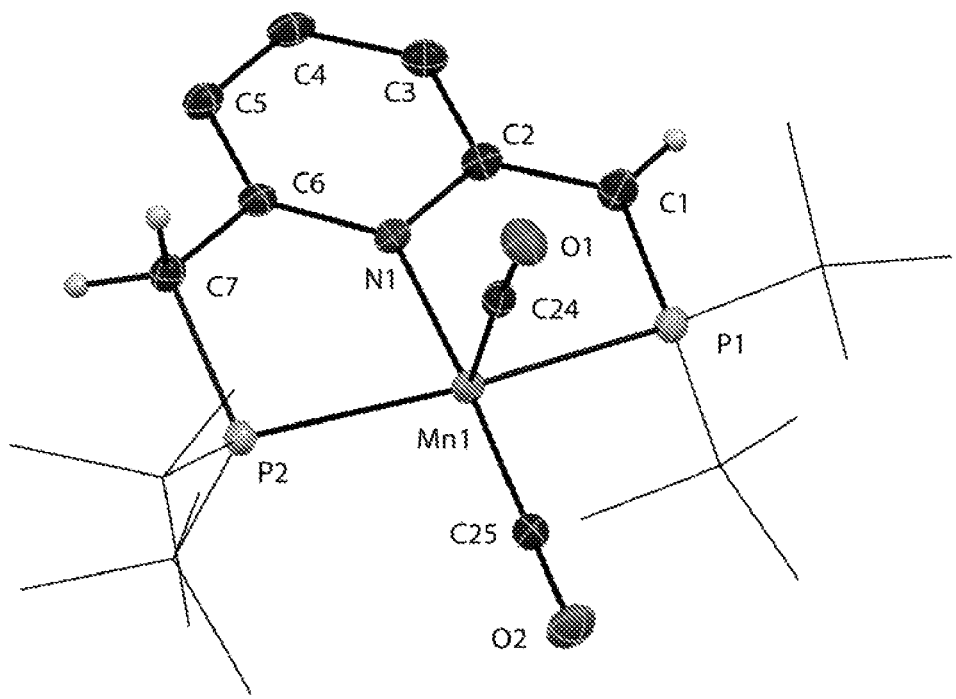
FIG. 2 depicts an ORTEP diagram of [Mn(PNPᵗBu2*(CO)₂] (2) with thermal ellipsoids at 30% probability. The P(ᵗBu)₂ groups are drawn as wire frames, and hydrogen atoms are partially omitted for clarity. Selected bond lengths: C1-C2=1.369(3) Å, C2-C3=1.449(3) Å, C3-C4=1.348(3) Å, C4-C5=1.407(3) Å, C5-C6=1.373(3) Å, C6-C7=1.498(3) Å, Mn1-N1=2.0333(16) Å, Mn1-P1=2.2950(7) Å, Mn1-P2=2.3117(7) Å, Mn1-C24=1.744(2) Å, Mn1-C25=1.768(2) Å, C24-O1=1.168(2) Å, C25-O2=1.171(2) Å.

Interestingly, in solution the manganese complex of formula 1 exists as a monomer, while in the solid state it exists as a dinitrogen-bridged dimer (7, FIG. 1). This was confirmed from DOSY NMR experiment. Moreover, at low temperature, a solution of the manganese complex of formula 1 revealed existance of an equilibrium between the monomer and dimer. The molecular structure of 7 exhibits a distorted octahedral geometry around Mn(I) center (FIG. 1).

TABLE 1

Selected bond lengths and angles of the manganese complex of formula 7 based on X-ray structure as presented in FIG. 1:

| Bond Distances [Å] | | Bond Angle [°] | |
| --- | --- | --- | --- |
| Mn1—P1 | 2.3023(5) | P1—Mn1—P2 | 163.15(2) |
| Mn1—P2 | 2.3091(5) | P3—Mn2—P4 | 164.11(2) |
| Mn2—P3 | 2.2892(6) | N1—Mn1—C21 | 177.94(7) |
| Mn2—P4 | 2.2970(6) | N2—Mn2—C42 | 178.01(7) |
| Mn1—N3 | 1.9393(13) | Mn1—N3—N4 | 175.81(12) |
| Mn2—N4 | 1.9405(13) | Mn2—N4—N3 | 177.74(12) |
| N3—N4 | 1.1135(18) | N3—Mn1—C20 | 176.02(7) |
| C22—C23 | 1.505(3) | N4—Mn2—C41 | 176.61(7) |
| C27—C28 | 1.384(2) | C1—P1—Mn1 | 98.63(6) |
| C1—C2 | 1.506(3) | C7—P2—Mn1 | 100.65(6) |
| C6—C7 | 1.385(2) | C22—P3—Mn2 | 100.23(6) |
| Mn1—N1 | 2.0845(14) | C28—P4—Mn2 | 100.19(6) |
| Mn2—N2 | 2.0837(14) | C1—C2—N1 | 115.42(15) |

Example 3

Figure 3:
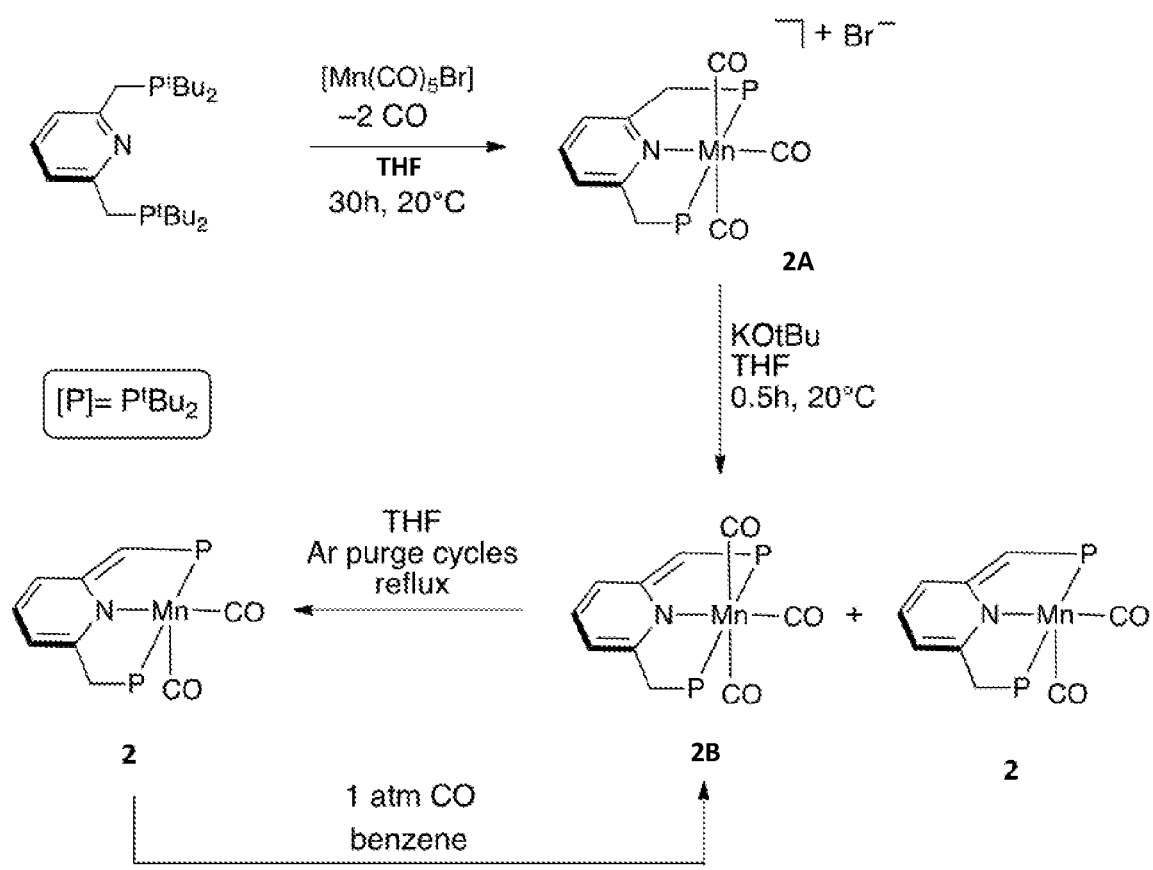
FIG. 3 is a schematic synthesis of the manganese complex 2.[P=ᵗBu₂P].

Synthesis of Manganese Complex of Formula 2 (FIG. 3)

mer-[Mn(PNP$^{tBu}$)(CO)$_3$]Br (2A):

2,6-bis(di-$^t$Butyl-phosphinomethyl)pyridine (PNP$^{t-Bu}$ ligand) (537 mg, 1.36 mmol) was dissolved in 9 mL of benzene and added to a stirred suspension of Mn(CO)$_5$Br (380 mg, 1.36 mmol) in 9 mL benzene in a 20 mL vial. The mixture was stirred at room temperature for 30 h. The obtained suspension was distributed equally between three vials, which were subsequently layered with n-pentene and kept at −38° C. The yellow precipitate was decanted, washed with n-pentane, and dried under reduced pressure (700 mg, 83% yield).

$^{31}$P{$^1$H} NMR (162.07 MHz, (CD$_3$)$_2$SO, 25° C.): δ 109.37 (s, 2P). $^1$H NMR (400.36 MHz, (CD$_3$)$_2$SO, 25° C.): δ 1.35 (d, $^3$J$_{PH}$=12.7 Hz, 36H, (CH$_3$)$_3$CP), 4.07 (d, $^2$J$_{HP}$=7.0 Hz, 4H, PCH$_2$), 7.65 (d, $^3$J$_{HH}$=7.7 Hz, 2H, CH$_{pyri(3,5)}$), 7.94 (t, $^3$J$_{HH}$=7.7 Hz, 1H, CH$_{pyri(4)}$).

$^{13}$C{$^1$H} QDEPT NMR (100.67 MHz, (CD$_3$)$_2$SO, 25° C.): δ 29.74 (s, 12C, (CH$_3$)$_3$CP), 36.76 (t, $^1$J$_{PC}$=6.7 Hz, 4C, (CH$_3$)$_3$CP)), 38.34 (t, $^1$J$_{PC}$=8.0 Hz, 2C, (CH$_2$P)), 122.76 (s, 2C, CH$_{pyri(3,5)}$), 139.68 (s, 1C, CH$_{pyri(4)}$), 163.23 (s, 2C, CH$_{pyri(2,6)}$), 220.46 (t, $^2$J$_{PC}$=15.9 Hz, 2C, Mn—CO), 223.91 (t, $^2$J$_{PC}$=12.8 Hz, 1C, Mn—CO).

IR (KBr, pellet, cm$^{-1}$): 1919, 1932 (overlapping) ($ν_{3CO\ asymmetric}$+$ν'_{3CO\ asymmetric}$), 2021 ($ν_{3CO\ symmetric}$) in 10:1 ratio.

Elemental analysis (C$_{26}$H$_{43}$BrMnNO$_3$P$_2$) calculated (found): C, 50.83 (50.80) H, 7.05 (7.04) N, 2.28 (2.26) %.

mer-[Mn(PNP*$^{tBu}$)(CO)$_3$] (2B)

Method A: via dearomatization of mer-[Mn(PNP$^{tBu}$)(CO)$_3$]Br (2): mer-[Mn(PNP$^{tBu}$)(CO)$_3$]Br (2) (50 mg, 0.08 mmol) was suspended in 4 mL THF. KO$^t$Bu (33 mg, 0.30 mmol) was dissolved in 2 mL THF and added dropwise to the suspension, which dissolved completely to give a brown homogeneous solution. The solution was allowed to stir for 0.5 h at ambient temperature. Subsequently all volatiles were evaporated in vacuo. The remaining brown residue was extracted with n-pentane (~10 mL) and filtered through a Teflon syringe filter (0.2 μm). Brown crystals and amorphous precipitate were formed upon storing the solution at −38C for 48 h. The solids were decanted and dried under reduced pressure to yield 38 mg of a 2:1 mixture of mer-[Mn(PNP*$^{tBu}$)(CO)$_3$] (2B) and cis-[Mn(PNP$^{tBu}$)(CO)$_2$] (2).

Method B: via CO addition to cis-[Mn(PNP*$^{tBu}$)(CO)$_2$] (2): cis-[Mn(PNP*$^{tBu}$)(CO)$_2$] (2) (8 mg, 0.016 mmol) was dissolved in 0.5 mL C$_6$D$_6$ and transferred to a J. Young NMR tube with Kontes valve. The tube was degassed and subsequently filled with 1 atm of CO gas, which resulted in a color change from dark blue to orange. Analysis by multinuclear NMR spectroscopy indicated the quantitative formation of mer-[Mn(PNP*$^{tBu}$)(CO)$_3$] (2B).

$^{31}$P{$^1$H} NMR (162.07 MHz, C$_6$D$_6$, 25° C.): δ 100.84 (br, 1P), 108.34 (br, 1P). $^1$H NMR (400.36 MHz, C$_6$D$_6$, 25° C.): δ 1.11 (d, $^3$J$_{PH}$=12.4 Hz, 18H, (CH$_3$)$_3$CP), 1.45 (d, $^3$J$_{PH}$=12.6 Hz, 18H, (CH$_3$)$_3$CP), 2.73 (d, $^2$J$_{HP}$=8.1 Hz, 2H, PCH$_2$), 3.78 (s, 1H, PCH), 5.54 (d, $^3$J$_{HH}$=6.4 Hz, 1H, CH$_{pyri(3)}$), 6.25 (d, $^3$J$_{HH}$=8.7 Hz, 1H, CH$_{pyri(5)}$), 6.48 (t, $^3$J$_{HH}$=7.3 Hz, 1H, CH$_{pyri(4)}$).

$^{13}$C{$^1$H} QDEPT NMR (100.67 MHz, C$_6$D$_6$, 25° C.): δ 30.49 (s, 12C, (CH$_3$)$_3$CP), 31.19 (s, 12C, (CH$_3$)$_3$CP), 37.29 (d, $^1$J$_{PC}$=14.1 Hz, 1C, CH$_2$P), 37.64 (d, $^1$J$_{PC}$=11.5 Hz, 2C, (CH$_3$)$_3$CP), 39.94 (d, $^1$J$_{PC}$=17.2 Hz, 2C, (CH$_3$)$_3$CP), 67.52 (d, $^1$J$_{PC}$=40.2 Hz, 1C, CHP), 102.11 (d, $^3$J$_{PC}$=7.6 Hz, 1C, CH$_{pyri(3)}$), 113.08 (d, $^3$J$_{PC}$=15.0 Hz, 1C, CH$_{pyri(5)}$), 131.96 (s, 1C, CH$_{pyri(4)}$), 157.85 (s, 1C, C$_{pyri(6)}$), 171.75 (d, $^2$J$_{PC}$=17.2 Hz, 21.0 Hz, 1C, C$_{pyri(2)}$), 224.66 (br, 2C, Mn—CO), 226.27 (br, 1C, Mn—CO).

IR (KBr, pellet, cm$^{-1}$): 1884, 1924, 2020 ((ν$_{3CO\ antisymmetric}$+ν$_{3CO\ antisymmetric}$)+ν$_{3CO\ symmetric}$ in 10:10:1 ratio).

Elemental analysis (C$_{26}$H$_{42}$MnNO$_3$P$_2$) calculated (found): C, 58.53 (59.27) H, 7.94 (8.25) N, 2.63 (2.60) %.

cis-[Mn(PNP*$^{tBu}$)(CO)$_2$] (2)

mer-[Mn(PNP$^{tBu}$)(CO)$_3$]Br (2A) (150 mg, 0.24 mmol) was suspended in 7 mL THF. KO$^t$Bu (27 mg, 0.24 mmol) was dissolved in 5 mL THF and added dropwise to the suspension to give a brown solution. The solution was subsequently transferred to a Schlenk tube. The closed vessel was heated (oil-bath temperature of 90° C.) and purged ten times in 5 min intervals with a stream of argon followed by careful degassing under reduced pressure. Eventually the solvent was removed completely under reduced pressure. The resulting dark blue powder was dissolved in 10 mL of n-pentane and filtered through a Teflon syringe filter (0.2 μm). The solution was kept at −38° C. in a freezer for 48 h to form dark blue crystals. The crystals were decanted and dried under vacuum. (77 mg, 60% yield).

$^{31}$P{$^1$H} NMR (202.5 MHz, C$_6$D$_6$, 25° C.): δ 87.15 (d, $^2$J$_{PP}$=68.2 Hz, 1P, PCH=C), 101.30 (d, $^2$J$_{PP}$=68.1 Hz, 1P, PCH$_2$C).

$^1$H NMR (500.13 MHz, C$_6$D$_6$, 25° C.): 1.00 (d, $^3$J$_{PH}$=12.7 Hz, 18H, ((CH$_3$)$_3$CP), 1.28 (d, $^3$J$_{PH}$=13.0 Hz, 18H, ((CH$_3$)$_3$CP), 2.77 (d, $^2$J$_{HP}$=9.2 Hz, 2H, PCH$_2$), 3.82 (s, 1H, PCH), 5.45 (d, $^3$J$_{HH}$=5.9 Hz, 1H, CH$_{pyri(3)}$), 6.36 (m, 1H, CH$_{pyri(4)}$), 6.40 (m, 1H, CH$_{pyri(5)}$).

$^{13}$C{$^1$H} QDEPT NMR (125.76 MHz, C$_6$D$_6$, 25° C.): 29.34 (d, $^2$J$_{CP}$=3.9 Hz, 6C, (CH$_3$)$_3$CP), 29.92 (d, $^2$J$_{CP}$=3.8 Hz, 6C, (CH$_3$)$_3$CP), 34.88 (d, $^1$J$_{CP}$=13.4 Hz, 1C, PCH$_2$), 36.11 (d, $^1$J$_{CP}$=13.7 Hz, 2C, (CH$_3$)$_3$CP), 37.65 (d, $^1$J$_{CP}$=21.6 Hz, 2C, (CH$_3$)$_3$CP), 71.42 (d, $^1$J$_{CP}$=43.9 Hz, 1C, PCH=C), 99.50 (d, $^3$J$_{PC}$=10.1 Hz, 1C, CH$_{pyri(3)}$), 117.06 (d, $^3$J$_{PC}$=17.3 Hz, 1C, CH$_{pyri(5)}$), 132.06 (s, 1C, CH$_{pyri(4)}$), 160.93 (dd, $^{2,3}$J$_{PC}$=5.2 Hz, 8.4 Hz, 1C, C$_{pyri(6)}$), 174.22 (dd, $^{2,3}$J$_{PC}$=5.8 Hz, 21.0 Hz, 1C, C$_{pyri(2)}$), 239.25(t, $^2$J$_{CP}$=17.3 Hz. 2C, Mn—CO).

IR (KBr, pellet, cm$^{-1}$): 1833, 1904 (ν$_{2CO\ symmetric}$+ν$_{2CO\ antisymmetric}$, 1:1 ratio).

Elemental analysis (C$_{25}$H$_{42}$MnNO$_2$P$_2$) calculated (found): C, 59.40 (59.72) H, 8.37 (8.46) N, 2.77 (2.70) %.

Example 4

Diffusion Ordered Spectroscopy (DOSY) NMR Experiments of the Manganese Complexes 1 and 2

Diffusion NMR measurements were carried out on a Bruker 400 MHz Avance III NMR spectrometer equipped with a z-gradient system capable of producing a maximal pulse gradient of about 50 gauss cm$^{-1}$ in the z-direction. These diffusion experiments were performed using the longitudinal eddy currents diffusion (LED) sequence with the following parameters: 4 ms duration of sine shape pulse-gradients, which were incremented from 0.7 to 33.4 G cm$^{-1}$ in ten steps and the pulse gradient separation was 30 ms. All measurements were performed three times and the reported diffusion coefficients are the average±standard deviation of three experiments. The measurements were performed at 298.0 K using C$_6$D$_6$ used as a solvent.

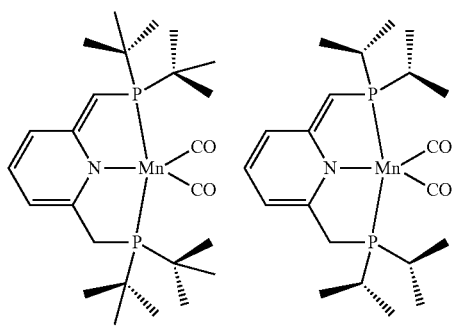

Molecular weight: 507.51    Molecular weight: 451.40

DOSY mesured diffusion coefficients:

$D = (0.705 \pm 0.01) \times 10^{-5} \text{ cm}^2 \text{ } S^{-1}$ $D = (0.735 \pm 0.02) \times 10^{-5} \text{ cm}^2 \text{ } S^{-1}$ The connection between diffusion coefficients and the mass of the molecoule, is given by the following relation:

$$\sqrt[3]{\frac{M_j}{M_i}} \le \frac{D_i}{D_j} \le \sqrt{\frac{M_j}{M_i}}$$

The ratio of mesured diffusion coefficients $D_2/D_1 = 1.04255$

Mass ratio range according to the measured diffusion coefficients $1.087 \le \frac{M_j}{M_i} \le 1.133$ The calculated mass ratio, is in between the range:

$\frac{M_{tBu}}{M_{iPr}} = \frac{507.5}{451.4} = 1.124$

The measured diffusion values suit the calculated mass ratio. Complex 2 exists as a monomer in both solution and solid state. DOSY experiment suggests that, complex 1 has similar diffusion values with that of 2, and hence it has a similar size. This confirms existence of 2 as a monomer in solution. (FIG. 9)

Example 5

Dehydrogenative Coupling of Benzyl Alcohol and Benzylamines Using the Manganese Complexes of this Invention The dehydrogenative coupling reaction of benzyl alcohol and benzylamine to give N-benzylidene-1-phenylmethanamine was chosen as a model system. Thus, a dry toluene solution containing equimolar amounts of benzyl alcohol and benzylamine, and a catalytic amount of complexes 1 or 2 was heated at 135° C. (bath temperature) for the specified time (Table 2). The products were analyzed by GC-MS and NMR spectroscopy and identified by comparison with authentic samples. Heating a solution of benzyl alcohol (0.5 mmol) and benzylamine (0.5 mmol) with the pyridine-based PNP manganese complex 2 (4 mol %) in a closed system under nitrogen atmosphere at 135° C. in toluene (2 mL) resulted in 76% conversion to N-benzylidene-1-phenylmethanamine after 30 h (Table 2, entry 1). Analysis of the gas phase by GC revealed the formation of $H_2$. Using complex 1, under the same conditions, 60% of N-benzylidene-1-phenylmethanamine was formed (Table 2, entry 2). No side products, like amide or ester were observed under the catalytic condition as seen in case of ruthenium catalysis [B. Gnanaprakasam, J. Zhang, D. Milstein, Angew. Chem. Int. Ed. 2010, 49, 1468.]. Interestingly, no hydrogenated product like, dibenzylamine was observed in this case. Moreover, when the reaction was carried out with complex 2 in benzene (2 mL) for 36 h in a closed system, it resulted in 85% consumption of benzyl alcohol and 82% yield of N-benzylidene-1-phenylmethanamine, together with a small amount of unreacted aldehyde, generated from the alcohol (Table 2, entry 3). Lowering the manganese complex (2) loading to 3 mol % or 2 mol % resulted in 89% and 62% yield of N-benzylidene-1-phenylmethanamine, respectively, after 48 h (Table 2, entries 4 and 5). However, prolonging the reaction time to 60 h using 3 mol % of complex 2 resulted in 92% yield of the desired imine (Table 2, entry 6). It is noteworthy that when the dehydrogenation reaction was carried out in an open system under an argon atmosphere, 94% of N-benzylidene-1-phenylmethanamine was furnished, comparable yield with that of the closed system (Table 2, entries 6 and 7). Use of polar solvents seems to have an adverse effect on the rate of the catalytic reaction. Thus, when the reaction was carried out using dioxane or THF as solvents, only <5% of N-benzylidene-1-phenylmethanamine was formed in both the cases (Table 2, entries 8 and 9), the rest being the starting compounds (Table 2).

TABLE 2

Optimization of the reaction conditions for the dehydrogenative coupling of benzyl alcohol and benzylamine.[a]

| Entry | Mn cat (mol %) | Solvent | Time (h) | Conv. (%)[b] | Yield of imine (%)[c] |
|---|---|---|---|---|---|
| 1 | 2 (4) | toluene | 30 | 76 | 76 |
| 2 | 1 (4) | benzene | 36 | 85 | 82 |
| 3 | 2 (3) | benzene | 48 | 90 | 89 |
| 4 | 2 (2) | benzene | 48 | 62 | 62 |
| 5 | 2 (3) | benzene | 60 | 92 | 92 |
| 6 | 2 (3) | benzene | 60 | 94 | 94[d] |
| 7 | 2 (3) | dioxane | 60 | <5 | <5 |
| 8 | 2 (3) | THF | 60 | <5 | <5 |

[a]Reaction condition: alcohol (0.5 mmol), amine (0.5 mmol), Mn cat, solvent (2 mL) at 135° C. (bath temperature) in a closed system under nitrogen atmosphere;
[b]based on the consumption of benzyl alcohol;
[c]yields were determined by $^1$H NMR spectroscopy with respect to toluene or dioxane as an internal standard or by GC-analysis;
[d]reaction was carried out under argon atmosphere in an open system.

Example 6

Dehydrogenative Coupling of Various Alcohols and Amines Using the Manganese Complexes of this Invention Under the optimized conditions (Table 2, entry 6), the substrate scope of the manganese-catalysed dehydrogenative coupling of alcohols and amines was explored. A variety of substituted benzyl alcohols undergo efficient dehydrogenative coupling with amines containing either electron-donating or -withdrawing substituents (Table 3). Thus, heating a solution of benzyl alcohol with cyclohexylamine or 2-phenylethylamine using catalyst 2 at 135° C. in benzene (2 mL) in a closed system resulted in the formation of the corresponding imines exclusively in 93% and 95% yields, respectively (Table 3, entries 1 and 2). Similarly, 4-methoxybenzylamine and 4-fluorobenzylamine react with benzyl alcohol under similar reaction conditions gave 97% and 52% of the corresponding imines (Table 3, entries 3 and 4). Analysis of the reaction mixture in latter case by $^1$H NMR and GC-MS indicated the presence of the starting materials and a small amount of aldehyde, generated in-situ from the corresponding alcohols by dehydrogenation. Complex 2 also catalysed effectively the reaction of 4-methoxybenzyl alcohol with benzylamine, cyclohexylamine, and 4-fluorobenzylamine to afford the corresponding imines in 93%0, 78%, and 73% yields, respectively (Table 3, entries 5-7). Use of amines bearing electron donating substituents resulted in higher yields than amines with electron withdrawing substituents, presumably because of higher nucleophilicity of the former. When hexylamine reacted with 4-methoxybenzyl alcohol only 50% of the corresponding imine was formed under analogous reaction conditions (Table 3, entry 8). Prolonging the reaction time slightly increased the yield of the desired imine. Reaction of 3,4-dimethoxybenzyl alcohol with 2-phenylethylamine or cyclohexylamine furnished the corresponding imines in 99% and 78% yields, respectively (Table 3, entries 9 and 10), 4-methylbenzyl alcohol reacted with the 4-fluorobenzylamine to yield the corresponding imine in 65% yield and traces of aldehyde (Table 3, entry 11). Alcohols with an electron withdrawing substituent at the para-position also underwent the catalytic reaction. Thus, reaction of 4-fluorobenzyl alcohol with benzylamine or cyclohexylamine using catalyst 2 produced 91% and 78% of the corresponding imines, respectively (Table 3, entries 12 and 13). Further, the catalytic reaction of 4-chlorobenzyl alcohol with benzylamine and cyclohexylamine under analogous reaction conditions yielded 99% and 70% of the corresponding imines, respectively (Table 3, entries 14 and 15). However, the reaction with aliphatic amines under analogous reaction conditions proceeds slowly and reaction of 4-cholorobenzyl alcohol with hexylamine produced the imine in 45% yield (Table 3, entry 16). The lower yield of hexylamine compared to cyclohexylamine could be attributed to the higher nucleophilicity of the latter. Aliphatic alcohols also react with an aliphatic amine under the reaction condition to give the imine, albeit slower rate. Thus, 1-hexanol reacts with cyclohexylamine to yield the corresponding imine in 30% yield (Table 3, entry 18). Prolonging the reaction time did not increase the yield of the desired amine appreciably.

TABLE 3

Dehydrogenative coupling of various alcohols and amines catalyzed by 2.[a]

R—OH + R$_1$—NH$_2$ $\xrightarrow[\text{benzene, 135° C. 60 h}]{\text{Mn cat 2 (3 mol \%)}}$ R—N—R$_1$ + H$_2$ + H$_2$O

| Entry | Alcohol | Amine | Imine | Conv. (%)[b] | Yield (%)[c] |
|---|---|---|---|---|---|
| 1 | benzyl alcohol | cyclohexylamine | N-benzylidene cyclohexylamine | 97 | 93 |
| 2 | benzyl alcohol | 2-phenylethylamine | N-benzylidene-2-phenylethylamine | 96 | 95 |
| 3 | benzyl alcohol | 4-methoxybenzylamine | N-benzylidene-4-methoxybenzylamine | 99 | 97 |
| 4 | benzyl alcohol | 4-fluorobenzylamine | N-benzylidene-4-fluorobenzylamine | 55 | 52 |
| 5 | 4-methoxybenzyl alcohol | benzylamine | N-(4-methoxybenzylidene)benzylamine | 93 | 93 |

TABLE 3-continued

Dehydrogenative coupling of various alcohols and amines catalyzed by 2.[a]

$$R\text{—}OH + R_1\text{—}NH_2 \xrightarrow[\substack{\text{benzene,}\\ 135°\text{C.}\\ 60\text{ h}}]{\substack{\text{Mn cat 2}\\ (3\text{ mol \%})}} R\text{—}CH\text{=}N\text{—}R_1 + H_2 + H_2O$$

| Entry | Alcohol | Amine | Imine | Conv. (%)[b] | Yield (%)[c] |
|---|---|---|---|---|---|
| 6 | 4-MeO-C6H4-CH2OH | cyclohexylamine | 4-MeO-C6H4-CH=N-cyclohexyl | 85 | 78 |
| 7 | 4-MeO-C6H4-CH2OH | 4-F-C6H4-CH2NH2 | 4-MeO-C6H4-CH=N-CH2-C6H4-4-F | 73 | 73 |
| 8 | 4-MeO-C6H4-CH2OH | n-pentyl-NH2 | 4-MeO-C6H4-CH=N-pentyl | 50 | 50 |
| 9 | 3,4-(MeO)2-C6H3-CH2OH | PhCH2CH2NH2 | 3,4-(MeO)2-C6H3-CH=N-CH2CH2Ph | >99 | >99 |
| 10 | 3,4-(MeO)2-C6H3-CH2OH | cyclohexylamine | 3,4-(MeO)2-C6H3-CH=N-cyclohexyl | 91 | 78 |
| 11 | 4-Me-C6H4-CH2OH | 4-F-C6H4-CH2NH2 | 4-Me-C6H4-CH=N-CH2-C6H4-4-F | 71 | 65 |
| 12 | 4-F-C6H4-CH2OH | PhCH2NH2 | 4-F-C6H4-CH=N-CH2Ph | 95 | 91 |
| 13 | 4-F-C6H4-CH2OH | cyclohexylamine | 4-F-C6H4-CH=N-cyclohexyl | 80 | 78 |

TABLE 3-continued

Dehydrogenative coupling of various alcohols and amines catalyzed by 2.[a]

$$R\text{-}CH_2OH + R_1\text{-}CH_2NH_2 \xrightarrow[\text{benzene, 135° C., 60 h}]{\text{Mn cat 2 (3 mol \%)}} R\text{-}CH=N\text{-}CH_2R_1 + H_2 + H_2O$$

| Entry | Alcohol | Amine | Imine | Conv. (%)[b] | Yield (%)[c] |
|---|---|---|---|---|---|
| 14 | 4-Cl-C6H4-CH2OH | PhCH2NH2 | 4-Cl-C6H4-CH=N-CH2Ph | >99 | >99 |
| 15 | 4-Cl-C6H4-CH2OH | CyNH2 | 4-Cl-C6H4-CH=N-Cy | 75 | 70 |
| 16 | 4-Cl-C6H4-CH2OH | n-C5H11-NH2 | 4-Cl-C6H4-CH=N-C5H11 | 57 | 45 |
| 17 | n-C5H11-CH2OH | CyNH2 | n-C4H9-CH=N-Cy | 42 | 30 |

[a]Reaction condition: alcohol (0.5 mmol), amine (0.5 mmol), Mn cat (3 mol %), benzene (2 mL) at 135° C. (bath temperature) for 60 h in a closed system under nitrogen atmosphere;
[b]based on the consumption of alcohol;
[c]yields were determined by $^1$H NMR spectroscopy with respect to toluene or dioxane as an internal standard or by GC-analysis.

Example 7

Proposed Mechanism for the Formation of Imines

To gain insight about possible intermediates and mechanistic implications during the reaction course, reaction of complex 2 with benzyl alcohol was monitored by $^{31}$P{$^1$H}NMR spectroscopy (FIG. 7). Complex 2 exhibits a set of two sharp doublets at δ 87.15 and 101.3 ppm ($^2J_{P\text{-}P}$=68.2 Hz) in the $^{31}$P{$^1$H} NMR spectrum (FIG. 7A). Upon dissolving it in benzyl alcohol (270 equivalents), a dramatic change in the $^{31}$P NMR spectrum was observed, with the appearance of a broad singlet at δ 104.5 ppm, signifying a dynamic process taking place (FIG. 7B). This could be due to the reversible formation of an alkoxo complex with concomitant aromatization of the pincer ligand. In order to verify this, independently the alkoxo complex [Mn(PNP$^{tBu2}$OCH$_2$Ph)(CO)$_2$] (9) was synthesized by adding 3 eq of benzyl alcohol into a saturated pentane solution of complex 2. Storing the reaction mixture at −38° C. for 72 h resulted formation of single crystals of complex 9. The molecular structure of 9 was unambiguously established by single crystal X-ray diffraction analysis (FIG. 5A), which revealed the activation of the O—H bond of the benzyl alcohol by complex 2. Complex 9 exhibits a Mn(I) center in a distorted octahedral geometry, with the alkoxo moiety bound in an axial position to the manganese center. The IR spectrum of 9 exhibits absorption bands at 1814 and 1891 cm$^{−1}$ that are characteristic of an octahedral di-carbonyl compound in a cis arrangement. In continuation of the NMR experiment, after 20 minutes from addition of benzyl alcohol to complex 2, a new set of two sharp AB doublets appeared in solution at δ 120.2 and 126.2 ppm ($^2J_{P\text{-}P}$=106.4 Hz, FIG. 7C), which was assigned to the aldehyde adduct, [Mn(PNP$^{tBu}$OCHPh)(CO)$_2$] (10, FIG. 5B), and was independently prepared. Formation of complex 10 presumably involves the dehydrogenation of benzyl alcohol to benzaldehyde by 2 through a double hydrogen transfer (FIG. 4). Accordingly, the proposed mechanism of this process suggests that the dehydrogenation of the alcohol proceeds through a (presumably concerted) bifunctional proton and hydride transfer, illustrated as transition state C (FIG. 4). It is noteworthy to mention that, formation of the aldehyde by direct β-H elimination of the alkoxy ligand of the coordinatively saturated complex 9 is less likely. The identity of 10 was also verified by its independent synthesis. Thus, treating a saturated THF solution of complex 2 with 2 eq of benzladehyde separately, followed by exposure to pentane vapour in a sealed 20 mL vial, after 72 h at room temperature formation of single crystals of 10 suitable for X-ray diffraction analysis was formed. The solid state structure of complex 10 shown in FIG. 5B indicates the aldehyde bound to the metal ligand framework in a cooperative fashion with Mn—O and C—O bonds. Complex 10 was separately dissolved in neat benzyl alcohol to verify the $^{31}$P NMR shift and was found to be in accordance with the NMR experiment (FIG. 7F). Moreover, in continuation of the NMR experiment, after 60 minutes a new singlet at δ 128.7 ppm appeared (FIGS. 7D and 7E). This was identified to be the hydride complex [Mn(PNP$^{tBu2}$—H)(CO)$_2$] (11). Interestingly, when this reaction mixture was pressurized with $H_2$, an increase in intensity of the singlet at δ 128.7 ppm was observed. This suggests the formation of the Mn—H complex 11. Moreover, complex 11 was separately synthesized by treatment of 2 with $H_2$ in $C_6D_6$. The $^1H$ NMR spectrum of complex 11 shows a hydride resonance at δ −4.19 ppm. The molecular structure of 11 as obtained from a single crystal x-ray analysis (FIG. 5C). It was separately dissolved in neat benzyl alcohol to verify the $^{31}P$ NMR shift and was found to be in accordance with the NMR experiment (FIG. 7F). Complex 11 then undergoes dehydrogenation under the catalytic condition to regenerate the active complex 2 which then enters into the second catalytic cycle (FIG. 4). On the other hand, the released aldehyde reacts with an amine to yield an unstable hemiaminal which releases a molecule of water to form the final imine product.

Example 8

Synthesis and Characterization of Intermediates in the Catalytic Dehydrogenation of Alcohols (Intermediate Complexes 9, 10 and 11)

Preparation of cis-[Mn(PNP$^{tBu}$—OCH$_2$Ph)CO)$_2$] (Intermediate Complex 9):

Benzyl alcohol (15 mg, 0.14 mmol) was added to 2.5 mL pentane solution of cis-Mn(PNP*$^{tBu}$)(CO)$_2$ (30 mg, 0.06 mmol) in 20 mL vial. The solution was kept at −38° C. in the freezer for 48 h. The obtained large red crystals were decanted, washed with pentane and dried under vacuum, Yield: 32 mg, 0.052 mmol, 86%.

Elemental analysis (C$_{32}$H$_{50}$MnNO$_3$P$_2$) calculated (found): C, 62.63 (62.52), H, 8.21 (8.32), N, 2.28 (1.90) %.

IR (KBr, pellet, cm$^{-1}$): 1814, 1891 ($\nu_{2CO\ symmetric}$+$\nu_{2CO\ antisymmetric}$, 1:1 ratio).

Figure 5A:
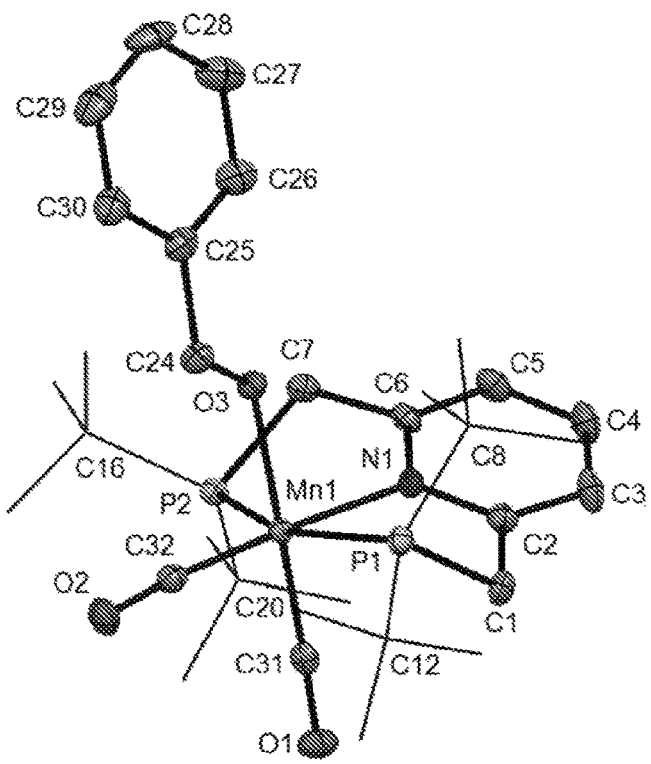
FIG. 5A-5C depict the molecular structures of complexes 9, 10, and 11 (which are intermediates in the cycle presented in FIG. 4) with thermal ellipsoids set at 50% probability. Hydrogen atoms were omitted for calrity, except the Mn—H in structure 11. The P(ᵗBu)₂ groups are drawn as wire frames.

FIG. 5A presents X-ray structure of the intermediate complex 9.

TABLE 4

Selected bond lengths and angles of the manganese intermediate complex 9:

| Bond Distances [Å] | | Bond Angle [°] | |
|---|---|---|---|
| Mn1—P1 | 2.3863(9) | P1—Mn1—P2 | 158.27(3) |
| Mn1—P2 | 2.3524(9) | P1—Mn1—O3 | 92.78(6) |
| Mn1—O3 | 2.0130(19) | P1—Mn1—N1 | 77.87(7) |
| Mn1—N1 | 2.078(2) | P2—Mn1—N1 | 80.67(7) |
| Mn1—C31 | 1.769(3) | N1—Mn1—C32 | 176.84(11) |
| Mn1—C32 | 1.776(3) | C31—Mn1—O3 | 176.64(10) |
| C1—C2 | 1.508(4) | C31—Mn1—C32 | 85.36(12) |
| C6—C7 | 1.500(4) | P1—C1—C2 | 105.99(18) |
| C31—O1 | 1.170(3) | P2—C7—C6 | 109.74(18) |
| C24—O3 | 1.380(3) | C2—N1—C6 | 118.9(2) |

Preparation of cis-[Mn(PNP$^{tBu}$—OCHPh)(CO)$_2$] (Intermediate Complex 10):

Benzaldehyde (15 mg, 0.14 mmol) was added to 2.5 mL pentane solution of cis-Mn(PNP*$^{tBu}$)(CO)$_2$ (30 mg, 0.06 mmol) in 20 mL vial. The solution was kept at −38° C. in the freezer for 48 h. The obtained large red crystals were decanted, washed with pentane and dried under vacuum. (76% yield, 28 mg, 0.046 mmol).

$^{31}P\{^1H\}$ NMR (202.44 MHz, $C_6D_6$, 7° C.): δ 124.48 (d, $^2J_{PP}$=111.6 Hz, 1P, PCH$_2$), 130.55 (d, $^2J_{PP}$=111.6 Hz, 1P, PCHC).

$^{31}P\{^1H\}$ NMR (162.07 MHz, benzyl alcohol, 7° C.): δ 120.2 (d, $^2J_{PP}$=106.4 Hz, 1P, PCH$_2$), 126.2 (d, $^2J_{PP}$=106.4 Hz, 1P, PCHC).

$^1H$ NMR (500.08 MHz, $C_6D_6$, 7° C.): 1.09 (br, 18H, ((CH$_3$)$_3$CP), 1.51 (d, $^3J_{PH}$=11.8 Hz, 9H, ((CH$_3$)$_3$CP), 1.60 (br, 9H, ((CH$_3$)$_3$CP), 2.74 (dd, $^2J_{HH}$=15.9 Hz, $^3J_{PH}$=10 Hz, 1H, CH$_2$P), 3.19 (d, $^2J_{HH}$=15.9 Hz, 1H, PCH$_2$), 2.60 (d, $^2J_{HH}$=9.6 Hz, 2H, PCH$_2$), 4.37 (d, $^3J_{PH}$=8.9 Hz 1H, PCHC), 5.95 (s, 1H, CHCO), 6.31 (d, 1H, $^3J_{HH}$=7.4 Hz, CH$_{pyri(3)}$), 6.53 (d, 1H, $^3J_{HH}$=7.6 Hz, CH$_{pyri(5)}$), 6.58 (t, 1H, $^3J_{HH}$=7.6 Hz, C$_{pyri(4)}$), 7.05 (t, 1H, $^3J_{HH}$=7.1 Hz, C$_{pyri(4)}$), 7.22 (t, 1H, $^3J_{HH}$=7.5 Hz, CH$_{pyri(3,5)}$), 7.62 (d, 1H, $^3J_{HH}$=7.6 Hz, CH$_{Ph(2,6)}$.

$^{13}C\{^1H\}$ QDEPT NMR (125.75 MHz, $C_6D_6$, 25° C.): 30.64 (s, 12C, (CH$_3$)$_3$CP), 36.79 (d, $^1J_{CP}$=10.6 Hz, 1C, PCH$_2$), 37.1 (d, $^1J_{CP}$=22.3 Hz, 2C, (CH$_3$)$_3$CP), 37.8 (d, $^1J_{CP}$=14.7 Hz, 2C, (CH$_3$)$_3$CP), 56.22 (d, $^1J_{CP}$=6.3 Hz, 1C, PCHC), 77.47 (s, 1C, PhCHO), 118.51 (s, 1C, C$_{pyri(3)}$), 121.9 (s, 1C, CH$_{pyri(5)}$), 125.36 (s, 2C, CH$_{Ph}$), 127.28 (s, 3C, CH$_{Ph}$), 135.05 (s, 1C, CH$_{pyri(4)}$), 148.94 (s, 1C, CPh(ipso)), 161.69 (s, 1C, CH$_{pyri(6)}$), 164.81 (s, 1C, CH$_{pyri(2)}$), 233.99 (s, 1C, Mn—CO), 235.08 (s, 1C, Mn—CO).

Elemental analysis (C$_{32}$H$_{18}$MnNO$_3$P$_2$) calculated (found): C, 62.84 (62.07), H, 7.91 (7.95), N, 2.29 (1.74) %.

IR (KBr, pellet, cm$^{-1}$): 1820, 1899 ($\nu_{2CO\ symmetric}$+$\nu_{2CO\ antisymmetric}$, 1:1 ratio).

Figure 5B:
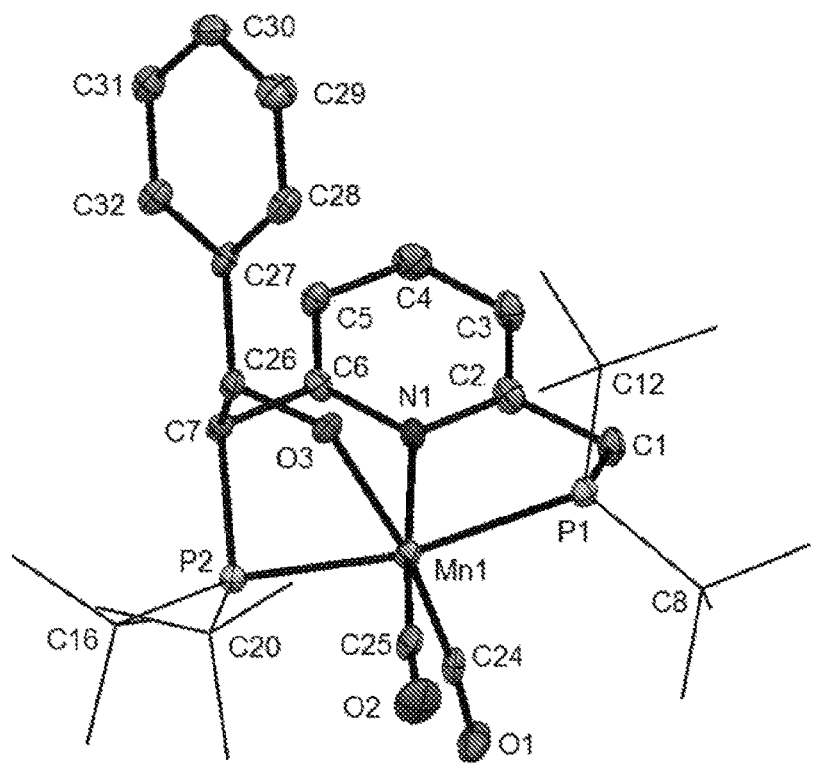
Figure 5C:
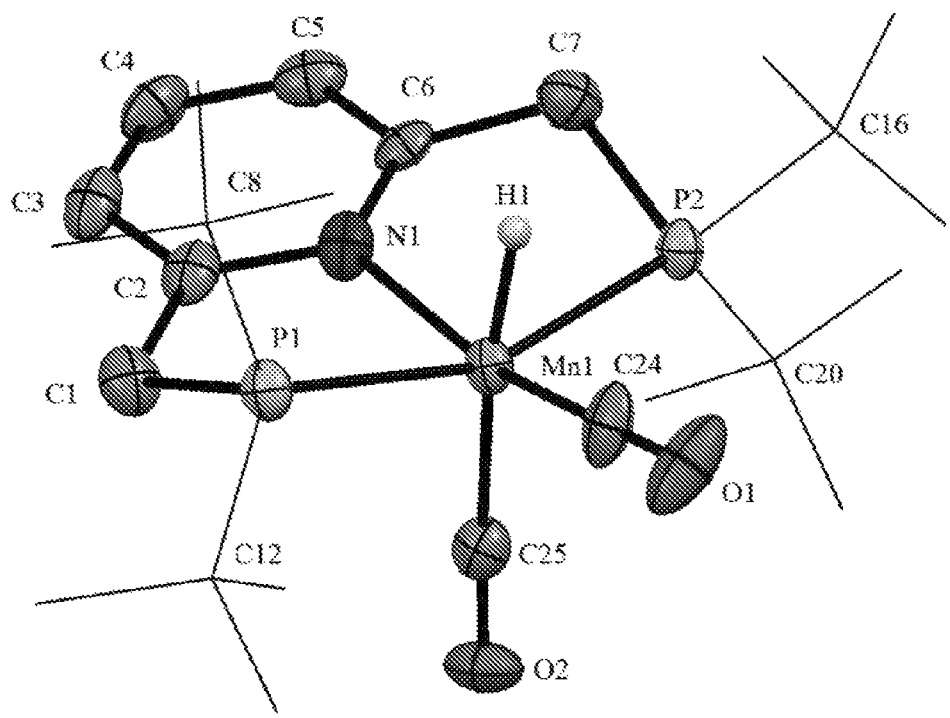
Figure 6:
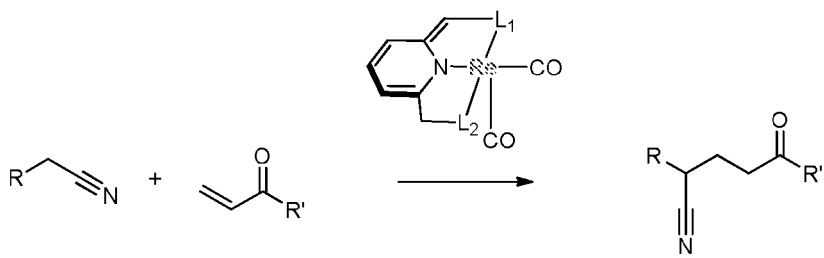
FIG. 6 is a schematic synthesis of Michael addition reaction: rhenium complex catalyzes conjugate addition of nitriles (where R is aryl) (up) and a manganese complex (2)
Figure 6:
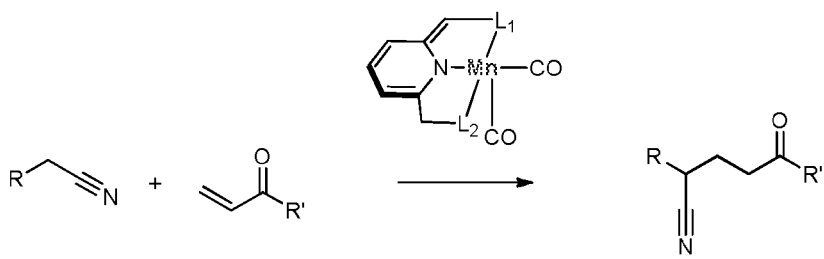

FIG. 5B presents X-ray structure of the intermediate complex 10.

TABLE 5

Selected bond lengths and angles of the manganese intermediate complex 10:

| Bond Distances [Å] | | Bond Angle [°] | |
|---|---|---|---|
| Mn1—P1 | 2.3161(15) | P1—Mn1—P2 | 162.77(6) |
| Mn1—P2 | 2.3325(15) | P1—Mn1—O3 | 97.18(10) |
| Mn1—O3 | 2.107(4) | P1—Mn1—N1 | 81.02(12) |
| Mn1—N1 | 2.057(4) | P2—Mn1—N1 | 81.78(12) |
| Mn1—C24 | 1.772(5) | N1—Mn1—C24 | 98.9(2) |
| Mn1—C25 | 1.792(5) | C24—Mn1—O3 | 170.21(19) |
| C7—C26 | 1.592(7) | N1—Mn1—C25 | 171.1(2) |
| C26—O3 | 1.392(6) | C25—Mn1—O3 | 93.44(18) |
| C1—P1 | 1.866(5) | P2—Mn1—N1 | 81.78(12) |
| C7—P2 | 1.871(4) | C7—C26—O3 | 109.7(4) |

Preparation of cis-[Mn(PNP$^{tBu}$—H)(CO)$_2$] (Intermediate Complex 11):

Hydrogen gas (2 atm) was pressured into a sealed 50 mL Schlenk tube containing 15 mL pentene solution of cis-Mn (PNP*$^{tBu2}$)(CO)$_2$ (30 mg, 0.06 mmol). The product precipitated as yellow powder, and transferred to 20 mL vial washed with pentane and dried under vacuum (92% yield, 28 mg, 0.055 mmol). Single crystal suitable for x-ray analysis received when concentrated (10 mg/mL), THF/pentene (1:1) solution of complex D was stored at the freezer (−38° C.) for 2 weeks.

$^{31}P\{^1H\}$ NMR (202.44 MHz, tol-d$_8$, 25° C.): δ 132.02 (s, 2P).

$^{31}P\{^1H\}$ NMR (162.07 MHz, benzyl alcohol, 25° C.): δ 128.7 (s, 2P).

$^1H$ NMR (500.08 MHz, tol-d$_8$, 25° C.): δ −4.19 (t, $^2J_{PH}$=52.9 Hz, Mn—H), 1.25 (s, 18H, (CH$_3$)$_3$CP), 1.38 (s, 18H, (CH$_3$)$_3$CP), 2.99 (d, $^2J_{HH}$=15.8 Hz, 2H, CH$_2$P), 3.12 (d, $^2J_{HH}$=16.1 Hz, 2H, CH$_2$P), 6.43 (s, 2H, CH$_{pyri(3,5)}$), 6.66 (s, 1H, CH$_{pyri(4)}$).

$^{13}C\{^1H\}$ QDEPT NMR (100.67 MHz, tol-d$_8$, 25° C.): δ 29.97 (s, 6C, (CH$_3$)$_3$CP), 30.33 (s, 6C, (C(H$_3$)$_3$CP), 36.25 (s, 2C, (CH$_3$)$_3$CP), 37.92 (s, 2C, (CH$_3$)$_3$CP), 39.07 (s, 2C, CH$_2$P), 118.59 (s, 2C, CH$_{pyri(3,5)}$), 133.26 (s, 1C, CH$_{pyri(4)}$), 163.66 (s, 2C, CH$_{pyri(2,6)}$), 230.22 (s, 1C, Mn—CO), 236.38 (s, 1C, Mn—CO).

FIG. 5C presents X-ray structure of the intermediate complex 11.

TABLE 6

Selected bond lengths and angles of the manganese intermediate complex 11:

| Bond Distances [Å] | | Bond Angle [°] | |
|---|---|---|---|
| Mn1—P1 | 2.2323(19) | P1—Mn1—P2 | 158.23(12) |
| Mn1—P2 | 2.265(2) | H1—Mn1—C25 | 164(4) |
| Mn1—H1 | 1.23(8) | P1—Mn1—N1 | 81.73(14) |
| Mn1—N1 | 2.105(6) | P2—Mn1—N1 | 83.26(15) |
| Mn1—C24 | 1.757(7) | N1—Mn1—C24 | 166.4(3) |
| Mn1—C25 | 1.810(7) | Mn1—C24—O1 | 179.4(6) |
| C1—C2 | 1.501(9) | N1—Mn1—C25 | 95.8(3) |
| C6—C7 | 1.501(9) | C24—Mn1—H1 | 88(3) |
| C1—P1 | 1.859(7) | P2—Mn1—N1 | 83.26(15) |
| C7—P2 | 1.840(6) | Mn1—C25—O2 | 176.8(6) |

Crystal data were measured at 100° K. on a Bruker Apex-II KappaCCD diffractometer equipped with [λ(Mo—Kα)=0.71073 Å] radiation, graphite monochromator and MiraCol optics. The data were processed with APEX-II collect package programs. Structures were solved by the AUTOSTRUCTURE module and refined with full-matrix least-squares refinement based on $F^2$ with SHELXL-97.

Example 9

Catalytic Michael Reactions with α-$CH_2$ Groups

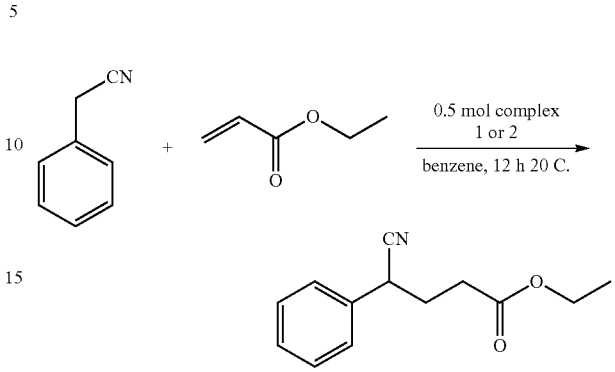

Mechanism:

The manganese complex 2 reacted with benzyl cyanide with formation of C—C and Mn—N bonds owing to a [1,3]-addition reaction mediated by a dearomatization/aromatization pathway as presented in the following scheme:

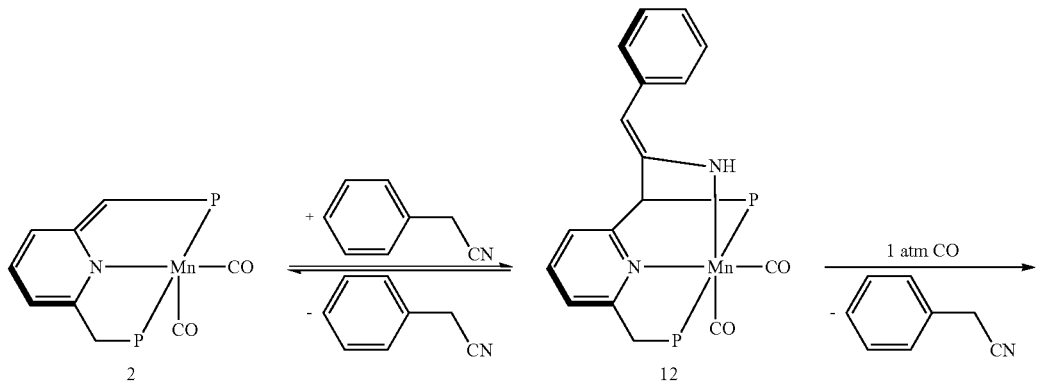

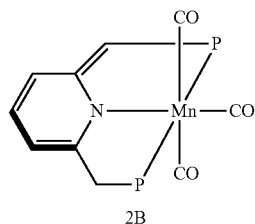

Upon addition of two equivalents of benzyl cyanide to a deep blue solution of complex 2 in THF a drastic color change to red is observed. Recrystallization from THF/n-pentane at −38° C. gives the enamido complex intermediate 12 [Mn(PNP$^{tBu}$—HNCH=CHPh)(CO)$_2$] as large red crystals in 85% yield. The $^{31}$P{$^1$H} NMR spectrum of 12 shows the expected two doublets of the AB-spin system for two phosphorus nuclei in different chemical environment at higher frequencies (126.6 and 140.1 ppm) and with a significantly larger coupling constant with respect to the dearomatized complex 2 ($^2J_{PP}$=100 Hz in 12 vs. 68 Hz in 2). The $^1$H NMR resonances centered at 4.39 ppm (s, amido 1H, Mn—NH) and 5.41 (s, olefinic 1H, C=CHPh) indicate the formation of an enamido motif in 12. The carbonyl stretches in the IR spectrum (KBr pellet) appear at 1832 and 1905 cm$^{-1}$ in a 1:1 ratio signifying a mutual cis-arrangement of both carbonyls.

An X-ray diffraction study of crystals of the enamido complex 12 (FIG. 8) exhibits a distorted octahedral coordination sphere, formed by the meridional PNP$^{tBu2}$ pincer ligand and two CO ligands in mutual cis-positions, and the amido moiety in an axial position. A short C26-C27 interatomic distance (1.383 Å) typical of a C=C double bond is observed, accompanied by a long C26-N2 (1.345 Å) bond indicating a C—N single bond adjacent to an sp$^2$ hybridized carbon. The [1,3]-addition of benzyl cyanide to 2 to form 12 is characterized by the newly formed C—C single bond between the exo-cyclic carbon of the pincer (C7-C26=1.540 Å), and a Mn—N bond (Mn1-N2=2.058 Å).

The [1,3]-addition of benzyl cyanide to 2 with C—C and Mn—N bond formation is reversible. This is clearly demonstrated when a solution of complex 12 in benzene is treated with one atmosphere of CO gas at ambient temperature. The dearomatized tris-carbonyl complex 3 is readily formed with concomitant displacement of benzyl cyanide. The reaction can be conveniently followed by $^{31}$P{$^1$H} NMR spectroscopy. Representative spectra of the transformation of 12 into 3 are shown in FIG. 10.

Catalytic Michael Reaction: As shown above, [Mn(PNP$^{tBu2}$*)(CO)$_2$] (2) readily reacts with benzyl cyanide to form the enamido complex 12. Both compounds 2 and 12 are potent catalysts for the Michael addition of benzyl cyanide to ethyl acrylate. At ambient temperature in benzene ethyl 4-cyano-4-phenylbutanoate is obtained within 12 h in 90% and 93% yield, respectively (1 mmol scale, 1:1 substrate ratio).

Example 10

Preparation of Manganese Complex 12 cis-[Mn(PNP$^{tBu}$—NHC=CHPh)(CO)$_2$] (12):

cis-Mn(PNP*$^{tBu}$)(CO)$_2$(2) (22 mg, 0.043 mmol) was dissolved in 1 mL THF in a 20 ml vial. Subsequently benzyl cyanide (10 mg, 0.085 mmol) was added resulting in a color change of the solution from dark blue to red. The solution was layered with 4 mL n-pentane and kept at −38° C. in the freezer for 48 h. The formed large red crystals were decanted, washed with n-pentane and dried under reduced pressure. (23 mg, 85% yield). $^{31}$P{$^1$H} NMR (162.07 MHz, C$_6$D$_6$, 25° C.): δ 126.64 (d, $^2J_{PP}$=98.6 Hz, 1P), 140.14 (d, $^2J_{PP}$=100.7 Hz, 1P). $^1$H NMR (400.36 MHz, C$_6$D$_6$, 25° C.): δ 0.69 (d(br), $^3J_{PH}$=10.7 Hz, 9H, (CH$_3$)$_3$CP), 1.00 (d, $^3J_{PH}$=10.5 Hz, 9H, (CH$_3$)$_3$CP), 1.39 (d, J$^3{}_{PH}$=12.1 Hz, 9H, (CH$_3$)$_3$CP), 1.58 (d, $^3J_{PH}$=11.7 Hz, 9H, (CH$_3$)$_3$CP), 2.76 (dd, $^2J_{HH}$=16.1 Hz $^2J_{HP}$=10.2 Hz, 1H, (CH$_2$)P), 3.21 (dd, $^2J_{HH}$=16.0 Hz, $^2J_{HP}$=3.7 Hz, 1H, (CH$_2$)P), 4.09 (d, $^2J_{HP}$=9.3 Hz 1H, PCH), 4.39 (s, 1H, Mn—NH), 5.41 (s, 1H, Ph-CH=C), 6.35 (d, $^3J_{HH}$=7.6 Hz, 1H, CH$_{(pyridine(3))}$), 6.73 (d, $^3J_{HH}$=7.6 Hz, 1H, CH$_{(pyridine(5))}$), 6.82 (t, $^3J_{HH}$=7.6 Hz, 1H, CH$_{(pyridine(4))}$), 6.90 (t, $^3J_{HH}$=7.3 Hz, 1H, CH$_{(aryl-para)}$), 7.29 (t, $^3J_{HH}$=7.7 Hz, 2H, CH$_{(aryl-meta)}$), 7.49 (d, $^3J_{HH}$=7.7 Hz, 2H, CH$_{(aryl-ortho)}$).$^{13}$C{$^1$H} NMR (100.67 MHz, C$_6$D$_6$, 25° C.): δ 30.02 (br, 3C, (CH$_3$)$_3$CP), 30.76, 30.98, 31.17 (3 peaks overlapping, 9C, (CH$_3$)$_3$CP), 36.84 (br, 2C, (CH$_3$)$_3$CP), 37.20 (d, $^1J_{PC}$=11.8 Hz, 1C, PCH$_2$), 37.81 (m, 2C, (CH$_3$)$_3$CP), 63.25 (d, $^1J_{PC}$=9.9 Hz, 1C, PCH), 91.19 (s, 1C, Ph-CH=C), 118.34 (d, $^2J_{PC}$=6.6 Hz, 1C CH$_{(pyridine(3))}$), 118.79 (d, $^2J_{PC}$=5.9 Hz, 1C CH$_{(pyridine(5))}$), 119.79 (s, 1C, CH$_{(aryl-para)}$), 123.30 (s, 2C, CH$_{(aryl-ortho)}$), 128.70 (s, 2C, CH$_{(aryl-meta)}$), 136.10 (d, $^2J_{PC}$=5.9 Hz, 1C CH$_{(pyridine(4))}$), 144.03 (s, 1C, C$_{iso\ (aryl)}$), 154.31 (d, $^2J_{PC}$=9.2 Hz, 1C, C$_{iso\ (pyridine)}$), 161.00 (d, $^2J_{PC}$=4.9 Hz, 1C, C$_{ipso\ (pyridine)}$), 165.18 (m, 1C, CH=C—NH), 232.83 (br, 1C, Mn—CO), 234.92 (br, 1C, Mn—CO). IR (KBr, pellet, cm$^{-1}$): 1832, 1905 (ν$_{2CO\ symmetric}$+ν$_{2CO\ antisymmetric}$, 1:1 ratio). Elemental analysis (C$_{33}$H$_{49}$MnN$_2$O$_2$P$_2$) calculated (found): C, 63.66 (64.25) H, 7.93 (8.24) N, 4.50 (4.11) %.

The X-ray structure of complex 12 is presented in FIG. 8.

Example 11

Catalytic Michael Reactions with Aliphatic Nitriles

Procedure for the Catalytic Reactions of Aliphatic Nitriles and Benzyl Cyanide with α,β-Unsaturated Esters and Ketones Procedure A (with Additional Solvent):

A stock solution containing 5 mg/mL (0.01 mmol/mL) of cis-[Mn(PNP*$^{tBu}$)(CO)$_2$] (2) in the particular reaction media (solvent: C$_6$H$_6$, THF, DCM, or n-pentane) was prepared. To 0.5 mL of the stock solution (0.005 mmol catalyst) 1 mmol of nitrile is added followed by the addition of 1 mmol of the specific α,β-unsaturated compound. The mixture stirred at room temperature (~22° C.) for the indicated time and quenched by introduction of non-dried n-pentane. The yield was determined by integration of $^1$H NMR signals with respect to the suitable standard either toluene for the reaction in THF, dichloromethane, and n-pentane, or dioxane for C$_6$H$_6$ (done before quenching). The products were purified according to the indicated method, isolated yields are reported.

Procedure B (Neat Nitrile):

A stock solution of propionitrile containing 5 mg/mL (0.01 mmol/mL) of cis-[Mn(PNP*$^{tBu2}$)(CO)$_2$] (2) was prepared. To 0.5 mL of stock solution (0.005 mmol catalyst) 1 mmol of the specific α,β-unsaturated compound is added. The mixture stirred at room temperature (~22° C.) for the indicated time and quenched by introduction of non-dried n-pentane. The yield was determined by integration of $^1$H NMR signals with respect to toluene as an external standard. The products were purified according to the indicated method, isolated yields are reported.

Results:

A variety of aliphatic nitriles (R—CN wherein R=Me, Et, n-Pr, n-Bu, Table 7; entries 1-5) went facile Michael addition to ethyl acrylate catalyzed by complex 2 (0.5 mol %). The catalytic reactions were performed on a 2.5 mmol scale with a nitrile:ethyl acrylate ratio of 1:1, using benzene as solvent. The γ-cyanoesters were obtained in moderate to excellent yields. A common observed side product was the double addition product of two nitrile donors to ethyl acrylate, resulting in moderate yields for the addition reactions of acetonitrile (entry 1) to ethyl acrylate. When acetonitrile was used as a solvent (entry 2) the mono addition product was formed exclusively. Remarkably, the addition reaction of propionitrile to ethyl acrylate occurs very selectively in high yield and short reaction time (entry 3).

rate and selectivity was observed in the addition of propionitrile to trans-methyl crotonate (entry 8). After an extended reaction time of 24 h only 40% conversion of the crotonate was detected and the desired addition product was

TABLE 7

Michael addition of aliphatic nitriles to ethyl acrylate catalyzed by 2.

| Entry | R | Time (h) | Conversion (%) | Yield (%) | Product |
|---|---|---|---|---|---|
| 1 | H | 20 | 69 | 26(21) | |
| | | | | 20(17) | |
| 2[a] | H | 40 | 90 | 89(83) | |
| 3 | CH$_3$ | 6 | >99 | 93(82) | |
| 4 | CH$_3$CH$_2$ | 40 | 57 | 48(29) | |
| 5 | CH$_3$CH$_2$CH$_2$ | 40 | 72 | 67(48) | |
| 6 | Ph | 12 | >99 | 94(84) | |

Reaction conditions: A solution containing 2.5 mmol of the substrates in a 1:1 ratio and 0.5 mol % complex 2 in 2 mL benzene was stirred under nitrogen at ambient temperature.
[a]acetonitrile used as a solvent.
Conversion with respect to the ethyl acrylate was determined by $^1$H NMR spectroscopic analysis with suitable internal reference. The yields are determined by 1H NMR spectroscopy analysis using reference substance (isolated yields are given in parenthesis).

α,β-unsaturated carbonyl compounds as suitable acceptors were studied. Table 8 exhibits reactions of propionitrile with various acrylates, methyl crotonate and cyclohex-2-enone (entries 1-8). The reactions were performed on a 1 mmol scale with respect to the Michael acceptor. The reactions given in entries 4-8 were performed in neat propionitrile as solvent. The reaction tolerates ketones (entry 2) as well as flourinated esters (entry 3), however the reaction with phenyl acrylate proceeds at a slow rate (entry 4). The effect of terminal substitution of the double bond in the Michael acceptor is significant. Reduction in the reaction formed in only 18% yield. In contrast, acceptors bearing a substituted terminal double bond react well. Thus, under the same reaction conditions, methyl methacrylate (entry 5) showed full conversion already after 12 h with the product obtained in 92% yield. Similarly, trifluoroethyl methacrylate resulted in 93% yield after 5 hours (entry 6). The very reactive Michael acceptor cyclohex-2-enone (entry 7) showed a tendency for homo-addition reactions to form [1,1'-bi(cyclohexan)]-6-ene-2,3'-dione causing low yield of the desired product.

TABLE 8

Michael addition reaction of propionitrile to α,β-unsaturated carbonyl compounds catalyzed by complex 2.

| Entry | Nitrile | Acceptor | Time (h) | Conversion (%) | Yield (%) | Product |
|---|---|---|---|---|---|---|
| 1 |  | 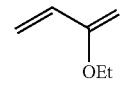 | 5 | >99 | 93(71)[a] | 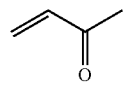 |
| 2 | | 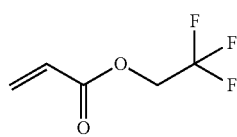 | 2 | >99 | 86(84)[a] | 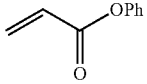 |
| 3 | | 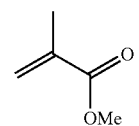 | 2 | >99 | 93(71)[a] | 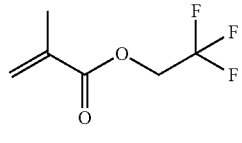 |
| 4 | | 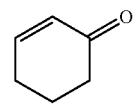 | 26 | 58 | 52 | 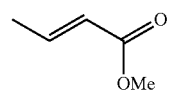 |
| 5 | | | 12 | >99 | 92(92)[a] | |
| 6 | | | 5 | >99 | 93(90)[a] | |
| 7 | | | 5 | >99 | 33 | |
| 8 | | | 24 | 40 | 18 | |

Reaction conditions: 1 mmol of substrates, ratio 1:1. Complex 2 0.5 mol %, ambient temperature, 0.5 mL solvent: for entries 1-3 benzene; and for entries 4-8 neat propionitrile. The conversion, with respect to the acceptor, is determined by $^1$H NMR spectroscopic analysis. The yields are determined by $^1$H NMR spectroscopic analysis using reference substance. [a]isolated yield. For details see Supporting Information (page S18).

Example 12

Mechanistic Studies of Michael Reaction Using Aliphatic Nitriles with Complex 2

Non-activated, aliphatic nitriles are suitable substrates for Michael-type C—C couplings catalyzed by complex 2. The binding of propionitrile to 2 by means of temperature dependent NMR spectroscopy was studied. The $^{31}P\{^1H\}$ NMR spectrum of a solution containing complex 2 and twelve equivalents of propionitrile in n-pentane at ambient temperature showed dynamic behavior with broad resonances assigned to the dearmomatized complex 2 (d 83.9 and d 98.9 ppm, $^2J_{PP}$=68 Hz). Upon cooling the sample stepwise to 235 K a new set of doublets at 126.5 and 163.8 ppm appears (AB system with $^2J_{PP}$=107 Hz, FIG. 11) indicating reversible binding of propionitrile to complex 2. The following thermochemical parameters for the binding of propionitrile to complex 2 were derived from a Vant Hoff plot: ΔH=−13.6 kcal/mol and ΔS=69.4 cal/molK.

In contrast to the reaction of 2 with benzyl cyanide (See Example 8), the $^{31}P\{^1H\}$ NMR spectrum of the reaction with propionitrile in n-pentane shows resonances significantly shifted to higher frequencies, when compared to the spectrum of 12 (d 140.1 and 126.6 ppm), signifying the formation of a ketimido complex rather than an enamido species. Note that the $^{31}P\{^1H\}$ NMR spectrum of the ketimido complex [Mn(PNP—N=CPh)(CO)$_2$], prepared from the reaction of 2 and benzonitrile has similar chemical shifts of the two phosphorus resonances (i.e. doublet at 165.6 ppm and 126.5 ppm with $^2J_{PP}$=106 Hz).

The $^{31}P\{^1H\}$ NMR spectrum of a sample of complex 2 dissolved in neat propionitrile shows similar broad resonances at room temperature. Cooling the sample stepwise to 225 K gives rise to the appearance of sharp resonances, consistent with the formation of the ketimido species 14 as the major compound (d, 128.1 ppm and 166.0 ppm, $^2J_{PP}$=106 Hz). However, these resonances are accompanied by the formation of new signals, assigned to the enamido compound 15 as a minor species (d, 127.7 and 134.1 ppm, $^2J_{PP}$=106 Hz). Representative $^{31}P\{^1H\}$ NMR spectra are shown in FIG. 14.

Evidently, propionitrile does not readily give the enamido compound 15, unlike the reaction of 2 with benzyl cyanide, which results in the enamido complex 12 However, there is evidence for the formation of an enamido moiety upon the reaction of 2 with a large excess of the nitrile at low temperature as presented in the following scheme:

Example 13

Solvent Effect in Michael's Reaction

Screening of different solvents in a Michael Reaction of propionitrile to ethyl acrylate in different solvents showed that non-polar solvents such as pentane and benzene are most suitable for the catalytic reaction as presented in Table 9 and in FIG. 13.

TABLE 9

| Solvent | Time (h) | Conversion[a] (%, NMR) | Yield[b] (%) |
|---|---|---|---|
| DCM | 2.5 | 47 | 39 |
| THF | 2.5 | 68 | 61 |
| benzene | 2.5 | 88 | 78 |
| n-pentane | 2.5 | >99 | 90 |
| Neat | 2 | >99 | 80[c] |

*Reaction conditions: 1 mmol ethyl acrylate and 1 mmol propionitrile in 0.5 mL solvent at RT. Catalyst load 0.5 mol %.
[a]Conversion relative to ethyl acrylate
[b]isolated yield (product contains traces of double addition byproduct).
[c]NMR yield.

Example 14

Computational Studies of Michael Reaction Using Aliphatic Nitriles

Computational Methods

All geometries were optimized with the BP86 generalized-gradient approximation (GGA) functional and the def2-SV(P) basis set together with corresponding core potential for ruthenium.[22-25] The D3 dispersion correction was used for the geometry optimizations.[26] Thermodynamic properties were obtained at the same level of theory from a frequency calculation. All free energies are calculated under standard conditions unless otherwise noted. Minima and transition states were characterized by the absence and presence of one imaginary frequency, respectively. Single point calculations were obtained with the TPSS meta-GGA functional in combination with the D3 dispersion correction and Becke-Johnson dumping and the larger triple-zeta def2-TZVP basis set.[24,26,27,28] The TPSS functional was recently shown to yield results very close to explicitly correlated coupled cluster benchmark calculations for reaction energies and barriers involving transition metal complexes with pin-

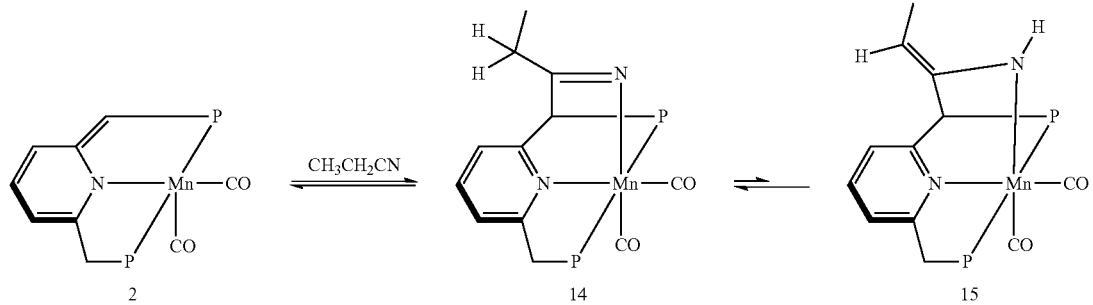

Undoubtedly, the enamido tautomer 12 is stabilized by conjugation with the aromatic ring, which is lacking in case of 15.

cer ligands.[28] In order to improve the computational efficient, the density fitting approximation with the W06 fitting basis sets, designed for use with the def2 basis sets, was used.[30,31] In order to take solvent effects into account, the SMD solvation model for benzene was used for both, the geometry optimizations and the single point calculations.[32] The "ultrafine" (i.e., a pruned (99,590)) grid was used for all calculations. All calculations were performed using Gaussian 09 Revision D.01

Results

To allow for a better understanding of the elementary steps involved in the catalytic transformation, DFT calculations at the TPSS-D3BJ/def2-TZVP//BP86-D3/def2-SV(P) level of theory were performed. Since zwitterionic intermediates might be involved, both the geometry optimizations and the single point energy calculations were performed using the SMD solvation model for benzene. Propionitrile and ethylacrylate were chosen as representative substrates.

Based on the calculations the nitrile first coordinates to 2 to give H, which can undergo C—C bond formation to give the aforementioned ketimido complex 14 (FIG. 14).

The formation of complex 14 is predicted to be endergonic at 298 K but is computed to be slightly exergonic at 235 K:

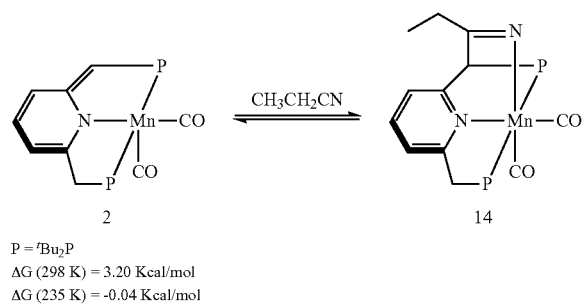

2      14

P = $^tBu_2P$
ΔG (298 K) = 3.20 Kcal/mol
ΔG (235 K) = -0.04 Kcal/mol

The calculated free energies agree with the observation made by NMR (FIG. 11) that in the presence of an excess of propionitrile only 2 can be observed at 298 K, whereas at 235 K 14 is detectable. Furthermore, the computed ΔH value of −10.3 kcal/mol is in favorable agreement with the value derived from the Vant Hoff plot analysis of the temperature dependent NMR investigation in pentane (ΔH=−13.6 kcal/mol). Next, we investigated the tautomerism pathway leading to the enamide 15 (FIG. 15). The ketimide nitrogen in complex 14 can be assumed to be basic; therefore we commenced to elucidate whether it could deprotonate an acidic CH of a second propionitrile molecule. Starting from the hydrogen bond complex I, a relaxed potential energy surface scan over the NH distance did not yield a barrier. The zwitterionic complex J could be localized as local minima. A second proton transfer via TS2 yields the tautomerized enamido complex K to which the second propionitrile is bound via a N—H—N hydrogen bond.

The overall barrier for this tautomerization via protonation-deprotonation of complex 14 is 32.6 kcal/mol. Assuming that even in carefully dried organic solvents traces of water can be present, we computed in alternative mechanism with water molecules as proton shuttle. A transition state with two water molecules (TS3) was found to lower the barrier for tautomerization to 21.0 kcal/mol. In agreement with the NMR investigations (see FIG. 12), complex 15 is predicted to be less stable than complex 14 by 1.2 kcal/mol. To gain a deeper understanding of the metal template strategy, the nitrile-ketimine-tautomerization of propionitrile itself was also calculated.

The calculations predict the nitrile form to be more stable by 22 kcal/mol.

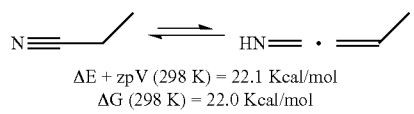

ΔE + zpV (298 K) = 22.1 Kcal/mol
ΔG (298 K) = 22.0 Kcal/mol

Therefore, these results indicate that a first effect of the template strategy is the stabilization of the nucleophilic tautomer of the nitrile substrate. Having established a possible pathway for the formation of complex 15, the C—C bond formation was studied. We assumed that hydrogen bond interactions may stabilize the zwitterionic intermediate, which results from the nucleophilic attack of 15 at the Michael acceptor. Indeed, a transition state for the C—C bond formation with a hydrogen bond between the NH group of G and the carboxylic oxygen of ethylacrylate could be localized (TS4 in FIG. 16). A proton transfer for which a relaxed potential energy surface scan over the OH bond length did not show a barrier, led to the enol intermediate M, which is high in energy. We therefore searched for alternative pathways avoiding the intermediate enol formation. After attack of 15 via TS5 a zwitterionic intermediate N is formed. Its energy is lower than that of the enol intermediate M.

Rotation of the enolate group around the new carbon-carbon bond via the staggered transition state TS6 leads to intermediate O. This intermediate can undergo a direct proton transfer from the NH group to the α-carbon of the enolate group via TS7 to directly yield the keto intermediate P, thus avoiding the formation of the high energy enol intermediate M. A similar transition state as located for the binding of the propionitrile to 2 results in the product complex Q. In this complex, the product is still bound to the manganese center via the nitrogen. Dissociation of the product finally regenerates the active catalyst 2. Notably, the pathway involving a zwitterionic intermediate not stabilized by hydrogen bonding is lower in energy than the one involving the enol intermediate. Regarding the overall transformation, the transition state for the waterassisted tautomerization is the one highest in energy with respect to the catalyst and the separated reactants. Furthermore, water is assumed to be present only in traces whereas an excess of substrates is used.

Thus, the tautomerization is rate determining. Based on the NMR investigations and the DFT calculations the mechanism to be operative is: after nitrile binding, a rate determining water-catalyzed tautomerization takes place. The carbon-carbon bond formation yields a zwitterionic intermediate. A direct proton transfer from the NH group leads directly to an intermediate in the keto form. No enol is involved in the cycle. Product release regenerates the active catalyst (FIG. 17).

Essentially, the proposed catalytic cycle (FIG. 17) outlines a cascade of a stepwise reduction and oxidation of the CN bond. The formal bond order decreases in the course of the activation of the nitrile (nitrile (b.o.=3)→ketimid (b.o.=2)→enamid (b.o.=1)). Upon addition of the reduced enamido moiety to the Michael acceptor, the CN bond order increases stepwise (ketimid (b.o.=2)→nitrile (b.o.=3)).

Example 15

Synthesis of Manganese Complex of Formula 6B and 6A'

Preparation and Characterization of [Mn(PNNH)(CO)$_2$Br] (6B).

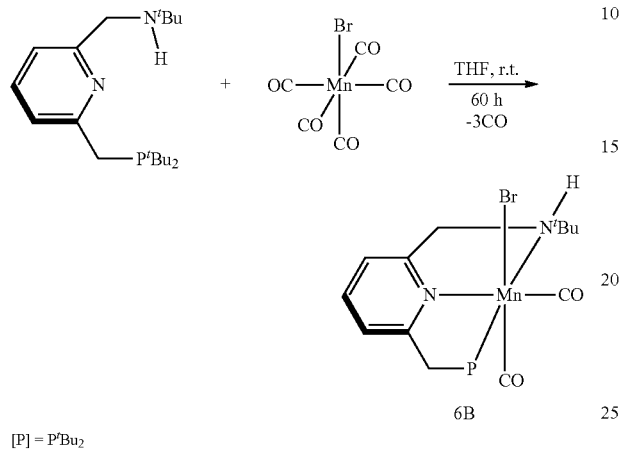

[P] = P$^t$Bu$_2$

N-((6-((di-tert-butylphos-phanyl)methyl)pyridine-2-yl)methyl)propan-2-amine (PNNH) ligand (1.60 g, 4.96 mmol) and [Mn(CO)$_5$Br] (1.36 g, 4.96 mmol) were dissolved in 10 mL of THF in a 20 mL vial. The vial was closed with a vial septum cap and two needles (0.8×40 mm) were connected through the septum in order to displace the CO gas liberated during the reaction. The mixture was stirred at room temperature for 60 h. The reaction mixture was concentrated to ~half of the volume and the orange precipitate was decanted, washed with diethyl ether, and dried under reduced pressure (2.01 g, 79% yield).

The N-((6-((di-tert-butylphos-phanyl)methyl)pyridine-2-yl)methyl)propan-2-amine (PNNH) ligand was prepared according to Fogler, E.; Garg, J. A.; Hu, P.; Leitus, G.; Shimon, L. J. W.; Milstein, D. *Chem. Eur. J.* 2014, 20, 15727

$^{31}$P{$^1$H} NMR (162.08 MHz, CDCl$_3$, 25° C.): δ 118.6 (s).

$^1$H NMR (400.36 MHz, CDCl$_3$, 25° C.): δ 1.16 (d, $^3J_{PH}$=11.5 Hz, 9H, (CH$_3$)$_3$CP), 1.49 (s, 9H, (CH$_3$)$_3$CN), 1.51 (d, $^3J_{PH}$=11.5 Hz, 9H, (CH$_3$)$_3$CP), 3.47 (m, 2H, NH, NCHH), 4.00 (dd, $^1J_{HH}$=16.3 Hz, $^2J_{HP}$=6.0 Hz, 1H, PCHH), 4.17 (d, $^1J_{HH}$=14.5 Hz, 1H, NCHH), 4.37 (t, J=13.6 Hz, 1H, PCHH), 7.22 (d, $^3J_{HH}$=6.7 Hz, 1H, CH$_{pyri(3)}$), 7.41 (d, $^3J_{HH}$=6.7 Hz, 1H, CH$_{pyri(5)}$), 7.66 (t, $^3J_{HH}$=6.7 Hz, 1H, CH$_{pyri(4)}$).

$^{13}$C{$^1$H} QDEPT NMR (100.67 MHz, CDCl$_3$, 25° C.): δ 29.1 (s, (CH$_3$)$_3$CN), 29.7 (d, $^2J_{PC}$=2.8 Hz, (CH$_3$)$_3$CP), 31.7 (d, $^2J_{PC}$=2.8 Hz, (CH$_3$)$_3$CP), 36.6 (m, (CH$_3$)$_3$CP, CH$_2$P), 37.6 (d, $^1J_{PC}$=14.7 Hz, (CH$_3$)$_3$CP), 54.0 (s, CH$_2$N), 56.9 (s, (CH$_3$)$_3$CN), 118.7 (s, CH$_{pyri(5)}$), 121.8 (d, $^3J_{PC}$=7.6 Hz, CH$_{pyri(3)}$), 137.2 (s, CH$_{pyri(4)}$), 159.1 (d, $^4J_{PC}$=2.6 Hz, CH$_{pyri(6)}$), 163.3 (d, $^2J_{PC}$=6.4 Hz, CH$_{pyri(2)}$), 233.7 (bs, Mn—CO), 237.6 (bs, Mn—CO). IR (KBr, pellet, cm$^{-1}$): 1828 ($v_{asym}$, C≡O), 1909 ($v_{sym}$, C≡O) in 1:1 ratio.

MS (ESI): m/z [M-Br]$^+$ 433.34, [M-(Br+CO)]$^+$ 405.35, [M-(Br+2CO)]$^+$ 377.35. MS (ESI$^-$): m/z [Br]$^-$ 78.96.

HRMS (ESI$^+$): m/z [M-Br]$^+$ (C$_{21}$H$_{33}$N$_2$O$_2$PMn) Calcd: 431.1660, Found: 431.1655.

HRMS (ESI$^-$): m/z [M+2Br]$^+$ (C$_{21}$H$_{35}$N$_2$O$_2$PMnBr$_2$) Calcd: 591.0183, Found: 591.0175.

The IR spectrum of 6B exhibits two strong absorption bands at 1828 ($v_{asym}$) and 1909 cm$^{-1}$ ($v_{sym}$) in 1:1 ratio in agreement with two carbonyls in cis position. The $^{31}$P{$^1$H} NMR spectrum shows a singlet at 118.7 ppm. Single crystals suitable for X-ray analysis were obtained by slow diffusion of pentane into a concentrated solution of complex 6B in CH$_2$Cl$_2$. The PNNH pincer ligand binds to the metal center in a meridional fashion with the two carbonyl ligands located cis to each other (C—Mn—C=86.250), and the bromide in an axial position, completing a distorted octahedral coordination sphere.

Preparation and Characterization of [Mn(PNN)(CO)$_2$] (6A').

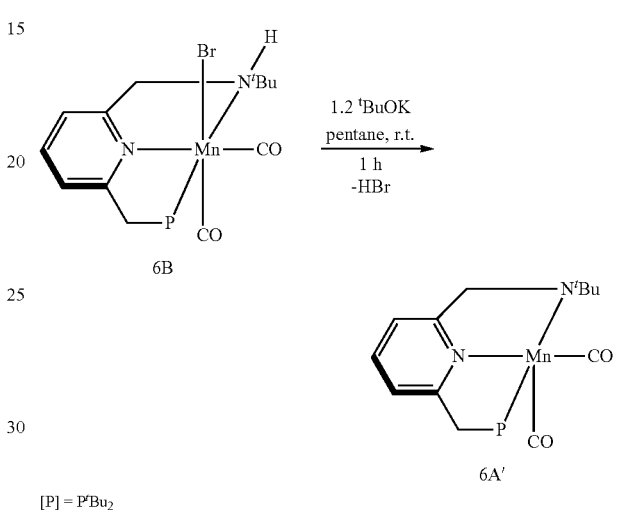

[P] = P$^t$Bu$_2$

[Mn(PNNH)(CO)$_2$(Br)] (6B) (200 mg, 0.39 mmol) and KO$^t$Bu (52 mg, 0.47 mmol) were suspended in 10 mL of pentane. The mixture was stirred at room temperature for 1 h. during the reaction time the original colorless suspension becomes a dark-green solution. After filtration through a Teflon syringe filter (0.2 μm), the pentane solution was kept at −19° C. in a freezer overnight to form dark green crystals. The crystals were decanted and dried under vacuum. (115 mg, 68% yield).

$^{31}$P{$^1$H} NMR(162.08 MHz, C$_6$D$_6$, 25° C.): δ 135.0 (s).

$^1$H NMR (400.36 MHz, C$_6$D$_6$, 25° C.): δ 1.14 (d, $^3J_{PH}$=12.4 Hz, 18H, (CH$_3$)$_3$CP), 1.78 (s, 9H, (CH$_3$)$_3$CN), 3.08 (d, $^2J_{HP}$=7.6 Hz, 2H, PCH$_2$), 4.53 (s, 2H, NCH$_2$), 6.62 (t, $^3J_{HH}$=7.7 Hz, 2H, CH$_{pyri(3,5)}$), 6.89 (t, $^3J_{HH}$=7.7 Hz, 1H, CH$_{pyri(4)}$).

$^{13}$C{$^1$H} QDEPT NMR (100.67 MHz, C$_6$D$_6$, 25° C.): δ 21.6 (d, $^2J_{PC}$=4.5 Hz, (CH$_3$)$_3$CP), 26.7 (s, (CH$_3$)$_3$CN), 27.9 (d, $^1J_{PC}$=10.8 Hz, CH$_2$P), 28.0 (d, $^1J_{PC}$=10.8 Hz., (CH$_3$)$_3$(P), 60.6 (s, CH$_2$N), 108.6 (s, CH$_{pyri(5)}$), 110.4 (d, $^3J_{PC}$=7.2 Hz, CH$_{pyri(3)}$), 125.8 (s, CH$_{pyri(4)}$), 153.9 (d, $^2J_{PC}$=7.8 Hz, CH$_{pyri(2)}$), 157.9 (d, $^4J_{PC}$=4.7 Hz, CH$_{pyri(6)}$), 207.8 (bs, Mn—CO), 212.9 (bs, Mn—CO).

IR (KBr, pellet, cm$^{-1}$): 1797 ($v_{asym}$, C≡O), 1874 ($v_{sym}$, C≡O) in 1:1 ratio. MS (ESI$^+$): m/z [M]$^+$ 433.34, [M-CO]$^+$ 405.36, [M-2CO]$^+$ 377.37.

HRMS (ESI$^+$): m/z [M]$^+$ (C$_{21}$H$_{33}$N$_2$O$_2$PMn) Calcd: 431.1660, Found: 431.1655.

The IR spectrum of 6A' (NaCl plates) showed two strong bands at 1797 ($v_{asym}$) and 1874 cm$^{-1}$ ($v_{sym}$) in 1:1 ratio, indicating a 90° C.—Mn—C angle. The $^{31}$P{$^1$H} NMR spectrum showed a singlet at 135.0 ppm, downfield shifted by ~16 ppm in comparison with 6B. The $^1$H NMR spectrum of 6A' exhibited only two distinct resonances in the aromatic regime. Two resonances were observed in $^1$H NMR for the protons at the two benzylic positions; a singlet at 4.53 ppm and a doublet at 3.08 ppm in 1:1 ratio. No resonance due to the N—H proton was observed, indicating deprotonation of the amine group. Two resonances were observed for the carbonyl ligands in the $^{13}$C{$^1$H} NMR spectrum at 212.9 ppm and 207.8 ppm. X-ray diffraction of single crystal of 6A' (FIG. 18) showed meridional coordination of the deprotonated PNNH pincer ligand. Both carbonyl ligands were located mutually cis (C20-Mn—C21=87.220), completing a distorted square pyramidal coordination sphere. The C—C bond lengths of the pyridine ring were almost equal, confirming that no de-aromatization of the pyridine ring occurred, in line with no deprotonation of the benzylic position. The Mn—N amido bond (1.889 Å) was significantly shorter from Mn-amine bond (2.171 Å) in 6B, confirming the amine-amide conversion upon deprotonation.

X-Ray Characterization

Single crystals suitable for X-ray analysis for the manganese complexes 6B and 6A' are presented in FIG. 18. Crystal data were measured at 100 K on a Nonius KappaCCD (6B) and Bruker Apex-II KappaCCD (6A') diffractometers equipped with [λ(Mo—Kα)=0.71073 Å] radiation, graphite monochromator and MiraCol optics. The data were processed with HKL2000 (6B) and APEX-II (6A') collect package programs. Structures were solved by the SHELXT-2013 (6B) and AUTOSTRUCTURE (6A') modules and refined with full-matrix least-squares refinement based on $F^2$ with SHELXL-2014.

Crystal Data, Data Collection, and Structure Refinement for 6B and 6A'.

| Crystal data | | |
|---|---|---|
| | 6B | 6A' |
| formula | $C_{21}H_{35}BrMnN_2O_2P$ | $C_{21}H_{34}MnN_2O_2P$ |
| $M_r$ | 513.33 | 432.41 |
| crystal system | monoclinic | monoclinic |
| space group | $P2_1/C$ | $P2_1/C$ |
| a (Å) | 9.2250(18) | 10.2774(4) |
| b (Å) | 15.306(3) | 10.5133(4) |
| c (Å) | 16.738(3) | 20.4008(7) |
| α(°) | 90 | 90 |
| β(°) | 92.37(3) | 93.609(2) |
| γ(°) | 90 | 90 |
| V (Å$^3$) | 2361.3(8) | 2199.92(14) |
| Z | 4 | 4 |
| $\rho_{calc}$ (g cm$^{-3}$) | 1.444 | 1.306 |
| μ(mm$^{-1}$) | 2.337 | 0.690 |
| F(000) | 1064 | 920 |
| crystal size (mm$^3$) | 0.18 × 0.12 × 0.08 | 0.20 × 0.20 × 0.20 |
| Data collection and Refinement | | |
| T/K | 100(2) | 100(2) |
| measd reflns | 9413 | 34343 |
| Unique reflns (Rint) | 4803 (0.0194) | 5033 (0.0315) |
| reflns used for refinement | 4803 | 9959 |
| refined parameters | 266 | 253 |
| GOF on $F^2$ | 1.076 | 1.038 |
| $R_1{}^a$ [I > 2σ (I)] | 0.0249 | 0.0384 |
| $wR_2{}^b$ all data | 0.0642 | 0.0999 |

$^a$R1 = Σ||Fo| − |Fc||/Σ|Fo|.
$^b$wR2 = [Σ[w(Fo$^2$ − Fc$^2$)$^2$]/Σ[w(Fo$^2$)$^2$]]$^{1/2}$.

Tables 10 and 11 provide selected bond length and bond angles respectively of these complexes.

TABLE 10

Selected bond lengths [Å] of 6B and 6A'.

| 6B | | 6A' | |
|---|---|---|---|
| Mn1—Br1 | 2.6193(6) | | |
| Mn1—P1 | 2.3159(9) | Mn1—P1 | 2.2622(6) |
| Mn1—N1 | 2.033(2) | Mn1—N1 | 2.018(2) |
| Mn1—N2 | 2.171(2) | Mn1—N2 | 1.889(2) |
| Mn1—C20 | 1.759(2) | Mn1—C20 | 1.775(2) |
| Mn1—C21 | 1.784(2) | Mn1—C21 | 1.821(2) |
| C1—C2 | 1.499(3) | C1—C2 | 1.501(3) |
| C6—C7 | 1.500(3) | C6—C7 | 1.492(3) |
| C1—P1 | 1.849(2) | C1—P1 | 1.850(2) |
| C7—N2 | 1.489(2) | C7—N2 | 1.464(3) |

TABLE 11

Selected bond angles [°] of 6B and 6A'.

| 6B | | 6A' | |
|---|---|---|---|
| Br1—Mn1—P2 | 95.21(2) | | |
| Br1—Mn1—N2 | 81.37(4) | | |
| P1—Mn1—N1 | 81.16(4) | P1—Mn1—N1 | 80.64(5) |
| P1—Mn1—N2 | 159.08(4) | P1—Mn1—N2 | 141.76(6) |
| N1—Mn1—C21 | 175.03(7) | N1—Mn1—C20 | 173.08(8) |
| N1—Mn1—C20 | 98.23(7) | N1—Mn1—C21 | 92.65(7) |
| N2—Mn1—C21 | 104.29(7) | N2—Mn1—C20 | 104.86(8) |
| N2—Mn1—C20 | 90.24(7) | N2—Mn1—C21 | 117.02(8) |
| C20—Mn1—C21 | 86.25(9) | C20—Mn1—C21 | 87.20(9) |

Example 16

Hydrogenation of Esters Using the Manganese Catalyst of this Invention

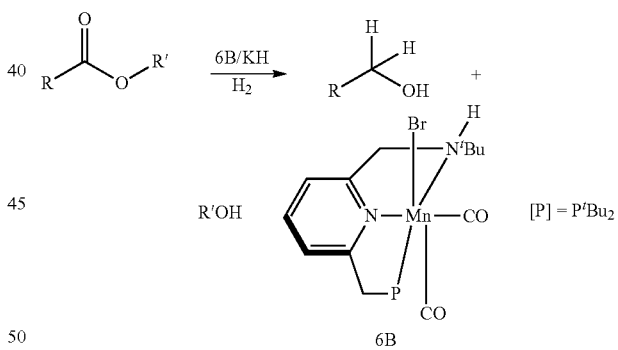

The manganese precatalyst 6B in the attempted hydrogenation of hexyl hexanoate under 20 bar of $H_2$ and catalyst loading of 1 mol % in toluene was not successful (Table 12, Entry 1). However, addition of a base (2 mol %), under the same conditions did result in hexanol formation. Using of $^t$BuOK or potassium bis(trimethylsilyl)amide, hexanol was obtained in 31% and 54% yields, respectively (Entries 2, 3). When KH was used as a base, full conversion to hexanol was observed under the same conditions (Entry 4). When preparing the reaction mixture at room temperature, addition of $^t$BuOK or KHMDS resulted in a dark green color, in line with ligand dearomatization by deprotonation. In contrast, no color change was observed at room temperature upon addition of KH, due to its insolubility under these conditions. The lack of immediate reaction with the 6B at ambient temperature, can be a practical advantage, avoiding handling the more sensitive active catalyst 6'. Moreover, using KH does not generate a conjugate base in solution, avoiding potential side reactions.

TABLE 12

Base optimization for manganese-catalyzed hydrogenation of hexyl hexanoate.

| Entry | Base  | Time (h) | Conv (%)[b] | Yield[b] |
|-------|-------|----------|-------------|----------|
| 1     | —     | 22       | —           | —        |
| 2     | tBuOK | 22       | 39          | 31       |
| 3     | KHMDS | 23       | 55          | 54       |
| 4     | KH    | 23       | 99          | 99       |

[a]Reaction conditions: substrate (1.0 mmol), toluene (1.0 mL), internal standard (xylene, 1 mmol), 100° C.
[b]Products confirmed by GC-MS. Conversions and Yields were determined by $^1$H NMR with an internal standard (xylene)

Method:

The scope of the reaction was examined with various esters using the precatalyst [Mn(PNNH)(CO)$_2$(Br)] (6B) (1 mol %) and KH (2 mol %) (Table 13). A suspension containing 0.01 mmol of the pre-catalyst 6B, 0.02 mmol of KH, 1 mmol of ester, 1 mmol of mesitylene (120 mg) in 1 mL of toluene were placed in a steel autoclave fitted with Teflon sleeve. The autoclave was pressurized with 20 bar H$_2$ and heated at 100° C. (bath temperature) with stirring for the specified time. After cooling to room temperature, the H$_2$ was vented off carefully. The solution was then filtered through Celite and the solution was analyzed by GC-MS and $^1$H NMR spectroscopy. The conversion and yield were determined by integration of $^1$H NMR signals with respect to the internal standard (mesitylene).

Results:

Hydrogenation of 1 mmol of hexyl hexanoate under 20 bar H$_2$ at 100° C. in toluene, resulted in 99% yield of hexanol (Entry 1). Under the same conditions ethyl butyrate was hydrogenated to give 98% yield of butanol and 91% yield of ethanol after 50 hours (Entry 2). When the reaction was performed at shorter reaction time (22 hours, Entry 2bis), small amounts of ethyl acetate and butyl butanoate were also formed, attributed to a transesterification reaction with the formed ethanol and butanol. Cyclohexylmethyl acetate gave 99% yield of cyclohexylmethanol and 60% yield of ethanol (Entry 3), and no transesterification products were observed. Hydrogenation of the secondary aliphatic ester heptan-2-yl acetate resulted in 98% yield of heptane-2-ol and 57% yield of ethanol (Entry 4). Ethyl 3-phenylpropanoate was smoothly hydrogenated, rendering 99% yield of 3-phenylpropan-1-ol and 70% yield of ethanol after 21 hours (Entry 5). Similarly, ethyl 3-phenylpropanoate gave 99% yield of phenylmethanol and 74% yield of butanol after 22 hours (Entry 6). In order to get full hydrogenation of benzyl benzoate longer reaction time was needed (43 hours, 99% yield benzyl alcohol, Entry 7). Similarly, methyl benzoate gave 96% yield of benzyl alcohol and 63% of methanol after 50 hours (Entry 8). ε-Caprolactone was smoothly and quantitatively hydrogenated to 1,6-hexanediol (99% yield, Entry 9). The activated benzyl trifluoroacetate gave 99% yield of benzyl alcohol and 78% of 2,2,2-trifluoroethanol (Entry 10), and no secondary products where observed. Gratifyingly, allyl trifluoroacetate gave 97% yield of 2,2,2-trifluoroethanol and 96% of allyl alcohol (Entry 11), showing high chemoselectivity to ester hydrogenation over C=C hydrogenation. Hydrogenation of ethyl 4-isocyanobenzoate required an increase of precatalyst loading to 3%, probably due to competing nitrile coordination, and resulted in 61% yield of (4-isocyanophenyl)methanol and 66% yield of ethanol, with no hydrogenation of the nitrile group detected (Entry 12).

TABLE 13

Catalytic hydrogenation of esters using the manganese precatalyst 6B

| Entry | Ester | Time (h) | Conv (%)[a] | Products[a] | Yield (%)[a] |
|-------|-------|----------|-------------|-------------|--------------|
| 1     | hexyl hexanoate | 23 | 99 | hexanol | 99 |
| 2[b]  | ethyl butyrate  | 50 | 99 | butanol + EtOH | 98/91 |
| 2 bis[b] | ethyl butyrate | 22 | 90 | butanol + EtOH | 32/35 |
|       | butyl butanoate + ethyl acetate |  |  |  | 12/11 |

TABLE 13-continued

Catalytic hydrogenation of esters using the manganese precatalyst 6B

| Entry | Ester | Time (h) | Conv (%)[a] | Products[a] | | Yield (%)[a] |
|---|---|---|---|---|---|---|
| 3[b] | acetate of cyclohexylmethanol | 43 | 99 | cyclohexylmethanol | EtOH | 99/60 |
| 4[b] | hexan-2-yl acetate | 43 | 99 | hexan-2-ol | EtOH | 98/57 |
| 5[b] | ethyl 3-phenylpropanoate | 21 | 99 | 3-phenylpropan-1-ol | EtOH | 99/70 |
| 6 | benzyl butyrate | 22 | 99 | benzyl alcohol | butan-1-ol | 99/74 |
| 7 | benzyl benzoate | 43 | 99 | benzyl alcohol | | 99 |
| 7 bis | benzyl benzoate | 22 | 80 | benzyl alcohol | | 80 |
| 8[b] | methyl benzoate | 50 | 99 | benzyl alcohol | MeOH | 98/63 |
| 9 | ε-caprolactone | 36 | 99 | hexane-1,6-diol | | 98[c] |
| 10 | benzyl trifluoroacetate | 28 | 99 | 2,2,2-trifluoroethanol | benzyl alcohol | 78/99 |

TABLE 13-continued

Catalytic hydrogenation of esters using the manganese precatalyst 6B $$R\text{—}C(=O)\text{—}O\text{—}R' \xrightarrow[100\,°C./20\,bar/Tol]{6B\,(1\%)/KH\,(2\%)} R\text{—}CH_2\text{—}OH + R'OH$$

| Entry | Ester | Time (h) | Conv (%)[a] | Products[a] | Yield (%)[a] |
|---|---|---|---|---|---|
| 11[d] | F₃C-C(=O)-O-CH₂-CH=CH₂ | 60 | 99 | F₃C-CH₂-OH ; HO-CH₂-CH=CH₂ | 97/96 |
| 12[b,e] | NC-C₆H₄-C(=O)-O-Et | 60 | 75 | NC-C₆H₄-CH₂-OH ; EtOH | 60/66 |

Reaction conditions: substrate (1.0 mmol), toluene (1.0 mL), internal standard (xylene, 1 mmol), 100° C.
[a]Conversions and Yields were determined by $^1$H NMR with an internal standard (xylene). Products confirmed by GC-MS.
[b]Lower yield of methanol and ethanol are attributed to evaporation during workup after catalysis.
[c]The diol is insoluble in the reaction mixture. Isolated yield.
[d]No hydrogenation of the vinyl group was observed.
[e]6B (3%)/KH (6%). No hydrogenation of the nitrile group was detected.

Example 17

Mechanistic Studies of Catalytic Hydrogenation of Esters Using the Manganese Catalyst of this Invention Mechanistically, the fact that benzyl benzoate and methyl benzoate undergo hydrogenation using the precatalyst 6B indicate that ester enolate intermediates are not involved in the catalysis. Aiming at gaining insight regarding the nature of the active catalyst, deprotonation of 6B was performed. 1.2 equivalents of KOtBu were added to a suspension of 6B in pentane, the solution became dark blue, yielding the novel amido complex 6A' (see Example 15):

Exploring the catalytic activity of the amido complex 6A', hydrogenation of hexyl hexanoate under the same previously described conditions, in presence of the precatalyst 6A' (1 mol %) in the absence of base gave 96% yield of hexanol after 22 hours, showing comparable catalytic activity as with the catalyst prepared in situ (Table 13, Entry 1), in line with 6A' being the likely catalytically active complex. No reaction was observed between hexyl hexanoate and complex 6A' in stoichiometric ratio, in toluene-d$^8$ at room temperature.

To gain more mechanistic insight, NMR investigations were carried out using complex 6A'. Under H$_2$ atmosphere (1 bar) at room temperature, in an NMR Young tube, complex 6A' in C$_6$D$_6$ reversibly activates H$_2$ to yield, after 10 min, a mixture of the hydride complex 16 and complex 6A' in a ratio of 6A': 16, 1.0:0.6, as determined by $^{31}$P{$^1$H} NMR

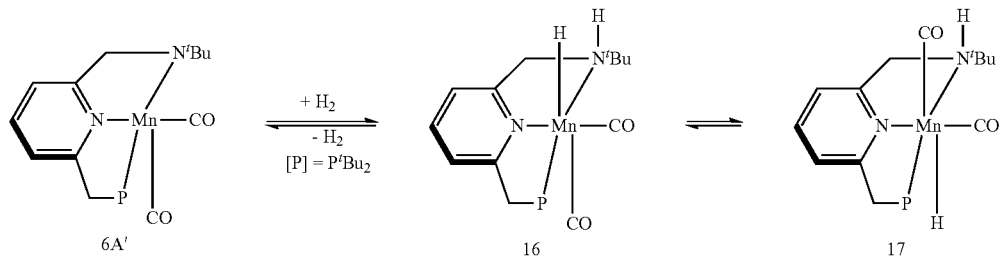

Preparation of Intermediate Complex 16:

To a suspension of complex 6B (40 mg, 0.08 mmol) in cold toluene-d$^8$ (−10° C., 0.8 mL) was added a cold THF solution of NaBHEt$_3$ (−10° C., NaBHEt$_3$ 1M in THF, 90 μL, 0.09 mmol), the mixture was stirred at −10° C. for 2 min, filtered through a Teflon syringe filter (0.2 μm) and the dark-red filtrate added to a Young NMR tube. The Young tube was evacuated by two freeze-pump-thaw cycles and back-filled with H$_2$ (1 bar). The reaction mixture was kept cold and characterized by low temperature NMR (0° C.).

$^{13}$P{$^1$H} NMR indicated 82% conversion to syn-[Mn (PNNH)(H)(CO)$_2$] (3). $^{31}$P{$^1$H} NMR (202.43 MHz, Tol-d$^8$, −10° C.): δ 142.6 (s).

$^1$H NMR (500.08 MHz, Tol-d$^8$, −10° C.): δ −1.91 (d, $^2J_{PH}$=53.6 Hz, 1H, Mn—H), 1.17 (d, $^3J_{PH}$=18.7 Hz, 9H, (CH$_3$)$_3$CP), 1.21 (s, 9H, (CH$_3$)$_3$CN), 1.37 (d, $^3J_{PH}$=11.4 HZ, 9H, (CH$_3$)$_3$CP), 2.85 (bs, 1H, NH), 3.04 (m, 2H, NCHH, PCHH), 3.32 (d, $^1J_{HH}$=10.5 Hz, 1H, NCHH), 3.56 (overlapped THF, 1H, PCHH), 6.46 (d, $^7J_{HH}$=7.2 Hz, 1H, CH$_{pyri(3)}$), 6.76 (d, $^3J_{HH}$=7.2 Hz, 1H, CH$_{pyri(5)}$), 7.10 (bs, 1H, CH$_{pyri(4)}$).

$^{13}$C{$^1$H} QDEPT NMR (125.74 MHz, Tol-d$^8$, −10° C.): δ 20.2 (bs, (CH$_3$)$_3$CP), 21.0 (bd, $^2J_{PC}$=3.4 Hz, (CH$_3$)$_3$CP), 22.7 (s, (CH$_3$)$_3$CN), 29.0 (d, $^1J_{PC}$=10.0 Hz, CH$_2$P), 29.6 (d, $^1J_{PC}$=7.8 Hz, (CH$_3$)$_3$CP), 46.5 (bs, CH$_2$N), 47.9 (bs, (CH$_3$)$_3$CN), 109.0 (s, CH$_{pyri(5)}$), 111.5 (d, $^3J_{PC}$=8.0 Hz, CH$_{pyri(3)}$), 125.6 (s, CH$_{pyri(4)}$), 151.2 (s, CH$_{pyri(6)}$), 153.7 (d, $^2J_{PC}$=6.9 Hz, CH$_{pyri(2)}$), 219.3 (bd, $^2J_{PC}$=12.6 Hz, Mn—CO), 230.4 (bd, $^2J_{PC}$=20.7 Hz, Mn—CO).

Characterization of anti-[Mn(PNNH)(H)(CO)$_2$] (17)

Complex 4 was characterized in the reaction mixture obtained by activation of H$_2$ at room temperature.

$^{31}$P{$^1$H} NMR (162.07 MHz, C$_6$D$_6$, 25° C.): δ 143.8 (s).

$^1$H NMR (400.36 MHz, C$_6$D$_6$, 25° C.): δ −1.34 (d, $^2J_{PH}$=55.3 Hz, 1H, Mn—H), 1.15 (s, 9H, (CH$_3$)$_3$CN), 1.25 (d, $^3J_{PH}$=18.7 Hz, 9H, (CH$_3$)$_3$CP), 1.36 (d, $^J J_{PH}$=11.4 Hz, 9H, (CH$_3$)$_3$CP), 2.95 (m, 2H, NCHH, NH), 3.43 (bd, $^1J_{HP}$=14.1 Hz, 1H, PCHH), 3.43 (bd, $^1J_{HP}$=15.6 Hz, 1H, PCHH), 3.87 (d, $^1J_{HH}$=7.2 Hz, 1H, PCHH), 6.18 (bs, 1H CH$_{pyri(3)}$), 6.73 (m, 2H, CH$_{pyri(5)}$, CH$_{pyri(4)}$).

$^{13}$C{$^1$H} QDEPT NMR (125.74 MHz, Tol-d$^8$, 25° C.): δ 19.2 (bs, (CH$_3$)$_3$CP), 21.4 (bd, $^2J_{PC}$=4.3 Hz, (CH$_3$)$_3$CP), 22.2 (s, (CH$_3$)$_3$CN), 29.3 (d, $^1J_{PC}$=11.4 Hz, CH$_2$P), 29.6 (d, $^1J_{PC}$=7.8 Hz, (CH$_3$)$_3$CP), 46.9 (bs, (H$_2$N), 47.6 (bs, (CH$_3$)$_3$CN), 108.7 (s, CH$_{pyri(5)}$), 111.2 (d, $^3J_{PC}$=8.2 Hz, CH$_{pyri(3)}$), 125.2 (s, CH$_{pyri(4)}$), 151.1 (bd, $^4J_{PC}$=3.6 Hz, CH$_{pyri(6)}$), 153.1 (d, $^2J_{PC}$=7.1 Hz, CH$_{pyri(2)}$), 218.1 (bd, $^2J_{PC}$=10.8 Hz, Mn—CO), 229.4 (bd, $^2J_{PC}$=19.6 Hz, Mn—CO). Accordingly syn-[Mn(PNNH)(H)(CO)$_2$] complex 17, which is formed in situ under the catalytic conditions, is an actual intermediate in the ester hydrogenation process.

$^{31}$P{$^1$H} NMR indicated 37% conversion to syn-[Mn(PNNH)(H)(CO)$_2$] (16) after 10 min at room temperature. With time a mixture of 16 and 17 was obtained. After 16 hours at room temperature, no changes in the ratio between 6A', 16 and 17 were observed. $^{31}$P{$^1$H} NMR indicated 36% conversion to syn-[Mn(PNNH)(H)(CO)$_2$] (16) and 33% conversion to anti-[Mn(PNNH)(H)(CO)$_2$] (17).

The hydride resonance appears at −1.71 ppm (d, $^2J_{PH}$=52.7 Hz) in $^1$H NMR and it showed a singlet at 143.4 ppm in the $^{31}$P{$^1$H} NMR spectrum, 7.6 ppm downfield shifted in comparison with complex 6A'. Complex 16 slowly isomerized to yield the hydride complex 17. Complex 17 exhibited a hydride resonance at −1.34 ppm (d, 2J$_{PH}$=55.2 Hz) in $^1$H NMR spectrum and a singlet at 143.8 ppm in $^{31}$P{$^1$H} NMR spectrum. After 16 hours no changes in the proportion of 6A', 16 and 17 complexes were observed (6A': 16:17; 1.0:1.1:1.2, determined by $^{31}$P{$^1$H} NMR). Complex 16 was independently prepared by treatment of complex 6B with NaHBEt$_3$ under H$_2$ atmosphere (1 bar) in Tol-d$^8$ at −10° C. and characterized by low temperature NMR (0° C.).

In line with the proposed geometry of 16, two resonances are observed in the carbonyl regime in the $^{13}$C{$^1$H} NMR spectrum at 219.3 ppm ($^2J_{PC}$=12.6 Hz) and 230.4 ppm ($^2J_{PC}$=20.7 Hz). When this cold solution containing complex 16 reaches room temperature it slowly forms a mixture of 6A', 16 and 17 complexes (after 12 hours, proportion 6A': 16:17; 1.0:0.8:0.9, was determined by $^{31}$P{$^1$H} NMR spectroscopy). Complex 17 exhibits the same pattern in $^{13}$C{$^1$H}NMR as complex 16 two resonances for the carbonyl ligands, at 218.4 ppm ($^2J_{PC}$=12.5 Hz) and 229.8 ppm ($^2J_{PC}$=19.7 Hz), slightly different in their chemical shift in comparison with 16.

The syn orientation of the N—H and Mn—H bonds in 16 is indicated by a NOE study, upon selective irradiation of the hydride resonance at −1.71 ppm, the NOE difference spectrum gives NOE enhancement for the resonance at 3.09 ppm (s), which corresponds to the NH group and also for the resonance at 1.42 ppm (d, $^3J_{Hp}$=12 Hz), due to the $^t$BuP group which points in the same direction as the Mn—H. Upon selective irradiation of the hydride resonance at −1.34 ppm, the NOE difference spectrum only shows NOE enhancement for the resonances at 1.37 ppm (d, $^3J_{HP}$=12 Hz) and 0.94 ppm (s), which correspond to the $^t$BuP and $^t$BuN groups, in agreement with the proposed anti orientation of the N—H and Mn—H bonds for 17 (FIG. 19).

Summary:

Complex 6B showed high selectivity for ester groups, C=C and CN groups not being affected. The actual catalytically active complex, the amido complex 6A', was prepared by deprotonation of 6B and was also generated in situ. H$_2$ activation takes place by metal-ligand cooperation (MLC), in which the manganese metal center and the PNNH-pincer ligand participate synergistically in H$_2$ activation, leading to syn and anti isomers.

Example 18

Synthesis of Manganese Complex of Formula 4 and 4B

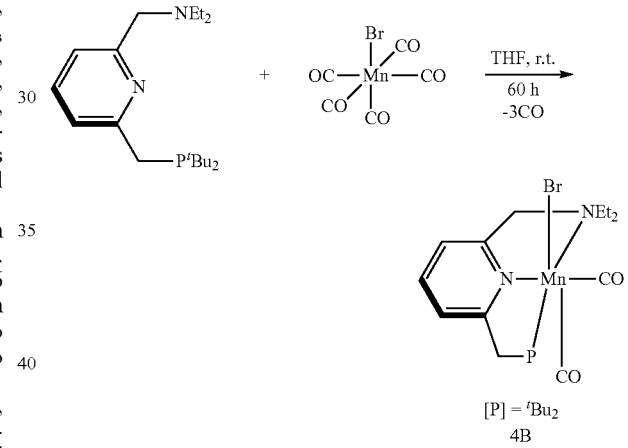

[P] = $^t$Bu$_2$
4B 2-(di-tert-butylphosphinomethyl)-6-diethylaminomethyl) pyridine (PNN) ligand (1.60 g, 4.96 mmol) and [Mn(CO)$_5$Br] (1.36 g, 4.96 mmol) were dissolved in 10 mL of THF in a 20 mL vial. The vial was closed with a vial septum cap and two needles (0.8×40 mm) were connected through the septum in order to displace the CO gas liberated during the reaction. The mixture was stirred at room temperature for 60 h. The reaction mixture was concentrated to ~half of the volume and the orange precipitate was decanted, washed with diethyl ether, and dried under reduced pressure (2.24 g, 88% yield).

The 2-(di-tert-butylphosphinomethyl)-6-diethylaminomethyl)pyridine (PNN) ligand was prepared according to Zhang, J; Leitus, G.; Ben-David, Y.; Milstein, D. J. Am. Chem. Soc. 2009, 131, 3146.

$^{31}$P{$^1$H} NMR (162.08 MHz, CDCl$_3$, 25° C.): δ 118.0 (s).

$^1$H NMR (400.36 MHz, CDCl$_3$, 25° C.): δ 1.09 (tbr, $^3J_{HH}$=6.6 Hz, 6H, N(CH$_2$CH$_3$)$_2$), 1.34 (d, $^3J_{PH}$=12.5 Hz, 18H, (CH$_3$)$_3$CP), 2.27 (mbr, 2H, N(CH$_2$CH$_3$)$_2$), 3.20 (mbr, 2H, N(CH$_2$CH$_3$)$_2$), 3.58 (mbr, 2H, NCH$_2$Py), 4.20 (mbr, 2H, PCH$_2$), 7.19 (sbr, 1H, CH$_{pyri(3)}$), 7.43 (sbr, 1H, CH$_{pyri(5)}$), 7.65 (sbr, 1H, CH$_{pyri(4)}$).

$^{13}$C{$^1$H} NMR (100.67 MHz, CDCl$_3$, 25° C.): δ 7.73 (s, N(CH$_2$CH$_3$)$_2$), 11.23 (s, N(CH$_2$CH$_3$)$_2$), 28.9 (d, $^2J_{PC}$=4.8

Hz, (CH$_3$)$_3$CP), 30.6 (d, $^2$J$_{PC}$=3.2 Hz, (CH$_3$)$_3$CP), 35.9 (d, $^1$J$_{PC}$=16.3 Hz, (CH$_3$)$_3$CP), 36.8 (d, $^1$J$_{PC}$=10.8 Hz, (CH$_3$)$_3$CP), 37.3 (d, $^1$J$_{PC}$=7.1 Hz, PCH$_2$), 52.8 (s, N(CH$_2$CH$_3$)$_2$), 53.4 (s, N(CH$_2$CH$_3$)$_2$), 66.4 (s, NCH$_2$Py), 117.2 (s, CH$_{pyri(5)}$), 118.8 (d, $^3$J$_{PC}$=7.6 Hz, CH$_{pyri(3)}$), 132.3 (s, CH$_{pyri(4)}$), 158.2 (d, $^4$J$_{PC}$=3.6 Hz, CH$_{pyri(6)}$), 161.7 (d, $^2$J$_{PC}$=7.2 Hz, CH$_{pyri(2)}$), 227.3 (d, $^2$J$_{PC}$=12.9 Hz, Mn—O), 238.6 (d, $^2$J$_{PC}$=12.9 Hz, Mn—CO).

IR (KBr, pellet, cm$^{-1}$): 1829 ($\nu_{sym}$. C≡O), 1916 ($\nu_{sym}$. C≡O) in 1:1 ratio.

Preparation and Characterization of [Mn(PNN*)(CO)$_2$] (4).

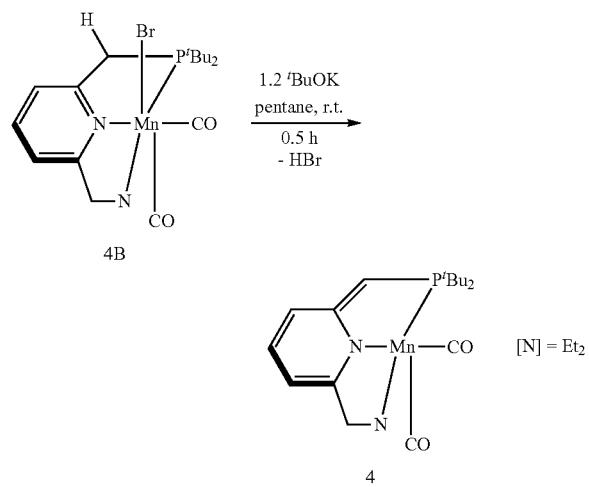

[Mn(PNN)(CO)$_2$(Br)] (4B) (200 mg, 0.39 mmol) and KO$^t$Bu (52 mg, 0.47 mmol) were suspended in 10 mL of pentane. The mixture was stirred at room temperature for 1 h. during the reaction time the original colorless suspension becomes a dark-blue solution. After filtration through a Teflon syringe filter (0.2 μm), the pentane solution was kept at −35° C. in a freezer overnight to form dark blue crystals. The crystals were decanted and dried under vacuum. (127 mg, 79% yield).

$^{31}$P{$^1$H} NMR (162.08 MHz, C$_6$D$_6$, 25° C.): δ 110.9 (s).

$^1$H NMR (400.36 MHz, C$_6$D$_6$, 25° C.): δ 0.62 (t, $^3$J$_{HH}$=7.2 Hz, 9H, N(CH$_2$CH$_3$)$_2$), 1.21 (d, $^3$J$_{PH}$=13.0 Hz, 18H, (CH$_3$)$_3$CP), 1.99 (m, 2H, N(CH$_2$CH$_3$)$_2$), 2.26 (m, 2H, N(CH$_2$CH$_3$)$_2$), 3.08 (sbr, 2H, NCH$_2$Py), 3.70 (sbr, 1H, PCHPy), 5.21 (mbr, 1H, CH$_{pyri(4)}$), 6.41 (m, 2H, CH$_{pyri(3,5)}$).

$^{13}$C{$^1$H} NMR (100.67 MHz, C$_6$D$_6$, 25° C.): δ 8.9 (s, N(CH$_2$CH$_3$)$_2$), 28.7 (d, $^2$J$_{PC}$=4.0 Hz, (CH$_3$)$_3$CP), 36.4 (d, $^1$J$_{PC}$=22.0 Hz, (CH$_3$)$_3$CP), 49.2 (s, N(CH$_2$CH$_3$)$_2$), 63.3 (s, NCH$_2$Py), 68.7 (d, $^1$J$_{PC}$=45.5 Hz, PCHPy), 96.9 (s, CH$_{pyri(5)}$), 115.9 (d, $^3$J$_{PC}$=16.2 Hz, CH$_{pyri(3)}$), 131.8 (s, CH$_{pyri(4)}$), 156.4 (d, $^4$J$_{PC}$=4.5 Hz, CH$_{pyri(6)}$), 171.1 (d, $^2$J$_{PC}$=19.3 Hz, CH$_{pyri(2)}$), 238.3 (d, $^2$J$_{PC}$=19.4 Hz, Mn—CO).

IR (KBr, pellet, cm$^{-1}$): 1819 ($\nu_{asym}$, C≡O), 1907 ($\nu_{sym}$, C≡O) in 1:1 ratio.

Characterization by X-Ray Diffraction.

Crystal data was measured at 100 K on a Bruker Apex-II KappaCCD diffractometer equipped with [λ(Mo—Kα)= 0.71073 Å] radiation, graphite monochromator and MiraCol optics. The data were processed APEX-II collect package program. Structure was solved (FIG. 20) by the AUTOSTRUCTURE module and refined with full-matrix least-squares refinement based on F$^2$ with SHELXL-2014.

Crystal Data, Data Collection, and Structure Refinement for 4.

| Crystal data | |
|---|---|
| | 4 |
| formula | C$_{21}$H$_{34}$MnN$_2$O$_2$P |
| M$_r$ | 432.41 |
| crystal system | monoclinic |
| space group | Cc |
| a (Å) | 14.1304(15) |
| b (Å) | 14.4105(14) |
| c (Å) | 11.1726(12) |
| α(°) | 90 |
| β(°) | 96.228(3) |
| γ(°) | 90 |
| V (Å$^3$) | 2161.6(4) |
| Z | 4 |
| ρ$_{calc}$ (g cm$^{-3}$) | 1.270 |
| μ(mm$^{-1}$) | 0.672 |
| F(000) | 920 |
| crystal size (mm$^3$) | 0.18 × 0.14 × 0.06 |
| Data collection and Refinement | |
| T/K | 100(2) |
| measd reflns | 6871 |
| Unique reflns (Rint) | 3443 (0.0386) |
| reflns used for refinement | 3443 |
| refined parameters | 252 |
| GOF on F$^2$ | 1.012 |
| R$_1$$^a$ [I > 2σ (I)] | 0.0367 |
| wR$_2$$^b$ all data | 0.0777 |

$^a$R1 = Σ||Fo| − |Fc||/Σ|Fo|.
$^b$wR2 = [Σ[w(Fo$^2$ − Fc$^2$)$^2$]/Σ[w(Fo$^2$)$^2$]]$^{1/2}$.

Tables 14 and 15 provide selected bond length and bond angles respectively of complex 4.

TABLE 14

| Selected bond lengths [Å] of 4. | |
|---|---|
| | 4 |
| Mn1—P1 | 2.3071(9) |
| Mn1—N1 | 1.969(3) |
| Mn1—N2 | 2.106(3) |
| Mn1—C20 | 1.764(4) |
| Mn1—C21 | 1.733(4) |
| C1—C2 | 1.499(5) |
| C6—C7 | 1.366(5) |
| C7—P1 | 1.778(4) |
| C1—N2 | 1.362(4) |

TABLE 15

| Selected bond angles [°] 4. | |
|---|---|
| | 4 |
| P1—Mn1—N1 | 82.05(8) |
| P1—Mn1—N2 | 158.61(8) |
| N1—Mn1—C20 | 165.94(16) |
| N1—Mn1—C21 | 108.77(15) |
| N2—Mn1—C20 | 96.88(14) |
| N2—Mn1—C21 | 98.58(14) |
| C20—Mn1—C21 | 85.25(18) |

Example 19

Dehydrogenative Coupling of Alcohols for the Preparation of Esters Using the Manganese Catalyst of this Invention The deprotonated complex 6B in presence of KH was found to be very active catalyst for acceptorless dehydrogenative esterification of alcohols, 5 mol % complex 6B with KH (5 mol %) in neat 1-hexanol (5 mmol) were placed in a Schlenk-bomb tube (50 ml volume), the tube was placed under vaccum (approx. 1 mm Hg) for ~5 minutes, sealed under vacuum, and heated at 100° C. (bath temperature) with strong stirring for 16 hours, 88% hexyl hexanoate was formed (Table 14, Entry 2). Starting from diols, formation of lactones is also possible, through two sequential reactions in the absence of external oxidants and generating molecular hydrogen as the only stoichiometrical waste. 1,4-butanediol was smoothly dehydrogenated, using the 6B (2 mol %) and KH (4 mol %) under reflux of benzene in an open system, yielding 99% of γ-butyrolactone (Entry 2). Complex 6B in presence of KH smoothly converted 1,2-benzenedimethanol into phtalide. Refluxing 1,2-benzenedimethanol (1 mmol) and toluene (2 mL) in the presence of 6B (50% mol) and KH (10 mol %) under argon atmosphere provided phtalide in 99% yield (Entry 4).

TABLE 16

Catalytic dehydrogenation of alcohols using the manganese precatalyst 6B $$2\ R\text{-}OH \xrightarrow[\text{Solvent}]{\text{6B/KH}} R\text{-}C(=O)\text{-}O\text{-}R + 2\ H_2$$

| Entry | Alcohol | Solvent | Temp (° C.) | Time (h) | Conv (%)[a] | Ester | Yield(%)[a] |
|---|---|---|---|---|---|---|---|
| 1[b] | 1-pentanol | neat | 100 | 16 | 92 | pentyl pentanoate | 88 |
| 2[c] | 1,4-butanediol | Benzene | reflux | 60 | 99 | γ-butyrolactone | 99 |
| 3[d] | 1,5-pentanediol | Toluene | reflux | 4 | 58 | δ-valerolactone | 52 |
| 4[d] | 1,2-benzenedimethanol | Toluene | reflux | 4 | 99 | phtalide | 99 |

[a]Conversions and Yields determined by $^1$H-NMR with an internal standard (mesitylene). Products confirmed by GC-MS.
[b]Reaction conditions: 6B (5 mol %)/KH (5 mol %) and substrate (5 mmol) were placed in a Schlenk tube, the tube was evacuated for 5 min, sealed, and heated at 100° C. (bath temperature) with strong stirring for 16 h.
[c]6B (2 mol %)/KH (4 mol %) and substrate (1 mmol) internal standard (1 mmol, mesitylene) and benzene (2 mL) were refluxed under argon.
[d]6B (5%)/KH (10%) and substrate (1 mmol) internal standard (1 mmol, mesitylene) and toluene (2 mL) were refluxed under Ar flow.

Complex 6A' was also found to be very active in the dehydrogenative esterification process. When a cyclohexane solution containing 2 mmol of 1-hexanol and 2.5 mol % of complex 6A' was refluxed under argon atmosphere, 86% conversion of 1-hexanol was observed after 48 hours, to give hexyl hexanoate in 84% (Table 15, Entry 1), showing comparable activity as with the catalyst prepared in situ (Table 16, Entry 1).

TABLE 17

Catalytic dehydrogenation of alcohols using the amido complex 6A'.

$$2\ R\text{-}OH \xrightarrow[\text{Solvent}]{\text{6A' (2.5\%)}} R\text{-}C(=O)\text{-}O\text{-}R + 2\ H_2$$

| Entry | Alcohol | Solvent | Temp (° C.) | Time (h) | Conv (%)[a] | Ester | Yield (%)[a] |
|---|---|---|---|---|---|---|---|
| 1 | 1-pentanol | cyclohexane | reflux | 48 | 86 | pentyl pentanoate | 84 |

[a]Conversions and Yields determined by 1H-NMR with an internal standard (mesitylene). Products confirmed by GC-MS.
[b]6A' (2.5 mol %) and substrate (2 mmol) internal standard (1 mmol, mesitylene) and cyclohexane (2 mL) were refluxed under argon.

Example 20

Dehydrogenative Coupling of Alcohols and Amines for the Preparation of Amides Using the Manganese Catalyst of this Invention A solution of methylcyclohexane (2 mL), complex 6B (5 mol %), KH (10 mol %), benzylamine (1 mmol) and 1-hexanol (1 mmol) was refluxed for 60 hours, 70% conversion of benzylamine was observed, rendering a mixture consisting of N-benzylhexanamide (A) in 40% yield and N-hexylidenebenzenemethanamine (B) in 28% yield (Table 16, Entry 1), with the rest of the alcohol being converted to hexyl hexanoate. Under the same conditions, when 1-hexanol reacts with 1-hexylamine, the corresponding imine was obtained in 99% yield (Entry 2). Refluxing of 1-hexanol, benzylamine and toluene in presence of complex 6B (5 mol %) and KH (10%) provided only the imine B in 80% yield (Entry 3), with the rest of the alcohol being converted to hexyl hexanoate.

Once having performed the synthesis of lactones from diols (Table 14, entries 2-4), this domino sequence was applied to the synthesis of other biologically relevant compounds. The similarity of their structures led us to focus on analogous lactams. When a toluene solution of 1 mmol of 4-amino-1-butanol and 5 mol % of complex 6B in presence of KH (100%) was refluxed under argon atmosphere, γ-butyrolactone was formed in 68% yield after 18 hours (Table 18, Entry 4). Under analogous conditions, intramolecular amidation was also carried out by using 5-amino-1-pentanol with full conversion to δ-valerolactam after 18 h (Entry 5).

TABLE 18

Direct amide synthesis by dehydrogenative coupling of alcohols and amines.

$$R_1\text{-OH} + R_2\text{-NH}_2 \xrightarrow[\text{reflux}]{\text{6B (5\%)/KH (10\%)}} R_1\text{C(O)NHR}_2 + R_1\text{CH=NR}_2 + 2H_2 + H_2O$$

| Entry | Alcohol | Amine | Solvent | Time (h) | Conv$^a$ (%) |
|---|---|---|---|---|---|
| 1$^c$ | hexanol (CH$_3$(CH$_2$)$_5$OH) | benzylamine (PhCH$_2$NH$_2$) | methyl cyclo hexane | 60 | 70 |
| 2$^c$ | hexanol | hexylamine | methyl cyclo hexane | 60 | 99 |
| 3$^c$ | benzyl alcohol | hexylamine | Tol | 39 | 99 |
| 4$^d$ | 4-amino-1-butanol (HO(CH$_2$)$_4$NH$_2$) | | Tol | 18 | 72 |
| 5$^d$ | 5-amino-1-pentanol (HO(CH$_2$)$_5$NH$_2$) | | Tol | 18 | 99 |

| Entry | Product(s) | | Yield$^b$ (%) |
|---|---|---|---|
| 1$^c$ | N-benzylhexanamide | A | 40 |
| | N-hexylidenebenzenemethanamine | B | 28 |
| 2$^c$ | N-hexylhexanamide | A | — |

TABLE 18-continued

Direct amide synthesis by dehydrogenative coupling of alcohols and amines.

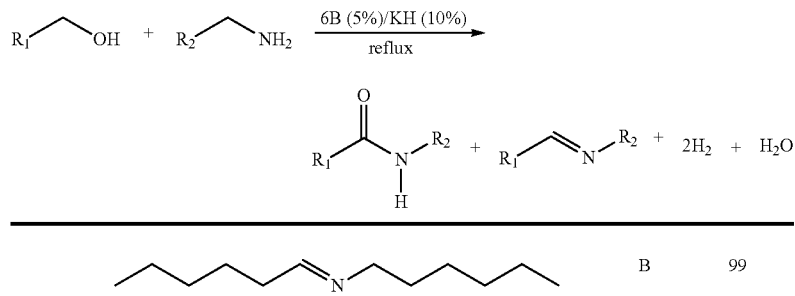

| | | | |
|---|---|---|---|
| | 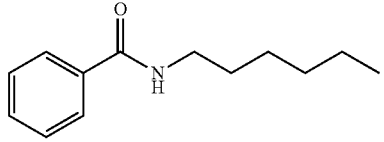 | B | 99 |
| 3[c] | 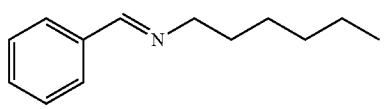 | A | — |
| | 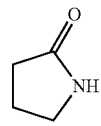 | B | 80 |
| 4[d] | 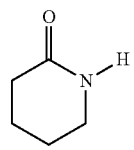 | | 68 |
| 5[d] | | | 99 |

[a]Based in consumption of amine.
[b]Conversions and yields determined by $^1$H-NMR with an internal standard (mesitylene). Products confirmed by GC-MS.
[c]Reaction conditions: substrates (1.0 mmol), solvent (2 mL), internal standard (mesitylene, 1.0 mmol) were refluxed under argon.
[d]Substrate (1 mmol) internal standard (1 mmol, mesitylene) and toluene (4 mL) were refluxed under argon.

Complex 6A' also exhibited reactivity in the amide synthesis under base-free conditions (Table 19). The reaction of 1-hexanol and benzylamine resulted in slightly better conversion to N-benzylhexanamide (A) as compared with 6B under reflux of methylcyclohexane after 48 hours (48% yield, Table 19, Entry 1) but with formation of imine B as well. In contrast, the reaction of 1-hexanol and 1-hexylamine was achieved the formation of the corresponding amide, in comparison with the reaction using the precatalyst 6B with base (Table 16, Entry 2), but if formed in low yield (10% yield, Entry 2) with formation of the imine (40% yield).

TABLE 19

Direct amide synthesis from alcohols and amines catalyzed by the complex 6A'.

R₁-CH₂-OH + R₂-CH₂-NH₂ →[6A' (5%)][reflux] R₁-C(=O)-NH-R₂ + R₁-CH=N-R₂ + 2H₂ + H₂O

| Entry | Alcohol | Amine | Solvent | Time (h) | Conv$^a$ (%) |
|---|---|---|---|---|---|
| 1$^c$ | pentyl-OH | benzylamine | cyclohexane | 48 | 86 |
| 2$^c$ | pentyl-OH | hexylamine | methylcyclohexane | 48 | 58 |

| Entry | Product(s) | | Yield$^b$ (%) |
|---|---|---|---|
| 1$^c$ | N-benzyl pentanamide | A | 48 |
|  | N-benzyl pentylidenimine | B | 29 |
| 2$^c$ | N-hexyl pentanamide | A | 10 |
|  | N-hexyl pentylidenimine | B | 42 |

$^a$Based in consumption of amine.
$^b$Conversions and yields determined by $^1$H-NMR with an internal standard (mesitylene). Products confirmed by GC-MS.
$^c$Reaction conditions: substrates (1.0 mmol), solvent (2 mL), internal standard (mesitylene, 1.0 mmol) were refluxed under argon.

Example 21

Amidation of Esters Using the Manganese Catalyst of this Invention

Results Using Complex 6B:

A solution of methylcyclohexane (2 mL), pyrrolidine (2 mmol), pentyl pentanoate (1 mmol), precatalyst 6B (5 mol %) and KH (10 mol %) was refluxed under an argon atmosphere, 88% consumption of pentyl pentoate was observed after 60h, to give the corresponding amide in 52% yield (Table 20, Entry 1) and pentanol as subproduct. Reaction of 4-benzylpyrrolidine and pentyl pentanoate under the same conditions resulted after 60h in 47% conversion of pentyl pentoate, with 26% yield of the corresponding amide (Table 20, Entry 2) and pentanol.

TABLE 20

Amidation of esters catalyzed by complex 6B.

R-C(=O)-O-CH2-R + 2 R1R2NH → (6B (5 mol %)/KH (10 mol %), methylcyclohexane reflux) → R-C(=O)-NR1R2 + 2 H2

| Entry | Ester | Amine | Time (h) | Conv (%)[a] |
|---|---|---|---|---|
| 1 | pentyl pentanoate | pyrrolidine | 60 | 88 |
| 2 | pentyl pentanoate | 4-benzylpiperidine | 60 | 47 |

| Entry | | Yield(%)[a] |
|---|---|---|
| 1 | 1-(pyrrolidin-1-yl)pentan-1-one | 52 |
| 2 | 1-(4-benzylpiperidin-1-yl)pentan-1-one | 26 |

Reaction conditions: pentyl pentanoate (1.0 mmol), amine (2.0 mmol), methylcyclohexane (2 mL), internal standard (mesitylene, 1.0 mmol) were refluxed under argon in an open system.
[a]Conversions and yields determined by $^1$H-NMR with an internal standard (mesitylene). Products confirmed by GC-MS.

Results Using Complex 6A':

Complex 6A' was also tested in this reaction. The reaction of pentyl pentanoate with piperidine gave 56% conversion of pentyl pentoate, with 42% yield of the amide after 48 hours (Table 21, Entry 1), using complex 6A' (5 mol %) in absence of base. Reaction of pentyl pentanoate with pyrrolidine in refluxing cyclohexane resulted after 17 hours in the corresponding amide (Entries 2). Higher conversions are expected at longer reaction times.

TABLE 21

Amidation of esters catalyzed by the amido complex 6A'.

R-C(=O)-O-CH2-R + 2 R1R2NH → (6A' (5 mol %), Solvent reflux) → R-C(=O)-NR1R2 + 2 H2

| Entry | Ester | Amine | Solvent | Time (h) | Conv (%)[a] | Amide | Yield(%)[a] |
|---|---|---|---|---|---|---|---|
| 1 | pentyl pentanoate | piperidine | methyl cyclohexane | 48 | 56 | 1-(piperidin-1-yl)pentan-1-one | 42 |

TABLE 21-continued

Amidation of esters catalyzed by the amido complex 6A'.

R-C(=O)-O-CH2-R + 2 R1-NH-R2 → [6A' (5 mol %), Solvent reflux] → R-C(=O)-N(R1)(R2) + 2 H2

| Entry | Ester | Amine | Solvent | Time (h) | Conv (%)$^a$ | Amide | Yield(%)$^a$ |
|---|---|---|---|---|---|---|---|
| 2 | pentyl pentanoate | pyrrolidine | cyclohexane | 17 | 38 | 1-(pyrrolidin-1-yl)pentan-1-one | 32 |

Reaction conditions: 2 mL of solvent, pentyl pentanoate (1.0 mmol), amine (2.0 mmol), methylcyclohexane (2 mL), internal standard (mesitylene, 1.0 mmol) were refluxed under Ar flow.
$^a$Conversions and yields determined by $^1$H-NMR with an internal standard (mesitylene). Products confirmed by GC-MS.

Results Using Complex 4

Complex 4 exhibited low activity in dehydrogenative coupling of primary alcohols to esters and also in the amidation reaction from alcohols and amines. It exhibited better reactivity in the amidation of esters, but it is still less active than the analogous complex 6B (Table 22). Exploring the scope of the ester amidation reaction, pentyl pentanoate and some amines were examined. Refluxing a methylcyclohexane solution containing pentyl pentanoate (1 mmol), piperidine (2 mmol), and 5 mol % of complex 4 under argon atmosphere for 48 hours resulted in 34% consumption of pentyl pentanoate, with formation of 1-(piperidin-1-yl)pentan-1-one in 28% yield as determined by $^1$H NMR and GC-MS (Entry 1).

Example 22

Synthesis of Cyclic Imides from Diols Using the Manganese Catalyst of this Invention Complex 6B was found to be active in the catalytic dehydrogenative coupling of diols and amines to form cyclic amides. The reaction between 1,4-butanediol and amine afford N-substituted succinimide derivatives in excellent yields (Table 23). When a toluene solution containing 1.2 mmol of 1,4-butanediol, 1 mmol of 2-phenethylamine, 5% of complex 6B and 10% of KH was refluxed under an argon atmosphere, quantitative conversion of the amine was observed by NMR and GC-MS after 40 hours, to give

TABLE 22

Amidation of esters catalyzed by the dearomatized complex 4.

R-C(=O)-O-CH2-R + 2 R1-NH-R2 → [4 (5 mol %), Solvent reflux] → R-C(=O)-N(R1)(R2) + 2 H2

| Entry | Ester | Amine | Solvent | Time (h) | Conv (%)$^a$ | Amide | Yield(%)$^a$ |
|---|---|---|---|---|---|---|---|
| 1 | pentyl pentanoate | piperidine | methyl cyclohexane | 42 | 34 | 1-(piperidin-1-yl)pentan-1-one | 28 |
| 2 | pentyl pentanoate | pyrrolidine | cyclohexane | 17 | 28 | 1-(pyrrolidin-1-yl)pentan-1-one | 22 |

Reaction conditions: 2 mL of solvent, pentyl pentanoate (1.0 mmol), amine (2.0 mmol), methylcyclohexane (2 mL), internal standard (mesitylene, 1.0 mmol) were refluxed under Ar flow.
$^a$Conversions and yields determined by $^1$H-NMR with an internal standard (mesitylene). Products confirmed by GC-MS.

1-(phenylethyl)succinimide (characterized by NMR and GC-MS) in 88% isolated yield after column purification (Table 23, Entry 1). Excellent relativities where observed with benzyl amines. Reaction of 1,4-butanediol with benzylamine in toluene in analogous conditions resulted in 99 conversion, and the corresponding succinimide was isolated in 69% yield (Table 23, Entry 2). Refluxing of 1,4-butanediol and 4-fluorobenzylamine and toluene in the presence of the mixture 6B/KH, provided the succinimide in 72% yield (Table 23, Entry 3). More electron rich benzyl amines favored the cyclization reactions than electron-poor ones (Table 23, entries 3 and 5). In the case of alkyl amines, the imide was obtained in lower yield under analogous conditions (Table 23, Entries 6-8). The catalyst was sensitive to steric hindrance, thus reaction of 1,4-butanediol and cyclohexylamine rendered N-cyclohexylsuccinimide in 46% yield.

It is noted that γ-Butyrolactone was observed, especially with low yielding substrates, along with other unidentified by-products, presumably from possible inter- and intra-molecular amidation and esterifications reactions.

TABLE 23

Synthesis of N-substituted succinimides from 1,4-butanediol

| Entry | Amine | Conv (%)[a] | Succinimide | Yield [%][b] |
|---|---|---|---|---|
| 1[c] | phenethylamine | 99 | N-phenethylsuccinimide | 88 |
| 2[c] | benzylamine | 99 | N-benzylsuccinimide | 69 |
| 3[c] | 4-methylbenzylamine | 99 | N-(4-methylbenzyl)succinimide | 92 |
| 4[c] | 4-fluorobenzylamine | 99 | N-(4-fluorobenzyl)succinimide | 72 |
| 5[c] | 4-methoxybenzylamine | 99 | N-(4-methoxybenzyl)succinimide | 82 |
| 6[d] | hexylamine | 96 | N-hexylsuccinimide | 62 |
| 7[d] | butylamine | 99 | N-butylsuccinimide | 58 |

TABLE 23-continued

Synthesis of N-substituted succinimides from 1,4-butanediol

HO~~~OH + R—NH₂ →[6B (5%)/KH (10%)][Tol] N-R succinimide + 4 H₂

| Entry | Amine | Conv (%)[a] | Succinimide | Yield [%][b] |
|---|---|---|---|---|
| 8[d] | MeO-CH₂CH₂-NH₂ | 99 | N-CH₂CH₂-OMe succinimide | 57 |
| 9[d] | cyclohexyl-NH₂ | 60 | N-cyclohexyl succinimide | 46 |
| 10[d] | cyclopentyl-NH₂ | 99 | N-cyclopentyl succinimide | 42 |
| 11[e] | H₂N-(CH₂)₅-NH₂ | 99 | bis-succinimide | 48 |

[a]Conversions based on consumption of amine, determined by ¹H NMR and GC-MS with an internal standard (mesitylene).
[b]Yields of isolated product. Reaction conditions: [Mn(PNNH)] (5 mol %), KH (10 mol %), toluene (2 mL), reflux, 40 hours.
[c]1,4-butanediol (1.0 mmol), amine (1.0 mmol), internal standard (mesitylene, 1 mmol).
[d]1,4-butanediol (0.5 mmol), amine (0.5 mmol), internal standard (mesitylene, 0.5 mmol).
[e]1,4-butanediol (0.5 mmol), amine (0.25 mmol), and internal standard (mesitylene, 0.5 mmol).

Since facile synthesis of succinimides derivates from 1,4-butanediol has been achieved, various diols were screened to synthesize cyclic amides. Phtalamide derives were obtained from 1,2-benzenedimethanol in moderate yields (Table 24). When a toluene solution of 1 mmol of 1,2-benzedimethanol, 1 mmol of benzylamine and mixture 6B/KH 5%/10% were refluxed under argon atmosphere, 81% conversion of the benzylamine was observed by GC-MS and NMR to give N-benzylphtalimide (A) in 34% yield (characterized by NMR and GC-MS) and N,N'-dibenzylphtalamide (B) in 24% isolated yield after purification (Table 24, entry 1). The remaining 1,2-benzenedimethanol was fully converted to phtalide. Complex 6B showed lower activity in the activation of alkyl amines than aryl amines (Table 24, entry 3). Use of phtalide, a presumably intermediate for the imide formation, showed to be beneficial for the reaction, but it still rendered a mixture of A and B. A toluene solution of 6B/KH (5%/10% mole percent) with butylamine and phtalide (1:1 ratio) was refluxed under a flow of argon for 18h. This setup resulted in the formation of N-butylphtalimide (A) in 46% yield and N,N'-dibutylphtalamide in 25% yield. Six-membered glutaramides were also formed in moderate yields (Table 21, entries 5-6). Reaction of 1,5-pentanediol (1.2 mmol) and 2-phenethylamine (1.0 mmol) under analogous conditions render 1-(2-phenylethyl)-2,6-piperidinedione in 62% isolated yield after column (Table 24, entry 5).

TABLE 24

Synthesis of cyclic imides from diols.

| Entry | Diol | Amine | Conv. Of amine(%)[a] | Products | | Yield (%) |
|---|---|---|---|---|---|---|
| 1 | benzene-1,2-diyldimethanol | benzylamine | 82 | N-benzylphthalimide | A | 34[b] |
| | | | | N,N'-dibenzylphthalamide | B | 24[c] |
| 2 | benzene-1,2-diyldimethanol | 4-fluorobenzylamine | 88 | N-(4-fluorobenzyl)phthalimide | A | 38[b] |
| | | | | N,N'-bis(4-fluorobenzyl)phthalamide | B | 22[c] |
| 3 | benzene-1,2-diyldimethanol | butylamine | <90[d] | N-butylphthalimide | A | 26[c] |
| | | | | N,N'-dibutylphthalamide | B | 18[c] |

TABLE 24-continued

Synthesis of cyclic imides from diols.

R¹R²CH(CH₂OH)₂ + R³CH₂NH₂ →[6B (5%)/KH (10%)][Tol] cyclic imide + 4 H₂

| Entry | Diol | Amine | Conv. Of amine(%)[a] | Products | Yield (%) |
|---|---|---|---|---|---|
| 4[e] | phthalide | butylamine | <99[d] | A: N-butylphthalimide; B: N,N'-dibutylphthalamide | A 46[c]; B 25[c] |
| 5[f] | 1,5-pentanediol | 2-phenethylamine | 99 | 1-(2-phenylethyl)-2,6-piperidinedione | 62[c] |
| 6[f] | 1,5-pentanediol | 4-fluorobenzylamine | 99 | 1-[(4-fluorophenyl)methyl]-2,6-piperidinedione | 32[c] |

Reaction conditions: 1,2-benzenedimethanol (1.0 mmol), amine (1.0 mmol), internal standard (mesitylene, 1.0 mmol) in 2 mL of toluene were refluxed under Ar flow for 40 hours
[a]Conversions of amine was determined by ¹H-NMR and GC-MS with an internal standard (mesitylene).
[b]Determined by ¹H-NMR and GC-MS with an internal standard (mesitylene).
[c]Isolated yield.
[d]Volatile amine.
[e]Phtalide (1.0 mmol), butylamine (1.2 mmol), internal standard (mesitylene, 1.0 mmol) in 2 mL of toluene were refluxed under Ar flow for 18 hours.
[f]1,5-pentanodiol (1.2 mmol), amine (1.0 mmol), internal standard (mesitylene, 1.0 mmol) in 2 mL, of toluene were refluxed under Ar flow for 40 hours.

A broader scope of N-substituted glutaramide derivates in good yields were afforded using higher catalytic loading in more diluted solutions (Table 25). When a toluene solution (4 mL) containing 0.5 mmol of 1,5-pentanediol, 0.5 mmol of 2-phenethylamine, 8% of complex 6B and 16% of KH was refluxed under an argon atmosphere, quantitative conversion of the amine was observed by NMR and GC-MS after 40 hours, to give 1-(2-phenylethyl)-2,6-piperidinedione in 72% isolated yield after column (Table 25, entry 1). Noticeable, more-electron-rich benzyl amines favorate the cyclization reaction than electron-poor ones (Table 25, entries 2-5). Thus reaction of 1,5-pentanediol (0.5 mmol) and 4-methoxybenzylamine (0.5 mmol) under analogous conditions render 1-[(4-methoxyphenyl)methyl]-2,6-piperidinedione in 76% isolated yield after column (Table 25, entry 5).

TABLE 25

Synthesis of N-glutarimides derivates.

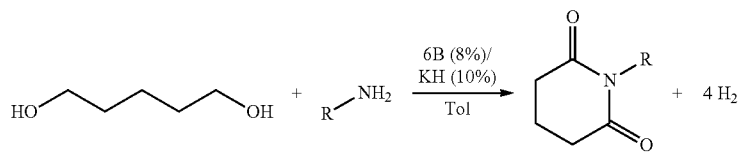

| Entry | Amine | Conv (%)[a] | Glutarimide | Yield [%][b] |
|---|---|---|---|---|
| 1[c] | PhCH₂CH₂NH₂ | 99 | N-phenethyl glutarimide | 72 |
| 2[c] | BnNH₂ | 99 | N-benzyl glutarimide | 50 |
| 3[c] | 4-Me-C₆H₄-CH₂NH₂ | 99 | N-(4-methylbenzyl) glutarimide | 57 |
| 4[c] | 4-F-C₆H₄-CH₂NH₂ | 99 | N-(4-fluorobenzyl) glutarimide | 52 |
| 5[c] | 4-MeO-C₆H₄-CH₂NH₂ | 99 | N-(4-methoxybenzyl) glutarimide | 76 |
| 6[d] | n-hexylamine | 99 | N-hexyl glutarimide | 60 |

[a]Conversions based on consumption of amine, determined by ¹H NMR and GC-MS with an internal standard (mesitylene).

[b]Yields of isolated product. Reaction conditions: [Mn(PNNH)] (8 mol %), KH (16 mol %), 1,5-pentanediol (0.5 mmol), amine (0.5 mmol), internal standard (mesitylene, 0.5 mmol), toluene (4 mL), reflux, 40 hours.

Example 23

Synthesis of Manganese Complex 19-Mn(iPr-PN$^H$P)(CO)$_2$Br

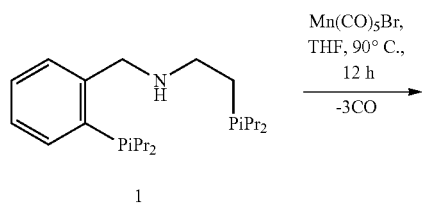

To a solution of the iPr-PN$^H$P ligand 1 (268 mg, 0.73 mmol) in 5 mL THF was added under argon atmosphere an orange solution of Mn(CO)$_5$Br (200 mg, 0.73 mmol) in 10 mL THF and the reaction mixture was kept stirring at 90° C. for 12 h (Note: The argon atmosphere need to be removed occasionally in vacuo). The solution was filtered through a pad of Celite and the solvent was concentrated in vacuo. The solid residue was washed with pentane (10 mL), which on drying gives a yellow solid. The yellow crude product was dissolved in toluene (15 mL), the solution was filtered and concentrated, layered with pentane and kept in the refrigerator to obtain mixture of orange and yellow crystals in 86% (348 mg) yield. $^1$H NMR (C$_6$D$_6$, 400 MHz): δ=1.09 (b, 3H, CH$_3$), 1.21 (b, 12H, CH$_3$), 1.44 (b, 2H, PCH$_2$), 1.52 (b, 3H, CH$_3$), 1.64 (3H, CH$_3$), 1.83 (m, 3H, CH$_3$), 2.08 (NCH$_2$), 2.55 (br, NH), 2.25 (2H. —CH), 2.91 (1H, CH), 3.25 (2H, CH and CH$_2$Ar overlapped), 4.16 (1H, —CH$_2$Ar), 6.83 (1H, Ar), 7.02 (1H, Ar), 7.09 (1H, Ar), 7.38 (1H, Ar). $^{13}${$^1$H} NMR (C$_6$D$_6$, 101 MHz): δ=18.6 (CH$_3$), 18.9 (CH$_3$), 19.2 (CH$_3$), 20.78 (CH$_3$), 23.7 (—CH$_2$P), 25 (CH), 29.2 (CH), 32.4 (CH), 55.4 (—CH$_2$N), 61.5 (d, J$_{CP}$=7.7 Hz, —CH$_2$Ar), 128.9 (Ar), 130.3 (d, J$_{CP}$=7.9 Hz, Ar), 131.9 (Ar), 140.8 (Ar). CO signals could not be found probably due to low concentration. $^{31}$P{$^1$H} NMR (C$_6$D$_6$, 162 MHz): δ=59.1 (d, $^2$J$_{PP}$=88 Hz,), 85.7 (d, $^2$J$_{PP}$=88 Hz). IR (thin film, NaCl)= 1828 cm$^{-1}$ (v$_{CO}$), 1913 cm$^{-1}$ (v$_{CO}$), 3210 cm$^{-1}$ (v$_{N-H}$). Anal. Calcd. for C$_{23}$H$_{39}$BrMnNO$_2$P$_2$: C, 49.48; H, 7.04; N, 2.51. Found: C, 50.53; H, 6.97; N, 2.01.

X-Ray Crystal Structure Determination:

Crystal data was measured at 100 K on a Bruker Apex-II Kappa CCD diffractometer equipped with [λ(Mo—Kα) =0.71073 Å] radiation, graphite monochromator and Mira Col optics. The data was processed with APEX-II collect package programs. Structures were solved (for ORTEP representation, see FIG. 21) by the AUTOSTRUCTURE module and refined with full-matrix least-squares refinement based on F2 with SHELXL-97.

TABLE 26

Selected bond lengths and bond angles of 19.

| Bond lengths [Å] | | Bond Angles [°] | |
|---|---|---|---|
| Br1—Mn1 | 2.5677(3) | P1—Mn1—P2 | 174.338(19) |
| Mn1—N1 | 2.1372(13) | N1—Mn1—P1 | 90.78(4) |
| Mn1—P1 | 2.3300(5) | C22—Mn1—P1 | 90.85(6) |
| Mn1—P2 | 2.3014(5) | C22—Mn1—N1 | 176.68(7) |
| Mn1—C23 | 1.7535(18) | C23—Mn1—C22 | 86.34(8) |
| Mn1—C22 | 1.7818(17) | N1—Mn1—Br1 | 84.12(4) |
| O1—C22 | 1.144(2) | | |
| N1—H1 | 1.0000 | | |

Example 24

Synthesis of Manganese Complex 20-Mn(iPr-PN$^H$PN$^H$P)(CO)$_2$

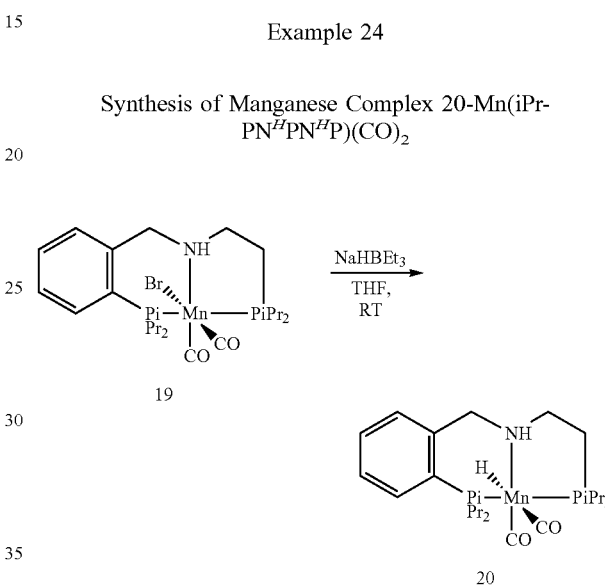

In a glove box under N$_2$ atmosphere, a 20 mL oven-dried vial equipped with a stirring bar was charged with a yellow solution of Mn(iPr-PN$^H$P)(CO)$_2$Br (19) (100 mg, 0.179 mmol) in 10 mL THF. Then 0.179 mL of cold NaHBEt$_3$ solution (0.179 mmol, 1 M in THF) was added dropwise, turning the solution color to light red. The solution was kept stirring for another 15 min followed by filtration and solvent evaporation in vacuo. The resulting yellowish red residue was washed with a minimum amount of pentane (2 mL) and dried to obtain a solid, which was extracted with benzene, and the solution filtered through a syringe filter and the solvent removed in vacuo. The light yellow powder complex 20 was afforded (65 mg) in 88% yield.

$^1$H NMR (C$_6$D$_6$, 400 MHz): δ=−5.5 (t, $^2$J p=60.2 Hz, Mn—H), 1.07 (3H, CH$_3$), 1.15 (2H, PCH$_2$), 1.32 (CH$_3$), 1.62 (m, 3H, CH$_3$), 1.82 (m, 2H, NCH$_2$), 2.04-2.16 (CH), 2.33 (2H, —CH), 2.64 (CH and CH$_2$Ar overlapped), 3.62 (1H, —CH$_2$Ar), 6.59 (1H, Ar), 6.99 (m, 1H, Ar), 7.08 (1H, Ar, merged with solvent signal), 7.41 (1H, Ar). $^{13}$C{$^1$H}-NMR (C$_6$D$_6$, 101 MHz): δ=18.2 (CH$_3$), 18.6 (CH$_3$), 18.8 (CH$_3$), 19.04 (CH$_3$), 19.3 (CH$_3$), 19.5 (CH$_3$), 23.6 (PCH$_2$), 29.3 (m, CH), 32.6 (CH), 56.3 (—CH$_2$N), 65.8 (—CH$_2$Ar), 130.2 (Ar), 130.8 (Ar), 143.8 (1H, Ar), 231.9 (CO), 227.5 (CO). $^{31}$P{$^1$H} NMR (C$_6$D$_6$, 162 MHz): δ=91 (d, $^2$J$_{PP}$=57 Hz), 114 (d, $^2$J$_{PP}$=57 Hz). IR (thin film, NaCl)=1805 cm$^{-1}$ (v$_{CO}$), 1879 cm$^{-1}$ (v$_{CO}$), 3290 cm$^{-1}$ (v$_{N-H}$). Anal. Calcd. for C$_{23}$H$_{40}$MnNO$_2$P$_2$: C, 57.62; H, 8.41; N, 2.92. Found: C, 58.30; H, 8.48; N, 2.52.

Example 25

Synthesis of Manganese Complex 18-(iPr-PNP)Mn(CO)$_2$

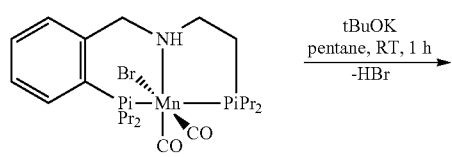

TABLE 27

Selected bond lengths and bond angles of 18.

| Bond lengths [Å] | | Bond Angles [°] | |
|---|---|---|---|
| Mn1—N1 | 1.9021(14) | P1—Mn1—P2 | 170.704(18) |
| Mn1—P1 | 2.2885(5) | N1—Mn1—P1 | 83.39(4) |
| Mn1—P2 | 2.2665(5) | C22—Mn1—P1 | 89.10(5) |
| Mn1—C23 | 1.7687(17) | C22—Mn1—N1 | 137.85(71) |
| Mn1—C22 | 1.7884(17) | C23—Mn1—C22 | 87.89(8) |
| O1—C22 | 1.169(2) | N1—Mn1—C23 | 133.90(7) |
| O2—C23 | 1.173(2) | | |

Example 26

Synthesis of Manganese Complex 21-(iPr-PN$^H$P)Mn(CO)$_2$

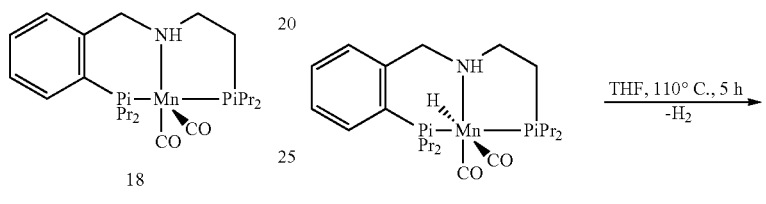

Under a nitrogen atmosphere, complex 19 (92 mg, 0.165 mmol), KOtBu (22 mg, 0.196 mmol) and 10 mL of pentane were charged in a vial equipped with a stirring bar. The color of the solution slowly changed to deep red. The reaction mixture was allowed to stir for 1 h at room temperature. Afterwards the solution was filtered through a pad of Celite and concentrated to 5 mL, filtered and kept in the refrigerator for several days. Deep red crystals of (iPr-PNP)Mn(CO)$_2$ 18 were obtained in 51% yield. Complex 18 is always accompanied by small amount of complex 21 and traces of complex 20. Moreover, complex 18 is very unstable and slowly transforms to complex 21 at room temperature after few hours (~12 h) or heating at 110° C. for 30 min.

$^1$H NMR (C$_6$D$_6$, 400 MHz): δ=0.87 (PCH$_2$), 1.06-1.10 (6H, CH$_3$), 1.12-1.19 (12H, CH$_3$), 1.23-1.29 (6H, CH$_3$), 1.45-1.51 (m, 2H, CH$_2$), 2.22-2.31 (m, 2H, CH), 2.67-2.76 (m, 2H, CH), 3.32-3.39 (m, 2H, NCH$_2$), 4.23 (s, 2H, —CH$_2$Ar), 7.02 (1H, Ar), 7.07 (m, 2H, Ar), 7.27-7.29 (1H, Ar). Due to instability of the complex $^{13}$C{$^1$H} was measured with concentrated freshly prepared sample for 1 h. Selected $^{13}$C{$^1$H}NMR (C$_6$D$_6$, 125.7 MHz): δ=17.4 (CH$_3$), 17.6 (CH$_3$), 17.7 (CH$_3$), 18.2 (CH$_3$), 20.3 (d, J$_{CP}$=9.4 Hz, CH$_2$), 25.6 (d, J$_{CP}$=20.6 Hz, CH), 27.9 (d, J$_{CP}$=23.5 Hz CH), 68.3 (—CH$_2$Ar), 69.6 (—CH$_2$N), 125.7 (Ar), 128.8 (Ar), 129.3 (Ar), 130.9 (Ar). $^{31}$P{$^1$H} NMR (C$_6$D$_6$, 162 MHz): δ=67.5 (d, $^2$J$_{PP}$=93 Hz), 113.6 (d, $^2$J$_{PP}$=93 Hz). IR (thin film, NaCl)=1816 cm$^{-1}$ (ν$_{CO}$), 1887 cm$^{-1}$ (ν$_{CO}$). Anal. Calcd. for C$_{23}$H$_{38}$MnNO$_2$P$_2$: C, 57.86; H, 8.02; N, 2.93. Found: C, 57.79; H, 8.30; N, 2.45.

X-Ray Crystal Structure Determination:

Crystal data was measured at 100 K on a Bruker Apex-II Kappa CCD diffractometer equipped with [λ(Mo—Kα)= 0.71073 Å] radiation, graphite monochromator and Mira Col optics. The data was processed with APEX-II collect package programs. Structures were solved (for ORTEP representation, see FIG. 22) by the AUTOSTRUCTURE module and refined with full-matrix least-squares refinement based on F2 with SHELXL-97.

The hydride complex (iPr-PN$^H$P)Mn(H)(CO)$_2$ (20) (10 mg) was dissolved in 0.5 mL THF in an oven-dried J-Young NMR tube under nitrogen atmosphere. The tube was taken out from the glove box and kept in a pre-heated (110° C.) oil bath. The $^{31}$P{$^1$H} NMR and $^1$H NMR monitoring of the reaction solution over certain time interval revealed disappearance of the hydride signal. The appearance of new signals in the $^{31}$P{$^1$H} NMR indicated formation of a yellow-colored new product in quantitative yield after 5 h. Crystallization upon toluene/pentane or concentrated solution of pentane at −30° C. and X-ray structure determination showed formation of the C—H activated (iPr-PN$^H$P)Mn(CO)$_2$ (5) complex.

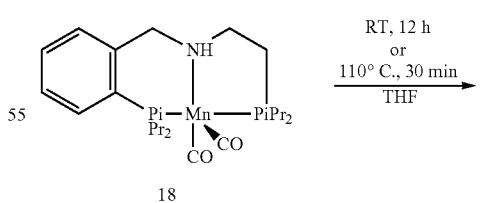

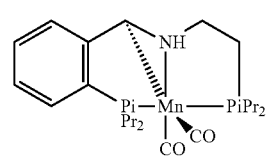

Alternative Procedure:

The amido complex 18 was heated at 110° C. for a few minutes (less than 30 min) in THF or stirred at room temperature in THF for a few hours (less than 12 h) to afford complex 21.

$^1$H NMR (C$_6$D$_6$, 400 MHz): δ=0.53 (1H, PCH$_2$), 0.73 (1H, PCH$_2$), 0.86-0.95 (3H, CH$_3$), 0.99-1.03 (CH$_3$), 1.07-1.11 (CH$_3$), 1.16-1.22 (m, 3H, CH$_3$), 1.29-1.37 (m, CH$_3$), 2.0 (NCH$_2$), 2.20 (benzylic CH), 2.38 (CH), 2.52-2.58 (CH), 6.97 (m, Ar), 7.1 (Ar, merged with solvent signal), 7.27 (Ar). $^{13}$C{$^1$H}NMR (C$_6$D$_6$, 101 MHz): δ=12.1 (CH$_2$), 17.0 (CH$_3$), 17.4 (CH$_3$), 17.5 (CH$_3$), 18.1 (CH$_3$), 18.7 (CH$_3$), 24.3 (m, CH), 26.9 (m, CH), 27.9 (m, CH), 50.0 (—CH$_2$N), 51.8 (—CHAr), 125.2 (Ar), 129.2 (Ar), 131.5 (1H, J$_{CP}$=18.3 Hz, Ar), 160 (J$_{CP}$=40 Hz, Ar), 231 (CO), 235 (CO). $^{31}$P{$^1$H} NMR (C$_6$D$_6$, 162 MHz): δ=103.5 (d, $^2$J$_{PP}$=73 Hz), 114.6 (d, $^2$J$_{PP}$=73 Hz). IR (thin film, NaCl)=1801 cm$^{-1}$ (ν$_{CO}$), 1881 cm$^{-1}$ (ν$_{CO}$), 3319 cm$^{-1}$ (ν$_{N-H}$).

X-Ray Crystal Structure Determination:

Crystal data were measured at 100 K on a Bruker Apex-II Kappa CCD diffractometer equipped with [λ(Mo—Kα)= 0.71073 Å] radiation, graphite monochromator and Mira Col optics. The data was processed with APEX-II collect package programs. Structures were solved (for ORTEP representation, see FIG. 23) by the AUTOSTRUCTURE module and refined with full-matrix least-squares refinement based on F2 with SHELXL-97.

TABLE 28

Selected bond lengths and bond angles of 21.

| Bond lengths [Å] | | Bond Angles [°] | |
|---|---|---|---|
| Mn1—N1 | 2.0338(14) | P1—Mn1—P2 | 171.830(19) |
| Mn1—P1 | 2.2426(5) | N1—Mn1—P1 | 82.81(4) |
| Mn1—P2 | 2.2536(5) | C22—Mn1—P1 | 97.82(6) |

TABLE 28-continued

Selected bond lengths and bond angles of 21.

| Bond lengths [Å] | | Bond Angles [°] | |
|---|---|---|---|
| Mn1—C23 | 1.7515(17) | C22—Mn1—N1 | 114.51(7) |
| Mn1—C22 | 1.7817(18) | C23—Mn1—C22 | 93.19(8) |
| O1—C22 | 1.169(2) | N1—Mn1—C3 | 41.66(6) |
| Mn1—C3 | 2.0695(17) | | |

TABLE 29

Crystal data summary of 19, 18, and 21.

| | 19 | 18 | 21 |
|---|---|---|---|
| CCDC | | | |
| empirical formula | C$_{99}$H$_{164}$Br$_4$Mn$_4$N$_4$O$_8$P$_8$ | C$_{23}$H$_{38}$MnNO$_2$P$_2$ | C$_{23}$H$_{38}$MnNO$_2$P$_2$ |
| formula weight (g · mol$^{-1}$) | 2325.49 | 477.42 | 477.42 |
| temperature (K) | 100(2) | 100(2) | 100(2) |
| wavelength (Å) | 0.71073 | 1.54184 | 0.71073 |
| crystal system, space group | Monoclinic, P2(1)/n | Orthorhombic, Pbca | Orthorhombic, Pbca |
| a (Å) | 16.6026(8) | 12.04030 | 10.8362 |
| b (Å) | 16.7674(8) | 14.79630 | 15.3484 |
| c (Å) | 20.1015(10) | 26.9293 | 29.1295 |
| α (deg) | 90 | 90 | 90 |
| β (deg) | 104.689 | 90 | 90 |
| γ (deg) | 90 | 90 | 90 |
| volume (Å$^3$) | 5413.0(5) | 4797.51(6) | 4844.8(4) |
| Z, density (calcd) Mg · m$^{-3}$ | 2, 1.427 | 8, 1.322 | 8, 1.309 |
| abs coefficient (mm$^{-1}$) | 2.104 | 5.875 | 0.696 |
| F(000) | 2420 | 2032 | 2032 |
| crystal size (mm$^3$) | 0.281 × 0.108 × 0.097 | 0.244 × 0.169 × 0.168 | 0.12 × 0.10 × 0.10 |
| θ range (deg) for data collection | 3.641 to 29.130 | 4.927 to 77.380 | 2.34 to 26.37 |
| reflections collected | 94338 | 45046 | 60849 |
| reflections unique | 14507/R$_{int}$ = 0.0368 | 5091/R$_{int}$ = 0.0514 | 4954/R$_{int}$ = 0.0503 |
| completeness to θ (%) | 99.7 | 100 | 100 |
| max/min transmission | 0.987 and 0.970 | 0.975 and 0.968 | 0.9337 and 0.9212 |
| data/restraints/parameters | 14507/0/632 | 5091/1/270 | 4954/0/278 |
| goodness-of-fit on F$^2$ | 1.029 | 1.028 | 1.072 |
| Final R$_1$ and wR$_2$ indices [I > 2σ(I)] | 0.0264, 0.0602 | 0.0337, 0.0907 | 0,0295, 0.0669 |
| R$_1$ and wR$_2$ indices (all data) | 0.0371, 0.0635 | 0.0351, 0.0917 | 0.0370, 0.0699 |
| largest diff. peak and hole (e · Å$^{-3}$) | 0.963 and −0.709 | 0.296 and −0.656 | 0.403 and −0.211 |

Example 27

Synthesis of Formamides from Methanol and Amines Using the Manganese Catalyst of this Invention Complex 20 was found to be catalytic in the dehydrogenative coupling of methanol and amines. Thus, reaction of 0.5 mmol of piperidine and complex 20 (2 mol %) in 1 ml of MeOH at 110° C. in a closed system resulted after 12 h in formation of N-formylpiperidine in 86% yield (Table 30, entry 1). The catalytic conditions of this reaction were further optimized, as represented in Table 30. Noteworthy, the reaction proceeds in the absence of any hydrogen acceptor. Analysis of the gas phase by GC indicated the formation of H$_2$. A small amount of N-methylpiperidine (13%) was also observed, as a result of reductive amination of formaldehyde intermediate with amine via hydrogen borrowing strategy.[D. van der Waals, L. E. Heim, C. Gedig, F. Herbrik, S. Vallazza, M. H. G. Prechtl, ChemSusChem 2016, 9, 2343-2347]. Therefore, it seemed that the N-methylation can be avoided by performing the reaction in an open system. However, when the reaction was carried out in an open system under reflux, N-formylpiperidine was observed in only 35% yield after 24h, possibly due to the lower temperature, along with an as yet unidentified product; as expected. N-methylation of piperidine was not observed (Table 30, entry 3). Next, the scope of this unprecedented base-metal catalyzed acceptorless dehydrogenative coupling reaction of methanol was probed with different amines. As shown in Table 31, the cyclic secondary amine pyrrolidine was converted to 1-formylpyrrolidine in good yield (61%, Table 30, entry 2). Dehydrogenative coupling of morpholine with methanol gave 50% 4-morpholinecarboxaldehyde (Table 31, entry 3) after 24 h. Reaction of N-methylbenzylamine with methanol afforded the corresponding N-benzyl-N-methylformamide in 78% yield after 15 h (Table 31, entry 4). Exploring the scope further, dehydrogenative reactions of methanol with various substituted primary benzylamines were studied. Thus, reaction of methanol with benzylamine (14 h) afforded the corresponding N-benzylformamide in 70% yield (Table 31, entry 5). Dehydrogenative coupling of 4-methoxybenzylamine and 4-methylbenzylamine with methanol led to 67%, and 74% yields of N-(4-methoxybenzyl)formamide and N-(4-methylbenzyl) formamide, respectively (Table 30, entries 6 and 7). Reaction of methanol with benzylic amines bearing electron withdrawing groups in the para positions (p-Cl, p-F) afforded the corresponding N-4-chlorobenzylformamide (56%), N-4-fluorobenzylformamide (57%) in moderate yields (Table 31, entries 9-10). Dehydrogenative coupling of the less basic 4-trifluoromethylbenzylamine with methanol resulted in 71% yield of N-(4-trifluoromethylbenzyl)formamide (Table 31, entry 8). The reaction of primary amines was not limited to benzyl amines. Reaction of methanol and cyclohexylamine furnished 66% yield of N-cyclohexylformamide (Table 31, entry 11). Similarly, 53% yield of N-(2-phenylethyl)formamide was obtained after 24 h heating of methanol and 2-phenethylamine (Table 30, entry 13). Butylamine gave N-butylformamide in good yield (64%, Table 31, entry 14). 1-naphthylmethylamine yielded N-(1-naphthmethyl)formamide in 62% yield after 15 h (Table 31, entry 12).

TABLE 30

Optimisation of the reaction conditions for N-formylation of piperidine using methanol catalyzed by 20:

| Entry | MeOH (mL) | Temp (° C.) | Time (h) | Conv.(%)[b] | Yield of formamide (%)[b] |
|---|---|---|---|---|---|
| 1 | 1 | 110 | 12 | 99[c] | 86 |
| 2 | 1 | 110 | 5 | 99[d] | 37 |
| 3 | 1 | Reflux (open) | 24 | 99[e] | 35 |
| 4 | 0.5 | 110 | 12 | 99 | 43 |
| 5 | 1 | 110 | 12 | 0 | 0 |

Conditions: piperidine (0.5 mmol), MeOH (1 mL), 20 (0.01 mmol), heated in an 100 mL closed Fischer Porter tube at 110° C. [b]Yields and conversions determined by GC or NMR analysis using toluene or m-xylene as internal standards. $C_{13}$% N-methylpiperidine formed. [d]Difference in conversion and yield indicated formation of N-methylpiperidine and an unidentified product. [e]Difference in conversion and yield indicated formation of an unidentified product. [f]The reaction was carried out without catalyst.

TABLE 31

N-formylation of amines using methanol catalyzed by 20

| Entry[a] | Amines | Products | Time (h) | Conv (%) | Yield (%)[b] |
|---|---|---|---|---|---|
| 1 | piperidine | N-formylpiperidine | 12 | 99 | 86 |
|  |  |  | 12 | 99 | 72[c] |
|  |  |  | 12 | 99 | 78[d] |
| 2 | pyrrolidine | 1-formylpyrrolidine | 14 | 97 | 61 |
| 3 | benzoxazine-CH₂NH₂ | benzoxazine-CH₂NHCHO | 24 | 99 | 50 |

TABLE 31-continued

N-formylation of amines using methanol catalyzed by 20

| Entry[a] | Amines | Products | Time (h) | Conv (%) | Yield (%)[b] |
|---|---|---|---|---|---|
| 4 | N-methylbenzylamine | N-methyl-N-benzylformamide | 15 | 99 | 78 |
| 5 | benzylamine | N-benzylformamide | 14 | 99 | 70 |
| 6 | 4-methoxybenzylamine | N-(4-methoxybenzyl)formamide | 12 | 99 | 67 |
| 7 | 4-methylbenzylamine | N-(4-methylbenzyl)formamide | 18 | 99 | 74 |
| 8 | 4-(trifluoromethyl)benzylamine | N-(4-(trifluoromethyl)benzyl)formamide | 12 | 83 | 71 |
| 9 | 4-chlorobenzylamine | N-(4-chlorobenzyl)formamide | 12 | 99 | 56 |
| 10 | 4-fluorobenzylamine | N-(4-fluorobenzyl)formamide | 14 | 99 | 57 |
| 11 | cyclohexylamine | N-cyclohexylformamide | 12 | 93 | 66 |
| 12 | | | 15 | 99 | 62 |
| 13 | phenethylamine | N-phenethylformamide | 24 | 99 | 53 |
| 14 | n-butylamine | N-butylformamide | 15 | 97 | 64 |

[a]Conditions: amines (0.5 mmol), MeOH (1 mL), 20 (0.01 mmol), heated in an 100 mL closed Fischer Porter tube at 110° C.
[b]Yields and conversions determined by GC or NMR analysis using toluene or m-xylene as internal standards, and conversion based on amine consumption.
[c]Complex 18 was used as catalyst.
[d]Complex 20 was used as catalyst.
Difference in yield and conversion indicates formation of N-methylated amine and also unidentified product.

Example 28

Proposed Mechanism for the Formation of Formamides

Freshly prepared complex (iPr-PNP)Mn(CO)$_2$ 18 (18 mg) was dissolved in 0.5 mL C$_6$D$_6$ giving a red solution. 2 equiv. of MeOH (3 µL) were added into the solution resulting in color change and instant disappearance of the $^{31}$P{$^1$H} NMR signals of the complex 18 and appearance of two new broad signals at 55.3 and 85.5 ppm. The obtained new species was assigned as the methoxy complex (iPr-PN$^H$P)Mn(CO)$_2$(OMe) 22. The $^1$H NMR showed overlapping broad signals at room temperature indicating equilibrium between free methanol and metal bound methoxy group. Therefore variable temperature NMR experiments were carried out in toluene-d$_8$.

Procedure for the Low Temperature NMR Experiment in Toluene-d$_8$:

A solution of freshly prepared complex (iPr-PNP)Mn(CO)$_2$ 18 (10 mg) was dissolved in 0.5 mL toluene-d$_8$. The $^1$H NMR spectrum was recorded at room temperature. Then 1 equiv. of MeOH (0.85 µL) was added into the solution and a slight color change was noticed. $^1$H NMR measurement showed overlapping broad signals at room temperature. Then $^1$H NMR and $^{31}$P{$^1$H} NMR measurements were carried out at low temperatures (FIG. 24). A sharp signal at δ=3.9 ppm in the $^1$H NMR that appeared at −30° C. was attributed to the methoxy ligand of complex 22. A signal at δ=3.1 ppm was assigned to the methoxy group of free methanol.

A 1D NOE study was also carried out at −30° C. by selective irradiation of the signal at δ =3.9 ppm, showing NOE enhancement of the resonance at δ=3.1 ppm corresponding to free methanol.

The $^{31}$P{$^1$H} NMR spectrum at −30° C. revealed two sharp doublets at δ=57.1 ($^2$J$_{PP}$=142 Hz) and 88.7 ($^2$J$_{PP}$=142 Hz) ppm for complex 22 along with the signals of complex 20 and 21. (FIG. 26)

An attempt to isolate complex 22 by removing the solvent in vacuo resulted in regeneration of the amido complex 18, free ligand and a small amount of an as yet unidentified product ($^{31}$P{$^1$H} NMR (THF)=71 ppm, 96 ppm).

Reaction of Complex 21 with Methanol:

Complex 21 (10 mg) was dissolved in 1 mL MeOH and kept stirring for 3 h. The $^{31}$P{$^1$H} NMR spectrum showed appearance of broad signals at 55.3 and 85.5 ppm attributed to the formed methoxy complex 22.

When complex 21 was heated at 100° C. for 30 min in MeOH partial formation of the hydrido complex 20 was observed initially, and after 1 h 20 and 21 converted to the methoxy complex 22. However, in this case when the MeOH solvent was removed in vacuo the $^{31}$P{$^1$H} NMR in THF revealed the signals of an unidentified product at 71 ppm and 96 ppm as the major product.

Reaction of the Amido Complex 18 with 1 Equiv. CD$_3$OD in Toluene:

A solution of freshly prepared amido complex (iPr-PNP)Mn(CO)$_2$ 18 (10 mg) was dissolved in 0.5 mL of toluene in a J Young NMR tube. Then 1 equiv. of CD$_3$OD (0.85 µL) was added and the NMR tube was shaken vigorously. A $^2$H NMR spectrum recorded at room temperature showed a broad signal at δ=3.2 ppm. Conducting the $^2$H NMR measurement at low temperature (−30° C.) showed the splitting of the broad signal to two signals at 3.9 ppm (attributed to metal bound OCD$_3$ ligand) and at δ=3.1 ppm (assigned to free CD$_3$OD (FIG. 25)). The N-D signal of the formed complex was not observed, probably due to overlap with the signals of OCD$_3$ or free CD$_3$OD.

To gain insight into the mechanism of the manganese catalyzed acceptorless dehydrogenative coupling of methanol and amines, the amine complex 19 was reacted with 1.2 equiv. tBuOK in pentane at room temperature, forming deep red crystals, of the amido species 18 (FIG. 27) and the structure was confirmed by X-diffraction studies (FIG. 27 and Example 25). Employing the freshly prepared amido complex 18 (2 mol %) as a catalyst in the dehydrogenative coupling reaction of methanol and piperidine at 110° C. yielded 72% of N-formylpiperidine after 12h (Table 30, entry 1, second row). However, complex 18 turned out to be unstable at room temperature (stable at −30° C. for several hours) and transformed to the thermodynamically more stable light yellow metallated complex 21 (FIG. 27) at room temperature in less than 12 h or upon heating at 110° C. just for 30 min. Thus, intramolecular C—H activation took place, involving cooperation between the metal center and the amido ligand of 18. Heating complex 20 at 110° C. in THF also resulted in formation of complex 21 (FIG. 27) and its structure was confirmed by an X-ray diffraction study and by detailed NMR spectroscopic studies (Example 26). Complex 21 was found active in the catalysis of dehydrogenative coupling reaction giving 78% of N-formylpiperidine after 12 h (Table 30, entry 1, third row).

Significantly, treatment of 18 with methanol (2 equiv.) in C$_6$D$_6$ at room temperature showed instant formation of a new complex which exhibited broad signals in the $^1$H NMR spectrum, and two broad $^{31}$P{$^1$H} NMR signals at δ=55 ppm and 85 ppm. Conducting the experiment in toluene-d$_8$ with 1 equiv. of methanol at −30° C. showed $^{31}$P NMR two sharp doublet signals at δ=57.1 ($^2$J$_{PP}$=142 Hz) and 88.7 ($^2$J$_{PP}$=142 Hz) ppm, attributable to the methoxy complex 22, and in the $^1$H NMR spectrum a sharp signal at 3.9 assigned to the resonance of a proton of the attached methoxy ligand. Another sharp minor signal at 3.1 ppm overlapping with other signals was observed due to free methanol. Upon irradiation of the signal at δ=3.9 ppm (1D NOE study) NOE showed enhancement of the resonances at 3.1 ppm, indicating exchange with free methanol. $^2$H NMR of the reaction of the amido complex 18 with 1 equiv. CD$_3$OD at −30° C. exhibited signals at δ=3.8 and 3.1 ppm (see ESI) for the coordinated methoxy ligand and free methanol. The N-D signal was not detected, likely due to overlap with CD$_3$O signals. Thus, these observations represent a rare direct observation on alkoxy intermediate in O—H activation by an amido-amine metal ligand cooperation. However, complex 22 turned out to be unstable, and removal of solvent regenerates the amido complex 18 along with a small amount of free ligand and an unidentified product showing in $^3$P{$^1$H} NMR signals at 71 and 96 ppm. Complex 21 requires excess methanol and longer reaction time (3 h) at room temperature to form the methoxy complex 22. In addition, when complex 21 was heated in methanol at 100° C., partial formation of the hydrido complex 20 was observed after 30 min, and after 1 h, it converted to the methoxy complex 22.

With these experimental results, there was a high importance in elucidating whether or not the benzylic CH group was involved in H$_2$ liberation in the actual catalytic transformation. Therefore, DFT calculations at the SMD (MeOH)-TPSS-D3BJ/def2-TZVPP//BP86-D3/def2-SV(P) level of theory were performed (FIG. 28). In agreement with the experimental results, 21 is predicted to be thermodynamically more stable than 18 by 9.7 kcal/mol. Reaction of 18 or 21 with methanol gives rise to the methoxy complex 22. H-abstraction from the methoxy ligand via ß-hydride elimination requires dissociation of the NH group and the formation of the agostic intermediate 23. This is due to the fact that by relaxed potential energy surface scans, no barrier for the methanol addition to 18 or 21 with respect to the separated reactants could be identified. A barrier resulting from solvent reorganization effects, intractable by DFT computations, cannot be excluded. Formaldehyde and the hydrido complex 20 is generated by this ß-hydride elimination via a barrier of 11.6 kcal/mol with respect to 18 and the free methanol. $H_2$ liberation from 20 involving 2 methanol molecules as proton shuttle requires only a low activation energy (8.1 kcal/mol with respect to 18). In contrast, a transition state for $H_2$ liberation involving the benzylic CH group is found to be higher in energy (41.8 kcal/mol with respect to 18). According to the computations, this transition state cannot be stabilized by additional methanol molecules, most likely due to the fact that the benzylic CH group is not capable of hydrogen bond formation to the methanol molecules. The formed formaldehyde reacts with the amine to generate a hemiaminal, which in another catalytic cycle liberates hydrogen to give the formamide (FIG. 28).

In conclusion, it has been demonstrated that N-formyl amines were formed by acceptorless dehydrogenative coupling of alcohol and amine, catalyzed by a base-metal catalyst. The reaction proceeds at low temperature under homogeneous conditions, without any additives using the catalysts of the invention.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

What is claimed is:

1. A manganese complex represented by a structure of formula I or its isomer or salt thereof:

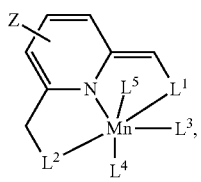

I wherein
$L^1$ is $(PR^aR^b)$;
$L^2$ is $(PR^aR^b)$;
$L^3$ is CO;
$L^4$ is CO;
$L^5$ is absent or CO;
Z represents zero, one, two or three substituents wherein each such substituent is independently selected from the group consisting of alkyl, cycloalkyl, aryl, heterocyclyl, heteroaryl, alkylcycloalkyl, alkylaryl, alkylheterocyclyl, alkylheteroaryl, halogen, nitro, amide, ester, cyano, alkoxy, alkylamino, arylamino, an inorganic support and a polymeric moiety; or Z forms a fused aromatic or heterocyclic ring with the nitrogen based ring;
$R^a$ and $R^b$ are each independently alkyl, cycloalkyl, aryl, heterocyclyl, heteroaryl, alkylcycloalkyl, alkylaryl, alkylheterocyclyl or alkylheteroaryl.

2. The complex of claim 1, $L^3$ and $L^4$ are CO and Z is zero substituents.

3. The complex of claim 1, wherein $R^a$ and $R^b$ are each independently selected from the group consisting of methyl, ethyl, propyl, isopropyl, n-butyl, sec-butyl, isobutyl, t-butyl and benzyl.

4. The complex of claim 3, wherein $R^a$ and $R^b$ are tert butyl or iso-propyl, or wherein said complex is represented by the structure of formula (1):

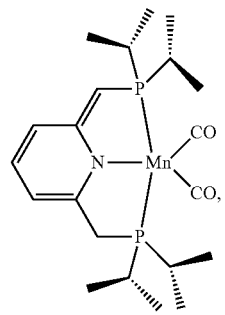

(1)

or
formula (2):

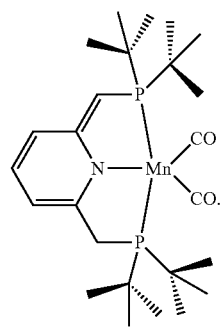

(2)

5. A catalytic process for preparing an imine comprising dehydrogenative coupling of an alcohol of the formula $RCH_2OH$ and an amine of the formula $R^1NH_2$:

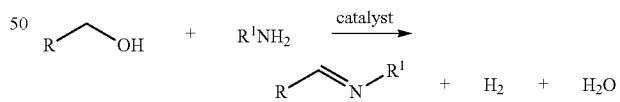

wherein
R is an unsubstituted or substituted alkyl, alkoxyalkyl, cycloalkyl, aryl, alkylaryl, heterocyclyl and heteroaryl;
$R^1$ is unsubstituted or substituted alkyl, alkoxyalkyl, cycloalkyl, aryl, alkylaryl, heterocyclyl and heteroaryl;
wherein said process comprising the step of reacting said alcohol and said amine in the presence of the manganese complex according to claim 1, thereby generating an imine.

6. The process of according to claim 5, wherein said alcohol is selected from the group consisting of: ethanol, n-propanol, n-butanol, n-pentanol, 2-pentanol, 3-pentanol, 1-hexanol, 2-methoxyethanol, 2,2,2-trifluoroethanol, 2-methyl-1-butanol, 3-methyl-1-butanol, benzyl alcohol, 2-methoxy benzyl alcohol, 4-fluoro benzyl alcohol, 4-chloro-benzyl alcohol, 3-methoxy benzyl alcohol, 3,4-methoxy benzyl alcohol, 4-methoxy benzyl alcohol, 1-phenylethanol, and cyclohexane methanol;

said amine is selected from the group consisting of cyclohexanamine, 2-phenylethanamine, (4-methoxyphenyl)methanamine, (4-fluorophenyl)methanamine phenylmethanamine and hexan-1-amine; and said complex is a complex of formula (1), or (2):

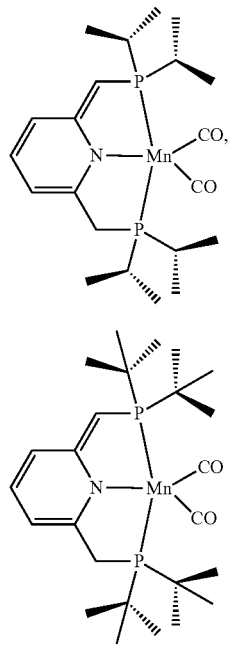

7. A catalytic process for C—C bond formation via Michael addition of unactivated nitriles of the formula $R^2CH_2CN$;

wherein said process comprises reacting an unactivated nitrile of formula $R^2CH_2CN$ and a Michael acceptor in the presence of the manganese complex according to claim 1; thereby generating a new C—C bond;

wherein said Michael acceptor is α, β unsaturated carbonyl, and wherein said process comprises reacting an unactivated nitriles of the formula $R^2CH_2CN$ and a Michael acceptor of the formula $R^3C(R^4)=C(R^5)EWG$:

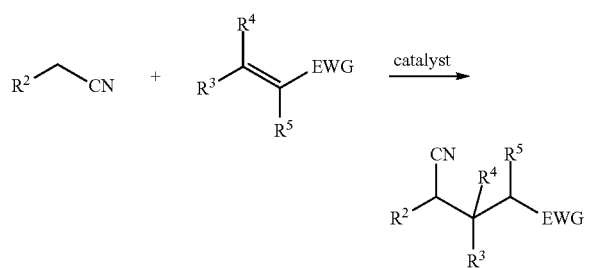

wherein $R^2$ is H, unsubstituted or substituted alkyl, cycloalkyl, aryl, alkylaryl or heterocyclyl; and $R^3$, $R^4$ and $R^5$ are each independently selected from H, unsubstituted or substituted alkyl, cycloalkyl, alkoxy (O-alkyl), aryloxy (O-aryl), aryl, alkylaryl or heterocyclyl or $R^3$ and $R^5$ form a cyclic ring; or $R^4$ and $R^5$ form a cyclic ring; or $R^3$ and $R^4$ form a cyclic ring;

wherein EWG is an electron withdrawing group comprising C(=O)R, C(=O)OR' $SO_2R'$, $CON(R)_2$, $NO_2$ or CN, wherein R is H, alkyl, aryl, heteroaryl, cycloalkyl or heterocycloalkyl; and R' is alkyl, aryl, heteroaryl, cycloalkyl or heterocycloalkyl.

8. The process according to claim 7, wherein said Michael acceptor is ethyl acrylate, but-3-en-2-one, 2,2,2-trifluoroethyl acrylate, phenyl acrylate, methyl methacrylate, cyclohex-2-enone or methyl but-2-enoate, and/or said complex is the complex of formula (1), or (2):

9. A catalytic process for hydrogenation of an ester to an alcohol wherein said process comprises reacting an ester, and a complex of claim 1, in the presence of hydrogen; wherein said complex reacts with said ester to obtain an alcohol;

wherein said ester is a lactone or an ester of formula $R^7C(O)OR^8$; wherein $R^7$ is selected from the group consisting of H, an unsubstituted or substituted alkyl, alkoxyalkyl, cycloalkyl, aryl, alkylaryl, heterocyclyl and heteroaryl; and $R^8$ is selected from the group consisting of an unsubstituted or substituted alkyl, alkoxyalkyl, cycloalkyl, aryl, alkylaryl, heterocyclyl and heteroaryl; and/or said ester of formula $R^7C(O)OR^8$ is hydrogenated to $R_7CH_2OH$; and/or $R^8OH$ is further obtained.

10. A catalytic process for the preparation of esters by dehydrogenative coupling of alcohols, said process comprises reacting an alcohol, and a complex of claim 1;

wherein said complex reacts with said alcohol to obtain an ester wherein said alcohol is a primary alcohol, a secondary alcohol or a dialcohol;

wherein said reaction of dialcohols yields a lactone or a polyester.

11. A catalytic process for the preparation of amides by dehydrogenative coupling of alcohols and amines, said process comprises reacting an alcohol and an amine, in the presence of a complex of claim 1; wherein said amine is a primary amine or a secondary amine or a diamine; or wherein said amine and alcohol is an aminoalcohol compound and said amidation product is a lactam; or wherein said amine is a diamine; said alcohol is a dialcohol and said amidation product is a polyester or polyamide.

12. A catalytic process for the preparation of amides comprising reacting an ester and an amine, in the presence of a complex of claim 1; to obtain an amide, wherein said ester is a lactone or an ester of formula $R^7C(O)OR^8$; wherein $R^7$ is selected from the group consisting of H, an unsubstituted or substituted alkyl, alkoxyalkyl, cycloalkyl, aryl, alkylaryl, heterocyclyl and heteroaryl; and $R^8$ is selected from the group consisting of an unsubstituted or substituted alkyl, alkoxyalkyl, cycloalkyl, aryl, alkylaryl, heterocyclyl and heteroaryl; and/or said amine is a primary amine or a secondary amine.

\* \* \* \* \*